US012509469B2

(12) United States Patent
Parrag et al.

(10) Patent No.: US 12,509,469 B2
(45) Date of Patent: Dec. 30, 2025

(54) COMPOSITIONS AND METHODS FOR THE TREATMENT OF PAIN AND DEPENDENCE DISORDERS

(71) Applicant: Ripple Therapeutics Corporation, Toronto (CA)

(72) Inventors: Ian Charles Parrag, Toronto (CA); Wendy Alison Naimark, Toronto (CA); Matthew Alexander John Statham, Milton (CA); Georgios Rizis, Toronto (CA); Kyle Giovanni Battiston, Toronto (CA)

(73) Assignee: Ripple Therapeutics Corporation, Toronto (CA)

(*) Notice: Subject to any disclaimer, the term of this patent is extended or adjusted under 35 U.S.C. 154(b) by 905 days.

(21) Appl. No.: 17/633,072

(22) PCT Filed: Aug. 6, 2020

(86) PCT No.: PCT/IB2020/000656

§ 371 (c)(1),
(2) Date: Feb. 4, 2022

(87) PCT Pub. No.: WO2021/024039

PCT Pub. Date: Feb. 11, 2021

(65) Prior Publication Data

US 2022/0274999 A1 Sep. 1, 2022

Related U.S. Application Data

(60) Provisional application No. 62/883,987, filed on Aug. 7, 2019, provisional application No. 63/019,181, filed on May 1, 2020.

(51) Int. Cl.

| | |
|---|---|
| ***C07D 489/04*** | (2006.01) |
| ***A61K 9/00*** | (2006.01) |
| ***A61K 31/485*** | (2006.01) |
| ***A61K 47/54*** | (2017.01) |
| ***A61K 47/55*** | (2017.01) |
| ***C07D 489/02*** | (2006.01) |
| ***C07D 489/08*** | (2006.01) |

(52) U.S. Cl.

CPC .......... *C07D 489/02* (2013.01); *A61K 9/0024* (2013.01); *A61K 47/542* (2017.08); *A61K 47/545* (2017.08); *A61K 47/55* (2017.08); *A61K 47/552* (2017.08); *C07D 489/08* (2013.01)

(58) Field of Classification Search

CPC ..... C07D 489/04; A61K 31/485; A61P 25/04; A61P 25/30

USPC ...................................... 546/45, 44; 514/282

See application file for complete search history.

(56) References Cited

U.S. PATENT DOCUMENTS

| | | | |
|---|---|---|---|
| 3,147,183 | A | 9/1964 | Joachim et al. |
| 3,591,612 | A | 7/1971 | Allais et al. |
| 3,663,579 | A | 5/1972 | Stache et al. |
| 4,024,871 | A | 5/1977 | Stephenson |
| 4,198,405 | A | 4/1980 | Enomoto et al. |
| 4,318,908 | A | 3/1982 | Enomoto et al. |
| 4,532,316 | A | 7/1985 | Henn |
| 4,833,215 | A | 5/1989 | Jedlinski et al. |
| 4,916,193 | A | 4/1990 | Tang et al. |
| 5,013,841 | A | 5/1991 | Matsumoto et al. |
| 5,217,493 | A | 6/1993 | Raad et al. |
| 5,250,524 | A | 10/1993 | Kramer et al. |
| 5,321,099 | A | 6/1994 | Goldwasser et al. |
| 5,387,598 | A | 2/1995 | Rossignol |
| 5,512,558 | A | 4/1996 | Enhsen et al. |
| 5,578,621 | A | 11/1996 | Rossignol |
| 5,798,115 | A | 8/1998 | Santerre et al. |
| 5,856,348 | A | 1/1999 | Rossignol |
| 5,859,038 | A | 1/1999 | Rossignol |
| 5,886,013 | A | 3/1999 | Rossignol |
| 5,965,590 | A | 10/1999 | Rossignol |
| 5,968,961 | A | 10/1999 | Rossignol |
| 6,020,353 | A | 2/2000 | Rossignol |
| 6,051,576 | A | 4/2000 | Ashton et al. |

(Continued)

FOREIGN PATENT DOCUMENTS

| | | | |
|---|---|---|---|
| AU | 2012258480 | A1 | 12/2012 |
| AU | 2017214071 | A1 | 8/2018 |

(Continued)

OTHER PUBLICATIONS

BE 616548, Chemical Abstract 1963, vol. 59, No. 1717 (1963) (English Abstract).

Rabouina et al. Synthesis and preliminary biological evaluation of estrone dimers. Letters in Drug Design & Discovery 4(3):171-174 (2007) (Abstract only).

(Continued)

*Primary Examiner* — Charanjit Aulakh

(74) *Attorney, Agent, or Firm* — Faegre Drinker Biddle & Reath LLP

(57) ABSTRACT

Provided herein are (e.g., controlled release) compositions for the treatment of acute or chronic diseases or disorders. Described herein are processable opioid conjugates. Also described herein are compositions and methods for the treatment of central nervous system (CNS) diseases or disorders including chronic pain (e.g., cancer pain), acute pain, opioid addiction, alcohol addiction, alcohol dependence, opioid-induced constipation, and narcotic depression. Said compositions and methods comprise opioid agonists and/or opioid antagonists, which demonstrate CNS activity and/or other desirable activities. Injection of said compositions subcutaneously or intraspinally provides therapeutic benefit to individuals suffering from CNS diseases or disorders.

13 Claims, 36 Drawing Sheets

(56) References Cited

U.S. PATENT DOCUMENTS

| | | | | |
|---|---|---|---|---|
| 6,096,525 | A | 8/2000 | Patnaik | |
| 6,117,894 | A | 9/2000 | Rossignol | |
| 6,127,507 | A | 10/2000 | Santerre | |
| 6,225,321 | B1 * | 5/2001 | Hu | C07D 498/04 546/45 |
| 6,299,604 | B1 | 10/2001 | Ragheb et al. | |
| 6,344,035 | B1 | 2/2002 | Chudzik et al. | |
| 6,429,300 | B1 | 8/2002 | Kurz et al. | |
| 6,602,915 | B2 | 8/2003 | Uhrich | |
| 6,689,350 | B2 | 2/2004 | Uhrich | |
| 6,703,037 | B1 | 3/2004 | Hubbell et al. | |
| 6,770,725 | B2 | 8/2004 | Santerre | |
| 8,062,657 | B2 | 11/2011 | Edelman et al. | |
| 8,349,309 | B2 | 1/2013 | Santerre et al. | |
| 8,722,739 | B2 | 5/2014 | Delong et al. | |
| 8,968,626 | B2 | 3/2015 | Pham et al. | |
| 9,056,048 | B2 | 6/2015 | Diamond et al. | |
| 9,089,579 | B2 | 7/2015 | Kalayoglu | |
| 9,120,738 | B2 | 9/2015 | Wu et al. | |
| 9,604,949 | B2 | 3/2017 | Ellis et al. | |
| 9,820,995 | B2 | 11/2017 | Edelman et al. | |
| 9,855,232 | B2 | 1/2018 | Wu et al. | |
| 9,895,384 | B1 | 2/2018 | Kydonieus et al. | |
| 9,994,543 | B2 | 6/2018 | Wei et al. | |
| 10,188,665 | B2 | 1/2019 | Edelman et al. | |
| 10,588,862 | B2 | 3/2020 | Parrag et al. | |
| 10,632,075 | B2 | 4/2020 | Parrag et al. | |
| 10,945,958 | B2 | 3/2021 | Parrag et al. | |
| 10,959,954 | B2 | 3/2021 | Parrag et al. | |
| 11,021,472 | B2 | 6/2021 | Josel et al. | |
| 11,147,855 | B2 | 10/2021 | Schiffman et al. | |
| 11,279,729 | B2 | 3/2022 | Parrag et al. | |
| 2003/0022876 | A1 * | 1/2003 | Ashton | A61K 31/485 540/107 |
| 2003/0035787 | A1 | 2/2003 | Uhrich | |
| 2003/0039689 | A1 | 2/2003 | Chen et al. | |
| 2003/0118528 | A1 | 6/2003 | Walters et al. | |
| 2003/0158598 | A1 | 8/2003 | Ashton et al. | |
| 2003/0203030 | A1 | 10/2003 | Ashton et al. | |
| 2004/0087664 | A1 | 5/2004 | Marcus et al. | |
| 2004/0180036 | A1 | 9/2004 | Ashton et al. | |
| 2004/0235811 | A1 | 11/2004 | Currie et al. | |
| 2005/0008695 | A1 | 1/2005 | Ashton et al. | |
| 2005/0031577 | A1 | 2/2005 | Uhrich | |
| 2005/0070470 | A1 | 3/2005 | Coy et al. | |
| 2005/0159609 | A1 | 7/2005 | King et al. | |
| 2005/0164994 | A1 | 7/2005 | Ashton et al. | |
| 2005/0220839 | A1 | 10/2005 | DeWitt et al. | |
| 2005/0255079 | A1 | 11/2005 | Santerre et al. | |
| 2006/0247216 | A1 | 11/2006 | Haj-Yehia | |
| 2007/0031472 | A1 | 2/2007 | Huang et al. | |
| 2009/0124591 | A1 | 5/2009 | Diamond et al. | |
| 2010/0062974 | A1 | 3/2010 | LaRonde et al. | |
| 2011/0243884 | A1 | 10/2011 | O'Shea et al. | |
| 2013/0096097 | A1 | 4/2013 | Kasai et al. | |
| 2013/0289223 | A1 | 10/2013 | Santerre et al. | |
| 2014/0256696 | A1 | 9/2014 | Sinha et al. | |
| 2016/0038651 | A1 | 2/2016 | Santerre et al. | |
| 2017/0028078 | A1 | 2/2017 | Mandell et al. | |
| 2018/0318318 | A1 | 11/2018 | Wang et al. | |
| 2019/0247311 | A1 | 8/2019 | Parrag et al. | |
| 2020/0071275 | A1 | 3/2020 | Delong et al. | |
| 2020/0276179 | A1 | 9/2020 | Kopczynski et al. | |
| 2021/0030667 | A1 | 2/2021 | Parrag et al. | |
| 2021/0113457 | A1 | 4/2021 | Parrag et al. | |
| 2021/0121455 | A1 | 4/2021 | He | |
| 2021/0121534 | A1 | 4/2021 | Schiffman et al. | |
| 2021/0205222 | A1 | 7/2021 | Parrag et al. | |
| 2022/0089635 | A1 | 3/2022 | Parrag et al. | |
| 2022/0106351 | A1 | 4/2022 | Parrag et al. | |
| 2022/0288277 | A1 | 9/2022 | Parrag et al. | |
| 2022/0289787 | A1 | 9/2022 | Parrag et al. | |
| 2022/0347305 | A1 | 11/2022 | Parrag et al. | |
| 2023/0225975 | A1 | 7/2023 | Parrag et al. | |

FOREIGN PATENT DOCUMENTS

| | | | |
|---|---|---|---|
| CA | 1148166 | A | 6/1983 |
| CA | 2461099 | A1 | 4/2003 |
| CA | 2467321 | A1 | 11/2005 |
| CA | 2571320 | A1 | 11/2005 |
| CA | 2906238 | A1 | 9/2014 |
| CH | 592687 | A5 | 11/1977 |
| CN | 101099867 | A | 1/2008 |
| CN | 1968715 | B | 12/2010 |
| CN | 105377319 | A | 3/2016 |
| CN | 110746593 | A | 2/2020 |
| EP | 3494955 | B1 | 1/2021 |
| FR | 2007815 | A1 | 1/1970 |
| IN | 201841029923 | A | 2/2020 |
| JP | S50123654 | A | 9/1975 |
| JP | H07501470 | A | 2/1995 |
| JP | H0924093 | A | 1/1997 |
| JP | 2000501318 | A | 2/2000 |
| JP | 2007537168 | A | 12/2007 |
| WO | WO-9010437 | A1 | 9/1990 |
| WO | WO-9511907 | A1 | 5/1995 |
| WO | WO-9520567 | A1 | 8/1995 |
| WO | WO-9528393 | A1 | 10/1995 |
| WO | WO-9729778 | A2 | 8/1997 |
| WO | WO-9807458 | A1 | 2/1998 |
| WO | WO-9850035 | A1 | 11/1998 |
| WO | WO-9906430 | A1 | 2/1999 |
| WO | WO-9912990 | A1 | 3/1999 |
| WO | WO-0209768 | A2 | 2/2002 |
| WO | WO-03028527 | A2 | 4/2003 |
| WO | WO-03040104 | A1 | 5/2003 |
| WO | WO-03043657 | A1 | 5/2003 |
| WO | WO-2004016214 | A2 | 2/2004 |
| WO | WO-2004033478 | A2 | 4/2004 |
| WO | WO-2005009480 | A2 | 2/2005 |
| WO | WO-2005110485 | A1 | 11/2005 |
| WO | WO-2007056457 | A2 | 5/2007 |
| WO | WO-2010040187 | A1 | 4/2010 |
| WO | WO-2010040188 | A1 | 4/2010 |
| WO | WO-2010062562 | A1 | 6/2010 |
| WO | WO-2011120044 | A1 | 9/2011 |
| WO | WO-2012109445 | A1 | 8/2012 |
| WO | WO-2012139164 | A1 | 10/2012 |
| WO | WO-2013106528 | A1 | 7/2013 |
| WO | WO-2014000033 | A1 | 1/2014 |
| WO | WO-2014134689 | A1 | 9/2014 |
| WO | WO-2014138190 | A1 | 9/2014 |
| WO | WO-2014139033 | A1 | 9/2014 |
| WO | WO-2015168014 | A1 | 11/2015 |
| WO | WO-2017041142 | A1 | 3/2017 |
| WO | WO-2017053638 | A1 | 3/2017 |
| WO | WO-2017083794 | A1 | 5/2017 |
| WO | WO-2018165710 | A1 | 9/2018 |
| WO | WO-2018165711 | A1 | 9/2018 |
| WO | WO-2019118924 | A1 | 6/2019 |
| WO | WO-2019148291 | A1 | 8/2019 |
| WO | WO-2019148293 | A1 | 8/2019 |
| WO | WO-2019148294 | A1 | 8/2019 |
| WO | WO-2019210215 | A1 | 10/2019 |
| WO | WO-2020154815 | A1 | 8/2020 |
| WO | WO-2021005417 | A1 | 1/2021 |
| WO | WO-2021014217 | A1 | 1/2021 |
| WO | WO-2021024039 | A1 | 2/2021 |
| WO | WO-2021024041 | A1 | 2/2021 |
| WO | WO-2021220061 | A2 | 11/2021 |

OTHER PUBLICATIONS

Saraiya et al. Dexamethasone for ocular inflammation. Expert Opin Pharmacother 12(7):1127-31 (2011).

U.S. Appl. No. 16/966,452 Office Action dated Dec. 2, 2022.

U.S. Appl. No. 16/966,453 Office Action dated Jul. 25, 2022.

U.S. Appl. No. 17/145,093 Office Action dated Dec. 19, 2022.

U.S. Appl. No. 18/170,403 Office Action dated Sep. 13, 2023.

Kalinowski et al. The influence of bolaamphiphilic steroid dimer on the formation and structure of bilayer lipid membranes. Cellular and Molecular Biology Letters 5(1):107-118 (2000).

U.S. Appl. No. 17/554,808 Office Action dated Nov. 7, 2023.

(56) References Cited

OTHER PUBLICATIONS

Bhattacharya et al.: Polymorphism in Pharmaceutical Solids: Thermoanalytical and Crystallographic Methods 334 (Brittain H. ed., 2nd ed. Informa Healthcare USA, Inc. 2009), 20 pp.
U.S. Appl. No. 17/426,779 Office Action dated Apr. 23, 2024.
U.S. Appl. No. 17/554,808 Office Action dated May 15, 2024.
U.S. Appl. No. 18/170,403 Office Action dated Feb. 26, 2024.
Carrilho et al. A new facile synthesis of steroid dimers containing 17,17'-dicarboxamide spacers. Tetrahedron Letters 54:2763-2765 (2013).
Bernstein, J. et al. Chapter 7.5: Powder diffraction and pharmaceuticals. International Tables for Crystallography H:767-781 (2019).
Co-pending U.S. Appl. No. 18/792,949, inventors Parrage; Ian Charles et al., filed Aug. 2, 2024.
U.S. Appl. No. 17/426,779 Office Action dated Nov. 4, 2024.
Bach et al., Retention of Antibacterial Activity and Bacterial Colonization of Antiseptic-Bonded Central Venous Catheters. J. Antimicrob. Chemother. 37:315-322 (1996).
Berge et al. Pharmaceutical Salts. Journal of Pharmaceutical Sciences 66(1):1-19 (Jan. 1977).
Blondeau. Fluoroquinolones: mechanism of action, classification, and development of resistance. Sury Ophthalmol. 49 Suppl 2:S73-8 (2004).
Budavari. The Merck Index—Fourteenth Edition Merck Research Laboratories. Whitehouse Station, NJ, pp. 1306-1307 (2006).
Burger. Isosterism and Bioisosterism in Drug Design, in Progress in Drug Research 287-328 (Ernst Jucker, ed., Birkhauser Verlag) (1991).
Chanphai et al. Conjugation of steroids with PAMAM nanoparticles. Colloids and Surfaces B: Biointerfaces 136:1035-1041 (2015).
Cheng et al., Intravitreal sustained-release dexamethasone device in the treatment of experimental uveitis. Invest Ophthalmol Vis Sci. 36(2):442-53 (1995).
Chirife et al., In vitro antibacterial activity of concentrated polyethylene glycol 400 solutions. Antimicrob Agents Chemother. 24(3):409-12 (1983).
Coessens et al., Synthesis and In Vitro Stability of Macromolecular Prodrugs of Norfloxacin. J. Cont. Release 47:283-291 (1997).
Dao et al. Targeting the Estrogen Receptor using Steroid-Therapeutic Drug Conjugates (Hy-brids). Bioconjugate Chemistry 23(11):2139-2158 (2012).
Ditizio et al., A Liposomal Hydrogel for the Prevention of Bacterial Adhesion to Catheters. Biomaterials 19:1877-1884 (1998).
Gaudana et al. Ocular drug delivery. AAPS J. 12(3):348-360 (2010).
Ghosh. Monomers and Polymers from Nalidixic Acid-Synthesis, Characterization, and Hydrolysis Study, in Progress in Biomedical Polymers, Ed. Gebekin et al., Plenum Press, New York, pp. 335-345 (1990).
Ghosh. Studies Directed Towards Polymeric Quinloone Antibiotics—Synthesis of Potential Monomers From Nalidixic Acid. Polymeric Mat. Sci. Engin. 59:790-793 (1988).
Gower et al. Drug discovery in ophthalmology: past success, present challenges, and future opportunities. BMC Ophthalmology 16:11 (Jan. 16, 2016).
Howard-Sparks et al. A Novel Chemical Delivery System Comprising an Ocular Sustained Re-lease Formulation of a 3a-17a-21-trihydroxy-5B-pregnan-20-one-BIS-5-Fluorouracil Coding. Drug Dev Ind Pharm 33:677-682 (2007).
Janout et al., Bioconjugate-Based Molecular Umbrellas. Bioconjugate Chemistry, 20(2):183-192 (E-Pub Nov. 20, 2008).
Janout et al. Molecular umbrella-amphotercin B conjugates. Bioconjugate Chemistry 25:1408-1411 (2014).
Jurček et al. Succinobucol's New Coat—Conjugation with Steroids to Alter Its Drug Effect and Bioavailability. 16(11):9404-9420 (2011).
Kanra et al., The short-term efficacy and safety of dexamethasone implant in a difficult-to-treat patient population with persistent diabetic macular edema. Ret Vit. 26(3):221-7 (2017) (English Abstract).
Kerns et al., Piperazinyl-linked fluoroquinolone dimers possessing potent antibacterial activity against drug-resistant strains of *Staphylococcus aureus*. Bioorg Med Chem Lett. 13(10):1745-9 (2003).
Li et al., Dimeric and Oligomeric Steroids. Chem Rev. 97(1):283-304 (1997).
Manolakis et el. Novel L-DOPA-derived poly(ester amide)s: monomers, polymers, and the first L-DOPA-functionalized biobased adhesive tape. Macromol Rapid Commun 35(1):71-6 (2014).
Michael et al. Enhanced RNA binding of dimerized aminoglycosides. Bioorg Med Chem 7:1361-1371 (1999).
Modak et al., A New Method for the Direct Incorporation of Antibiotic in Prosthetic Vascular Grafts. Surg. Gynecol. Obstet. 164:143-147 (1987).
Morimoto et al. New dimeric morphine from opium poppy (*Papaver somuniferum*) and its physiological function. J Nat Prod 66(7):987-989 (2003).
Nahar et al. A review on steroid dimers: 2011-2019. Steroids 164:108736 (2020).
Nahar et al. A review on synthetic and natural steroid dimers: 1997-2006. Current Medicinal Chemistry 14:1349-1370 (2007).
Nathan et al., Copolymers of Lysine and Polyethylene Glycol: A New Family of Functionalized Drug Carriers, Bioconjug. Chem. 4:54-62 (1993).
Navacchia et al. Bile Acid Conjugates with Anticancer Activity: Most Recent Research. Molecules 26(1):25 (2020).
Nishida et al., Studies on synthesis of antibacterial agent (NM441). I. Kinetics and mechanism of the reaction of 4-(bromomethyl)-5-methyl-1,3-dioxol-2-one with 1-substituted piperazine (NM394). Bull Chem Soc Jpn. 67:1419-26 (1994).
Nosova et al., Synthesis of new fluorinated derivatives of quinolinecarboxylic acids. Chem Heterocycl Compd 38(8):922-8 (2002).
Odian (Principles of Polymerization, 4th ed.(2004).
Paris et al. Glycerides as prodrugs. 3. Synthesis and antiinflammatory activity of [1-(p-chlorobenzoyl)-5-methoxy-2-methylindole-3-acetyl]glycerides (indomethacin glycerides). J Med Chem 23(1):9-13 (1980).
Paryze et al., A new approach to steroid dimers and macrocycles by the reaction of 3-chlorocarbonyl derivatives of bile acids with 0,0-, N,N-, and S,S-dinucleophiles. Tetrahedron Lett. 53(46):6212-5 (2012).
Patani et al. Bioisosterism: A Rational Approach in Drug Design. Chem. Rev. 96:3147-3176 (1996).
PCT/CA2014/050284 International Search Report and Written Opinion dated Jun. 2, 2014.
PCT/CA2019/050133 International Search Report and Written Opinion dated Apr. 29, 2019.
PCT/CA2019/050135 International Search Report and Written Opinion dated Apr. 29, 2019.
PCT/CA2019/050136 International Search Report and Written Opinion dated Apr. 29, 2019.
PCT/CA2020/050117 International Search Report and Written Opinion dated Apr. 15, 2020.
PCT/IB2020/000620 International Search Report and Written Opinion dated Oct. 30, 2020.
PCT/IB2020/000656 International Search Report and Written Opinion dated Nov. 16, 2020.
PCT/IB/2020/000659 International Search Report and Written Opinion dated Dec. 14, 2020.
PCT/IB2020/000663 International Search Report and Written Opinion dated Dec. 1, 2020.
PCT/IB2021/000332 International Search Report and Written Opinion dated Nov. 17, 2021.
Peng et al. Pharmacological properties of bivalent ligands containing butorphan linked to nalbuphine, naltrexone, and naloxone at mu, delta, and kappa opioid receptors. J Med Chem 50(9):2254-2258 (2007).
Ren et al., Macromolecular prodrug of dexamethasone prevents particle-induced peri-implant osteolysis with reduced systemic side effects. J Control Release. 175:1-9 (2014) (24 pages).
Robin et al. Medication adherence in patients with ocular hypertension or glaucoma. Exp. Rev. Ophth. 14:4-5, 199-210 (2019).
Roseeuw et al., Polymeric Prodrugs of Antibiotics with Improved Efficiency. J. Mater. Sci. Mater. Med. 10:743-746 (1999).

(56) References Cited

OTHER PUBLICATIONS

Sarker et al. Chapter 6: Applications of Steroid Dimers. in Steroid Dimer: Chemistry and Applications in Drug Design and Delivery, John Wiley & Sons Ltd. pp. 379-407 (2012).
Sinha. New findings on biological factors predicting addiction relapse vulnerability. Curr Psychiatry Rep 13(5):398-405 (2011).
Step-growth Polymerization. http://en.wikipedia.org/wiki/Step-growth_polymerization, retrieved on Jan. 12, 2012 (11 pages).
Svobodova et al. Recent advances in steroidal supramolecular gels. RSC Advances 2:4985-5007 (2012).
U.S. Appl. No. 16/396,135 Office Action dated Jul. 3, 2019.
U.S. Appl. No. 16/396,400 Office Action dated Jun. 24, 2019.
U.S. Appl. No. 16/396,400 Office Action dated Oct. 15, 2019.
U.S. Appl. No. 16/396,400 Response to Non-Final Office Action dated Sep. 24, 2019.
U.S. Appl. No. 16/698,372 Office Action dated Jan. 21, 2020.
U.S. Appl. No. 16/698,372 Office Action dated May 26, 2020.
U.S. Appl. No. 16/699,305 Office Action dated Feb. 3, 2020.
U.S. Appl. No. 16/699,305 Office Action dated May 26, 2020.
U.S. Appl. No. 17/145,093 Office Action dated Mar. 14, 2022.
U.S. Appl. No. 17/350,888 Office Action dated Oct. 7, 2021.
Woo et al., Biological characterization of a novel biodegradable antimicrobial polymer synthesized with fluoroquinolones, J. Biomat. Res., 59(1):35-45 (2002).
Woo et al., Synthesis and characterization of a novel biodegradable antimicrobial polymer, Biomaterials, 21:1235-1246 (2000).
Xue et al., New dimeric cholesteryl-based A(LS)2 gelators with remarkable gelling abilities: organogel formation at room temperature. J Colloid Interface Sci. 361(2):556-64 (2011).
Yang et al. Utilization of quinolone drugs as monomers: characterization of the synthesis reaction products for poly(norfloxacin diisocyanatododecane polycaprolactone). Biomacromolecules 2(1):134-41 (2001).

* cited by examiner

COMPOSITIONS AND METHODS FOR THE TREATMENT OF PAIN AND DEPENDENCE DISORDERS

CROSS-REFERENCES

This application is filed pursuant to 35 U.S.C. § 371 as a United States National Phase Application of International Application Ser. No. PCT/IB2020/000656, filed Aug. 6, 2020, which claims the benefit of U.S. Provisional Application No. 62/883,987, filed Aug. 7, 2019, and U.S. Provisional Application No. 63/019,181, filed May 1, 2020, which are hereby incorporated by reference in their entirety herein.

BACKGROUND OF THE INVENTION

Opioid (receptor) agonists are a front-line medication in the treatment of pain. However, use of opioid agonists are very often abused, which leads to adverse societal effects, addiction, overdose, and death. In some instances, opioid (receptor) antagonists are utilized in the treatment of (e.g., opioid) addiction, and/or overdose. Opioids (opioid receptor agonists and/or antagonists) are administered through a number of methods, including via oral or subcutaneous delivery methods. To provide efficacy, however, frequent or emergency administration of opioids is often required. For example, opioid (receptor) agonist oxycodone may be given twice a day (e.g., extended release). Frequent use of opioid (receptor) antagonists may also be administered frequently in order to deter opioid agonist abuse and/or administered in emergency situations to avoid overdose and/or death.

SUMMARY OF THE INVENTION

Provided in certain embodiments herein are compounds comprising a first radical (D1) and a second radical (D2) (e.g., having the formula: D1-L-D2). In certain instances, at least one of (e.g., both of) D1 and D2 is an opioid group (also referred to herein as an opioid radical) (e.g., opioid antagonists) and L is a linker. In certain embodiments, L is a hydrolyzable linker, such that when the compound of formula D1-L-D2 is (e.g., subcutaneously or intraspinal) administered (or when present in or otherwise exposed to an aqueous environment, such as a buffering solution, serum, or the like), D1 and D2 are released (e.g., in their free, non-radical form). In certain instances, the (e.g., covalent) joining of a D1 and a D2 through a linker L provides a compound comprising a processable form.

In some instances, compounds provided herein are processable into forms (e.g., implants, coatings, or other bodies), such as that are capable of being administered to an individual in need thereof. In some instances, such compounds are processable without the need for additional excipients or materials (e.g., controlled release polymers, matrices, or other components). In certain instances, the no or low amounts of additional excipients or materials facilitates high overall quantities of drug delivery (e.g., over an extended period), while limiting impact of drug delivery (e.g., a small implant can have high quantities of drug).

In certain instances, such compounds (or implants comprising such compounds) are administered to (e.g., implanted into) an individual, such that sustained and/or otherwise controlled (e.g., local or systemic) delivery of the drug is achieved. In some instances, delivery of the compounds (e.g., in the form of an implant, coating, etc.) facilitate delivery of a drug component or radical thereof for an extended period of time, such as for weeks, months, or more. In certain instances, compounds, formulations, and implants provided herein facilitate the long term delivery of drugs to an individual in need thereof, such as without the need for frequent dosing. For example, as discussed herein, opioids are often formulated and administered orally, such as with daily administration. In some instances, without rigid compliance to frequent administration is required to maintain (e.g., optimal) therapeutic efficacy. With the compounds provided herein, however, long term delivery of such drugs can be achieved from weeks, months, or more, with infrequent administration (e.g., once a year, twice a year, or the like). Further, in the case of opioid antagonists, patient compliance is a particular concern. For example, an opioid addict is likely to avoid taking an opioid antagonist in a time period where the addict desires to abuse an opioid agonist. Thus, in some instances, a long-lasting implant releasing an opioid antagonist over a long period of time will facilitate improved compliance with addiction rehabilitation that involve the use of opioid antagonist therapies.

Provided in certain embodiments herein are compounds, such as described herein, (e.g., pharmaceutical) compositions comprising compounds described herein, and methods of making and using compounds provided herein. In some embodiments, methods of using the compounds provided herein include methods of treating disorders in individuals in need thereof, such as disorders treatable by a drugs D1 and/or D2 (e.g., in its free form). It is to be understood that disclosures of methods provided herein explicitly include disclosures of pharmaceutical compositions comprising (e.g., an effective amount) of a compound provided herein for such uses.

As such, provided herein are compounds, compositions, methods, and formulations for the treatment of chronic pain (e.g., cancer pain), acute pain, opioid addiction, alcohol addiction, alcohol dependence, opioid-induced constipation, narcotic depression, or the like.

In certain embodiments, provided herein is an article comprising a compound of formula (A-I):

D1-L-D2 (A-I), or a pharmaceutically acceptable salt thereof.

In some embodiments each of D1 and D2 is, independently, a radical formed from a drug bearing a hydroxyl, primary amino, secondary amino, enolizable ketone, or carboxyl functional group for covalent attachment to L. In some embodiments, L is a linker covalently linking D1 to D2. In some embodiments, at least 70% (w/w) (e.g., 75±5%, 80±5%, 85±5%, 90±5%, 95±5% (w/w), or more) of the article is the compound of formula (A-I). In some embodiments, D1 and D2 are not radicals formed from a steroid.

In some embodiments, the article is a fiber, a fiber mesh, a woven fabric, a non-woven fabric, a film, a surface coating, a pellet, a cylinder, a hollow tube, a microparticle, a nanoparticle, or a shaped article. In some embodiments, the compound, D1, D2, or any combination thereof are released from the article through surface erosion. In certain embodiments, the article is free of controlled release polymer. In certain instances, D1 and D2 are released from the article at 37° C. in 100% bovine serum or at 37° C. in PBS (e.g., at a rate such that $t_{10}$ is greater than or equal to 1/10 of $t_{50}$).

Provided in certain embodiments herein is a method of forming an article provided herein, the method comprising (a) heating the compound (e.g., a crystalline form (e.g., a solid or a powder)), or a pharmaceutically acceptable salt thereof, (e.g., to form a melt or a glass); and (b) heat molding the compound (e.g., the melt or the glass) to form the article.

In certain embodiments, the method comprises (a) heating the compound, or a pharmaceutically acceptable salt thereof, (e.g., to form a melt or a glass); and (b) molding (e.g., injection molding or blow molding) the compound (e.g., the melt or the glass) to form the article. In some embodiments, the method comprises (a) dissolving the compound, or a pharmaceutically acceptable salt thereof, e.g., in a solvent (e.g., to form a solution); and (b) evaporating the solvent to form the article. For example, step (b) can include solvent casting to form a film or a fiber. In certain embodiments, the method comprises (a) dissolving the compound, or a pharmaceutically acceptable salt thereof, e.g., in a solvent (e.g., to form a solution); and (b) electrospinning or electrospraying the compound (e.g., dissolved in the solution) to form the article. In some embodiments, the method comprises (a) heating the compound, or a pharmaceutically acceptable salt thereof, (e.g., to form a melt or a glass); and (b) electrospinning or electrospraying the compound (e.g., the melt or the glass) to form the article. In certain embodiments, the method comprises (a) heating the compound, or a pharmaceutically acceptable salt thereof, (e.g., to form a melt); (b) extruding the compound (e.g., the melt or the glass) to form the article. In some embodiments, the article is further annealed.

Provided in certain embodiments herein is a compound comprising a first radical and a second radical, the first radical and the second radical each comprising a structure of Formula (I):

(I)

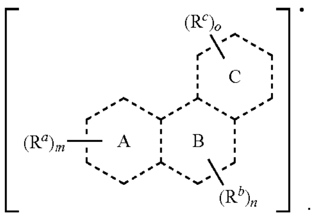

In certain embodiments, each ⸝⸝ is, independently, a single bond or a double bond. In some embodiments, each $R^a$, $R^b$, and $R^c$ are independently selected from the group consisting of oxo, halogen, —CN, —$NO_2$, azide, alkyl, heteroalkyl, cycloalkyl, heterocycloalkyl, alkoxy, aryloxy, ester, amino, hydrazone, oxime, hydroxy, or thiol, wherein the alkyl, heteroalkyl, cycloalkyl, alkoxy, aryloxy, hydrazone, or heterocycloalkyl is optionally substituted.

In some embodiments, any one of an $R^a$, $R^b$, or $R^c$ is independently taken together with another of $R^a$, $R^b$, or $R^c$ to form a substituted or unsubstituted cycloalkyl, heterocycloalkyl, aryl, or heteroaryl. In some embodiments, an $R^a$ is taken together with $R^c$ to form an optionally substituted heterocycloalkyl. In some embodiments, an $R^a$ or an $R^b$ is taken together with another $R^a$ or $R^b$ to form an optionally substituted cycloalkyl or an optionally substituted heterocycloalkyl. In some embodiments, an $R^b$ is taken together with another $R^b$ to form a substituted heterocycloalkyl. In some embodiments, $R^b$ is amino and combines with another $R^b$ to form an optionally substituted heterocycloalkyl. In some embodiments, $R^b$ is amino and combines with one of $R^b$ to form a heterocycloalkyl substituted with optionally substituted alkyl.

In some embodiments, each of m, n, and o are independently 0-6. In some embodiments, m is 4. In some embodiments, m is 3. In some embodiments, m is 2. In some embodiments, m is 1. In some embodiments, n is 2. In some embodiments, n is 1. In some embodiments, o is 2. In some embodiments, o is 1.

In some embodiments, the first and second radicals are non-steroidal. In some embodiments, the first and second radicals are both opioid radicals (e.g., the same opioid radical). Also provided in certain embodiments herein are pharmaceutical salts or solvates of a compound of Formula (I). In some embodiments, the structure of Formula (I) is processable at a temperature of at least 20° C. (e.g., 20° C., 25° C., 30° C., 37° C., or more) in its free form.

In some embodiments, $R^a$, $R^b$, and $R^c$ are each optionally and independently substituted with one or more groups, each group independently selected from —OH, oxo, alkyl (e.g., alkenyl), heteroalkyl, cycloalkyl, or alkoxy, wherein the alkyl, heteroalkyl, cycloalkyl, or alkoxy, is further optionally substituted. In certain embodiments, the alkyl, heteroalkyl, cycloalkyl, or heterocycloalkyl of each $R^a$, $R^b$, or $R^c$ is, independently, substituted or not substituted. In some embodiments, each group is independently not substituted or substituted with any one or more substituent described herein. In specific embodiments, each group is independently not substituted or substituted with one or more substituent, wherein each substituent is selected from the group consisting of —OH, oxo, alkyl (e.g., alkenyl), heteroalkyl, cycloalkyl, or alkoxy, wherein the alkyl, heteroalkyl, cycloalkyl, or alkoxy, is further optionally substituted.

In some embodiments, the substituted or unsubstituted cycloalkyl, heterocycloalkyl, aryl, or heteroaryl are each optionally and independently substituted with one or more groups, each group independently selected from —OH, oxo, alkyl (e.g., alkenyl), heteroalkyl, cycloalkyl, or alkoxy, wherein the alkyl, heteroalkyl, cycloalkyl, or alkoxy, is further optionally substituted. In certain embodiments, substituted or unsubstituted cycloalkyl, heterocycloalkyl, aryl, or heteroaryl are, independently, substituted or not substituted. In some embodiments, each group is independently not substituted or substituted with any one or more substituent described herein. In specific embodiments, each group is independently not substituted or substituted with one or more substituent, wherein each substituent is selected from the group consisting of —OH, oxo, alkyl (e.g., alkenyl), heteroalkyl, cycloalkyl, or alkoxy, wherein the alkyl, heteroalkyl, cycloalkyl, or alkoxy, is further optionally substituted. In some embodiments, the heterocycloalkyl is substituted with optionally substituted alkyl. In some embodiments, the alkyl is substituted with alkyl (e.g., alkenyl) or cycloalkyl. In some embodiments, the alkyl is methyl.

In some embodiments, provided herein is a compound comprising a first (opioid) radical and a second (opioid) radical, the first (opioid) radical and the second (opioid) radical each (e.g., independently) having a structure of Formula (IA):

(IA)

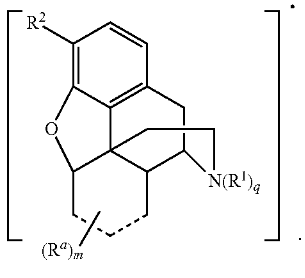

In some embodiments, the structure of Formula (I) or Formula (IA) is a radical of an opioid agonist or a radical of an opioid antagonist. In some embodiments, the structure of Formula (I) or Formula (IA) is a radical of an opioid agonist. In some embodiments, the structure of Formula (I) or Formula (IA) is a radical of an opioid antagonist. In some embodiments, the first (opioid) radical (e.g., an opioid agonist or an opioid antagonist) and the second (opioid) radical (e.g., an opioid agonist or an opioid antagonist) are joined by a linker (e.g., hydrolyzable linker).

In some embodiments, the first (opioid) radical and the second (opioid) radical are joined by a linker (e.g., comprising at least one oxo). In some embodiments, the first (opioid) radical is joined to the second (opioid) radical through any one of $R^a$, $R^1$, or $R^2$ of the first (opioid) radical. In some embodiments, the first (opioid) radical is joined to the second (opioid) radical through any one of $R^a$, $R^1$, or $R^2$, and the $R^a$, $R^1$, or $R^2$ through which the first (opioid) radical is joined to the second (opioid) radical comprises a hydroxyl radical (e.g., when together with the linker or second (opioid) radical (where the linker comprises at least one oxo), forms an ether) or a carboxylate radical (e.g., when taken together with the linker or second (opioid) radical, forms an ester or carbonate). In some embodiments, the connection between the carboxylate radical forms an anhydride. In some embodiments, the first (opioid) radical is joined to the second (opioid) radical through any one of $R^a$, $R^1$, or $R^2$, and the $R^a$, $R^1$, or $R^2$ through which the first (opioid) radical is joined to the second (opioid) radical comprises an amino radical (e.g., when together with the linker or second (opioid) radical (where the linker is a bond), forms an amide, carbamate, or thiocarbamate).

In some embodiments, provided herein is a compound of Formula (II):

(II)

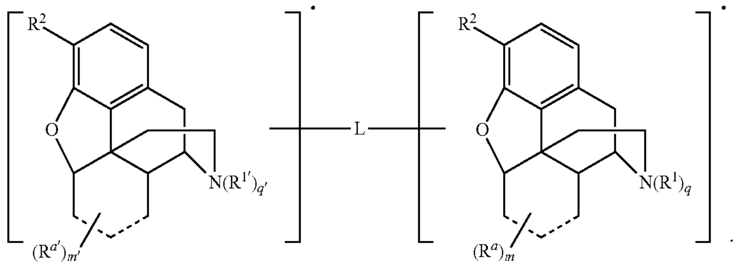

In some embodiments, a hydroxyl radical or a carboxylate radical of any one of Formula (I), Formula (IA), or Formula (II) is attached to a hydroxyl radical or a carboxylate radical of another of any one of Formula (I), Formula (IA), or Formula (II) through a linker. In some embodiments, a hydroxyl radical or a carboxylate radical of any one of Formula (I), Formula (IA), or Formula (II) is attached to a hydroxyl radical or a carboxylate radical of any one of Formula (I), Formula (IA), or Formula (II) through a linker. In some embodiments, a hydroxyl radical of any one of Formula (I), Formula (IA), or Formula (II) is attached to a hydroxyl radical of any one of Formula (I), Formula (IA), or Formula (II) through a linker. In some embodiments, a hydroxyl radical of any one of Formula (I), Formula (IA), or Formula (II) is attached to a carboxylate radical of any one of Formula (I), Formula (IA), or Formula (II) through a linker. In some embodiments, a carboxylate radical of any one of Formula (I), Formula (IA), or Formula (II) is attached to a hydroxyl radical of any one of Formula (I), Formula (IA), or Formula (II) through a linker. In some embodiments, a carboxylate radical of any one of Formula (I), Formula (IA), or Formula (II) is attached to a carboxylate radical of any one of Formula (I), Formula (IA), or Formula (II) through a linker. In some embodiments, the linker comprises at least one oxo. In some embodiments, the linker comprises two oxo groups.

In some embodiments, any one of $R^a$, $R^1$, or $R^2$ is an ester radical, a hydroxyl radical, or a carboxylate radical, and any one of $R^a$, $R^{a'}$, $R^1$, $R^2$, or $R^{2'}$ is an ester radical, a hydroxyl radical, or a carboxylate radical. In some embodiments, any one of $R^a$ or $R^2$ is an ester radical, a hydroxyl radical, or a carboxylate radical, and any one of $R^{a'}$ or $R^{2'}$ is an ester radical, a hydroxyl radical or a carboxylate radical.

In some embodiments, any radical of $R^a$, $R^1$, or $R^2$ is adjoined to any radical of $R^a$, $R^{a'}$, $R^1$, $R^{1'}$, $R^2$, or $R^{2'}$ by a linker. In some embodiments, any radical of $R^a$ or $R^2$ is adjoined to any radical of $R^{a'}$ or $R^{2'}$ by a linker. In some embodiments, a radical of $R^2$ is adjoined to a radical of $R^{2'}$ by a linker. In some embodiments, any radical of $R^a$ is adjoined to any radical of $R^{a'}$ by a linker. In some embodiments, the linker comprises at least one oxo. In some embodiments, the linker comprises two oxo groups.

In some embodiments, provided herein is a compound of Formula (IIA):

(IIA)

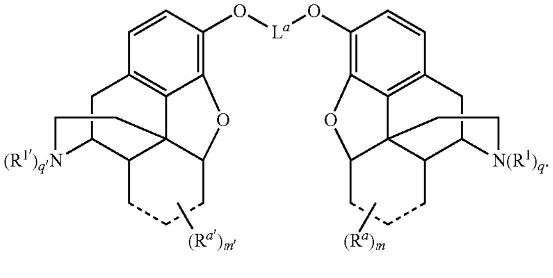

In some embodiments, provided herein is a compound of Formula (IIB):

(IIB)

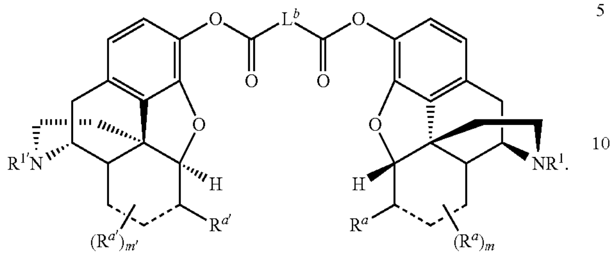

In some embodiments, provided herein is a compound of Formula (IIC):

(IIC)

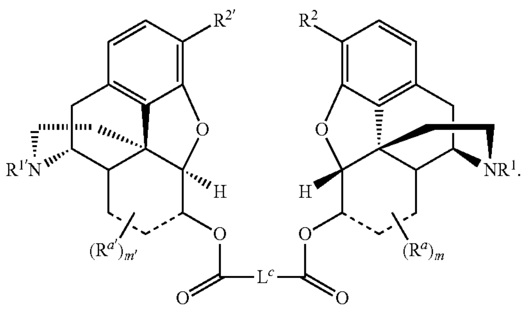

In some embodiments, provided herein is a compound of Formula (IID):

(IID)

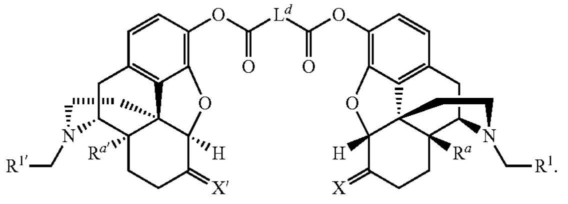

In some embodiments, X is O. In some embodiments, X is $CH_2$.

In some embodiments, provided herein is a compound of Formula (IIE):

(IIE)

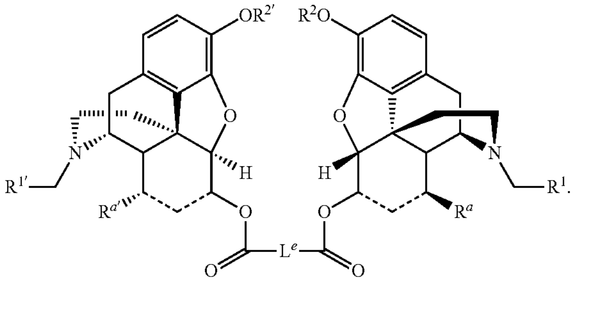

In some embodiments, provided herein is a compound of Formula (IIF):

(IIF)

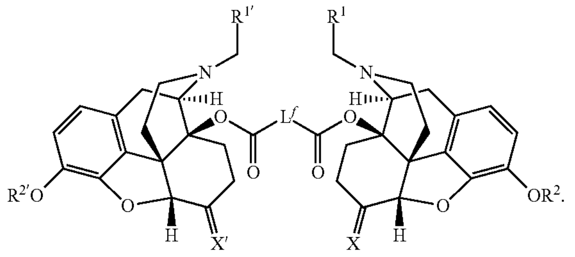

In some embodiments, X is O. In some embodiments, X is $CH_2$.

In some embodiments, each - - - of Formula (IA), Formula (II), Formula (IIA), Formula (IIB), Formula (IIC), Formula (IID), Formula (IIE), or Formula (IIF) is, independently, a single bond or a double bond. In some embodiments, each $R^a$ or $R^{a'}$ of Formula (IA), Formula (II), Formula (IIA), Formula (IIB), Formula (IIC), Formula (IID), Formula (IIE), or Formula (IIF) are independently selected from the group consisting of oxo, halogen, —CN, —$NO_2$, azide, alkyl, heteroalkyl, cycloalkyl, heterocycloalkyl, alkoxy, aryloxy, ester, amino, hydroxy, hydrazone, oxime, or thiol, wherein the alkyl, heteroalkyl, cycloalkyl, alkoxy, aryloxy, hydrazone, or heterocycloalkyl is optionally substituted. In some embodiments, each $R^a$ or $R^{a'}$ of Formula (IA), Formula (II), Formula (IIA), Formula (IIB), Formula (IIC), Formula (IID), Formula (IIE), or Formula (IIF) are independently selected from the group consisting of —OH, oxo, CHCH, optionally substituted alkoxy (e.g., heteroalkyl), and optionally substituted alkyl (e.g., optionally substituted with oxo, alkyl, or NH-optionally substituted alkyl). In some embodiments, any one of $R^a$ and/or $R^{a'}$ of Formula (IA), Formula (II), Formula (IIA), Formula (IIB), Formula (IIC), Formula (IID), Formula (IIE), or Formula (IIF) is unsaturated alkyl (e.g., alkenyl). In some embodiments, at least one of $R^a$ or $R^{a'}$ of Formula (IA), Formula (II), Formula (IIA), Formula (IIB), Formula (IIC), Formula (IID), Formula (IIE), or Formula (IIF) are unsaturated alkyl (e.g., alkenyl). In some embodiments, each $R^a$ or $R^{a'}$ of Formula (IA), Formula (II), Formula (IIA), Formula (IIB), Formula (IIC), Formula (IID), Formula (IIE), or Formula (IIF) are each independently H or —OH. In some embodiments, m and m' of Formula (IA), Formula (II), Formula (IIA), Formula (IIB), or Formula (IIC) are each independently 0-8. In some embodiments, m and m' of Formula (IA), Formula (II), Formula (IIA), Formula (IIB), or Formula (IIC) are each independently 4. In some embodiments, m and m' of Formula (IA), Formula (II), Formula (IIA), Formula (IIB), or Formula (IIC) are each independently 3. In some embodiments, m and m' of Formula (IA), Formula (II), Formula (IIA), Formula (IIB), or Formula (IIC) are each independently 2. In some embodiments, m and m' of Formula (IA), Formula (II), Formula (IIA), Formula (IIB), or Formula (IIC) are each independently 1.

In some embodiments, a first $R^a$ of Formula (IA), Formula (II), Formula (IIA), Formula (IIB), or Formula (IIC) is taken together with another $R^a$ to form an optionally substituted cycloalkyl, heterocycloalkyl, aryl, or heteroaryl. In some embodiments, a first $R^a$ of Formula (IA), Formula (II), Formula (IIA), Formula (IIB), or Formula (IIC) is taken together with another $R^a$ to form an optionally substituted cycloalkyl. In some embodiments, a first $R^a$ of Formula (IA), Formula (II), Formula (IIA), Formula (IIB), or Formula (IIC) is taken together with another $R^a$ to form an unsubstituted cycloalkyl. In some embodiments, the cycloalkyl is a bicycloalkyl. In some embodiments, the bicycloalkyl is bicyclo[2.2.2]octane. In some embodiments, a first $R^a$ of Formula (IA), Formula (II), Formula (IIA), Formula (IIB), or Formula (IIC) is taken together with another $R^a$ to form an unsubstituted cycloalkyl and a third $R^a$ of Formula (IA), Formula (II), Formula (IIA), Formula (IIB), or Formula (IIC) is attached to the same carbon atom to which the first $R^a$ of Formula (IA), Formula (II), Formula (IIA), Formula (IIB), or Formula (IIC) is attached. In some embodiments, the third $R^a$ of Formula (IA), Formula (II), Formula (IIA), Formula (IIB), or Formula (IIC) is alkoxy (e.g., methoxy).

In some embodiments, a first $R^{a'}$ of Formula (II), Formula (IIA), Formula (IIB), or Formula (IIC) is taken together with another $R^{a'}$ to form an optionally substituted cycloalkyl, heterocycloalkyl, aryl, or heteroaryl. In some embodiments, a first $R^{a'}$ of Formula (II), Formula (IIA), Formula (IIB), or Formula (IIC) is taken together with another $R^{a'}$ to form an optionally substituted cycloalkyl. In some embodiments, a first $R^{a'}$ of Formula (II), Formula (IIA), Formula (IIB), or Formula (IIC) is taken together with another $R^{a'}$ to form an unsubstituted cycloalkyl. In some embodiments, the cycloalkyl is a bicycloalkyl. In some embodiments, the bicycloalkyl is bicyclo[2.2.2]octane. In some embodiments, a first $R^{a'}$ of Formula (II), Formula (IIA), Formula (IIB), or Formula (IIC) is taken together with another $R^{a'}$ to form an unsubstituted cycloalkyl and a third $R^{a'}$ of Formula (II), Formula (IIA), Formula (IIB), or Formula (IIC) is attached to the same carbon atom to which the first $R^{a'}$ of Formula (II), Formula (IIA), Formula (IIB), or Formula (IIC) is attached. In some embodiments, the third $R^{a'}$ of Formula (II), Formula (IIA), Formula (IIB), or Formula (IIC) is alkoxy (e.g., methoxy).

In some embodiments, each $R^1$ and $R^{1'}$ of Formula (IA), Formula (II), Formula (IIA), Formula (IIB), Formula (IIC), Formula (IID), Formula (IIE), or Formula (IIF) are independently H, alkyl, heteroalkyl, cycloalkyl, or heterocycloalkyl, wherein the alkyl, heteroalkyl, cycloalkyl, or heterocycloalkyl are optionally substituted. In some embodiments, q and q' of Formula (IA), Formula (II), or Formula (IIA) are each independently 2. In some embodiments, each $R^1$ and $R^{1'}$ of Formula (IA), Formula (II), Formula (IIA), Formula (IIB), Formula (IIC), Formula (IID), Formula (IIE), or Formula (IIF) are optionally substituted alkyl. In some embodiments, one $R^1$ of Formula (IA), Formula (II), Formula (IIA), Formula (IIB), Formula (IIC), Formula (IID), Formula (IIE), or Formula (IIF) is optionally substituted alkyl and the other is unsubstituted alkyl. In some embodiments, one $R^{1'}$ of Formula (IA), Formula (II), Formula (IIA), Formula (IIB), Formula (IIC), Formula (IID), Formula (IIE), or Formula (IIF) is optionally substituted alkyl and the other is unsubstituted alkyl. In some embodiments, q and q' of Formula (IA), Formula (II), or Formula (IIA) are each independently 1. In some embodiments, each $R^1$ and $R^{1'}$ of Formula (IA), Formula (II), Formula (IIA), Formula (IIB), Formula (IIC), Formula (IID), Formula (IIE), or Formula (IIF) are optionally substituted alkyl. In some embodiments, each $R^1$ and $R^{1'}$ of Formula (IA), Formula (II), Formula (IIA), Formula (IIB), Formula (IIC), Formula (IID), Formula (IIE), or Formula (IIF)) are unsubstituted alkyl. In some embodiments, either or both $R^1$ and/or $R^{1'}$ of Formula (IA), Formula (II), Formula (IIA), Formula (IIB), Formula (IIC), Formula (IID), Formula (IIE), or Formula (IIF) is unsaturated alkyl (e.g., alkenyl). In some embodiments, $R^1$ and $R^{1'}$ of Formula (IA), Formula (II), Formula (IIA), Formula (IIB), Formula (IIC), Formula (IID), Formula (IIE), or Formula (IIF) are unsaturated alkyl (e.g., alkenyl). In some embodiments, the unsubstituted alkyl is methyl. In some embodiments, the alkyl is substituted with alkyl (e.g., alkene) or cycloalkyl. In some embodiments, the alkyl is substituted with CHCH. In some embodiments, the alkyl is substituted with cyclopropyl or cyclobutyl.

In some embodiments, $R^2$ and $R^{2'}$ of Formula (IA), Formula (II), Formula (IIC), Formula (IIE), or Formula (IIF) is optionally substituted alkyl and the other is unsubstituted alkyl. are each independently H, hydroxy, alkyl, heteroalkyl, alkoxy, cycloalkyl, or heterocycloalkyl, wherein the alkyl, heteroalkyl, cycloalkyl, alkoxy, or heterocycloalkyl are optionally substituted. In some embodiments, $R^2$ and $R^{2'}$ of Formula (IA), Formula (II), Formula (IIC), Formula (IIE), or Formula (IIF) is —OH or optionally substituted alkoxy (e.g., methoxy or alkyl further substituted with aryl (e.g., phenyl)).

In some embodiments, any one of $R^a$, $R^1$, $R^2$, $R^{a'}$, $R^{1'}$, or $R^{2'}$ of Formula (IA), Formula (II), Formula (IIA), Formula (IIB), Formula (IIC), Formula (IID), Formula (IIE), or Formula (IIF) are each optionally and independently substituted with one or more groups, each group independently selected from —OH and optionally substituted alkyl (e.g., alkenyl or aryl). In certain embodiments, any one of $R^a$, $R^1$, $R^2$, $R^{a'}$, $R^{1'}$, or $R^{2'}$ of Formula (IA), Formula (II), Formula (IIA), Formula (IIB), Formula (IIC), Formula (IID), Formula (IIE), or Formula (IIF) are, independently, substituted or not substituted. In some embodiments, each group is independently not substituted or substituted with any one or more substituent described herein. In specific embodiments, each group is independently not substituted or substituted with one or more substituent, wherein each substituent is selected from the group consisting of —OH and optionally substituted alkyl (e.g., alkenyl). In some embodiments, the alkyl is substituted with —OH, alkyl, heteroalkyl, cycloalkyl, or aryl. In some embodiments, the alkyl is substituted with alkyl (e.g., alkenyl) or cycloalkyl. In some embodiments, the alkyl is methyl.

In some embodiments, the first radical and the second radical of Formula (IA), Formula (II), Formula (IIA), Formula (IIB), Formula (IIC), Formula (IID), Formula (IIE), or Formula (IIF) are both opioid radicals. In some embodiments, the first radical and the second radical of Formula (IA), Formula (II), Formula (IIA), Formula (IIB), Formula (IIC), Formula (IID), Formula (IIE), or Formula (IIF) are the same. In some embodiments, the first radical and the second radical of Formula (IA), Formula (II), Formula (IIA), Formula (IIB), Formula (IIC), Formula (IID), Formula (IIE), or Formula (IIF) are different.

In certain aspects, provided herein is a compound comprising:

a) a first opioid (e.g., opioid agonist radical, opioid antagonist radical, partial opioid agonist radical);

b) a second opioid (e.g., opioid agonist radical, opioid antagonist radical, partial opioid agonist radical); and c) a linker (e.g., hydrolyzable linker), wherein the linker adjoins (e.g., covalently) the first opioid (e.g., radical) and the second opioid (e.g., radical), or a pharmaceutically acceptable salt or solvate thereof.

In some embodiments, the first (opioid) radical (e.g., an opioid agonist or an opioid antagonist) and the second (opioid) radical (e.g., an opioid agonist or an opioid antagonist) are joined by a linker (e.g., hydrolyzable linker (e.g., L, $L^a$, $L^b$, $L^c$, $L^d$, $L^e$, or $L^f$)).

In some embodiments, the linker is alkyl, heteroalkyl, or alkoxy, wherein the alkyl, heteroalkyl, or alkoxy is optionally substituted. In some embodiments, the alkyl, heteroalkyl, or alkoxy are each independently substituted with one or more groups, each group being independently selected from the group consisting of —O— (e.g., hydroxyl or alkoxy), —S— (e.g., thiol or thioalkoxy), silicone, amino, alkyl, heteroalkyl, cycloalkyl, heterocycloalkyl, aryl or heteroaryl, wherein the alkyl, heteroalkyl, cycloalkyl, heterocycloalkyl, aryl or heteroaryl are optionally substituted (e.g., with oxo, halogen, or hydroxyl). In some embodiments, the linker comprises one or more linker groups, each linker group being independently selected from the group consisting of —O—, —S—, optionally substituted alkylene (e.g., alkenyl, alkynyl, branched (e.g., polypropylene), haloalkyl), optionally substituted heteroalkylene (e.g, polyTHF), and optionally substituted cycloalkylene. In some embodiments, the linker is optionally substituted with oxo, hydroxyl, or halogen. In some embodiments, the linker comprises one or more linker groups, each linker group being independently selected from the group consisting of alkyl, alkoxy, and cycloalkyl, wherein the alkyl, alkoxy, or cycloalkyl are optionally substituted. In some embodiments, the linker is optionally substituted with oxo, hydroxyl, or halogen. In some embodiments, the linker is alkyl (alkylene) and the alkyl (alkylene) is substituted with one or more groups selected from —OH, halo, oxo, alkyl, heteroalkyl, cycloalkyl, and heterocycloalkyl. In some embodiments, the linker is an unsubstituted alkyl (alkylene). In some embodiments, the linker is heteroalkyl (heteroalkylene) and the heteroalkyl (heteroalkylene) is substituted with one or more groups selected from halo or alkyl. In some embodiments, the linker is unsubstituted heteroalkyl (heteroalkylene). In some embodiments, the linker comprises at least one oxo. In some embodiments, the linker comprises two oxo groups. In some embodiments, the linker comprises at least one carbamate. In some embodiments, the linker comprises at least one ester. In some embodiments, the linker comprises two or more esters.

In some embodiments, the linker comprises one or more linker groups. In some embodiments, the linker comprises one or more linker groups selected from oxo, —O—, —S—, unsubstituted alkylene, $(CH_2CH_2)_n$, $(CHCH)_n$, $O(CH_2CH_2O)_n$, $(CH_2CH_2O)_n$, and $(CH(CH_3)C(=O)O)_n$, wherein n is 1-20. In some embodiments, the linker is unsubstituted alkylene, $(CH_2CH_2)_n$, $(CHCH)_n$, $O(CH_2CH_2O)_n$, $(CH_2CH_2O)_n$, $(CH(CH_3)C(=O)O)_n$, or $(CH_2CH_2)_nC{=}O(CH(CH_3)C(=O))_n$, wherein n is 1-20. In some embodiments, the linker is alkyl (alkylene) substituted with one or more groups selected from —OH, halo, oxo, alkyl, heteroalkyl, cycloalkyl, and heterocycloalkyl In some embodiments, n is 1-10. In some embodiments, n is 6. In some embodiments, n is 5. In some embodiments, n is 4. In some embodiments, n is 3. In some embodiments, n is 2. In some embodiments, n is 1.

In some embodiments, the linker is selected from the group consisting of: $-(CR_2)_y-$, $-O(CR_2)_yO-$, $-O(CR_2)_y-$, $-(CR_2)_yO-$, and $-O(CH_2CH_2O)_y-$, wherein y is 1-20 and each R is independently selected from the group consisting of H, halogen, alkyl, or is taken together with another R to form an optionally substituted cycloalkyl (e.g., a monocycloalkylene or a bicycloalkylene). In some embodiments, the linker is selected from the group consisting of: $-(CR_2)_y-$, $-O(CR_2)_yO-$, $-O(CR_2)_y-$, $-(CR_2)_yO-$, and $-O(CH_2CH_2O)_y-$, wherein y is 1-10 and each R is independently selected from the group consisting of H, halogen, alkyl, or is taken together with another R to form an optionally substituted cycloalkyl (e.g., a monocycloalkylene or a bicycloalkylene). In some embodiments, the linker is $-(CR_2)_y-$, y is 2, 4, or 8, and each R is hydrogen. In some embodiments, the linker is $-(CR_2)_y-$, y is 4-8, and each R is fluorine. In some embodiments, the linker is $-(CR_2)_y-$, y is 4-8, and each R is independently selected from hydrogen and alkyl (e.g., methyl). In some embodiments, the linker is $-O(CH_2CH_2O)_y-$, y is 2-4, and each R is hydrogen. In some embodiments, the linker is $-O(CR_2)_yO-$, y is 2-8, at least one R is taken together with another R to form an unsubstituted cycloalkyl, and each other R is hydrogen. In some embodiments, the linker is $-O(CR_2)_yO-$, y is 2-8, each R is hydrogen. In some embodiments, y is 8. In some embodiments, y is 7. In some embodiments, y is 6. In some embodiments, y is 5. In some embodiments, y is 4. In some embodiments, y is 3. In some embodiments, y is 2.

In some embodiments, the linker is hydrolyzable by an aqueous medium. In some embodiments, the aqueous medium is a buffered solution, water, a biological or physiological environment (e.g., subcutaneous), serum, blood, or the like. In some embodiments, the linker is hydrolytically labile. In some embodiments, the linker is hydrolyzed by an enzyme. In some embodiments, the enzyme is a hydrolase (e.g., a protease or an esterase). In some embodiments, the enzyme is an esterase.

In some embodiments, the structure of Formula (II), Formula (IIA), and Formula (IIB) comprise a first (opioid) radical and a second (opioid) radical joined by a linker (e.g., provided herein). In some embodiments, both the first (opioid) radical and the second (opioid) radical are each an opioid agonist or an opioid antagonist in their free form. In some embodiments, both the first (opioid) radical and the second (opioid) radical are each an opioid agonist in their free form. In some embodiments, both the first (opioid) radical and the second (opioid) radical are each an opioid antagonist in their free form. In some embodiments, the first (opioid) radical is an opioid agonist (e.g., selected from the group consisting of morphine, oxycodone, hydrocodone, codeine, buprenorphine, etc.) in its free form. In some embodiments, the first (opioid) radical is an opioid antagonist (e.g., selected from the group consisting of naloxone, naltrexone, nalmefene; methylnaltrexone, 8β-naltrexol, etc.) in its free form. In some embodiments, the opioid agonist is a partial opioid agonist (e.g., buprenorphine) or a mixed opioid agonist/antagonist.

In some embodiments, the first (opioid) radical and the second (opioid) radical are each (e.g., independently) a radical (e.g., a hydroxyl radical) selected from the group consisting of:

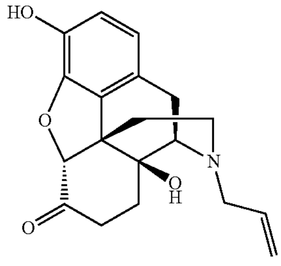
,

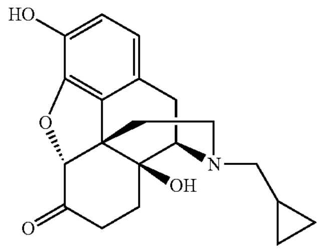
,
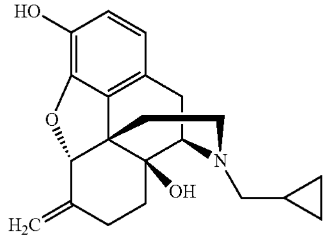
,
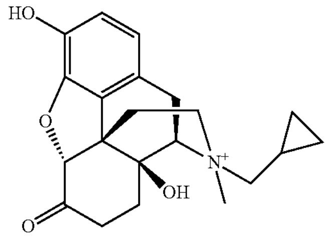
,
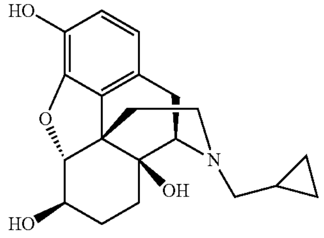
,
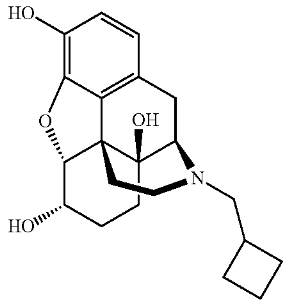
,
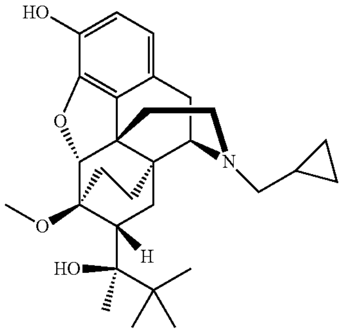
,
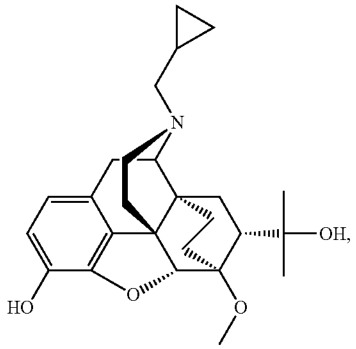
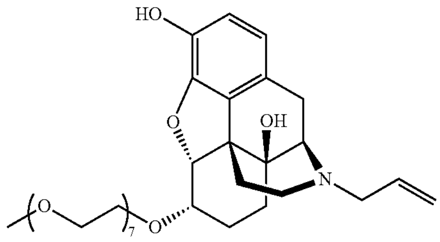
,
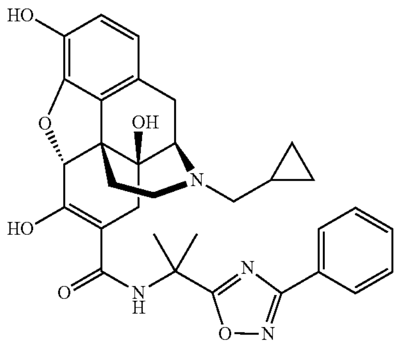
,
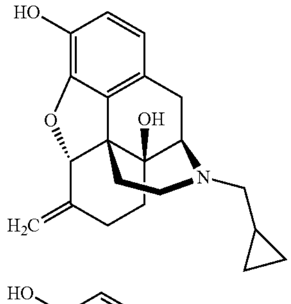
,
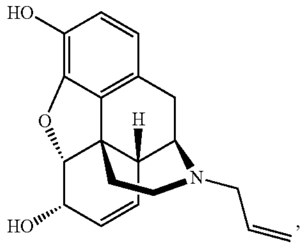
,
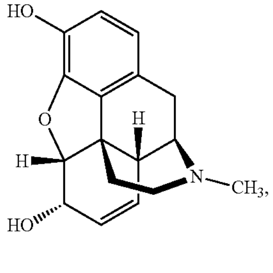

-continued
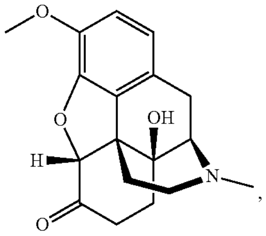
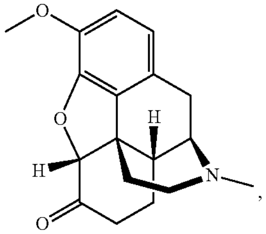
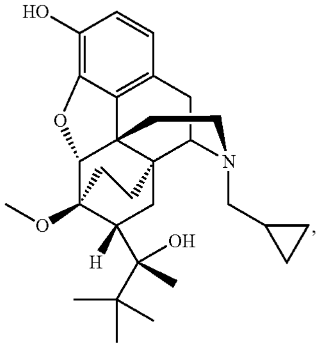
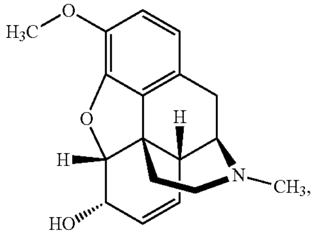
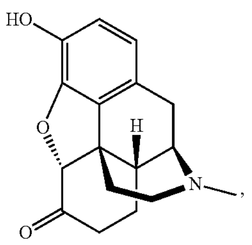
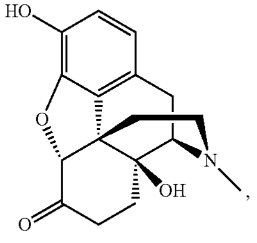
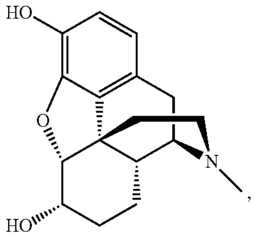
-continued
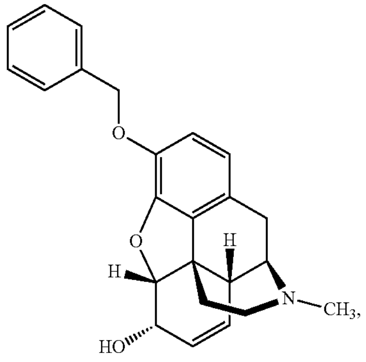
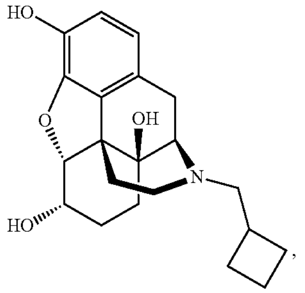
and
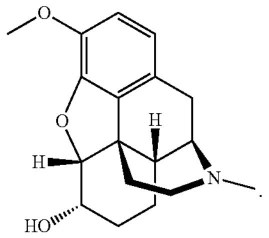
In some embodiments, the first radical (e.g., an opioid agonist) is a radical (e.g., a hydroxyl radical) selected from the group consisting of:
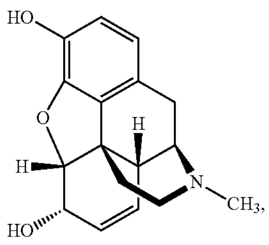
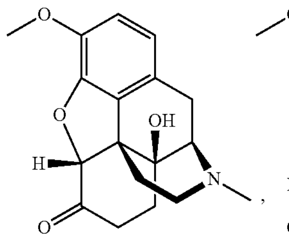
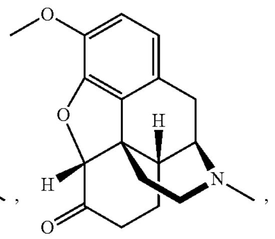

-continued
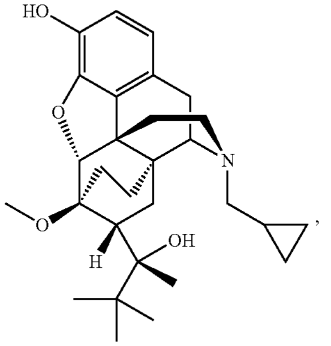
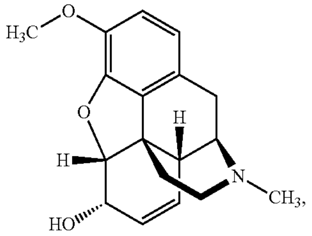
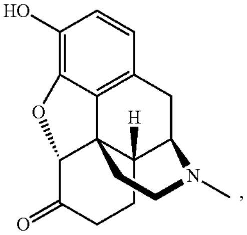
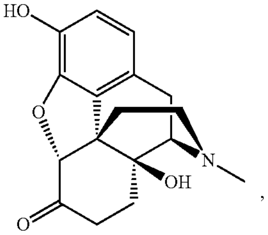
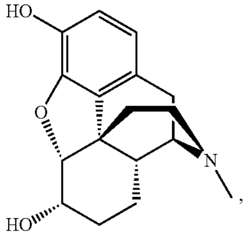
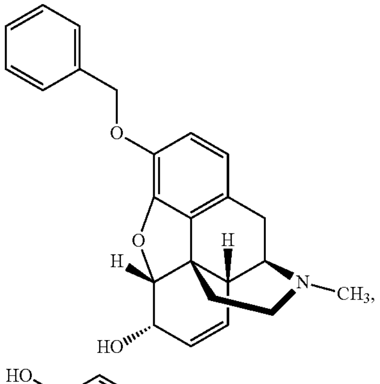
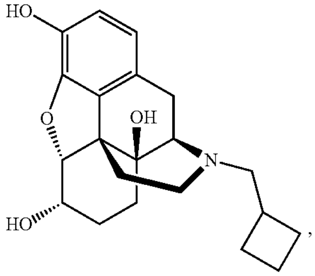
and
-continued
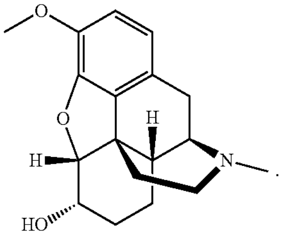
In some embodiments, the second radical (e.g., an opioid antagonist) is a radical (e.g., a hydroxyl radical) selected from the group consisting of:
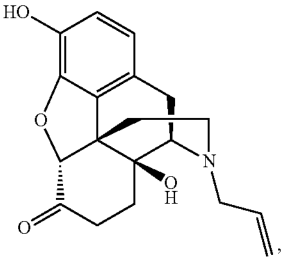
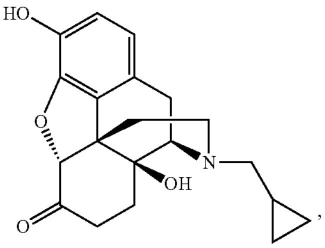
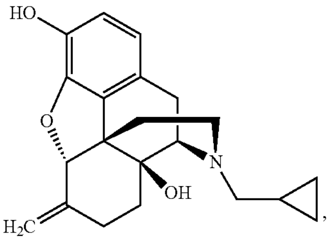
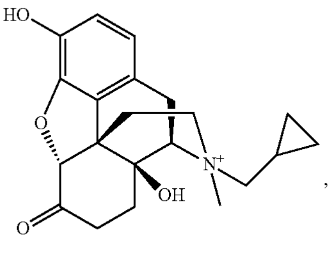
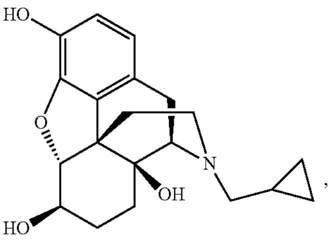

-continued

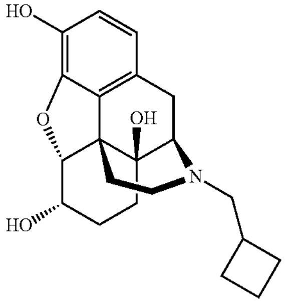

,

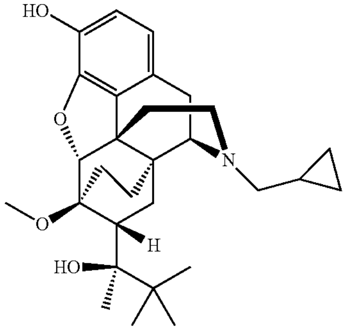

,

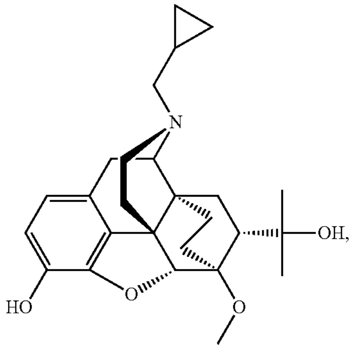

,

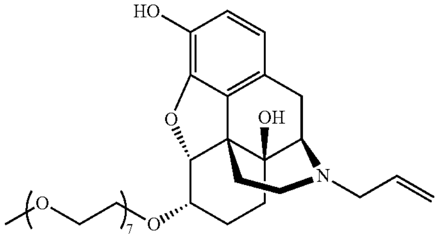

,

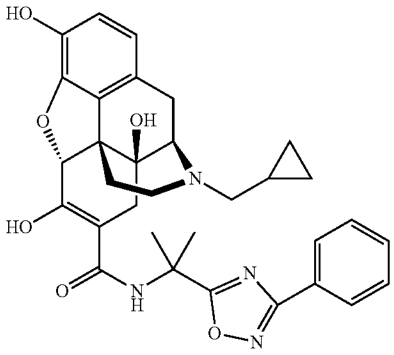

,

-continued

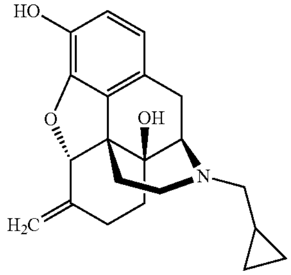

, and

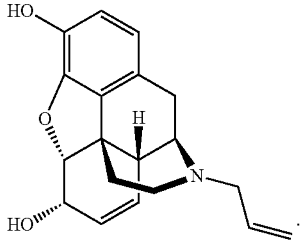

.

In some embodiments, provided herein is a pharmaceutical composition comprising any compound provided herein, such as a compound having the structure of any one of Formula (I), Formula (IA), Formula (II), Formula (IIA), Formula (IIB), Formula (IIC), Formula (IID), Formula (IIE), or Formula (IIF), or a pharmaceutically acceptable salt thereof. In some embodiments, the pharmaceutical composition comprises at least one pharmaceutically acceptable excipient.

Another embodiment provides the pharmaceutical composition, wherein the pharmaceutical composition is suitable for subcutaneous administration. Another embodiment provides the pharmaceutical composition, wherein the pharmaceutical composition is suitable for intraspinal administration.

Another embodiment provides a pharmaceutical implant or article comprising any compound provided herein, such as a compound having the structure of any one of Formula (I), Formula (IA), Formula (II), Formula (IIA), Formula (IIB), Formula (IIC), Formula (IID), Formula (IIE), or Formula (IIF) or a pharmaceutically acceptable salt thereof.

In some embodiments, the implant or article comprises at least 50 wt. % (at least 60 wt. %, at least 70 wt. %, at least 80 wt. %, at least 90 wt. %, at least 95 wt. %, at least 98 wt. %, or the like) of the compound and/or pharmaceutically acceptable salt thereof. In some embodiments, the implant or article undergoes surface erosion to release the compound, the first radical, and/or the second radical (e.g., in their free form). In some embodiments, first radical and the second radical are released (e.g., in their free form) from the pharmaceutical implant or article at near zero-order in solution (e.g., buffer solution, serum, biological environment, in vivo, or the like). In some embodiments, the first radical and the second radical are released (e.g., in their free form) from the pharmaceutical implant or article at 37° C. in 100% bovine serum or at 37° C. in phosphate buffered saline (PBS) at a rate such that $t_{10}$ is greater than or equal to 1/10 of $t_{50}$.

In some embodiments, the compound (e.g., D1-L-D2) is released from the article. In some embodiments, the first radical and the second radical are released (e.g., in their free form) from the compound (e.g., D1-L-D2) subsequent to the compound being released from the article. In some embodiments, the first radical and the second radical are released (e.g., in their free form) from the compound (e.g., D1-L-D2)

prior to the compound being released from the article. In some embodiments, the first radical and the second radical are released (e.g., in their free form) from the article or the compound by passive (e.g., in PBS) or active (in a biological environment (e.g., by an esterase)) hydrolysis. In some embodiments, the first radical and/or the second radical are released (e.g., in their free form) from the article or the compound by hydrolysis of a linker (e.g., at least one hydrolysable group thereof) adjoining the first radical and the second radical. In some embodiments, the linker comprises at least one hydrolysable group. In some embodiments, the at least one hydrolysable group is an ester or an anhydride.

In some embodiments, a compound or a pharmaceutical composition comprising any compound provided herein, such as a compound having the structure of any one of Formula (I), Formula (IA), Formula (II), Formula (IIA), Formula (IIB), Formula (IIC), Formula (IID), Formula (IIE), or Formula (IIF) or a pharmaceutically acceptable salt thereof. In certain embodiments, the composition further comprises an amount of a free form of a radical having the structure of any one of Formula (I), Formula (IA), Formula (II), Formula (IIA), Formula (IIB), Formula (IIC), Formula (IID), Formula (IIE), or Formula (IIF) or the like (such as wherein the free form is the radical, wherein R is a negative charge or an H). In some embodiments, a composition provided herein comprises a (e.g., weight or molar) ratio of a compound provided herein to a free form of a radical having the structure of any one of Formula (I), Formula (IA), or a pharmaceutically acceptable salt thereof (e.g., wherein R is a negative charge or an H) is about 1:99 to about 100:0 (e.g., the amount of the free form of the radical relative to the overall amount of free form of the radical plus the conjugate is between 0% (weight or molar) and 99%). In some embodiments, the relative amount of the free form of the radical is 0% to about 50%, such 0% to about 20%, 0% to about 10%, about 0.1% to about 10%, about 0.1% to about 5%, less than 5%, less than 2.5%, less than 2%, or the like (percentages being weight/weight or mole/mole percentages). Further, in some instances, compounds provided herein release free form of a radical of a compound having the structure of any one of Formula (I), Formula (IA), (e.g., wherein R is a negative charge or H), such as when administered to an individual subcutaneous or intraspinal administration).

Provided in some embodiments herein is a method for treating or preventing a disease or disorder (e.g., or the symptoms thereof) in an individual in need thereof, the method comprising implanting the article, implant, or composition of any one of the any compound provided herein, such as a compound having the structure of any one of Formula (I), Formula (IA), Formula (II), Formula (IIA), Formula (IIB), Formula (IIC), Formula (IID), Formula (IIE), or Formula (IIF), Formula (III), Formula (IIIA), Formula (IIIB), or Formula (IIIC), or a pharmaceutically acceptable salt thereof, into the individual. In some embodiments, the disease or disorder is an acute or a chronic disease or disorder.

In certain embodiments, provided herein is a method of treating a CNS disease or disorder in an individual in need of thereof, comprising administering to the individual a composition comprising any compound provided herein, such as a compound having the structure of any one of Formula (I), Formula (IA), Formula (II), Formula (IIA), Formula (IIB), Formula (IIC), Formula (IID), Formula (IIE), or Formula (IIF), or a pharmaceutically acceptable salt thereof. Another embodiment provides the method wherein the disease or disorder is selected from the group consisting of chronic pain (e.g., cancer pain), acute pain, opioid addiction, alcohol addiction, alcohol dependence, opioid-induced constipation, gambling disorders, and narcotic depression. Another embodiment provides the method wherein the CNS disease or disorder is pain (e.g., chronic pain), addiction (e.g., opioid addiction), or overdose. Another embodiment provides the method wherein the CNS disease or disorder is acute or chronic pain. Another embodiment provides the method wherein the CNS disease or disorder is addiction or dependence.

In some embodiments, a composition provided herein (e.g., used in a method provided herein) comprises a compound provided herein in a therapeutically effective amount (e.g., at a concentration effective to treat a CNS disease or disorder in an individual in need thereof, the method comprising administering to the individual a compound, pharmaceutically acceptable salt, implant, article, or composition having the structure of any one of Formula (I), Formula (IA), Formula (II), Formula (IIA), Formula (IIB), Formula (IIC), Formula (IID), Formula (IIE), or Formula (IIF). In some embodiments, a composition provided herein (e.g., used in a method provided herein) comprises a compound provided herein in a therapeutically effective amount (e.g., at a concentration effective to treat pain (e.g., chronic pain), addiction (e.g., opioid addiction), or overdose) systemically. In certain embodiments, a (e.g., pharmaceutical, subcutaneous, or intraspinal) composition provided herein comprises about 0.1 wt. % to about 10 wt. % of a compound provided herein.

In some instances, provided herein is a compound comprising a first radical and a second radical, both the first radical and the second radical each comprising a structure of Formula (I'):

Formula (I')

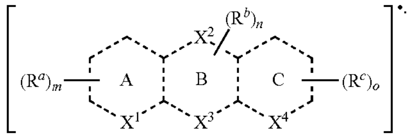

In some embodiments, each  is, independently, a single bond or a double bond. In some embodiments, each $R^a$, $R^b$, and $R^c$ are independently selected the group consisting of oxo, halogen, —CN, —$NO_2$, alkyl, heteroalkyl, cycloalkyl, heterocycloalkyl, alkoxy, amino, hydroxy, or thiol, wherein the alkyl, heteroalkyl, cycloalkyl, or heterocycloalkyl is optionally substituted. In some embodiments, any one of $R^a$, $R^b$, or $R^c$ are taken together with another of $R^a$, $R^b$, or $R^c$ to form a substituted or an unsubstituted cycloalkyl or heterocycloalkyl. In some embodiments, $X^1$, $X^2$, $X^3$, and $X^4$ are each independently selected from the group consisting of a bond and $Q_y$, wherein each Q is independently selected from the group consisting of —O—, —NR—, —$S(R)_x$—, and —$C(R)_z$—. In some embodiments, each of m, n, and o are independently 0-6. In some embodiments, each x is independently 0-5. In some embodiments, each y is independently 1-3. In some embodiments, each z is independently 1 or 2. In some embodiments, each R is independently selected from the group consisting of H, halogen, alkyl, heteroalkyl, cycloalkyl, heterocycloalkyl, alkoxy, amino, hydroxy, and thiol, or is taken together with another R to form an oxo. In some embodiments, the first and second radicals are non-steroidal. Also provided in certain embodiments herein are pharmaceutical salts or solvates of a compound of Formula (I').

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION OF THE INVENTION

Certain Definitions

Figure 1A:
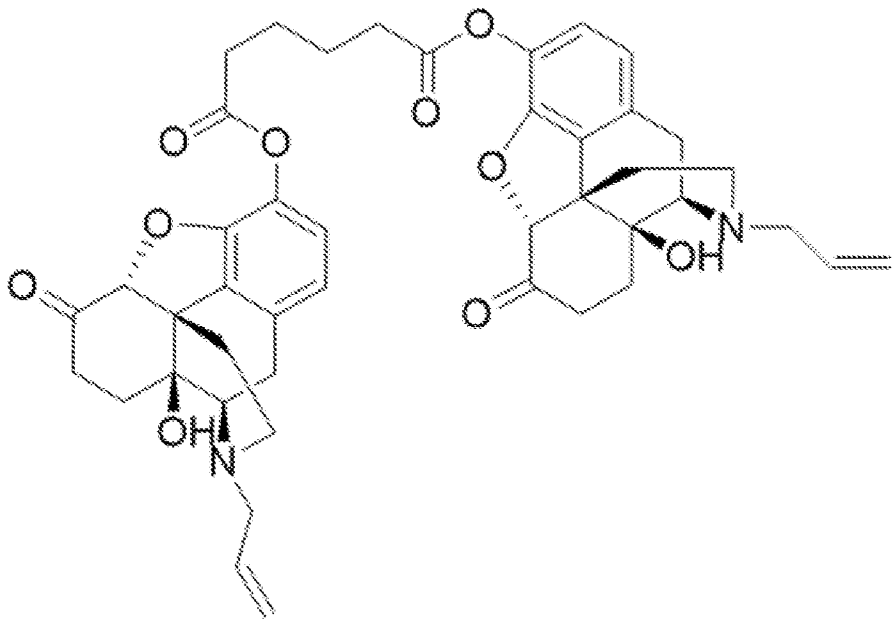
FIG. 1 shows the chemical structure (FIG. 1A) and the heat processed pellet (FIG. 1B) of an opioid composition (naloxone-adipate-naloxone, Compound 1) exemplified herein.
FIG. 1C shows the drug release profile for Compound 1 (pellet) in phosphate-buffered saline (PBS) over 20 days.
FIG. 1D represents the 20-day progression of the surface erosion drug release profile for the pellet of Compound 1 in PBS.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The terms "treat," "treating," or "treatment" as used herein, include reducing, alleviating, abating, ameliorating, relieving, or lessening the symptoms associated with a disease, disease sate, or indication (e.g., addiction, such as opioid addiction, or pain) in either a chronic or acute therapeutic scenario. Also, treatment of a disease or disease state described herein includes the disclosure of use of such compound or composition for the treatment of such disease, disease state, or indication.

"Amino" refers to the —$NH_2$ radical.

"Cyano" refers to the —CN radical.

"Nitro" refers to the —$NO_2$ radical.

"Oxa" refers to the —O— radical.

"Oxo" refers to the ═O radical.

"Thioxo" refers to the ═S radical.

"Imino" refers to the ═N—H radical.

"Oximo" refers to the ═N—OH radical.

"Hydrazino" refers to the ═N—$NH_2$ radical.

"Alkyl" generally refers to a straight or branched hydrocarbon chain radical consisting solely of carbon and hydrogen atoms, such as having from one to fifteen carbon atoms (e.g., $C_1$-$C_{15}$ alkyl). Unless otherwise state, alkyl is saturated or unsaturated (e.g., an alkenyl, which comprises at least one carbon-carbon double bond). Disclosures provided herein of an "alkyl" are intended to include independent recitations of a saturated "alkyl," unless otherwise stated. Alkyl groups described herein are generally monovalent, but may also be divalent (which may also be described herein as "alkylene" or "alkylenyl" groups). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (isobutyl), 1,1-dimethylethyl (tert-butyl), 1-pentyl (n-pentyl). The alkyl is attached to the rest of the molecule by a single bond. In general, alkyl groups are each independently substituted or unsubstituted. Each recitation of "alkyl" provided herein, unless otherwise stated, includes a specific and explicit recitation of an unsaturated "alkyl" group. Similarly, unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is optionally substituted as described for "alkyl" groups.

"Alkylene" or "alkylene chain" generally refers to a straight or branched divalent alkyl group linking the rest of the molecule to a radical group, such as having from one to twelve carbon atoms, for example, methylene, ethylene, propylene, i-propylene, n-butylene, and the like. Unless stated otherwise specifically in the specification, an alkylene chain is optionally substituted as described for alkyl groups herein.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" or "aryl-alkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl or cycloalkyl is saturated (i.e., containing single C—C bonds only) or unsaturated (i.e., containing one or more double bonds or triple bonds). Examples of saturated cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)O$R^a$, —$R^b$—C(O)N$(R^a)_2$, —$R^b$—O—$R^c$—C(O)N$(R^a)_2$, —$R^b$—N($R^a$)C(O)O$R^a$, —$R^b$—N($R^a$)C(O)$R^a$, —$R^b$—N($R^a$)S$(O)_tR^a$ (where t is 1 or 2), —$R^b$—S$(O)_tR^a$ (where t is 1 or 2), —$R^b$—S$(O)_tOR^a$ (where t is 1 or 2) and —$R^b$—S$(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkenyl" refers to a radical of the formula —$R^c$-carbocyclyl where $R^c$ is an alkenylene chain as defined above. The alkenylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

The term "heteroalkyl" refers to an alkyl group as defined above in which one or more skeletal carbon atoms of the alkyl are substituted with a heteroatom (with the appropriate number of substituents or valencies—for example, —$CH_2$— may be replaced with —NH— or —O—). For example, each substituted carbon atom is independently substituted with a heteroatom, such as wherein the carbon is substituted with a nitrogen, oxygen, selenium, or other suitable heteroatom. In some instances, each substituted carbon atom is independently substituted for an oxygen, nitrogen (e.g. —NH—, —N(alkyl)-, or —N(aryl)- or having another substituent contemplated herein), or sulfur (e.g. —S—, —S(=O)—, or —S$(=O)_2$—). In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a $C_1$-$C_{18}$ heteroalkyl. In some embodiments, a heteroalkyl is a $C_1$-$C_{12}$ heteroalkyl. In some embodiments, a heteroalkyl is a $C_1$-$C_6$ heteroalkyl. In some embodiments, a heteroalkyl is a $C_1$-$C_4$ heteroalkyl. Representative heteroalkyl groups include, but are not limited to —$OCH_2OMe$, or —$CH_2CH_2OMe$. In some embodiments, heteroalkyl includes alkoxy, alkoxyalkyl, alkylamino, alkylaminoalkyl, aminoalkyl, heterocycloalkyl, heterocycloalkyl, and heterocycloalkylalkyl, as defined herein. Unless stated otherwise specifically in the specification, a heteroalkyl group is optionally substituted as defined above for an alkyl group.

"Heteroalkylene" refers to a divalent heteroalkyl group defined above which links one part of the molecule to another part of the molecule. Unless stated specifically otherwise, a heteroalkylene is optionally substituted, as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)_tOR^a$ (where t is 1 or 2) and $—R^b—S(O)_tN(R^a)_2$ (where is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $—R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula $—O—R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetra hydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term “heteroaryl” is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

“N-heteroaryl” refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

“C-heteroaryl” refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

“Heteroarylalkyl” refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

“Heteroarylalkoxy” refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term “geometric isomer” refers to E or Z geometric isomers (e.g., cis or trans) of an alkene double bond. The term “positional isomer” refers to structural isomers around a central ring, such as ortho-, meta-, and para-isomers around a benzene ring.

In general, optionally substituted groups are each independently substituted or unsubstituted. Each recitation of an optionally substituted group provided herein, unless otherwise stated, includes an independent and explicit recitation of both an unsubstituted group and a substituted group (e.g., substituted in certain embodiments, and unsubstituted in certain other embodiments). Unless otherwise stated, substituted groups may be substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)$OR^a$, —C(O)N($R^a$)$_2$, —N($R^a$)C(O)$OR^a$, —OC(O)—N($R^a$)$_2$, —N($R^a$)C(O)$R^a$, —N($R^a$)S(O)$_t$$R^a$ (where t is 1 or 2), —S(O)$_t$$OR^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

The compounds disclosed herein, reference to any atom includes reference to isotopes thereof. For example, reference to H includes reference to any isotope thereof, such as a $^1H$, $^2H$, $^3H$, or mixtures thereof.

“Pharmaceutically acceptable salt” includes both acid and base addition salts. A pharmaceutically acceptable salt of any one of the pharmacological agents described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, meta phosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Processable Compounds and Pharmaceutical Agents

Often the final hurdle of drug development, producing a final medicinal product from an active pharmaceutical ingredient (API) that is a solid or a liquid at room temperature is an extensive and costly process. APIs that are solids at room temperature are often used for pharmaceutical formulations, incurring significant cost to formulation to a final medicinal product. The cost of formulating APIs limit the efficacy and/or adoption of potentially beneficial therapeutics.

Furthermore, patient compliance is an often unresolved issue in the clinic. In some embodiments, modified-release pharmaceuticals can improve patient compliance. For example, extended-release (ER) dosage forms, such as sustained-release (SR) or controlled-release (CR) dosage forms, may facilitate compliance with a therapeutic regimen in some instances. SR and CR dosage forms are generally designed to liberate an API at a certain rate, such as to maintain a particular drug concentration over a period of time. For example, SR maintains drug release over a sustained period but not at a constant rate, while CR maintains drug release over a sustained period at a more consistent (e.g., nearly constant) rate (e.g., zero-order). Despite their ability to extend the dosing of an active agent, such dosage forms can be difficult to develop. Moreover, such dosage forms often include controlled release excipients (e.g., polymers) and/or controlled release matrices to facilitate controlled release. In the case of liquid or otherwise low melting point active agents, controlled release formulations can be even more difficult to develop. Moreover, even in the best circumstances, many controlled release forms have limited durations of active release (e.g., 24-hour release windows), so patient compliance remains an issue.

Provided in certain embodiments herein is a processable compound that addresses the burden of medicinal product formulation as well as patient compliance. In certain instances, a processable compound provided herein is a compound that is manipulatable (e.g., as a solid, such as above a glass transition temperature, or as a melt) at a temperature of at least 20° C. (e.g., at least 30 C, at least 37 C, at least 40 C, at least 50 C) (e.g., such as 150° C. or less, 125° C. or less, 110° C. or less, 100° C. or less, 90° C. or less, or 80° C. or less).

In certain instances, the free form of a radical is the compound represented by the formula or radical referenced in its non-radical form (e.g., without the linker attachment).

In certain embodiments, a compound described herein is a solid at body temperature (e.g., about 37° C., or lower). In some embodiments, a compound provided herein comprises two processable groups (e.g., two radicals that are processable in their free form) (e.g., a structure provided in any one of Formula (I), Formula (IA), Formula (IA'), Formula (II), Formula (IIA), Formula (IIB), Formula (IIC), Formula (IID), Formula (IIE), or Formula (IIF)) (e.g., covalently) joined (e.g., conjugated) to each other (e.g., through a linker). In some embodiments, a compound (e.g., conjugate (e.g., processable conjugate)) comprises a first radical and a second radical. In some embodiments, either one or both of the first and/or second radicals of the compound (e.g., conjugate (e.g., processable conjugate)) are released (e.g., in their free form), the release being controlled release (e.g., near zero-order) and/or extended release. In some embodiments, either one or both of the first and/or second radicals of the compound (e.g., conjugate (e.g., processable conjugate)) are released (e.g., in their free form) for at least 15 days (e.g., a buffer solution, serum, biological environment (e.g., under the skin or in the spine), in vivo, or the like). In some embodiments, either one or both of the first and/or second radicals of the compound (e.g., conjugate (e.g., processable conjugate)) are released (e.g., in their free form)

for at least 14 days (e.g., a buffer solution, serum, biological environment (e.g., under the skin or in the spine), in vivo, or the like).

In some embodiments, the compound is formed into an implantable article (e.g., a pellet), such as using methods provided herein (e.g., described in the examples). The term "article," as used herein, generally refers to a pharmaceutical composition that is machined, molded, heat-processed, emulsion-processed, electrospun, electrosprayed, blow molded, or extruded to form a fiber, fiber mesh, woven fabric, non-woven fabric, film, surface coating, pellet, cylinder, rod, microparticle, nanoparticle, or another shaped article. In some embodiments, the implantable article has a (e.g., zero-order) controlled release rate over an extended period (e.g., 1 week, 2 weeks, 3 weeks, 4 weeks, 6 weeks, 12 weeks, 52 weeks, or more) in an aqueous medium (e.g., a buffer solution, serum, biological environment (e.g., under the skin or in the spine), in vivo, or the like). In some embodiments, a compound provided herein (or implant comprising such compound) is administered to an individual suffering an acute or a chronic disease or condition (e.g., as a therapy for the acute or chronic disease or condition) in any suitable manner (e.g., route of administration, such as by implanting, and/or frequency of dosing), such as a single dose or a series of doses (e.g., once or twice every 1 week, 2 weeks, 3 weeks, 4 weeks, 6 weeks, 12 weeks, 52 weeks, or more).

In certain instances, a compound (e.g., conjugate (e.g., processable conjugate)) provided herein is used to improve treatment options and/or compliance for acute diseases and/or disorders. In some embodiments, a processable compound described herein is used to improve treatment options and/or compliance for chronic diseases and/or disorders. In some embodiments, the processable compound provided herein is used to improve treatment options and/or patient for acute pain, chronic pain, post-operative pain, opioid addiction, opioid dependence, gambling disorders, or the like.

Provided herein is a compound (e.g., conjugate (e.g., processable conjugate)) that is processable (e.g., into an article). In some embodiments, the compound (e.g., conjugate (e.g., processable conjugate)) has any suitable morphology, such as to facilitate processing and/or pharmacodynamic effects (e.g., release profile). In certain embodiments, the compound (or implant or pharmaceutical composition comprising the compound) is amorphous (or comprises a highly amorphous content). In some embodiments, a compound (e.g., morphology) provided herein is a solid, such as at a physiological temperature (e.g., having a melting point ($T_m$) and/or glass transition temperature ($T_g$) of at least 37° C.). In some embodiments, the compound is a crystalline solid, film, glass, or amorphous solid (e.g., at a temperature of at least 37° C.) are solids (e.g., has a melting point (e.g., $T_m$ or $T_g$) of at least 37° C.). In some embodiments, the compound (or composition, article, or coating comprising the compound) has a crystallinity of at most 15% (e.g., determined by PXRD, DSC, or polarized light microscopy). In some embodiments, the compound (or composition, article, or coating comprising the compound) is substantially non-crystalline (e.g., determined by PXRD, DSC, or polarized light microscopy). In some embodiments, the compound (or composition, article, or coating comprising the compound) is amorphous (e.g., determined by PXRD, DSC, or polarized light microscopy). In some embodiments, the compound (e.g., morphology) has a thermal melting point ($T_m$) that is greater than or equal to the glass transition temperature ($T_g$). In some embodiments, the compound has a melting point of at least 37° C. In some embodiments, the compound (e.g., morphology) has a melting point of at least 100° C.

Opioids are a predominant treatment option for managing an individual's pain (e.g., acute or/or chronic). For example, an estimated 168,158,611 opioid prescriptions were dispensed in 2018. Pain management (e.g., acute and/or chronic) with therapeutic agents (e.g., opioids) often leads use disorders (e.g., addiction and dependence) given their highly addictive properties. For example, as of 2015, increased rates of recreational use and addiction are attributed to over-prescription of opioid medications and inexpensive illicit heroin. In addition, fears about over-prescribing, exaggerated side effects, and addiction from opioids are similarly blamed for under-treatment of pain. Furthermore, the prescription rate and sale of such therapeutic agents (e.g., opioids) creates a significant burden on the (e.g., global) healthcare system.

Use (e.g., opioid use) disorders (e.g., addiction and dependence) typically require long-term treatment and care. Therapeutic as well as behavioral strategies have been developed for treating use disorders. An individual's behavior (e.g., compliance) can significantly affect how an individual responds to treatment (e.g., relapse is a major unresolved issue with current treatment options). Some strategies aim to reduce drug use and lead to abstinence from opioids, while others attempt to stabilize on prescribed treatments (e.g., methadone, naloxone, or buprenorphine) with continued replacement therapy indefinitely. Some goals of treatment options include: reducing risks for the individual, reducing criminal behavior, and/or improving the long-term physical and psychological condition of the person. However, the relapse rate for substance use disorders is estimated to remain between 40% and 70% (Sinha, R. (2011) *Current Psychiatry Reports,* 13(5), 398-405).

Provided in certain embodiments herein is a processable compound that, for example, addresses the issues with pain management therapeutics and/or the lack of treatment options (e.g., long term treatment options that address issues with relapse) for drug addiction and/or dependence. Provided in some embodiments herein is a processable compound that, for example, has an extended (e.g., controlled (e.g., zero-order)) release profile that addresses the extensive prescription of opioids for pain management and/or that addresses the lack of an individual's compliance for drug addiction and dependence therapeutic treatment options (e.g., by decreasing the frequency of administration and/or controlling the release rate (e.g., and concentration) of the therapeutic agent).

In some instances, an opioid provided herein (e.g., as a radical in a compound herein) is a ligand that binds (e.g., in its free form) to an opioid receptor, such as, for example, the delta (δ)-opioid receptor (DOR), the kappa (η)-opioid receptor (KOR), mu (μ)-opioid receptor (MOR), nociceptin opioid receptor (NOR), zeta (ζ)-opioid receptor (ZOR), or any combination thereof. In some embodiments, the opioid is an opioid agonist, an opioid antagonist, or a mixed opioid agonist/antagonist of an opioid receptor. In some embodiments, the opioid agonist is a partial opioid agonist or an inverse opioid agonist. In some embodiments, the opioid is an opioid radical. In some embodiments, the opioid radical is joined to a radical of another opioid radical by a linker, as described herein, forming an opioid dimer. In some embodiments, each opioid radical of the opioid dimer is the same or different.

Provided herein is a processable compound (e.g., opioid conjugates) formed from two (e.g., processable) groups or radicals. In some embodiments, the processable compound (e.g., opioid conjugate) provided herein is processable into a solid (e.g., at a temperature of at least 20° C. (e.g., such as 150° C. or less, 125° C. or less, 110° C. or less, 100° C. or less, 90° C. or less, or 80° C. or less)). The processable compound (e.g., opioid conjugate) provided herein have a controlled release profile (e.g., zero order) and/or over an extended period (e.g., at least 1 day, 2 days, 3 days, 4 days, 5 days, 6 days, 7 days, 15 days, 30 days, or more) in solution (e.g., a buffer solution, serum, biological environment (e.g., under the skin or in the spine), in vivo, or the like). In some embodiments, a compound (e.g., an opioid conjugate) provided herein (or implant comprising such compound) is administered to an individual suffering an acute or a chronic disease or condition (e.g., as a therapy for the acute or chronic disease or condition) in any suitable manner (e.g., route of administration, such as by implanting, and/or frequency of dosing), such as a single dose or a series of doses (e.g., once or twice every 1 week, 2 weeks, 3 weeks, 4 weeks, 6 weeks, 12 weeks, 52 weeks, or more). The compound (e.g., opioid conjugate) is generated and tested, in certain embodiments, using the assays and methods provided herein (e.g., as described in the examples). The opioid conjugates provided herein represent a significant advance in the art as the opioid conjugates that produce a controlled (e.g., near zero-order) and extended release profile that is beneficial for treating acute and/or chronic diseases or disorders (e.g., acute pain, chronic pain, post-operative pain, opioid addiction, opioid dependence, or the like) with a single administration (e.g., once or twice every 1 week, 2 weeks, 3 weeks, 4 weeks, 6 weeks, 12 weeks, 52 weeks, or more).

In some instances, provided herein is a compound comprising a first radical and a second radical, both the first radical and the second radical each comprising a structure of Formula (I'):

Formula (I')

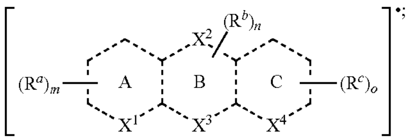

wherein:

each ⸝⸝ is, independently, a single bond or a double bond;

each $R^a$, $R^b$, and $R^c$ are independently selected the group consisting of oxo, halogen, —CN, —$NO_2$, alkyl, heteroalkyl, cycloalkyl, heterocycloalkyl, alkoxy, amino, hydroxy, or thiol, wherein the alkyl, heteroalkyl, cycloalkyl, or heterocycloalkyl is optionally substituted;

or any one of $R^a$, $R^b$, or $R^c$ are taken together with another of $R^a$, $R^b$, or $R^c$ to form a substituted or an unsubstituted cycloalkyl or heterocycloalkyl;

$X^1$, $X^2$, $X^3$, and $X^4$ are each independently selected from the group consisting of a bond and $Q_y$, wherein each Q is independently selected from the group consisting of —O—, —NR—, —$S(R)_x$—, and —$C(R)_z$—;

each of m, n, and o are independently 0-6;

each x is independently 0-5;

each y is independently 1-3;

each z is independently 1 or 2;

each R is independently selected from the group consisting of H, halogen, alkyl, heteroalkyl, cycloalkyl, heterocycloalkyl, alkoxy, amino, hydroxy, and thiol, or is taken together with another R to form an oxo; and or a pharmaceutically salt or solvate thereof, wherein the first and second radicals are non-steroidal.

In some instances, provided herein is a compound comprising a first radical and a second radical, both the first radical and the second radical each comprising a structure of Formula (I):

(I)

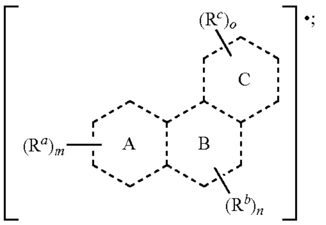

wherein:

each ⸝⸝ is, independently, a single bond or a double bond;

each $R^a$, $R^b$, and $R^c$ are independently selected from the group consisting of oxo, halogen, —CN, –$NO_2$, azide, alkyl, heteroalkyl, cycloalkyl, heterocycloalkyl, alkoxy, aryloxy, ester, amino, hydrazone, oxime, hydroxy, or thiol, wherein the alkyl, heteroalkyl, cycloalkyl, alkoxy, aryloxy, hydrazone, or heterocycloalkyl is optionally substituted;

or any one of an $R^a$, $R^b$, or $R^c$ is independently taken together with another of $R^a$, $R^b$, or $R^c$ to form a substituted or unsubstituted cycloalkyl, heterocycloalkyl, aryl, or heteroaryl; and each of m, n, and o are independently 0-6, or a pharmaceutically salt or solvate thereof, wherein the first and second radicals are non-steroidal.

In some embodiments, Ring A, B, or C of Formula (I) or Formula (I'), each optionally and independently comprise one or more heteroatom (e.g., O, S, or N) within the ring. In some embodiments, Ring A or Ring C of Formula (I) or Formula (I'), each optionally and independently, comprises one or more optionally substituted heteroatom (e.g., O, S, or N) within the ring. In some embodiments, Ring C of Formula (I) or Formula (I') comprises an O within the ring. In some embodiments, Ring A, B, or C of Formula (I) or Formula (I'), each optionally and independently, is aromatic. In some embodiments, Ring A or Ring C is aromatic. In some embodiments, Ring C is aromatic.

In some embodiments, provided herein is a first (opioid) radical and a second (opioid) radical, both the first (opioid) radical and the second (opioid) radical comprising a structure of Formula (IA):

(IA)

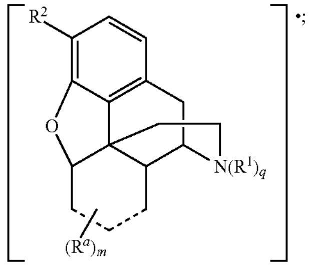

wherein:

each ⸝⸝ is, independently, a single bond or a double bond;

each $R^a$ is independently selected from the group consisting of oxo, halogen, —CN, —$NO_2$, azide, alkyl, heteroalkyl, cycloalkyl, heterocycloalkyl, alkoxy, aryloxy, ester, amino, hydroxy, hydrazone, oxime, or thiol, wherein the alkyl, heteroalkyl, cycloalkyl, alkoxy, aryloxy, hydrazone, or heterocycloalkyl is optionally substituted;

or a first $R^a$ is taken together with another $R^a$ to form an optionally substituted cycloalkyl, heterocycloalkyl, aryl, or heteroaryl;

each $R^1$ is independently H, alkyl, heteroalkyl, cycloalkyl, or heterocycloalkyl, wherein the alkyl, heteroalkyl, cycloalkyl, or heterocycloalkyl are optionally substituted;

$R^2$ is H, hydroxy, alkyl, heteroalkyl, alkoxy, cycloalkyl, or heterocycloalkyl, wherein the alkyl, heteroalkyl, cycloalkyl, alkoxy, or heterocycloalkyl are optionally substituted;

m is 0-8; and q is 1 or 2, or a pharmaceutically salt or solvate thereof.

In some embodiments, the structure of Formula (I) or Formula (IA), each optionally and independently, is a radical of an opioid agonist or an opioid antagonist. In some embodiments, the first radical and the second radical are each independently an opioid agonist or an opioid antagonist in their free form. In some embodiments, the first radical and the second radical are each an opioid agonist in their free form. In some embodiments, the first radical and the second radical are the same opioid agonist in their free form. In some embodiments, the first radical and the second radical are each an opioid antagonist in their free form. In some embodiments, the first radical and the second radical are the same opioid antagonist in their free form.

In some embodiments, the first (opioid) radical and the second (opioid) radical are joined by a linker. In some embodiments, the linker comprises one or more linker groups. In some embodiments, the first (opioid) radical and the second (opioid) radical are released from the opioid conjugate subsequent to hydrolysis of one or more of the linker groups.

In some instances, provided herein is a compound comprising a structure of Formula (II):

Formula (II)

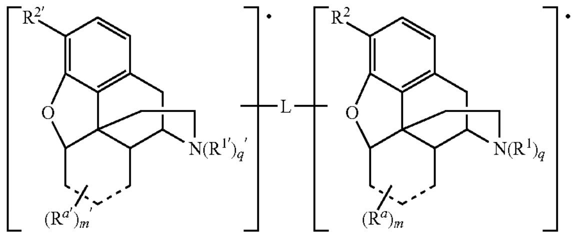

wherein:

each ⸝⸝ is, independently, a single bond or a double bond;

each $R^a$ and $R^{a'}$ are independently selected from the group consisting of oxo, halogen, —CN, —$NO_2$, azide, alkyl, heteroalkyl, cycloalkyl, heterocycloalkyl, alkoxy, aryloxy, ester, amino, hydroxy, hydrazone, oxime, or thiol, wherein the alkyl, heteroalkyl, cycloalkyl, alkoxy, aryloxy, hydrazone, or heterocycloalkyl is optionally substituted;

or a first $R^a$ is taken together with another $R^a$ to form an optionally substituted cycloalkyl, heterocycloalkyl, aryl, or heteroaryl;

or a first $R^{a'}$ is taken together with another $R^{a'}$ to form an optionally substituted cycloalkyl, heterocycloalkyl, aryl, or heteroaryl;

each $R^1$ and $R^{1'}$ are independently H, alkyl, heteroalkyl, cycloalkyl, or heterocycloalkyl, wherein the alkyl, heteroalkyl, cycloalkyl, or heterocycloalkyl are optionally substituted;

$R^2$ and $R^{2'}$ are each independently H, hydroxy, alkyl, heteroalkyl, cycloalkyl, alkoxy, or heterocycloalkyl, wherein the alkyl, heteroalkyl, cycloalkyl, alkoxy, or heterocycloalkyl are optionally substituted;

m and m' are each independently 0-8;

q and q' are each independently 1 or 2; and

L is a linker (e.g., a hydrolysable linker), or a pharmaceutically salt or solvate thereof.

In some embodiments, any one of $R^1$, $R^2$, or $R^a$ is a hydroxyl radical or a carboxylate radical, and any one of $R^{1'}$, $R^{2'}$, or $R^{a'}$ is a hydroxyl radical or a carboxylate radical. In some embodiments, any one of $R^1$, $R^2$, or $R^a$ is a hydroxyl radical, and any one of $R^{1'}$, $R^{2'}$, or $R^{a'}$ is a hydroxyl radical. In some embodiments, any one of $R^1$, $R^2$, or $R^a$ is adjoined to any one of $R^{1'}$, $R^{2'}$, or $R^{a'}$ by a linker. In some embodiments, any one of $R^2$ or $R^a$ is adjoined to any one of $R^{2'}$ or $R^{a'}$ by a linker. In some embodiments, $R^2$ is adjoined to $R^{2'}$ by a linker. In some embodiments, $R^{a'}$ is adjoined to $R^{a'}$ by a linker.

In some embodiments, provided herein is a compound comprising a structure of Formula (IIA):

(IIA)

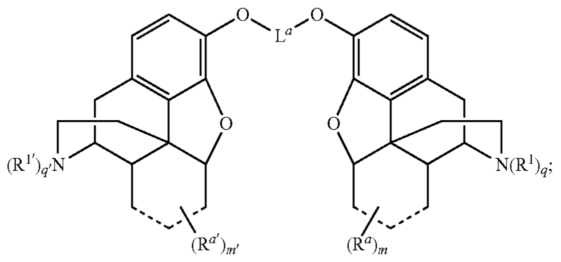

wherein:

each ---- is, independently, a single bond or a double bond;

each $R^a$ and $R^{a'}$ are independently selected from the group consisting of oxo, halogen, —CN, —$NO_2$, azide, alkyl, heteroalkyl, cycloalkyl, heterocycloalkyl, alkoxy, aryloxy, ester, amino, hydroxy, hydrazone, oxime, or thiol, wherein the alkyl, heteroalkyl, cycloalkyl, alkoxy, aryloxy, hydrazone, or heterocycloalkyl is optionally substituted;

or any one of an $R^a$ is independently taken together with another $R^a$ to form an optionally substituted substituted cycloalkyl, heterocycloalkyl, aryl, or heteroaryl;

or any one of an $R^{a'}$ is independently taken together with another $R^{a'}$ to form an optionally substituted cycloalkyl, heterocycloalkyl, aryl, or heteroaryl;

each $R^1$ and $R^{1'}$ are independently H, alkyl, heteroalkyl, cycloalkyl, or heterocycloalkyl, wherein the alkyl, heteroalkyl, cycloalkyl, or heterocycloalkyl are optionally substituted;

m and m' are each is independently 0-8;

q and q' are each independently 1 or 2; and $L^a$ is a linker (e.g., a hydrolyzable linker), or a pharmaceutically salt or solvate thereof.

In some embodiments, provided herein is a compound comprising a structure of Formula (IIA'):

(IIA')

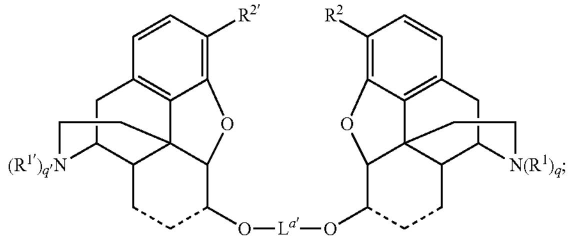

wherein:

each ---- is, independently, a single bond or a double bond;

each $R^a$ and $R^{a'}$ are independently selected from the group consisting of oxo, halogen, —CN, —$NO_2$, azide, alkyl, heteroalkyl, cycloalkyl, heterocycloalkyl, alkoxy, aryloxy, ester, amino, hydroxy, hydrazone, oxime, or thiol, wherein the alkyl, heteroalkyl, cycloalkyl, alkoxy, aryloxy, hydrazone, or heterocycloalkyl is optionally substituted;

or any one of an $R^a$ is independently taken together with another $R^a$ to form an optionally substituted substituted cycloalkyl, heterocycloalkyl, aryl, or heteroaryl;

or any one of an $R^{a'}$ is independently taken together with another $R^{a'}$ to form an optionally substituted cycloalkyl, heterocycloalkyl, aryl, or heteroaryl;

each $R^1$ and $R^{1'}$ are independently H, alkyl, heteroalkyl, cycloalkyl, or heterocycloalkyl, wherein the alkyl, heteroalkyl, cycloalkyl, or heterocycloalkyl are optionally substituted;

m and m' are each is independently 0-8;

q and q' are each independently 1 or 2; and $L^{a'}$ is a linker (e.g., a hydrolyzable linker), or a pharmaceutically salt or solvate thereof.

In some embodiments, the linker comprises at least one oxo. In some embodiments, the linker comprises two oxo groups.

In some embodiments, provided herein is a compound comprising a structure of Formula (IIB):

Formula (IIB)

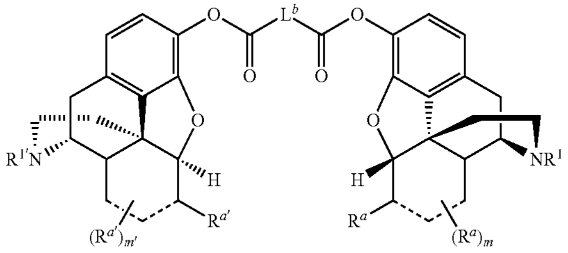

wherein:

each ---- is, independently, a single bond or a double bond;

each $R^a$ and $R^{a'}$ are independently selected from the group consisting of oxo, halogen, azide, alkyl, heteroalkyl, cycloalkyl, heterocycloalkyl, alkoxy, aryloxy, ester, amino, hydrazone, oxime, or hydroxy, wherein the alkyl, heteroalkyl, cycloalkyl, alkoxy, aryloxy, hydrazone, or heterocycloalkyl is optionally substituted;

or a first $R^a$ is taken together with another $R^a$ to form an optionally substituted cycloalkyl, heterocycloalkyl, aryl, or heteroaryl;

or a first $R^{a'}$ is taken together with another $R^{a'}$ to form an optionally substituted cycloalkyl, heterocycloalkyl, aryl, or heteroaryl;

each $R^1$ and $R^{1'}$ are independently H, alkyl, heteroalkyl, cycloalkyl, or heterocycloalkyl, wherein the alkyl, heteroalkyl, cycloalkyl, or heterocycloalkyl are optionally substituted;

$L^b$ is alkyl, heteroalkyl, or alkoxy, wherein the alkyl, heteroalkyl, or alkoxy is optionally substituted; and m and m' are each independently 0-4, or a pharmaceutically salt or solvate thereof.

In some embodiments, provided herein is a compound comprising a structure of Formula (IIC):

Formula (IIC)

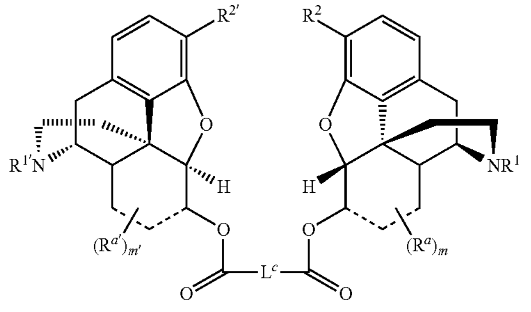

wherein:

each ---- is, independently, a single bond or a double bond;

each $R^a$ and $R^{a'}$ are independently selected from the group consisting of oxo, halogen, azide, alkyl, heteroalkyl, cycloalkyl, heterocycloalkyl, alkoxy, aryloxy, ester, amino, hydrazone, oxime, or hydroxy, wherein the alkyl, heteroalkyl, cycloalkyl, alkoxy, aryloxy, hydrazone, or heterocycloalkyl is optionally substituted;

or a first $R^a$ is taken together with another $R^a$ to form a substituted or unsubstituted cycloalkyl or heterocycloalkyl;

or a first $R^{a'}$ is taken together with another $R^{a'}$ to form a substituted or unsubstituted cycloalkyl or heterocycloalkyl;

each $R^1$ and $R^{1'}$ are independently H, alkyl, heteroalkyl, cycloalkyl, or heterocycloalkyl, wherein the alkyl, heteroalkyl, cycloalkyl, or heterocycloalkyl are optionally substituted;

$R^2$ and $R^{2'}$ are each independently H, hydroxy, alkyl, heteroalkyl, or alkoxy, wherein the alkyl, heteroalkyl, or alkoxy is optionally substituted;

$L^c$ is alkyl, heteroalkyl, or alkoxy, wherein the alkyl, heteroalkyl, or alkoxy is optionally substituted; and m and m' are each independently 0-4, or a pharmaceutically salt or solvate thereof.

Any list of options for a variable (e.g., R group, etc.) herein includes disclosure that each such variable, where more than one such variable is present, is independently selected from the list of options.

In some embodiments, adjacent ⸗⸗ are not, concurrently, double bond.

In some embodiments, an opioid dimer described herein comprises a first (opioid) radical and a second (opioid) radical. In some embodiments, the first (opioid) radical and the second (opioid) radical are each a solid at a temperature of at least 20° C. or more (e.g., at least 30° C., at least 37° C., at least 40° C., at least 50° C., at least 100° C., or more) in their free form. In some embodiments, the first (opioid) radical and the second (opioid) radical have the same structure in their free form.

In some embodiments, the first (opioid) radical and the second (opioid) radical are each independently an opioid agonist or opioid antagonist in their free form. In some embodiments, the opioid agonist is an inverse agonist, a mixed opioid agonist/antagonist or a partial opioid agonist. In some embodiments, the first (opioid) radical and the second (opioid) radical are each an opioid agonist in their free form. In some embodiments, the first (opioid) radical and the second (opioid) radical are each an opioid antagonist in their free form. In some embodiments, the first (opioid) radical and the second (opioid) radical are the same opioid agonist in their free form. In some embodiments, the first (opioid) radical and the second (opioid) radical are the same opioid antagonist in their free form.

In some embodiments, provided herein is a compound comprising:

a) a first opioid (e.g., opioid agonist, opioid antagonist, partial opioid agonist);

b) a second opioid (e.g., opioid agonist, opioid antagonist, partial opioid agonist); and c) a linker (e.g., hydrolyzable linker), wherein the linker adjoins (e.g., covalently) the first opioid and the second opioid, or a pharmaceutically acceptable salt or solvate thereof.

In some embodiments, the opioid agonist is an opium alkaloid. In some embodiments, the opioid agonist is selected from the group consisting of codeine, morphine, and oripavine, or the like.

In some embodiments, the opioid agonist is a semisynthetic opioid deriving from morphine. In some embodiments, the opioid agonist is selected from the group consisting of 14-hydroxymorphine, 2,4-dinitrophenylmorphine, 6-methyldihydromorphine, 6-methylenedihydrodesoxymorphine, 6-acetyldihydromorphine, azidomorphine, chlornaltrexamine, chloroxymorphamine, desomorphine, dihydromorphine, ethyldihydromorphine, hydromorphinol, methyldesorphine, morphine methylbromide, N-phenethylnordesomorphine, N-phenethyl-14-ethoxymetopon, N-phenethylnormorphine, 6-nicotinoyldihydromorphine, and RAM-378, or the like.

In some embodiments, the opioid agonist is a codeinedionine derivative. In some embodiments, the opioid agonist is selected from the group consisting of benzylmorphine, codeine methylbromide, ethyldihydromorphine, methyldihydromorphine, ethylmorphine, heterocodeine, isocodeine, pholcodine, and transisocodeine, or the like.

In some embodiments, the opioid agonist is a morphinone or a morphol derivative. In some embodiments, the opioid agonist is selected from the group consisting of 14-cinnamoyloxycodeinone, 14-ethoxymetopon, 14-methoxymetopon, 14-phenylpropoxymetopon, 3-acetyloxymorphone, 3,14-diacetyloxymorphone, 7-spiroindanyloxymorphone, 8,14-dihydroxydihydromorphinone, acetylmorphone, α-hydrocodol, codeinone, codoxime, conorfone, IBNtxA, thebacon, hydrocodone, hydromorphone, hydroxycodeine, metopon, morphinone, N-phenethyl-14-ethoxymetopon, noroxymorphone, oxycodone, oxymorphol, oxymorphone, pentamorphone, and semorphone, or the like.

In some embodiments, the opioid agonist is a morphide derivative. In some embodiments, the opioid agonist is selected from the group consisting of bromomorphide and chloromorphide, or the like.

In some embodiments, the opioid agonist is a dihydrocodeine. In some embodiments, the opioid agonist is selected from the group consisting of 14-hydroxydihydrocodeine, dihydrocodeine, and dihydroisocodeine, or the like.

In some embodiments, the opioid agonist is an N-oxide opioid derivative. In some embodiments, the opioid agonist is selected from the group consisting of codeine-N-oxide and morphine-N-oxide, or the like.

In some embodiments, the opioid agonist is a hydrazone. In some embodiments, the opioid agonist is oxymorphazone, or the like.

In some embodiments, the opioid agonist is a halogenated opioid derivative. In some embodiments, the opioid agonist is 1-iodomorphine, or the like.

In some embodiments, the opioid agonist is an opiate metabolite. In some embodiments, the opioid agonist is selected from the group consisting of codeine-6-glucuronide codeine-N-oxide, morphine-6-glucuronide, 3-monoacetylmorphine, 6-monoacetylmorphine, morphine-N-oxide, naltrexol, norcodeine, and normorphine, or the like.

In some embodiments, the opioid agonist is a morphinan derivative. In some embodiments, the opioid agonist is selected from the group consisting of 3-hydroxymorphinan, 4-chlorophenylpyridomorphinan, cyclorphan, levargorphan, levorphanol, morphanol, norlevorphanol, oxilorphan, phenomorphan, proxorphan, Ro4-1539, and xorphanol In some embodiments, the opioid agonist is selected from the group consisting of 1-nitroaknadinine, 14-episinomenine, 5,6-dihydronorsalutaridine, 6-keto nalbuphine, aknadinine, butorphanol, cephakicine, cephasamine, cyprodime, drotebanol, fenfangjine G, ketorfanol, nalbuphine, nalbuphone, and tannagine, or the like.

In some embodiments, the opioid agonist is a oripavin derivative. In some embodiments, the opioid agonist is selected from the group consisting of 7-PET, acetorphine, alletorphine, BU48, buprenorphine, buprenorphine-3-glucuronide, cyprenorphine, dihydroetorphine, etorphine, homprenorphine, 18,19-dehydrobuprenorphine, N-cyclopropylmethylnoretorphine, nepenthone, norbuprenorphine, norbuprenorphine-3-glucuronide, thevinone, and thienorphine, or the like.

In some embodiments, the opioid antagonist or the inverse opioid agonist is selected from the group consisting of 4-caffeoyl-1,5-quinide5'-guanidinonaltrindole, β-funaltrexamine, 6β-naltrexol, binaltorphimine, buprenorphine, chlornaltrexamine, clocinnamox, cyprodime, diacetylnalorphine, diprenorphine, levallorphan, methocinnamox, methylnaltrexone, naldemedine, nalfurafine, nalmefene, nalmexone, nalodeine, naloxazone, naloxegol, naloxol, naloxonazine, naloxone, naloxone benzoylhydrazone, nalorphine, naltrexone, naltriben, naltrindole, norbinaltorphimine, oxilorphan, S-allyl-3-hydroxy-17-thioniamorphinan, and samidorphan, or the like.

In some embodiments, the first (opioid) radical and the second (opioid) radical are each independently a radical (e.g., a hydroxyl radical) selected from the group consisting of:

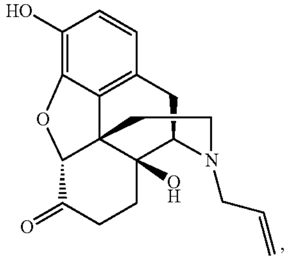

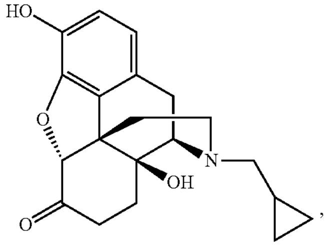

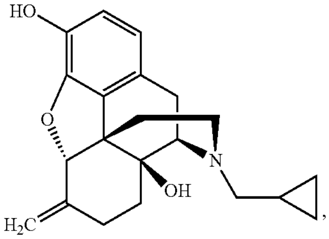

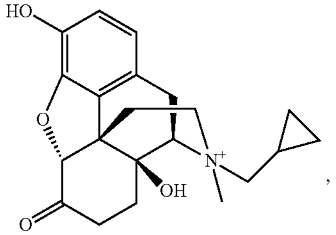

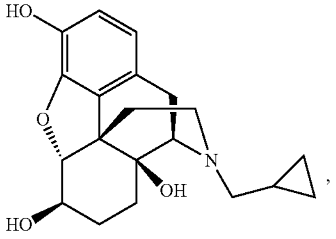

-continued

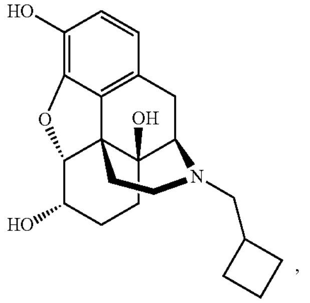

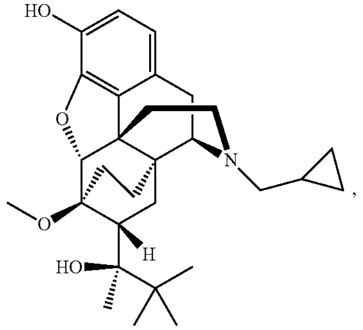

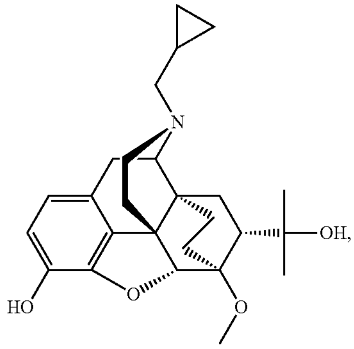

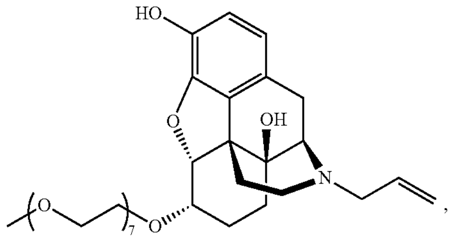

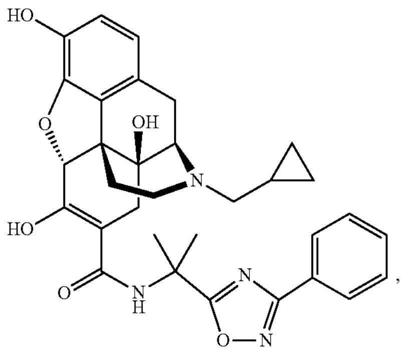

-continued
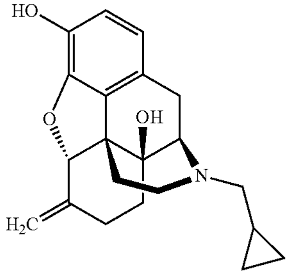
,
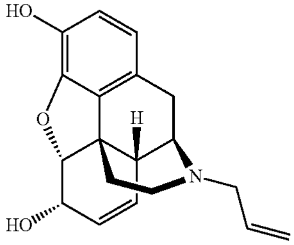
,
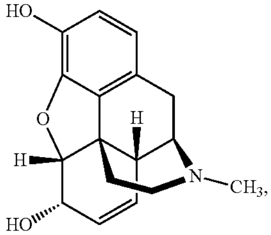
,
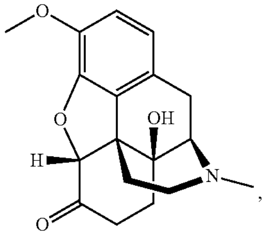
,
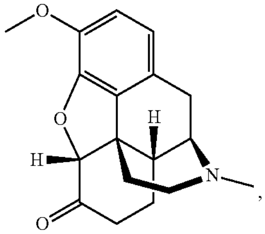
,
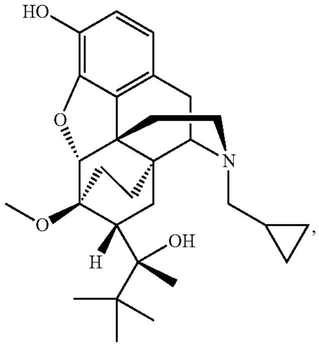
,
-continued
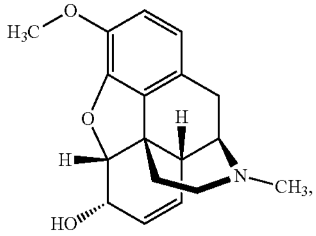
,
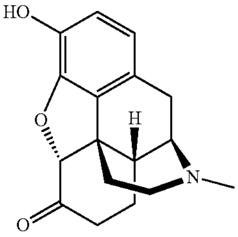
,
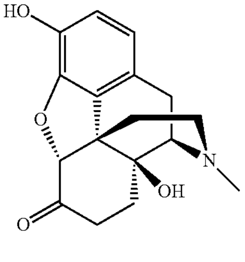
,
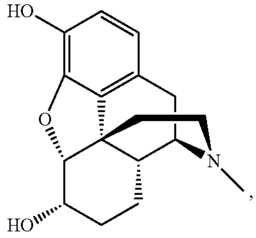
,
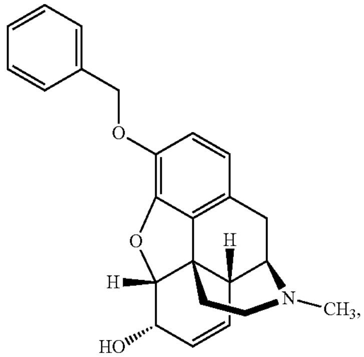
,
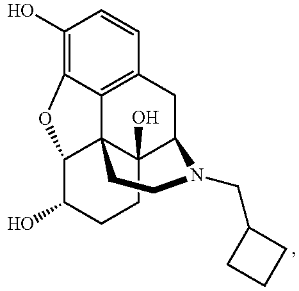
, and
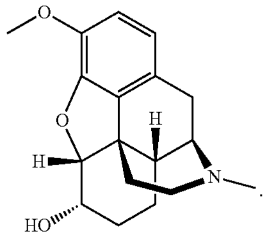
.

In some embodiments, the first radical or the second radical (e.g., an opioid agonist) is independently a radical (e.g., a hydroxyl radical) selected from the group consisting of:
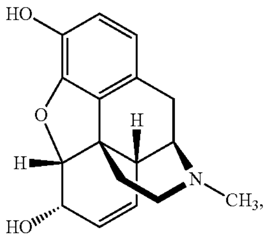
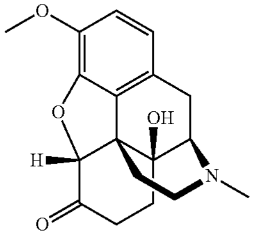
,
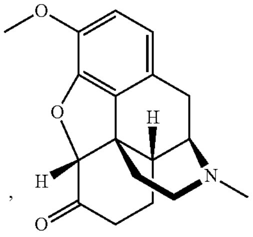
,
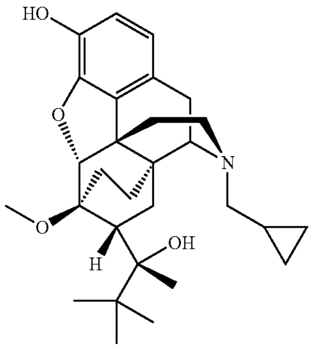
,
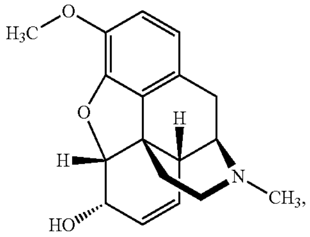
-continued
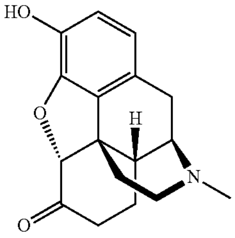
,
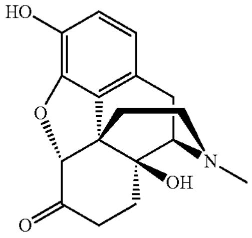
,
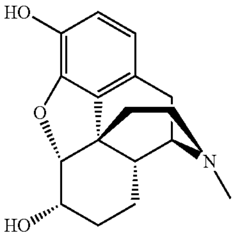
,
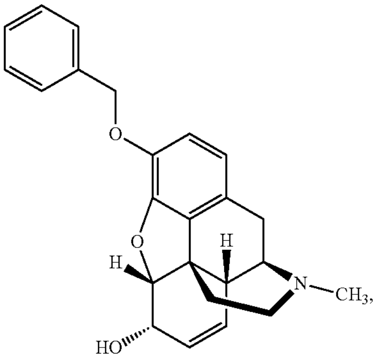
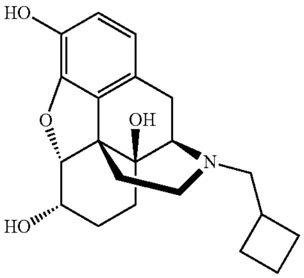
, and
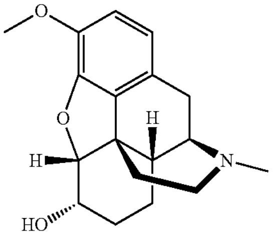
.

In some embodiments, the first radical or the second radical (e.g., an opioid antagonist) is independently a radical (e.g., a hydroxyl radical) selected from the group consisting of:
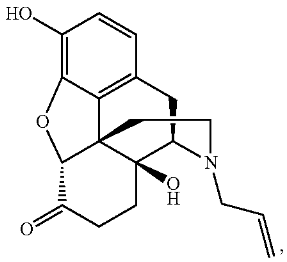
,
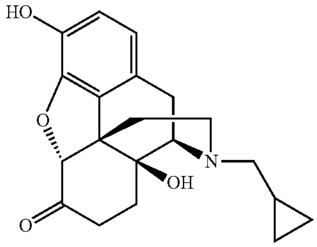
,
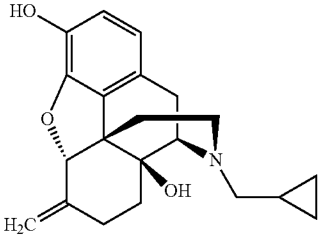
,
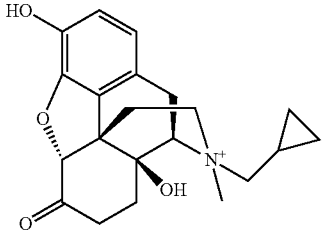
,
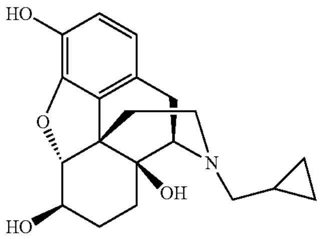
,
-continued
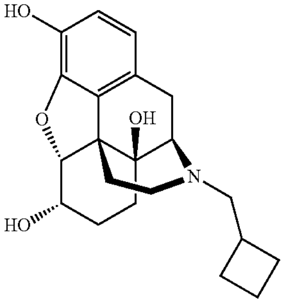
,
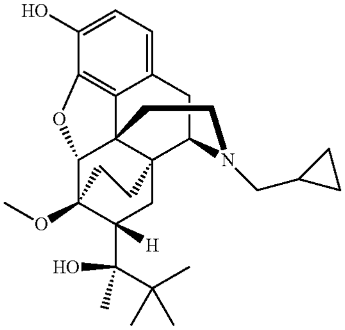
,
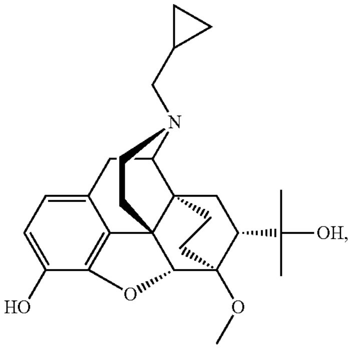
,
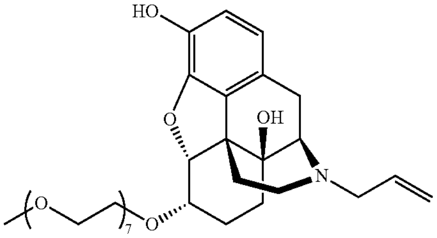
,
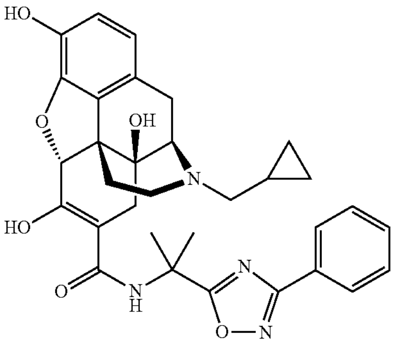
, -continued

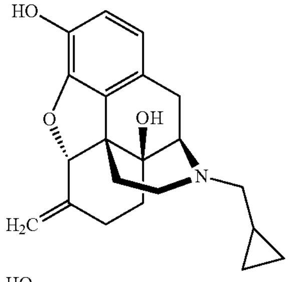

, and

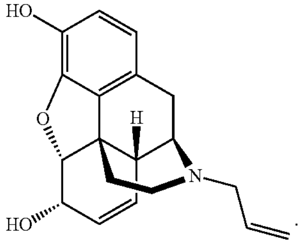

.

In some embodiments, provided herein is a compound comprising a structure of Formula (IID):

(IID)

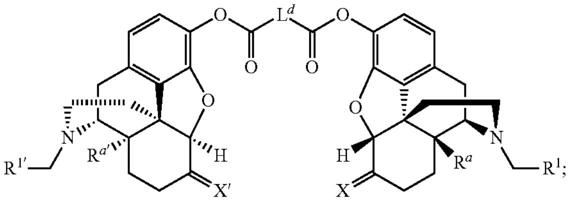

wherein:

$R^1$ and $R^{1'}$ are each independently unsaturated alkyl (e.g., alkenyl) or cycloalkyl;

$R^a$ and $R^{a'}$ are each independently H or —OH;

$L^d$ is selected from the group consisting of $—(CR_2)_y—$, $—O(CR_2)_yO—$, $—O(CR_2)_y—$, $—(CR_2)_yO—$, and $—O(CH_2CH_2O)_y—$, wherein y is 1-10 and each R is independently selected from the group consisting of H, hydroxyl, halogen, alkyl, or is taken together with another R to form an optionally substituted cycloalkyl; and X and X' are each independently O or $CH_2$, or a pharmaceutically salt or solvate thereof.

In some embodiments, $L^d$ is selected from the group consisting of $—(CR_2)_y—$, $—O(CR_2)_yO—$, $—O(CR_2)_y—$, $—(CR_2)_yO—$, and $—O(CH_2CH_2O)_y—$, wherein y is 1-10 and each R is independently selected from the group consisting of H, halogen, alkyl, or is taken together with another R to form an optionally substituted cycloalkyl.

In some embodiments, $R^1$ or $R^{1'}$, each optionally and independently, is unsaturated alkyl (e.g., alkenyl (e.g., allyl)). In some embodiments, $R^1$ or $R^{1'}$, each optionally and independently, is cycloalkyl (e.g., cyclopropyl).

In some embodiments, the compound (e.g., opioid conjugate), or pharmaceutically acceptable salt thereof, provided in Table 1 comprises both a first (opioid) radical and a second (opioid) radical, which when combined in a dimer are processable (e.g., wherein the radicals may or may not be processable themselves, when in their free form). In some embodiments, the compound (e.g., opioid conjugate), or pharmaceutically acceptable salt thereof, provided in Table 1 comprises a first (opioid) radical and a second (opioid) radical that are the same. In some embodiments, the compound (e.g., opioid conjugate), or pharmaceutically acceptable salt thereof, provided in Table 1 comprises a first (opioid) radical and a second (opioid) radical that are different. In some embodiments, both the first (opioid) radical and the second (opioid) radical of the compound (e.g., opioid conjugate), or pharmaceutically acceptable salt thereof, provided in Table 1 is attached to the linker at a phenolic position of each the first (opioid) radical and the second (opioid) radical.

TABLE 1

| Example | Structure | Name |
|---|---|---|
| 1 | 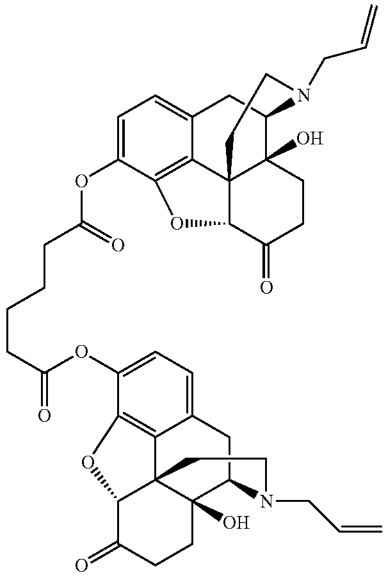 [SMILES: C=CCN1CC[C@]23c4c5ccc(OC(=O)CCCCC(=O)Oc6ccc7c8c6O[C@H]6C(=O)CC[C@@]9(O)[C@@H](C7)N(CC=C)CC[C@]869)c4O[C@H]2C(=O)CC[C@@]3(O)[C@H]1C5] | bis((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl)adipate |

TABLE 1-continued
| Example | Structure | Name |
|---|---|---|
| 2 | 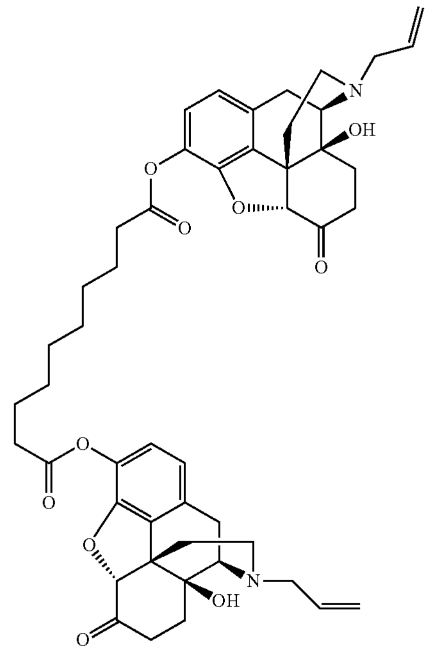 [SMILES: C=CCN1CC[C@]23c4c5ccc(OC(=O)CCCCCCCCC(=O)Oc6ccc7c8c6O[C@H]6C(=O)CC[C@@]9(O)[C@@H](C7)N(CC=C)CC[C@]869)c4O[C@H]2C(=O)CC[C@@]3(O)[C@H]1C5] | bis((4R,4aS,4aR,7aR,12bS)-3-allyl-4a-hydroxy-7-oxo-2,3,4,4a,5,6,7,7a-octahydro-1H-4,12-methanobenzofuro[3,2-e]isoquinolin-9-yl)decanedioate |
| 3 | 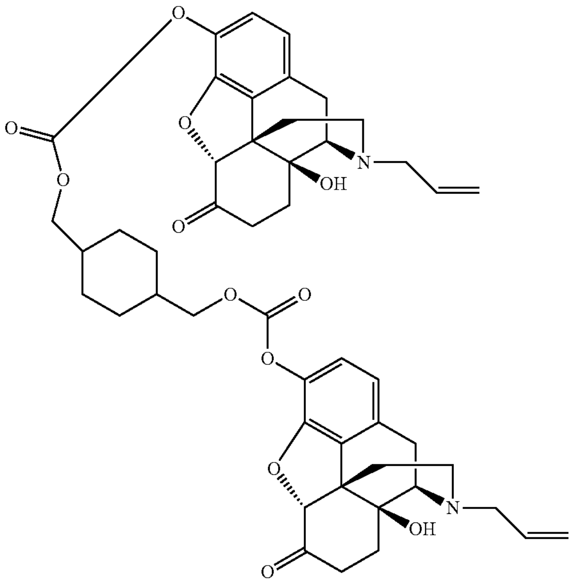 [SMILES: C=CCN1CC[C@]23c4c5ccc(OC(=O)OCC6CCC(COC(=O)Oc7ccc8c9c7O[C@H]7C(=O)CC[C@@]%10(O)[C@@H](C8)N(CC=C)CC[C@]97%10)CC6)c4O[C@H]2C(=O)CC[C@@]3(O)[C@H]1C5] | bis((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl)(cyclohexane-1,4-diylbis(methylene)) bis(carbonate) |

TABLE 1-continued

| Example | Structure | Name |
|---|---|---|
| 4 | 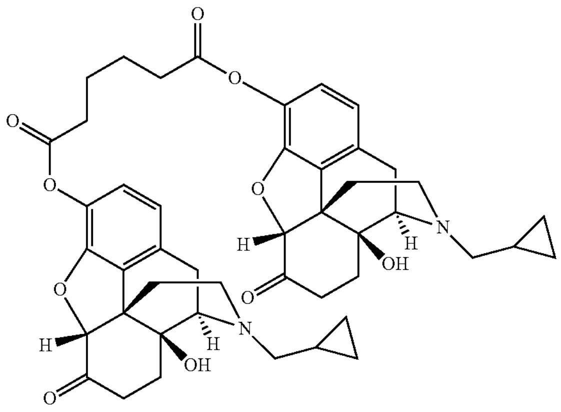 [SMILES: O=C(CCCCC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) adipate |
| 5 | 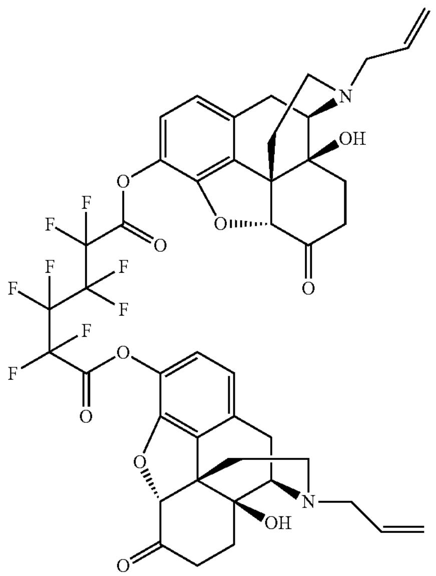 [SMILES: C=CCN1CC[C@]23c4c5ccc(OC(=O)C(F)(F)C(F)(F)C(F)(F)C(F)(F)C(=O)Oc6ccc7c8c6O[C@H]6C(=O)CC[C@@]9(O)[C@@H](C7)N(CC=C)CC[C@]869)c4O[C@H]2C(=O)CC[C@@]3(O)[C@H]1C5] | bis((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl) 2,2,3,3,4,4,5,5-octafluorohexanedioate |
| 6 | 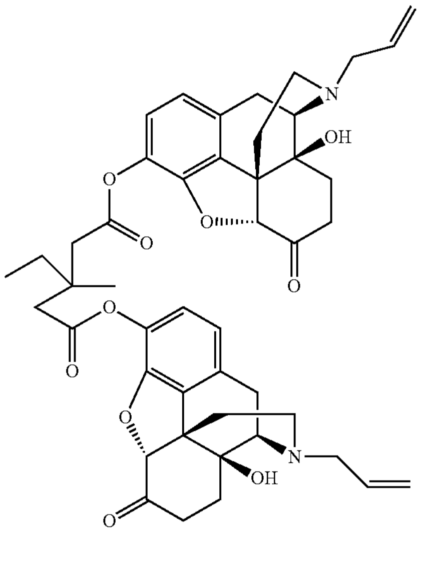 [SMILES: C=CCN1CC[C@]23c4c5ccc(OC(=O)CC(C)(CC)CC(=O)Oc6ccc7c8c6O[C@H]6C(=O)CC[C@@]9(O)[C@@H](C7)N(CC=C)CC[C@]869)c4O[C@H]2C(=O)CC[C@@]3(O)[C@H]1C5] | bis((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl) 3-ethyl-3-methylpentanedioate |

TABLE 1-continued
| Example | Structure | Name |
|---|---|---|
| 7 | 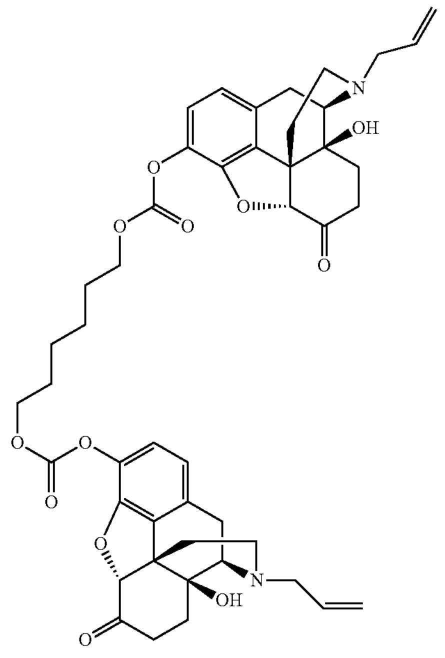 [SMILES: C=CCN1CC[C@]23c4c5ccc(OC(=O)OCCCCCCOC(=O)Oc6ccc7c8c6O[C@H]6C(=O)CC[C@@]9(O)[C@@H](C7)N(CC=C)CC[C@]869)c4O[C@H]2C(=O)CC[C@@]3(O)[C@H]1C5] | bis((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl) hexane-1,6-diyl bis(carbonate) |
| 8 | 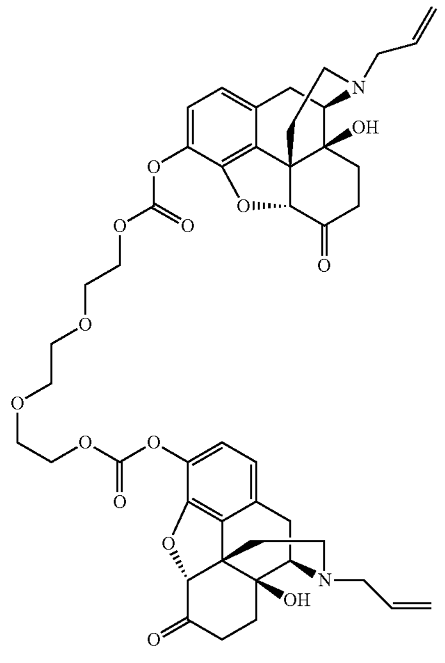 [SMILES: C=CCN1CC[C@]23c4c5ccc(OC(=O)OCCOCCOCCOC(=O)Oc6ccc7c8c6O[C@H]6C(=O)CC[C@@]9(O)[C@@H](C7)N(CC=C)CC[C@]869)c4O[C@H]2C(=O)CC[C@@]3(O)[C@H]1C5] | bis((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl) ((ethane-1,2-diylbis(oxy))bis(ethane-2,1-diyl)) bis(carbonate) |

TABLE 1-continued
| Example | Structure | Name |
| --- | --- | --- |
| 9 | 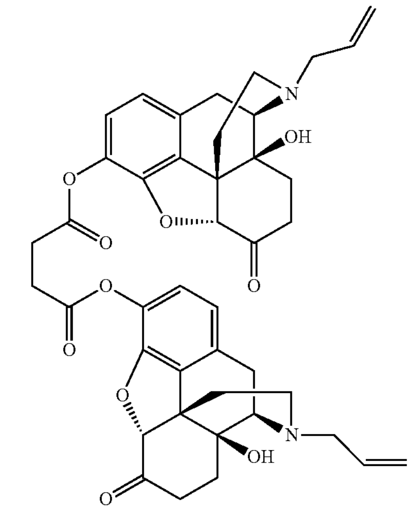 [SMILES: C=CCN1CC[C@]23c4c5ccc(OC(=O)CCC(=O)Oc6ccc7c8c6O[C@H]6C(=O)CC[C@@]9(O)[C@@H](C7)N(CC=C)CC[C@]869)c4O[C@H]2C(=O)CC[C@@]3(O)[C@H]1C5] | bis((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl) succinate |
| 10 | 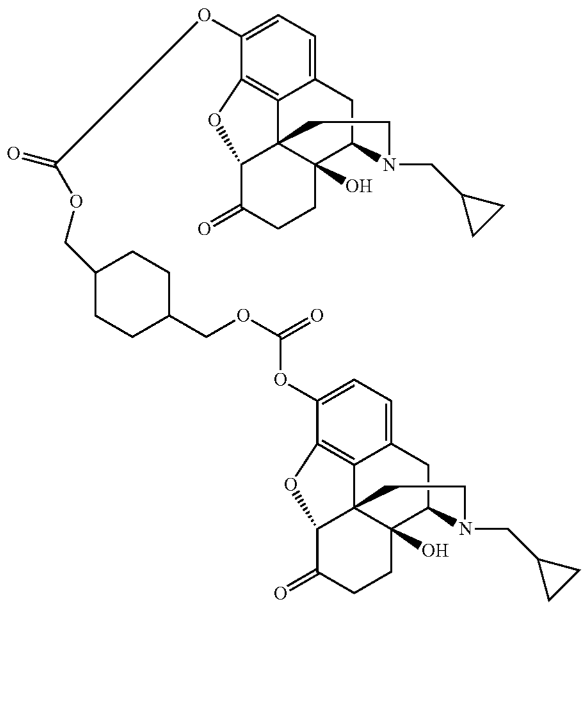 [SMILES: O=C(OCC1CCC(COC(=O)Oc2ccc3c4c2O[C@H]2C(=O)CC[C@@]5(O)[C@@H](C3)N(CC3CC3)CC[C@]425)CC1)Oc1ccc2c3c1O[C@H]1C(=O)CC[C@@]4(O)[C@@H](C2)N(CC2CC2)CC[C@]314] | cyclohexane-1,4-diylbis(methylene) bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) bis(carbonate) |

TABLE 1-continued

| Example | Structure | Name |
|---|---|---|
| 11 | 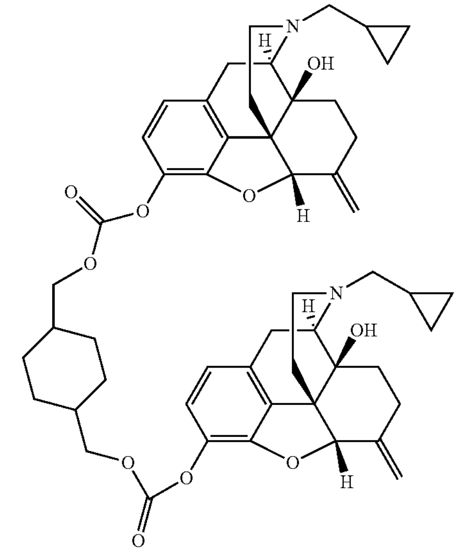 [SMILES: C=C1CC[C@@]2(O)[C@H]3Cc4ccc(OC(=O)OCC5CCC(COC(=O)Oc6ccc7c8c6O[C@H]6C(=C)CC[C@@]9(O)[C@@H](C7)N(CC7CC7)CC[C@]869)CC5)c5c4[C@@]2(CCN3CC2CC2)[C@H]1O5] | cyclohexane-1,4-diylbis(methylene) bis((4R,4aS,7aS,12bS)-3-(cyclopropylmethyl)-4a-hydroxy-7-methylene-2,3,4,4a,5,6,7,7a-octahydro-1H-4,12-methanobenofuro[3,2-e]isoquinolin-9-yl) bis(carbonate) |
| 12 | 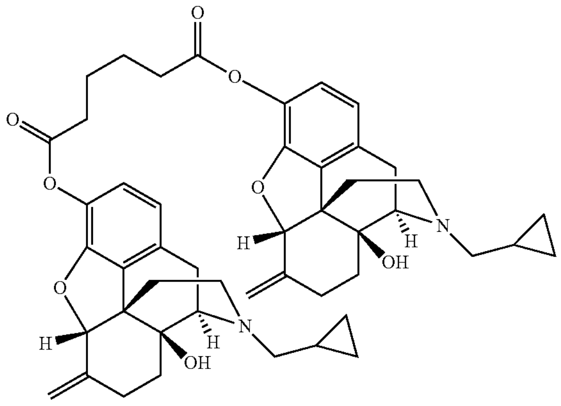 [SMILES: C=C1CC[C@@]2(O)[C@H]3Cc4ccc(OC(=O)CCCCC(=O)Oc5ccc6c7c5O[C@H]5C(=C)CC[C@@]8(O)[C@@H](C6)N(CC6CC6)CC[C@]758)c5c4[C@@]2(CCN3CC2CC2)[C@H]1O5] | bis((4R,4aS,7aS,12bS)-3-(cyclopropylmethyl)-4a-hydroxy-7-methylene-2,3,4,4a,5,6,7,7a-octahydro-1H-4,12-methanobenzofuro[3,2-e]isoquinolin-9-yl) adipate |
| 13 | 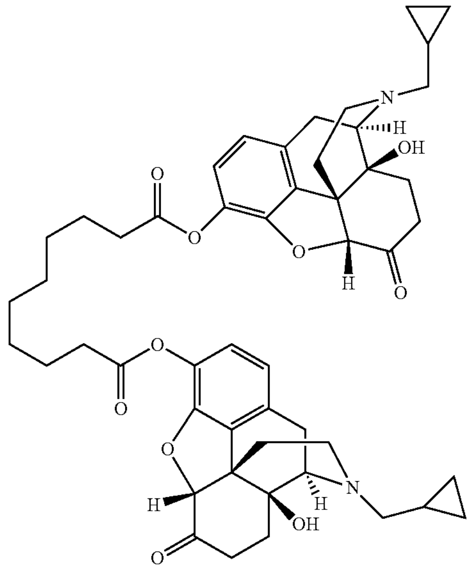 [SMILES: O=C(CCCCCCCCC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) decanedioate |

TABLE 1-continued

| Example | Structure | Name |
| --- | --- | --- |
| 14 | 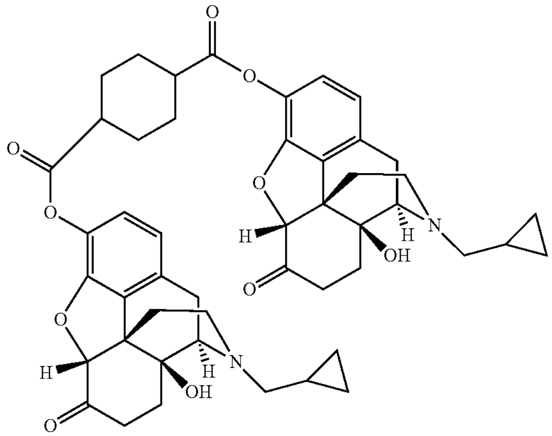 [SMILES: O=C(Oc1ccc2c3c1O[C@H]1C(=O)CC[C@@]4(O)[C@@H](C2)N(CC2CC2)CC[C@]314)C1CCC(C(=O)Oc2ccc3c4c2O[C@H]2C(=O)CC[C@@]5(O)[C@@H](C3)N(CC3CC3)CC[C@]425)CC1] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) cyclohexane-1,4-dicarboxylate |
| 15 | 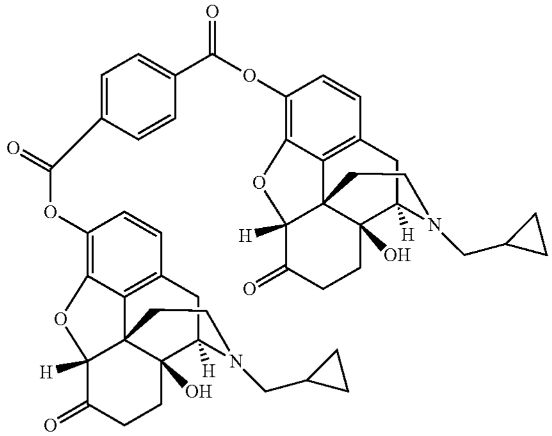 [SMILES: O=C(Oc1ccc2c3c1O[C@H]1C(=O)CC[C@@]4(O)[C@@H](C2)N(CC2CC2)CC[C@]314)c1ccc(C(=O)Oc2ccc3c4c2O[C@H]2C(=O)CC[C@@]5(O)[C@@H](C3)N(CC3CC3)CC[C@]425)cc1] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) terephthalate |
| 16 | 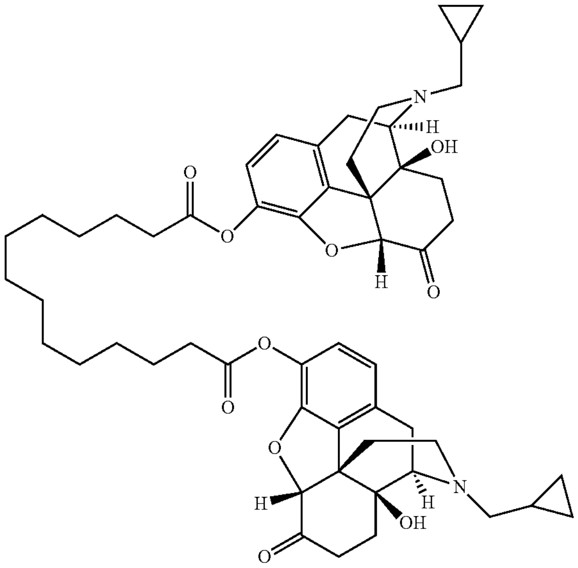 [SMILES: O=C(CCCCCCCCCCCCC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) tetradecanedioate |

TABLE 1-continued

| Example | Structure | Name |
| --- | --- | --- |
| 17 | 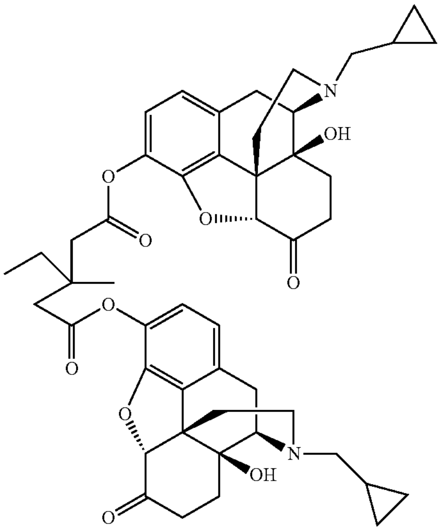 [SMILES: CCC(C)(CC(=O)Oc1ccc2c3c1O[C@H]1C(=O)CC[C@@]4(O)[C@@H](C2)N(CC2CC2)CC[C@]314)CC(=O)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 3-ethyl-3-methylpentanedioate |
| 18 | 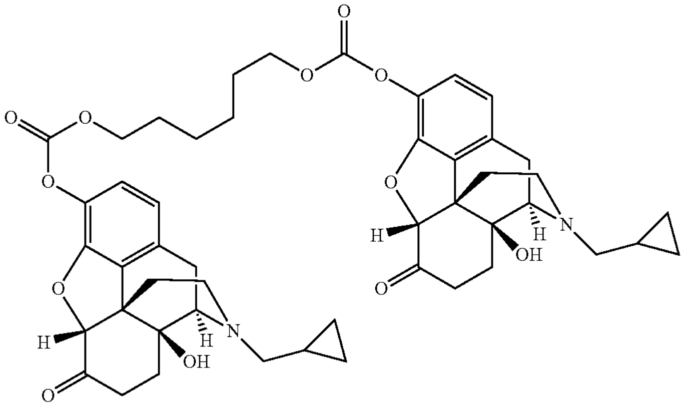 [SMILES: O=C(OCCCCCCOC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) hexane-1,6-diyl bis(carbonate) |
| 19 | 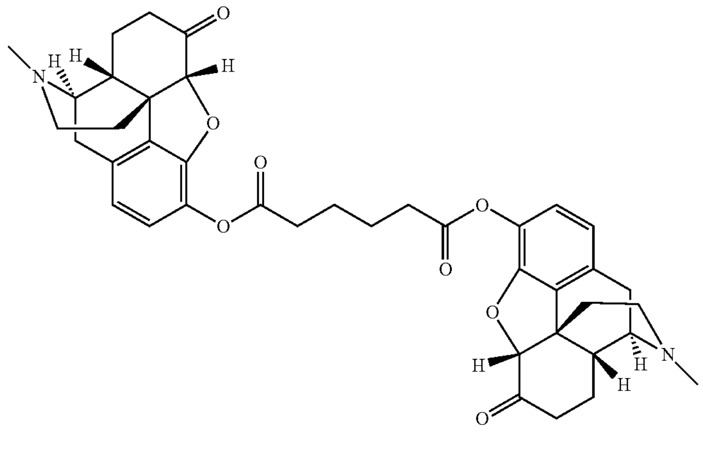 | bis((4R,4aR,7aR,12bS)-3-methyl-7-oxo-2,3,4,4a,5,6,7,7a-octahydro-1H-4,12-methanobenzofuro[3,2-e]isoquinolin-9-yl) adipate |

TABLE 1-continued
| Example | Structure | Name |
|---|---|---|
| 20 | 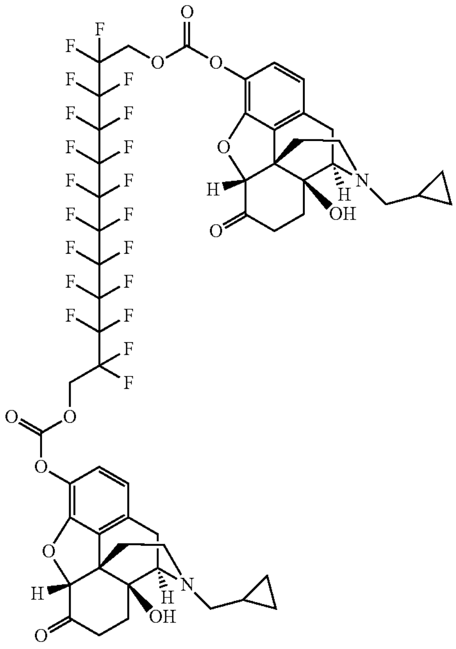 [SMILES: O=C(OCC(F)(F)C(F)(F)C(F)(F)C(F)(F)C(F)(F)C(F)(F)C(F)(F)C(F)(F)C(F)(F)C(F)(F)COC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) (2,2,3,3,4,4,5,5,6,6,7,7,8,8,9,9,10,10,11,11-icosafluorododecane-1,12-diyl) bis(carbonate) |
| 21 | 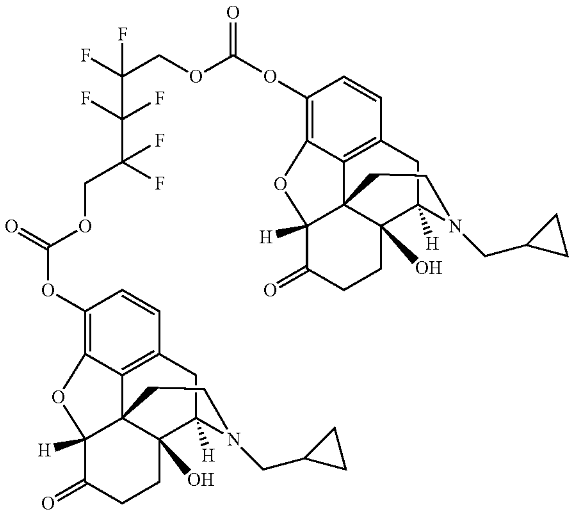 [SMILES: O=C(OCC(F)(F)C(F)(F)C(F)(F)COC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) (2,2,3,3,4,4-hexafluoropentane-1,5-diyl) bis(carbonate) |

TABLE 1-continued
| Example | Structure | Name |
| --- | --- | --- |
| 22 | 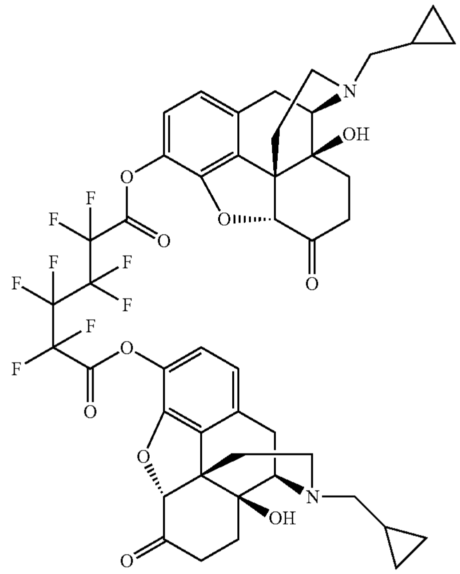 [SMILES: O=C1CC[C@@]2(O)[C@H]3Cc4ccc(OC(=O)C(F)(F)C(F)(F)C(F)(F)C(F)(F)C(=O)Oc5ccc6c7c5O[C@H]5C(=O)CC[C@@]8(O)[C@@H](C6)N(CC6CC6)CC[C@]758)c5c4[C@@]2(CCN3CC2CC2)[C@H]1O5] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 2,2,3,3,4,4,5,5-octafluorohexanedioate |
| 23 | 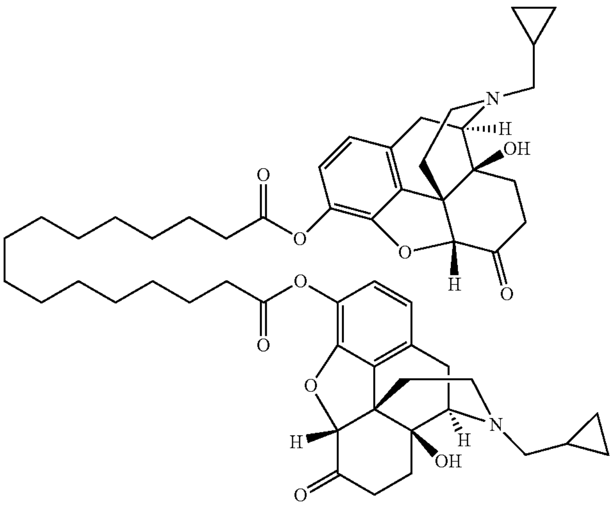 [SMILES: O=C(CCCCCCCCCCCCCCC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) hexadecanedioate |

TABLE 1-continued

| Example | Structure | Name |
| --- | --- | --- |
| 24 | 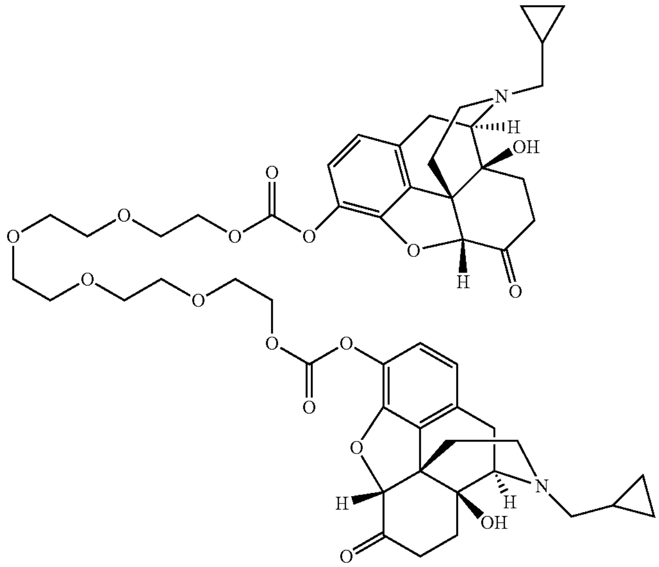 [SMILES: O=C(OCCOCCOCCOCCOCCOC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) (3,6,9,12-tetraoxatetradecane-1,4-diyl) bis(carbonate) |
| 25 | 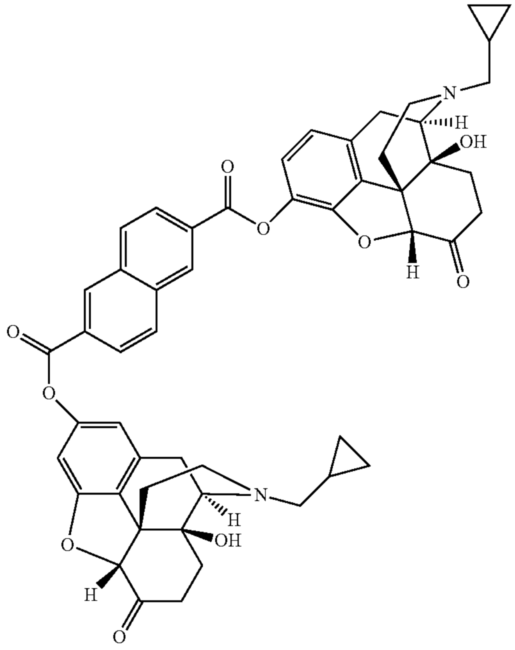 [SMILES: O=C(Oc1cc2c3c(c1)O[C@H]1C(=O)CC[C@@]4(O)[C@@H](C2)N(CC2CC2)CC[C@]314)c1ccc2cc(C(=O)Oc3ccc4c5c3O[C@H]3C(=O)CC[C@@]6(O)[C@@H](C4)N(CC4CC4)CC[C@]536)ccc2c1] | 2-((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-10-yl) 6-((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) naphthalene-2,6-dicarboxylate |

TABLE 1-continued

| Example | Structure | Name |
| --- | --- | --- |
| 26 | 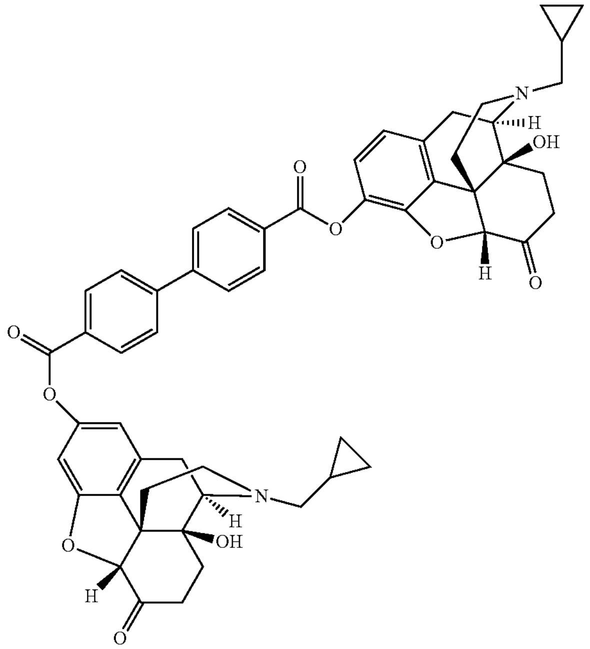 [SMILES: O=C(Oc1cc2c3c(c1)O[C@H]1C(=O)CC[C@@]4(O)[C@@H](C2)N(CC2CC2)CC[C@]314)c1ccc(-c2ccc(C(=O)Oc3ccc4c5c3O[C@H]3C(=O)CC[C@@]6(O)[C@@H](C4)N(CC4CC4)CC[C@]536)cc2)cc1] | 4-((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-10-yl) 4'-((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) [1,1'-biphenyl]-4,4'-dicarboxylate |
| 27 | 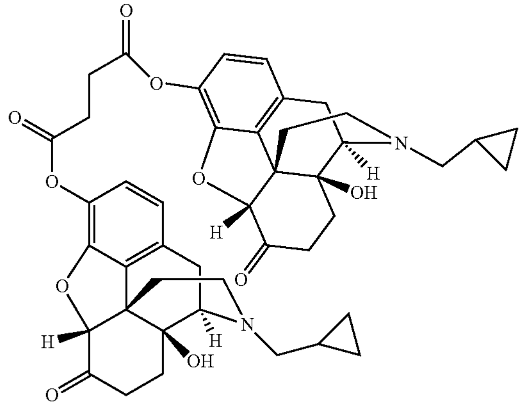 [SMILES: O=C(CCC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) succinate |

TABLE 1-continued

| Example | Structure | Name |
| --- | --- | --- |
| 28 | 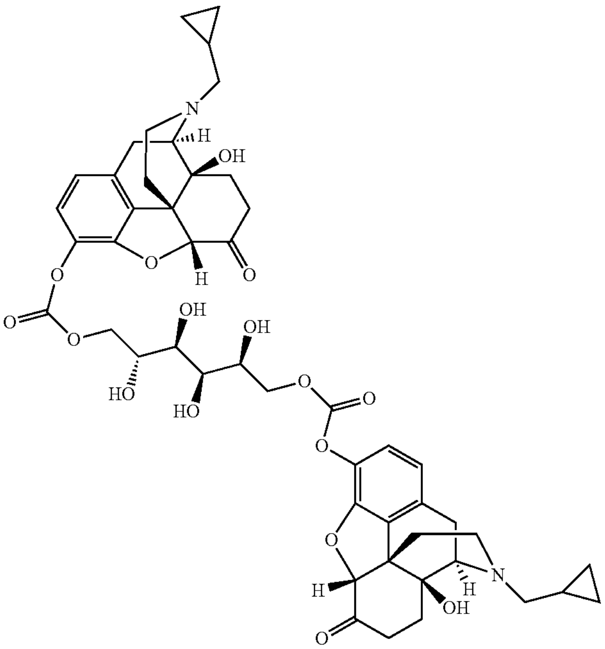 [SMILES: O=C(OC[C@@H](O)[C@@H](O)[C@H](O)[C@@H](O)COC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) ((2R,3R,4R,5S)-2,3,4,5-tetrahydroxyhexane-1,6-diyl) bis(carbonate) |
| 29 | 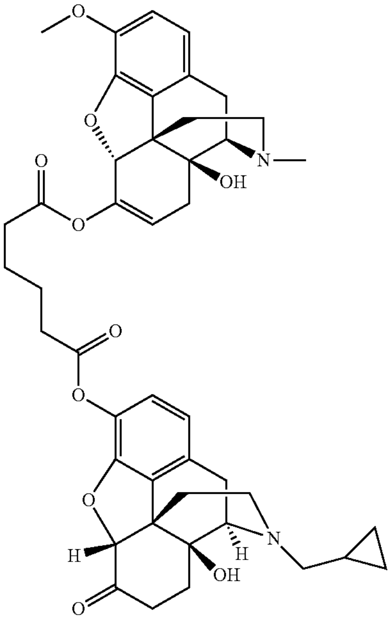 [SMILES: COc1ccc2c3c1O[C@H]1C(OC(=O)CCCCC(=O)Oc4ccc5c6c4O[C@H]4C(=O)CC[C@@]7(O)[C@@H](C5)N(CC5CC5)CC[C@]647)=CC[C@@]4(O)[C@@H](C2)N(C)CC[C@]314] | (4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl ((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) adipate |

TABLE 1-continued
| Example | Structure | Name |
|---|---|---|
| 30 | 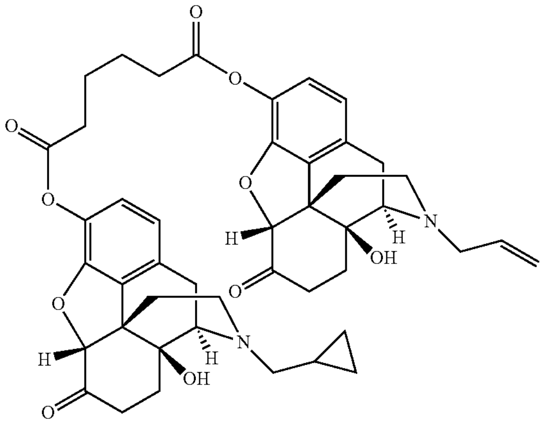 [SMILES: C=CCN1CC[C@]23c4c5ccc(OC(=O)CCCCC(=O)Oc6ccc7c8c6O[C@H]6C(=O)CC[C@@]9(O)[C@@H](C7)N(CC7CC7)CC[C@]869)c4O[C@H]2C(=O)CC[C@@]3(O)[C@H]1C5] | (4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl ((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) adipate |
| 31 | 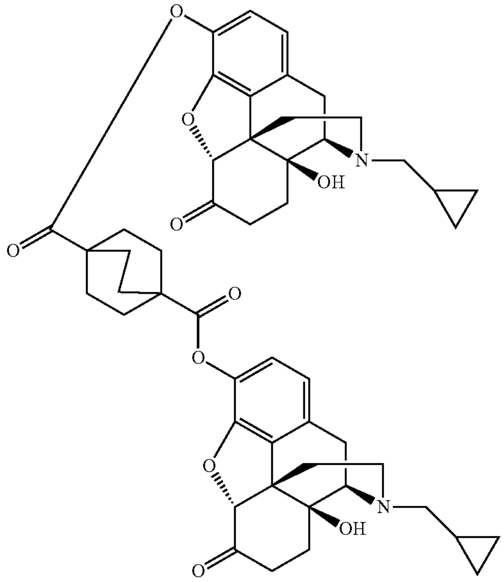 [SMILES: O=C1CC[C@@]2(O)[C@H]3Cc4ccc(OC(=O)C56CCC(C(=O)Oc7ccc8c9c7O[C@H]7C(=O)CC[C@@]%10(O)[C@@H](C8)N(CC8CC8)CC[C@]97%10)(CC5)CC6)c5c4[C@@]2(CCN3CC2CC2)[C@H]1O5] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) bicyclo[2.2.2]octane-1,4-dicarboxylate |

TABLE 1-continued

| Example | Structure | Name |
| --- | --- | --- |
| 32 | 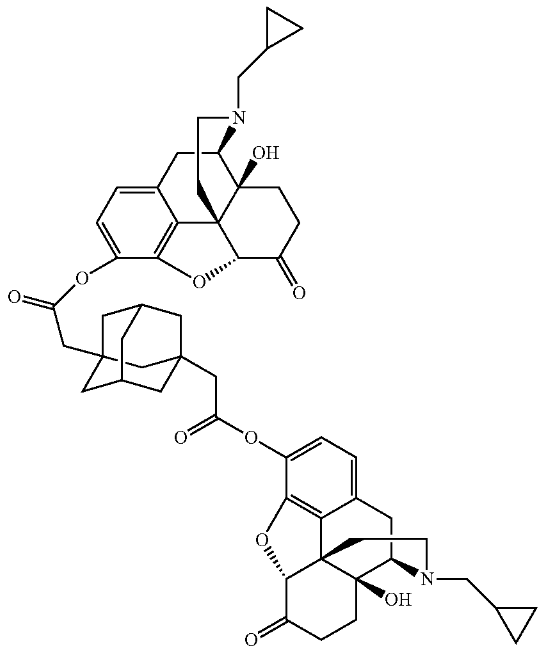 [SMILES: O=C(CC12CC3CC(C1)CC(CC(=O)Oc1ccc4c5c1O[C@H]1C(=O)CC[C@@]6(O)[C@@H](C4)N(CC4CC4)CC[C@]516)(C3)C2)Oc1ccc2c3c1O[C@H]1C(=O)CC[C@@]4(O)[C@@H](C2)N(CC2CC2)CC[C@]314] | bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) 2,2'-((1S,3S,5R,7R)-adamantane-1,3-diyl)diacetate |

In some embodiments, provided herein is a compound comprising a structure of Formula (IIE):

Formula (IIE)

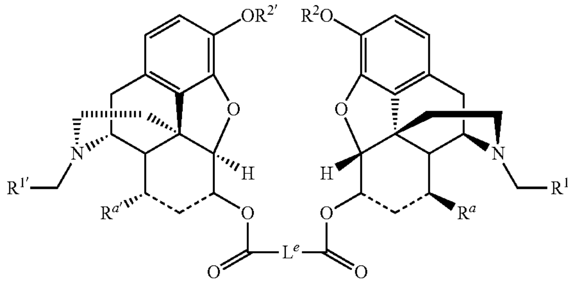

wherein:

$R^1$ and $R^{1'}$ are each independently H, unsaturated alkyl (e.g., alkenyl), or cycloalkyl;

$R^a$ and $R^{a'}$ are each independently H or —OH;

$R^2$ and $R^{2'}$ are each independently H or optionally substituted alkyl; and $L^e$ is selected from the group consisting of $—(CR_2)_y—$, $—O(CR_2)_yO—$, $—O(CR_2)_y—$, $—(CR_2)_yO—$, and $—O(CH_2CH_2O)_y—$, wherein y is 1-10 and each R is independently selected from the group consisting of H, hydroxyl, halogen, alkyl, or is taken together with another R to form an optionally substituted cycloalkyl, or a pharmaceutically salt or solvate thereof.

In some embodiments, the compound (e.g., opioid conjugate), or pharmaceutically acceptable salt thereof, provided in Table 2 comprises both a first (opioid) radical and a second (opioid) radical, which when combined in a dimer are processable (e.g., wherein the radicals may or may not be processable themselves, when in their free form). In some embodiments, the compound (e.g., opioid conjugate), or pharmaceutically acceptable salt thereof, provided in Table 2 comprises a first (opioid) radical and a second (opioid) radical that are the same. In some embodiments, both the first (opioid) radical and the second (opioid) radical of the opioid conjugate, or pharmaceutically acceptable salt thereof, provided in Table 2 is attached to the linker at a reactive oxo position (e.g., enolizable or 1,4 nucleophilic addition) of each the first (opioid) radical and the second (opioid) radical. In some embodiments, the compound (e.g., opioid conjugate), or pharmaceutically acceptable salt thereof, provided in Table 2 is has an extended release profile (e.g., configured to release an opioid agonist for an extended period of time (e.g., 1 day or more, 1 week or more, or 1 month or more) to an individual in need thereof (e.g., an individual with chronic pain or in need of long-term pain relief)).

TABLE 2
| Example | Structure | Name |
|---|---|---|
| 33 | 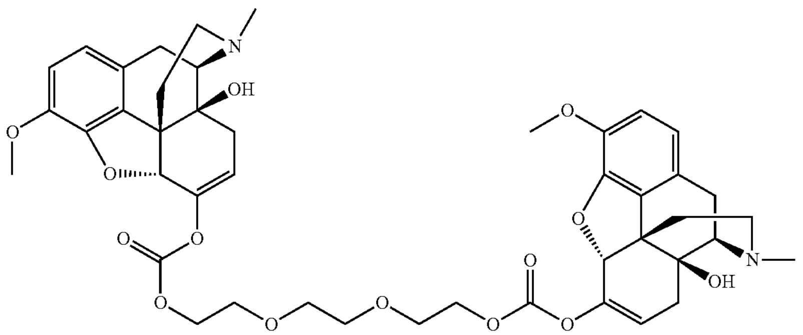 [SMILES: COc1ccc2c3c1O[C@H]1C(OC(=O)OCCOCCOCCOC(=O)OC4=CC[C@@]5(O)[C@H]6Cc7ccc(OC)c8c7[C@@]5(CCN6C)[C@H]4O8)=CC[C@@]4(O)[C@@H](C2)N(C)CC[C@]314] | (ethane-1,2-diylbis(oxy))bis(ethane-2,1-diyl) bis((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) bis(carbonate) |
| 34 | 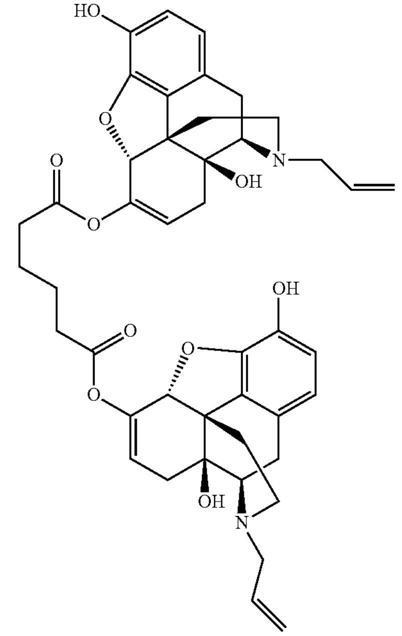 [SMILES: C=CCN1CC[C@]23c4c5ccc(O)c4O[C@H]2C(OC(=O)CCCCC(=O)OC2=CC[C@@]4(O)[C@H]6Cc7ccc(O)c8c7[C@@]4(CCN6CC=C)[C@H]2O8)=CC[C@@]3(O)[C@H]1C5] | bis((4R,4aS,7aR,12bS)-3-allyl-4a,9-dihydroxy-2,3,4,4a,5,7a-hexahydro-1H-4,12-methanobenzofuro[3,2-e]isoquinolin-7-yl) adipate |
| 35 | 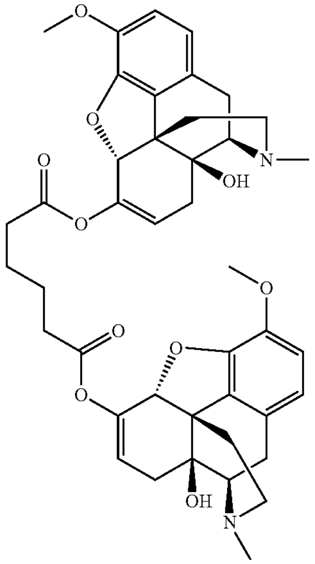 [SMILES: COc1ccc2c3c1O[C@H]1C(OC(=O)CCCCC(=O)OC4=CC[C@@]5(O)[C@H]6Cc7ccc(OC)c8c7[C@@]5(CCN6C)[C@H]4O8)=CC[C@@]4(O)[C@@H](C2)N(C)CC[C@]314] | bis((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) adipate |

TABLE 2-continued

| Example | Structure | Name |
| --- | --- | --- |
| 36 | 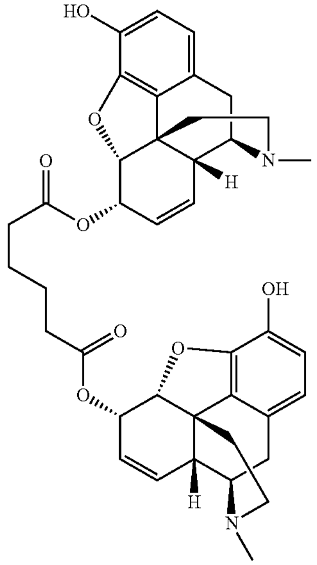 [SMILES: CN1CC[C@]23c4c5ccc(O)c4O[C@H]2[C@@H](OC(=O)CCCCC(=O)O[C@H]2C=C[C@H]4[C@H]6Cc7ccc(O)c8c7[C@@]4(CCN6C)[C@H]2O8)C=C[C@H]3[C@H]1C5] | bis((4R,4aR,7S,7aR,12bS)-9-hydroxy-3-methyl-2,3,4,4a,7,7a-hexahydro-1H-4,12-methanobenzofuro[3,2-e]isoquinolin-7-yl) adipate |
| 37 | 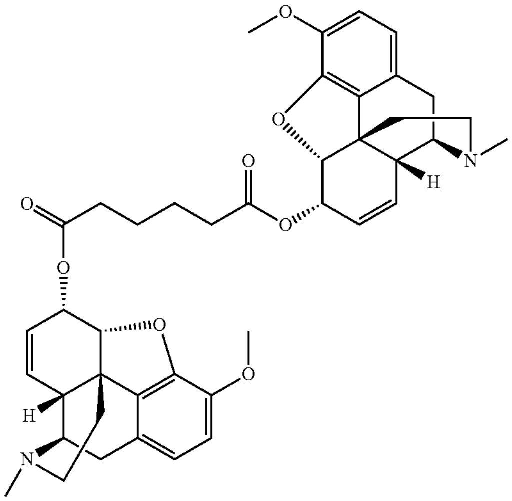 | bis((4R,4aR,7S,7aR,12bS)-9-methoxy-3-methyl-2,3,4,4a,7,7a-hexahydro-1H-4,12-methanobenzofuro[3,2-e]isoquinolin-7-yl) adipate |

In some embodiments, provided herein is a compound comprising a structure of Formula (IIF):

Formula (IIF)

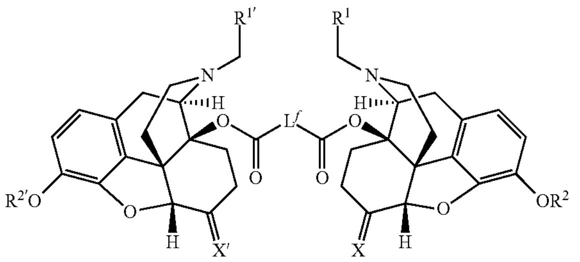

wherein:

$R^1$ and $R^{1'}$ are each independently H, unsaturated alkyl (e.g., alkenyl), or cycloalkyl;

$R^a$ and $R^{a'}$ are each independently H or —OH;

$R^2$ and $R^{2'}$ are each independently H or optionally substituted alkyl;

$L^f$ is selected from the group consisting of $—(CR_2)_y—$, $—O(CR_2)_yO—$, $—O(CR_2)_y—$, $—(CR_2)_yO—$, and $—O(CH_2CH_2O)_y—$, wherein y is 1-10 and each R is independently selected from the group consisting of H, hydroxyl, halogen, alkyl, or is taken together with another R to form an optionally substituted cycloalkyl; and X and X' are each independently O or $CH_2$, or a pharmaceutically salt or solvate thereof.

In some embodiments, the compound (e.g., opioid conjugate), or pharmaceutically acceptable salt thereof, provided in Table 3 comprises both a first (opioid) radical and a second (opioid) radical, which when combined in a dimer are processable (e.g., wherein the radicals may or may not be processable themselves, when in their free form). In some embodiments, the compound (e.g., opioid conjugate), or pharmaceutically acceptable salt thereof, provided in Table 3 comprises a first (opioid) radical and a second (opioid)

radical that are the same. In some embodiments, both the first (opioid) radical and the second (opioid) radical of the opioid conjugate, or pharmaceutically acceptable salt thereof, provided in Table 3 is attached to the linker at a tertiary alcohol of each the first (opioid) radical and the second (opioid) radical. In some embodiments, the compound (e.g., opioid conjugate), or pharmaceutically acceptable salt thereof, provided in Table 3 is less susceptible to hydrolysis (e.g., has a longer half-life) than a compound of Table 1 or Table 2.

TABLE 3

| Example | Structure | Name |
|---|---|---|
| 38 | 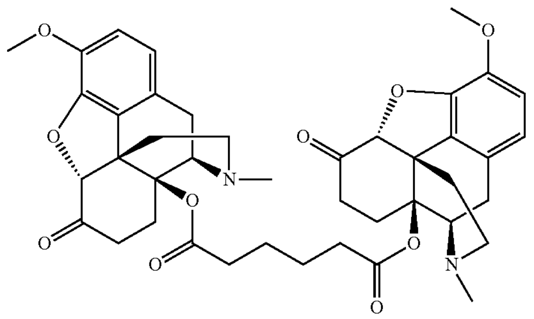 [SMILES: COc1ccc2c3c1O[C@H]1C(=O)CC[C@@]4(OC(=O)CCCCC(=O)O[C@@]56CCC(=O)[C@@H]7Oc8c(OC)ccc9c8[C@@]75CCN(C)[C@@H]6C9)[C@@H](C2)N(C)CC[C@]314] | bis((4R,4aS,7aR,12bS)-9-methoxy-3-methyl-7-oxo-1,2,3,4,5,6,7,7a-octahydro-4aH-4,12-methanobenzofuro[3,2-e]isoquinolin-4a-yl) adipate |
| 39 | 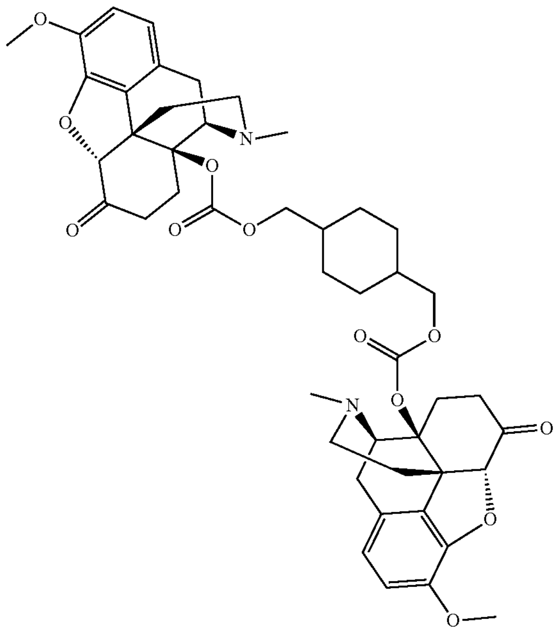 [SMILES: COc1ccc2c3c1O[C@H]1C(=O)CC[C@@]4(OC(=O)OCC5CCC(COC(=O)O[C@@]67CCC(=O)[C@@H]8Oc9c(OC)ccc%10c9[C@@]86CCN(C)[C@@H]7C%10)CC5)[C@@H](C2)N(C)CC[C@]314] | cyclohexane-1,4-diylbis(methylene) bis((4R,4aS,7aR,12bS)-9-methoxy-3-methyl-7-oxo-1,2,3,4,5,6,7,7a-octahydro-4aH-4,12-methanobenzofuro[3,2-e]isoquinolin-4a-yl) bis(carbonate) |
| 40 | 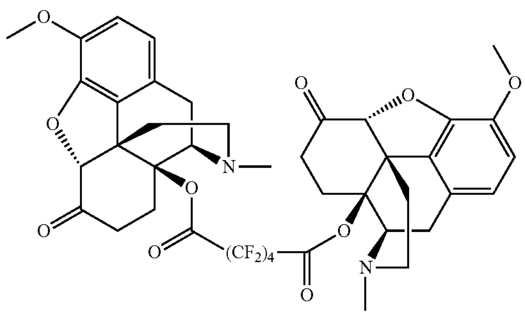 | bis(4R,4aS,7aR,12bS)-9-methoxy-3-methyl-7-oxo-1,2,3,4,5,6,7,7a-octahydro-4aH-4,12-methanobenzofuro[3,2-e]isoquinolin-4a-yl (1,2,2,3,3,4,4-heptafluoro-5-(((4R,4aS,7aR,12bS)-9-methoxy-3-methyl-7-oxo-1,2,3,4,5,6,7,7a-octahydro-4aH-4,12-methanobenzofuro[3,2-e] isoquinolin-4a-yl)oxy)-<br>5-oxo-1l3-pentyl)-l2-<br>fluoranecarboxylate |

TABLE 3-continued

| Example | Structure | Name |
|---|---|---|
| 41 | 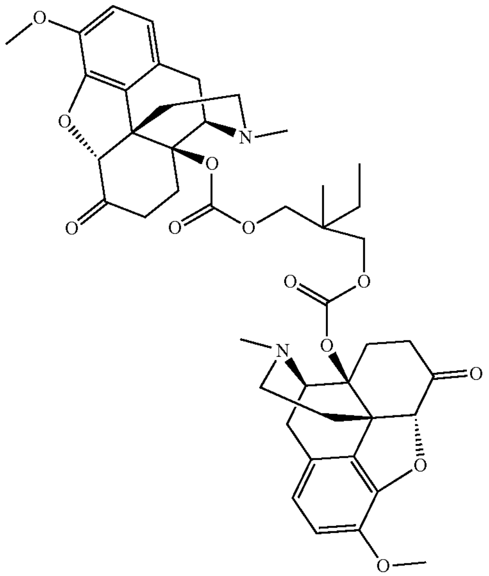 [SMILES: CCC(C)(COC(=O)O[C@@]12CCC(=O)[C@@H]3Oc4c(OC)ccc5c4[C@@]31CCN(C)[C@@H]2C5)COC(=O)O[C@@]12CCC(=O)[C@@H]3Oc4c(OC)ccc5c4[C@@]31CCN(C)[C@@H]2C5] | 2-ethyl-2-methylpropane-1,3-diyl bis((4aR,4aS,7aR,12bS)-9-methoxy-3-methyl-7-oxo-1,2,3,4,5,6,7,7a-octahydro-4aH-4,12-methanobenzofuro[3,2-e]isoquinolin-4a-yl) bis(carbonate) |
| 42 | 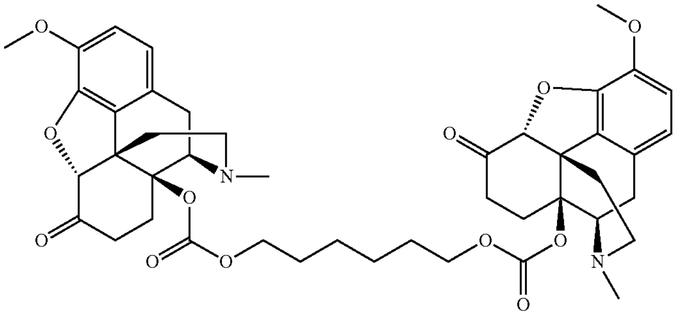 [SMILES: COc1ccc2c3c1O[C@H]1C(=O)CC[C@@]4(OC(=O)OCCCCCCOC(=O)O[C@@]56CCC(=O)[C@@H]7Oc8c(OC)ccc9c8[C@@]75CCN(C)[C@@H]6C9)[C@@H](C2)N(C)CC[C@]314] | hexane-1,6-diyl bis((4R,4aS,7aR,12bS)-9-methoxy-3-methyl-7-oxo-1,2,3,4,5,6,7,7a-octahydro-4aH-4,12-methanobenzofuro[3,2-e]isoquinolin-4a-yl) bis(carbonate) |

In some embodiments, the linker is alkyl, heteroalkyl, or alkoxy, wherein the alkyl, heteroalkyl, or alkoxy is optionally substituted. In some embodiments, the alkyl, heteroalkyl, or alkoxy are each independently substituted with one or more groups, each group being independently selected from the group consisting of oxo, —O— (e.g., hydroxyl or alkoxy), —S— (e.g., thiol or thioalkoxy), silicone, amino, alkyl, heteroalkyl, cycloalkyl, heterocycloalkyl, aryl or heteroaryl, wherein the alkyl, heteroalkyl, cycloalkyl, heterocycloalkyl, aryl or heteroaryl are optionally substituted (e.g., with halogen or hydroxyl). In some embodiments, the alkyl, heteroalkyl, or alkoxy are each independently substituted with one or more groups, each group being independently selected from the group consisting of —O—, —S—, silicone, amino, alkyl, heteroalkyl, cycloalkyl, heterocycloalkyl, aryl or heteroaryl, wherein the alkyl, heteroalkyl, cycloalkyl, heterocycloalkyl, aryl or heteroaryl are optionally substituted.

In some embodiments, the linker comprises at least one oxo. In some embodiments, the linker comprises two oxo groups. In some embodiments, the linker comprises one or more ester, carbonate, anhydride, carbamate, ester, or any combination thereof. In some embodiments, the linker comprises at least one carbamate. In some embodiments, the linker comprises at least one carbonate. In some embodiments, the linker comprises at least one ester. In some embodiments, the linker comprises two or more esters.

In some embodiments, the linker comprises one or more linker groups, each linker group being independently selected from the group consisting of —O—, —S—, optionally substituted alkylene (e.g., alkenyl, alkynyl, branched (e.g., polypropylene), haloalkyl), optionally substituted heteroalkylene (e.g, polyTHF), and optionally substituted cycloalkylene. In some embodiments, the linker comprises one or more linker groups, each linker group being independently selected from the group consisting of alkyl, alkoxy, and cycloalkyl, wherein the alkyl, alkoxy, or cycloalkyl are optionally substituted.

In some embodiments, the linker comprises a cycloalkylene. In some embodiments, the cycloalkylene is a monocycloalkylene or a bicycloalkylene (e.g., a spirocycloalkylene, a fused bicycloalkylene, or a bridged bicycloalkylene). In some embodiments, the cycloalkylene is an optionally substituted cyclohexylene. In some embodiments, the cycloalkylene is an optionally substituted bicyclo [2.2.2]octanene, bicyclo[2.2.1]heptanene, or tricyclo [3.3.1.13,7]decane.

In some embodiments, the linker is not aromatic. In some embodiments, the one or more groups (e.g., attached to the linker) is not an aromatic group. In some embodiments, provided herein is a conjugate comprising an aromatic linker or a linker comprising an aromatic group. In some embodiments, the conjugate comprising an aromatic linker or a linker comprising an aromatic group is not processable (e.g., into an article or implant provided herein).

In some embodiments, the linker comprises one or more linker groups selected from —O—, —S—, unsubstituted alkylene, $(CH_2CH_2)_n$, $(CHCH)_n$, $O(CH_2CH_2O)_n$, $(CH_2CH_2O)_n$, and $(CH(CH_3)C({=}O)O)_n$, wherein n is 1-20. In some embodiments, the linker is unsubstituted alkylene, $(CH_2CH_2)_n$, $(CHCH)_n$, $O(CH_2CH_2O)_n$, $(CH_2CH_2O)_n$, $(CH(CH_3)C({=}O)O)_n$, or $(CH_2CH_2)_nC{=}O(CH(CH_3)C({=}O)O)_n$, wherein n is 1-20.

In some embodiments, the linker is alkyl (alkylene) substituted with one or more groups selected from —OH, halo, oxo, alkyl, heteroalkyl, cycloalkyl, and heterocycloalkyl. In some embodiments, the linker is unsubstituted alkyl (alkylene). In some embodiments, the linker is heteroalkyl (heteroalkylene) substituted with one or more groups selected from halo or alkyl. In some embodiments, the linker is unsubstituted heteroalkyl (heteroalkylene). In some embodiments, the linker is selected from the group consisting of: $—(CR_2)_y—$, $—O(CR_2)_yO—$, $—O(CR_2)_y—$, $—(CR_2)_yO—$, and $—O(CR_2CR_2O)_y—$, wherein y is 1-10 and each R is independently selected from the group consisting of H, halogen, alkyl, or is taken together with another R to form an optionally substituted cycloalkyl. In some embodiments, each R is independently selected from H, alkyl, or is taken together with another R to form an optionally substituted cycloalkyl. In some embodiments, the one or more R is taken together with one or more other R to form a bridged cycloalkyl (e.g., a bridged cycloalkylene).

In some embodiments, longer linkers (e.g., at least 3-4 (e.g., carbon) atoms between an —O—) are preferred because, e.g., in some instances, shorter linkers result in increased melting point, increased Tg, increased crystallinity, decreased processability, or any combination thereof.

In some embodiments, $-(CH_2)_x$-cycloalkyl-$(CH_2)_y$—, wherein x and y are each independently 0-3. In some embodiments, x and y are each independently 0-2. In some embodiments, x and y are each independently 0 or 1. In some embodiments, x and y are each 0. In some embodiments, x and y are each 1.

In some embodiments, the optionally substituted cycloalkyl (e.g., cycloalkylene) is a monocycloalkyl (monocycloalkylene) or a bicycloalkyl (bicycloalkyl) (e.g., a spirocycloalkyl (spirocycloalkylene), a fused bicyloalkyl (bicycloalkylene), or a bridged bicycloalkyl (bicycloalkylene)). In some embodiments, the cycloalkyl (cycloalkylene) is an optionally substituted cyclohexyl (cyclohexylene). In some embodiments, the cycloalkyl (cycloalkylene) is an optionally substituted bicyclo[2.2.2]octanene, bicyclo[2.2.1]heptanene, or tricyclo[3.3.1.13,7]decane.

In some embodiments, the linker is hydrolyzed in a buffered solution. In some embodiments, the linker is hydrolyzed by an enzyme. In some embodiments, the enzyme is a hydrolase (e.g., a protease or an esterase).

Provided in some embodiments herein are articles that demonstrate unique properties for drug release applications. In some embodiments, the release of an opioid radical in its free form or a opioid conjugate provided herein from an article provided herein is beneficial (e.g., for drug release applications). In some embodiments, a compound provided herein have near zero-order release kinetics for an extended period of time (e.g., 1 day or more, 2 days or more, 3 days or more, 4 days or more, 5 days or more, 6 days or more, 7 days or more, 14 days or more, or 30 days or more) (e.g., in an individual in need thereof). In some embodiments, a compound provided herein releases at least one radical in its free form or a conjugate provided herein by surface erosion from the articles (e.g., pellets and coatings) provided herein. In some embodiments, the compounds provided herein are differentiated and unique from those disclosed by Singh (Pharmaceutically active dimers linked through phenolic hydroxyl groups; WO 2015/168014 A1). In certain embodiments, a conjugate provided herein comprises a linker comprising at least one group (e.g., not an ether, an amine, or the like) that is configured to release a radical in its free form or a conjugate provided herein. In some embodiments, an ether group confers stability to a conjugate provided herein, thereby providing properties that are not suitable for drug delivery applications provided herein. In some embodiments, provided herein is a compound that is conjugated through a labile linking group such as, for example, an ester and/or a carbonate.

In certain embodiments, provided herein is an opioid conjugate, or pharmaceutically acceptable salt thereof, having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3. Provided herein is an opioid conjugate, or pharmaceutically acceptable salt thereof, having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, that is processable (e.g., into an article or implant provided herein).

In some embodiments, the opioid conjugate, or pharmaceutically acceptable salt thereof, provided herein, having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, is a symmetrical opioid conjugate (e.g., the first radical and the second radical have the same structure, biological function, or a combination thereof). In some embodiments, the symmetrical opioid conjugate comprises a first opioid radical and a second opioid radical that each have the same biological function in their free form. In some embodiments, the symmetrical opioid conjugate comprises a first opioid radical and a second opioid radical that are each an opioid agonist in their free form. In some embodiments, the symmetrical opioid conjugate comprises a first opioid radical and a second opioid radical that are each an opioid antagonist in their free form. In some embodiments, the first opioid radical and the second opioid radical have the same structure (e.g., as a radical or in their free form).

In some embodiments, the opioid conjugate, or pharmaceutically acceptable salt thereof, provided herein, having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, is an asymmetrical opioid conjugate (e.g., the first radical and the second radical have a different structure, a different biological function, or a combination thereof). In some embodiments, the asymmetrical opioid conjugate comprises a first opioid radical and a second opioid radical that each have the same biological function in their free form. In some embodiments, the asymmetrical opioid conjugate comprises a first opioid radical and a second opioid radical that each have a different biological function in their free form. In some embodiments, the asymmetrical opioid conjugate comprises a first opioid radical and a second opioid radical that are each an opioid agonist in their free form. In some embodiments, the asymmetrical opioid conjugate comprises a first opioid radical and a second opioid radical that are each an opioid antagonist in their free form. In some embodiments, the asymmetrical opioid conjugate comprises a first opioid radical that is an opioid agonist in its free form and a second opioid radical that is an opioid antagonist in its free form. In some embodiments, the first opioid radical and the second opioid radical have the same structure (e.g., as a radical or in their free form). In some embodiments, the first opioid radical and the second opioid radical have a different structure (e.g., as a radical or in their free form).

In some embodiments, the opioid conjugate, or pharmaceutically acceptable salt thereof, having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, provided herein is a solid, such as at a physiological temperature (e.g., having a melting point ($T_m$) and/or glass transition temperature ($T_g$) of at least 37° C.). In some embodiments, the solid is a crystalline solid, a film, a glass, or an amorphous solid (e.g., at a temperature of at least 37° C.). In some embodiments, the opioid conjugate, or pharmaceutically acceptable salt thereof, having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, provided herein is not an oil.

In some embodiments, the opioid conjugate (e.g., or article thereof), or pharmaceutically acceptable salt thereof, having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, has a crystallinity of at most 15% (e.g., determined by PXRD, DSC, or polarized light microscopy). In some embodiments, the opioid conjugate (e.g., or article thereof), or pharmaceutically acceptable salt thereof, having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, is substantially crystalline (e.g., determined by PXRD, DSC, or polarized light microscopy). In some embodiments, opioid conjugate (e.g., or article thereof), or pharmaceutically acceptable salt thereof, having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, is amorphous (e.g., determined by PXRD, DSC, or polarized light microscopy).

In some embodiments, the opioid conjugate (e.g., or article thereof), or pharmaceutically acceptable salt thereof, having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, has a thermal melting point ($T_m$) that is greater than or equal to the glass transition temperature ($T_g$). In some embodiments, the opioid conjugate (e.g., or article thereof), or pharmaceutically acceptable salt thereof, provided herein (e.g., having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3) has a melting point of less than or equal to either one or both of the first and/or second radicals (e.g., in their free form) of the opioid conjugate.

In some embodiments, the opioid conjugate (e.g., in any morphology), or pharmaceutically acceptable salt thereof, (e.g., having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3) has a melting point of at least 37° C. In some embodiments, the opioid conjugate (e.g., in any morphology), or pharmaceutically acceptable salt thereof, provided herein (e.g., having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3) has a melting point of at least 100° C. In some embodiments, the opioid conjugate (e.g., in any morphology), or pharmaceutically acceptable salt thereof, provided herein (e.g., having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3) has a melting point of at least 160° C. In some embodiments, the opioid conjugate (e.g., in any morphology), or pharmaceutically acceptable salt thereof, provided herein (e.g., having a structure of any one of Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3) has a melting point of at most 220° C.

In some embodiments, an opioid conjugate provided herein forms an article provided herein (e.g., an implant, a pellet, or a coating). In some embodiments, the article has a melting point of at least 37° C. (e.g., at least 100° C., at least 160° C., or at least 200° C.). In some embodiments, the article has a melting point of at most 220° C. In some embodiments, an article with a melting point greater than 220° C. decomposes (e.g., and is not processable into an article (e.g., a pellet) provided herein) subsequent to heat processing or solvent processing methods provided herein. In some embodiments, the article provided herein has a melting point that is less than or equal to either one or both of the first and/or second radicals (e.g., in their free form) of the article.

In some embodiments, an article (e.g., which comprises an opioid conjugate comprising a linker that is aromatic (e.g., or has an aromatic group)) does not form an article provided herein. In some embodiments, the release profile of the article provided herein is modified by the linker (e.g., L, $L^a$, $L^b$, $L^c$, $L^d$, $L^e$, or $L^f$). For example, in certain embodiments, a linker that is less susceptible to hydrolysis (e.g., steric effects, electronic effects, etc.) provides an article that releases (e.g., from the article) an opioid conjugate or an opioid radical in its free form at a slower (e.g., extended-release) rate compared to an article that is more susceptible to hydrolysis (e.g., providing an article that releases (e.g., from the article) an opioid conjugate or an opioid radical in its free form at a faster (e.g., immediate-release) rate).

In some embodiments, the article has a melting point (e.g., a Tm or a Tg) and/or a release profile (e.g., in PBS) provided by, for example, Table 4.

TABLE 4

Figure 1B:
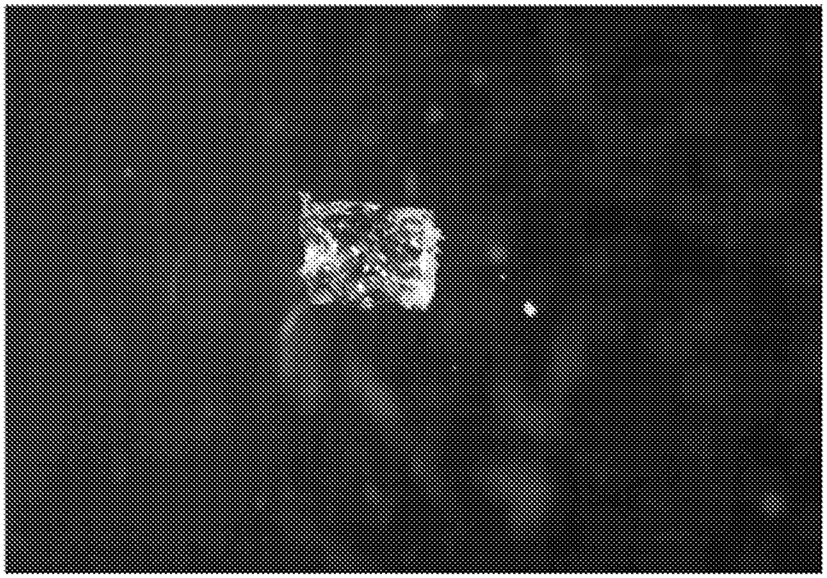
Figure 3:
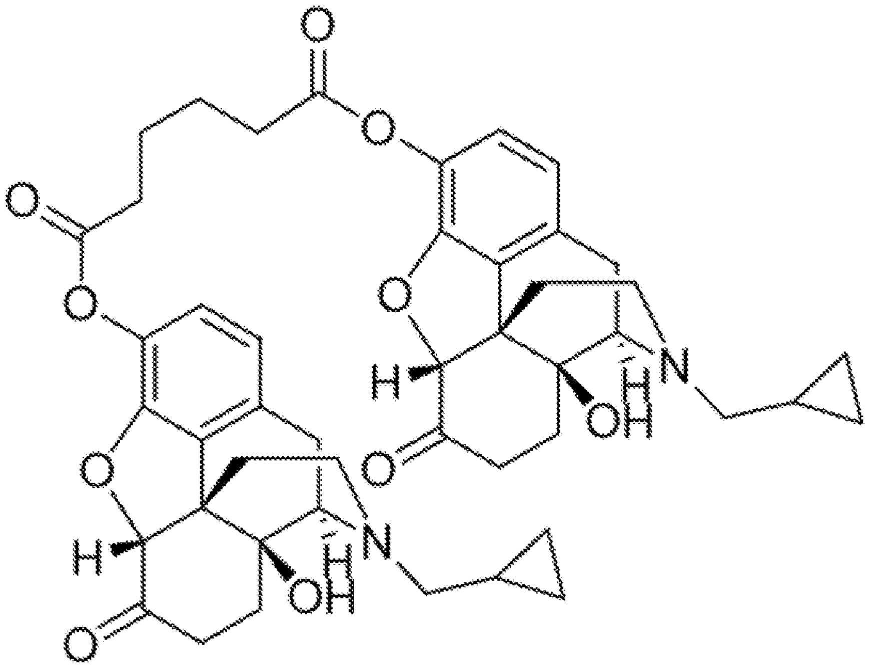
FIG. 3 shows the chemical structure (an opioid composition (naltrexone-adipate-naltrexone, Compound 2) provided herein.

| Compound | Melting point | Pellet formation? | Release in phosphate buffered saline (PBS) |
|---|---|---|---|
| 1 (FIG. 1A) | 120° C. | ✓ (FIG. 1B) | Near zero order for > 7 days (FIG. 1C & FIG. 1D) |
| 2 (FIG. 3A) | 187° C. | X (FIG. 3B) | N/A |

TABLE 4-continued

Figure 4A:
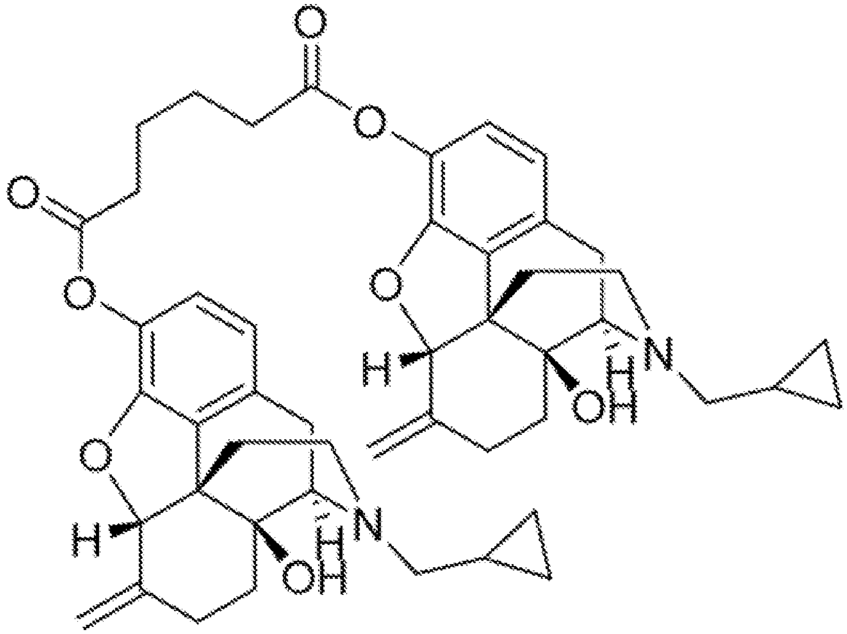
FIG. 4 shows the chemical structure (FIG. 4A) and the heat processed pellet (FIG. 4B) of an opioid composition (Nalmefene-Adip-Nalmefene, Compound 3) exemplified herein.
FIG. 4C shows the drug release profile for Compound 3 (pellet) in phosphate-buffered saline (PBS) over 14 days.
FIG. 4D represents the 14-day progression of the surface erosion drug release profile for the pellet of Compound 3 in PBS.
Figure 4B:
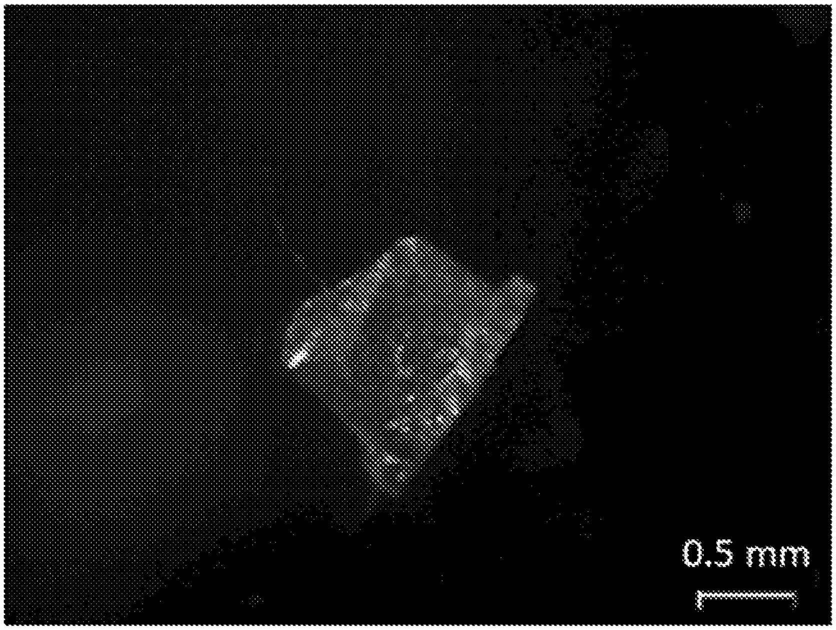
Figure 4C:
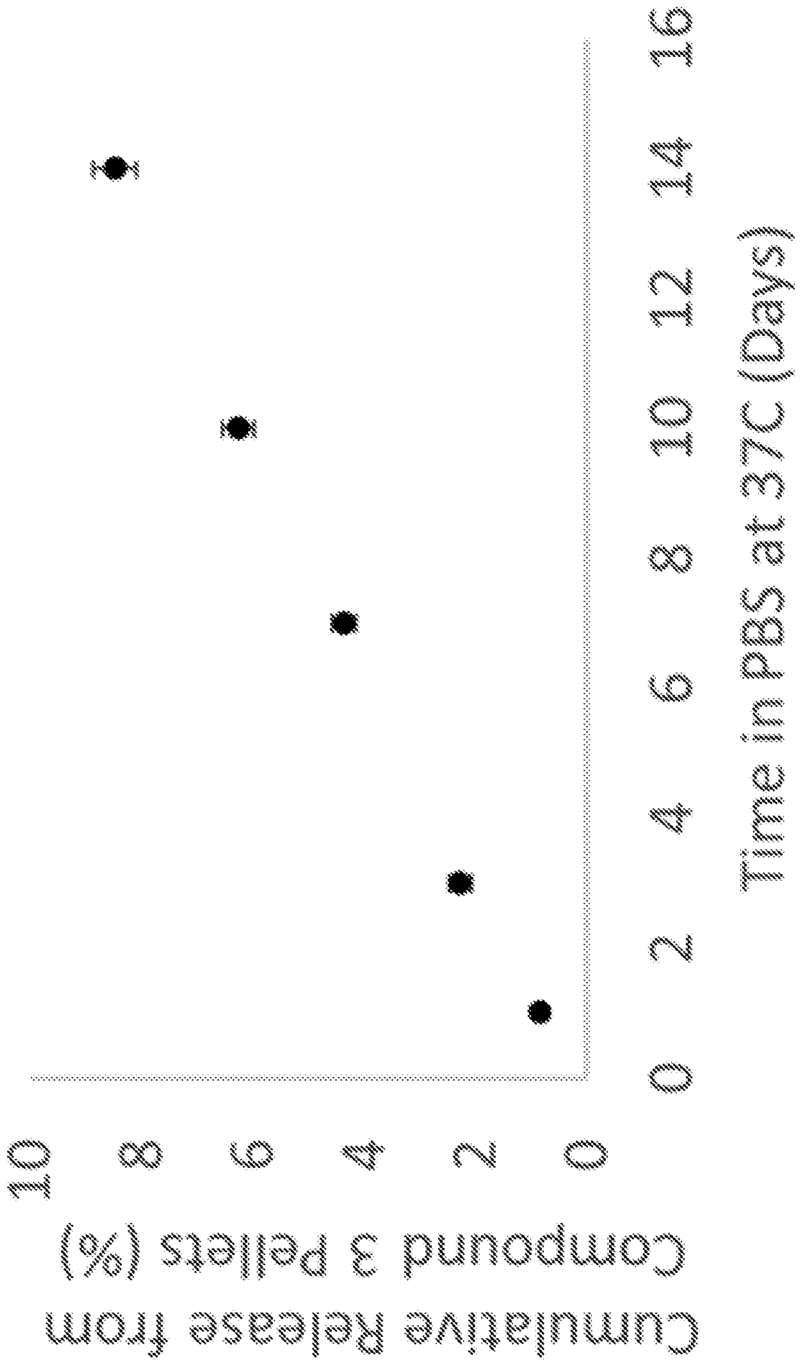
Figure 4D:
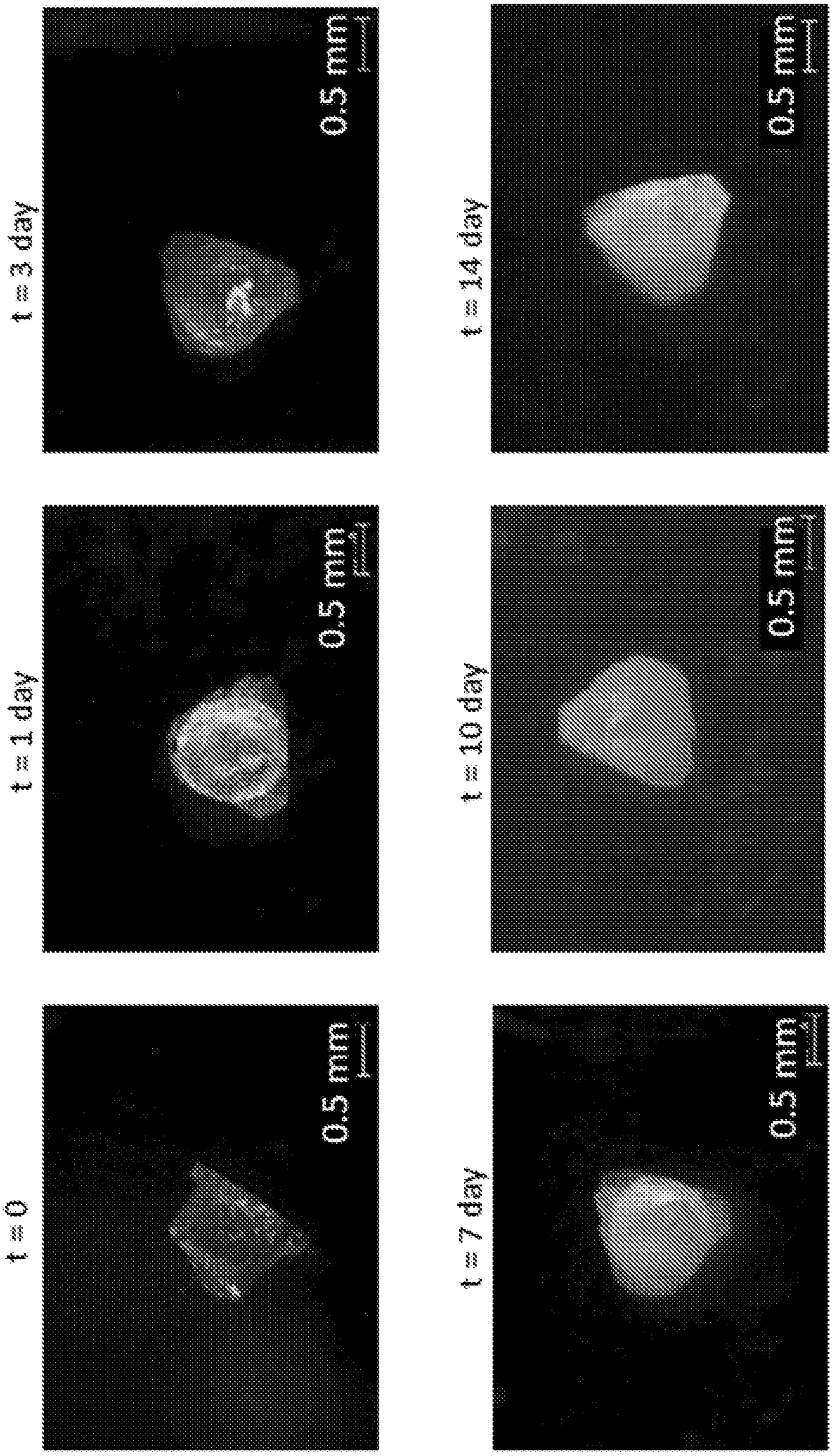
Figure 5A:
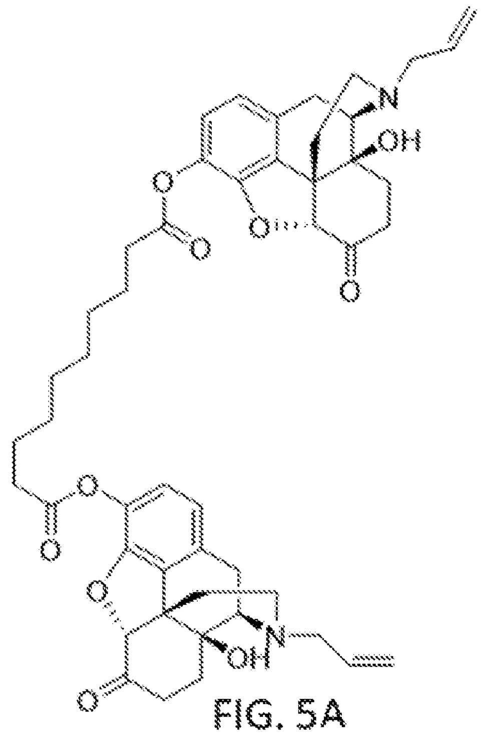
FIG. 5 shows the chemical structure (FIG. 5A) and the heat processed pellet (FIG. 5B) of an opioid composition (Naloxone-Seb-Naloxone, Compound 4) exemplified herein.
FIG. 5C shows the drug release profile for Compound 4 (pellet) in phosphate-buffered saline (PBS) over 14 days.
FIG. 5D represents the 14-day progression of the surface erosion drug release profile for the pellet of Compound 4 in PBS.
Figure 5B:
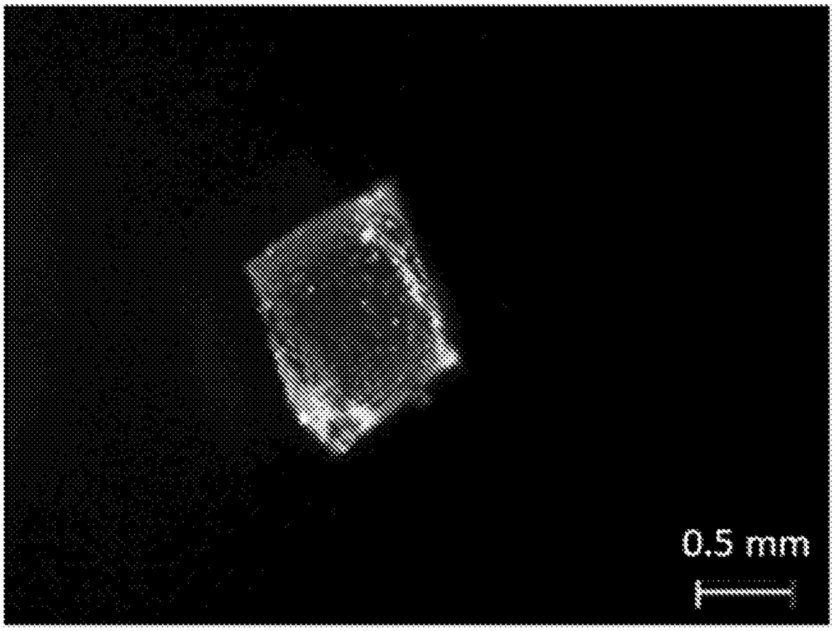
Figure 5C:
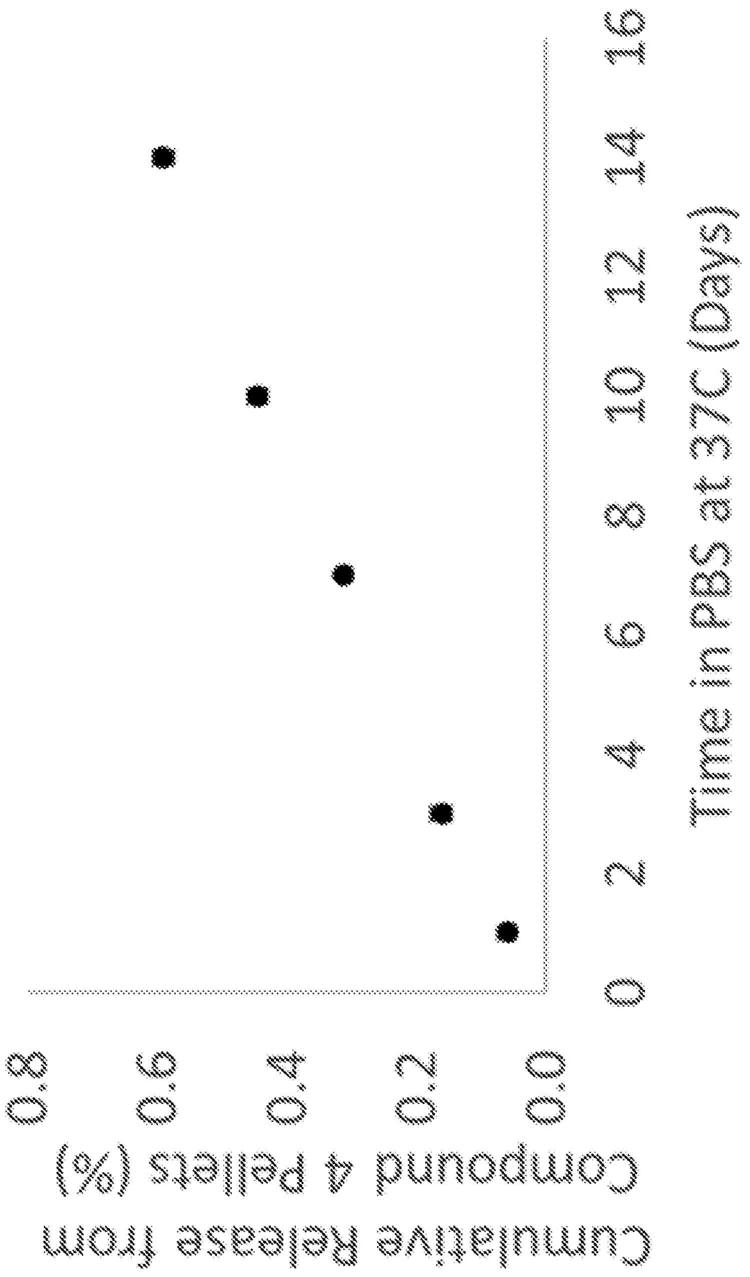
Figure 5D:
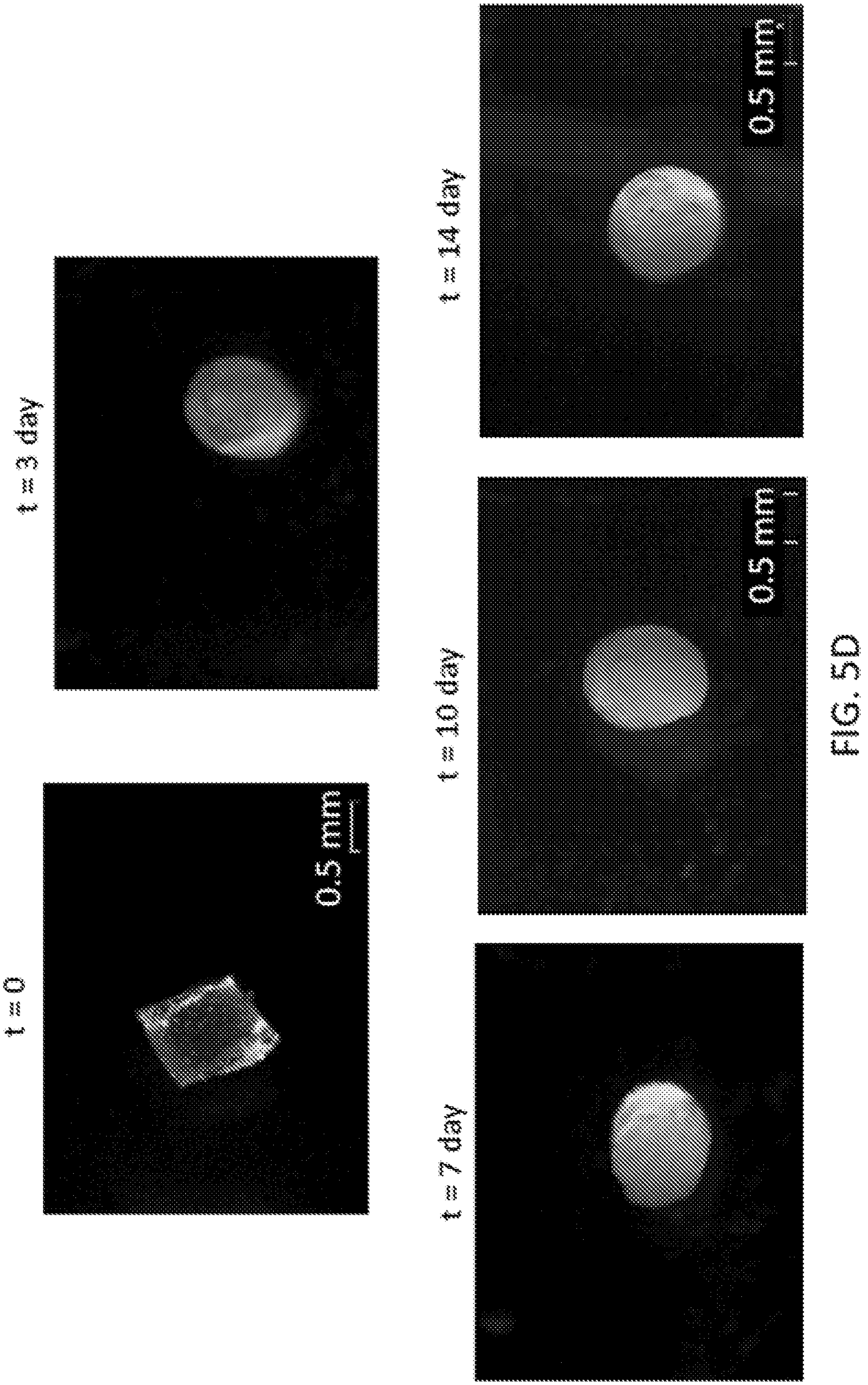
Figure 6A:
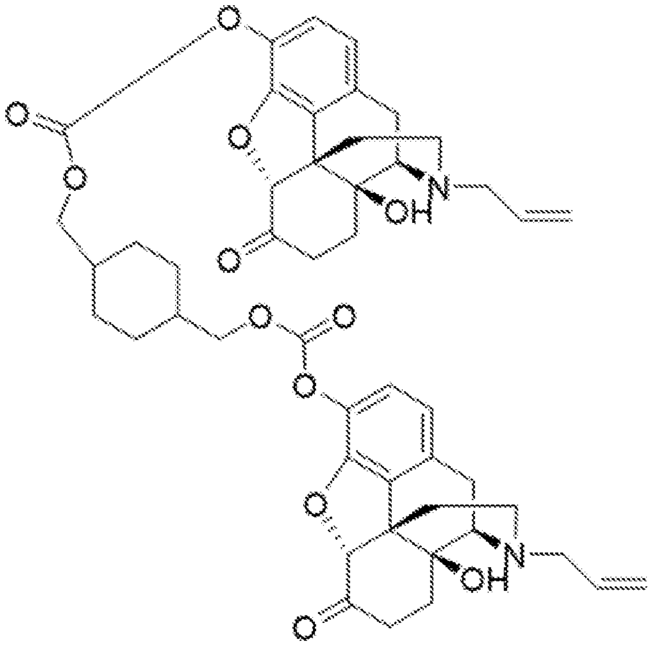
FIG. 6 shows the chemical structure (FIG. 6A) and the heat processed pellet (FIG. 6B) of an opioid composition (Naloxone-CDM-Naloxone, Compound 5) exemplified herein.
FIG. 6C shows the drug release profile for Compound 5 (pellet) in phosphate-buffered saline (PBS) over 14 days.
FIG. 6D represents the 14-day progression of the surface erosion drug release profile for the pellet of Compound 5 in PBS.
Figure 6B:
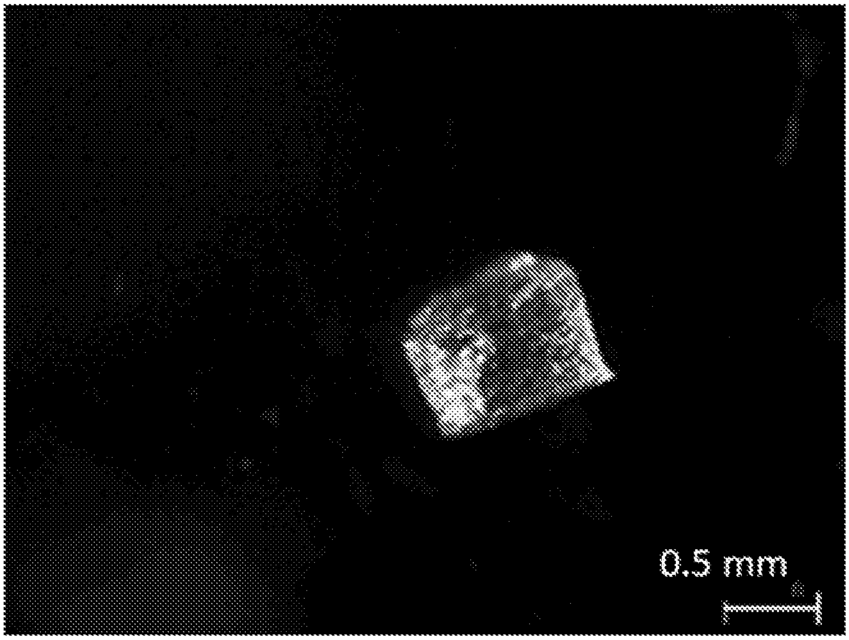
Figure 6C:
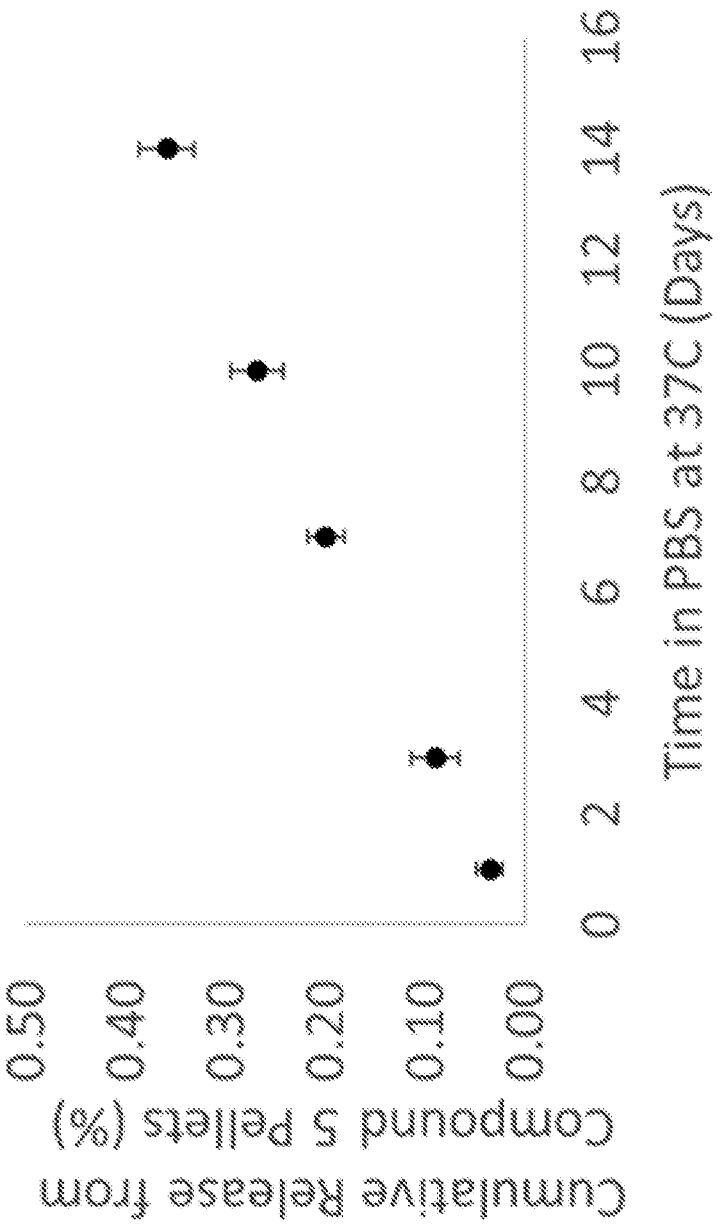
Figure 6D:
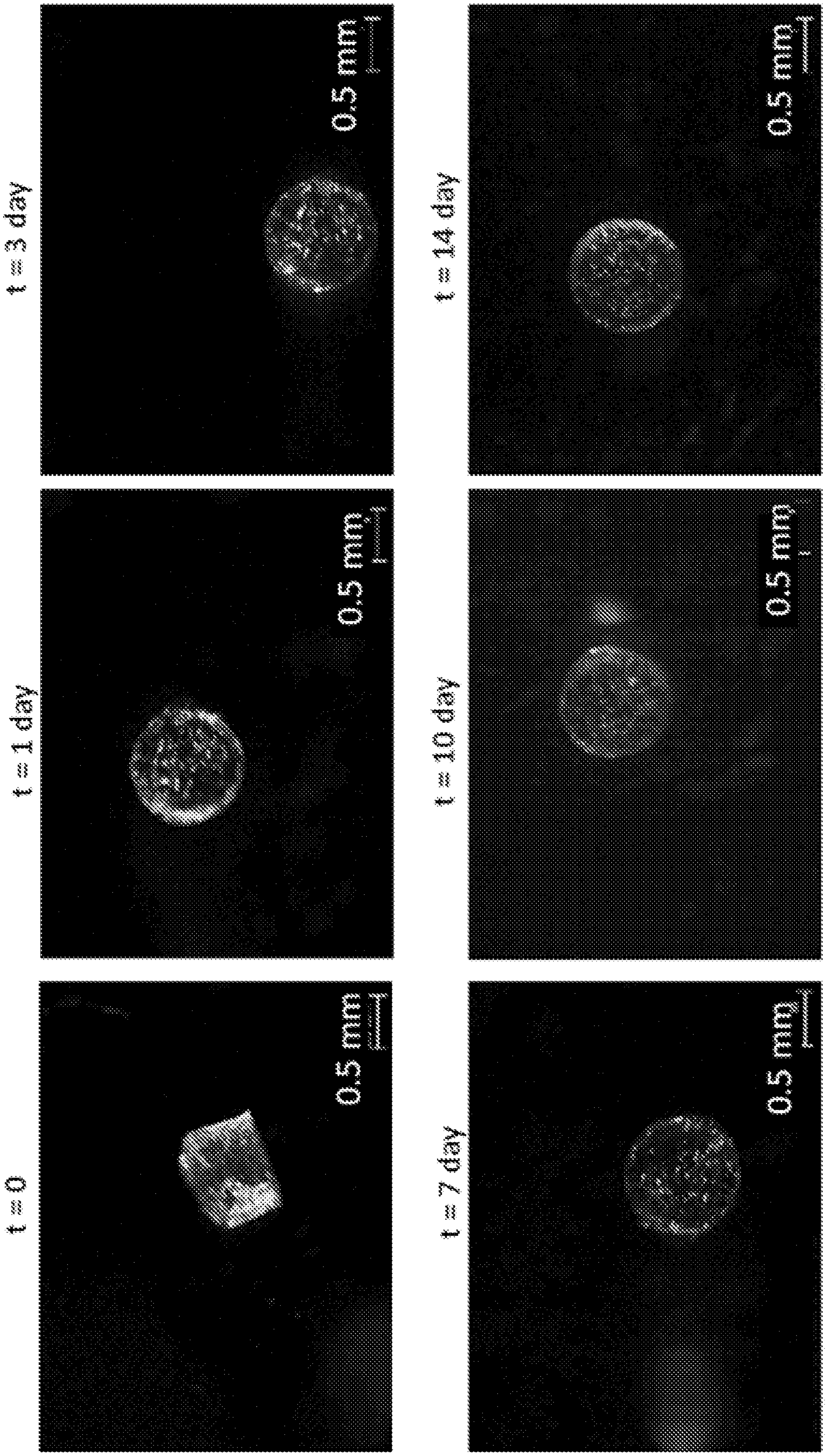
Figure 7A:
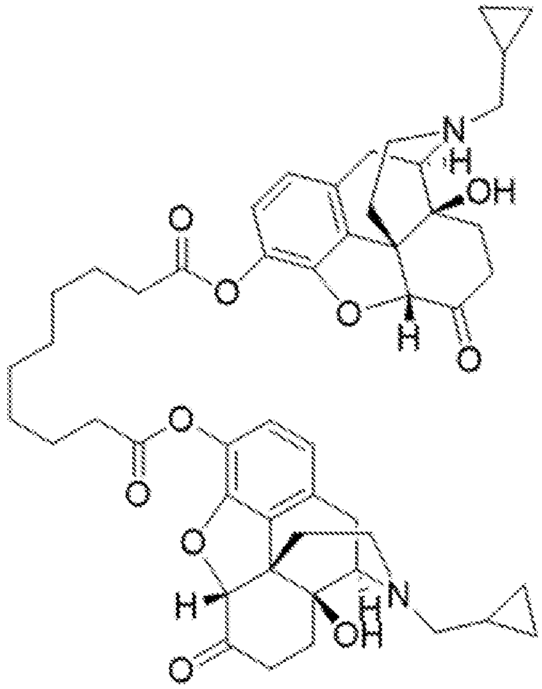
FIG. 7 shows the chemical structure (FIG. 7A) and the heat processed pellet (FIG. 7B) of an opioid composition (Naltrexone-Seb-Naltrexone, Compound 6) exemplified herein.
FIG. 7C shows the drug release profile for Compound 6 (pellet) in phosphate-buffered saline (PBS) over 14 days.
FIG. 7D represents the 14-day progression of the surface erosion drug release profile for the pellet of Compound 6 in PBS.
Figure 7B:
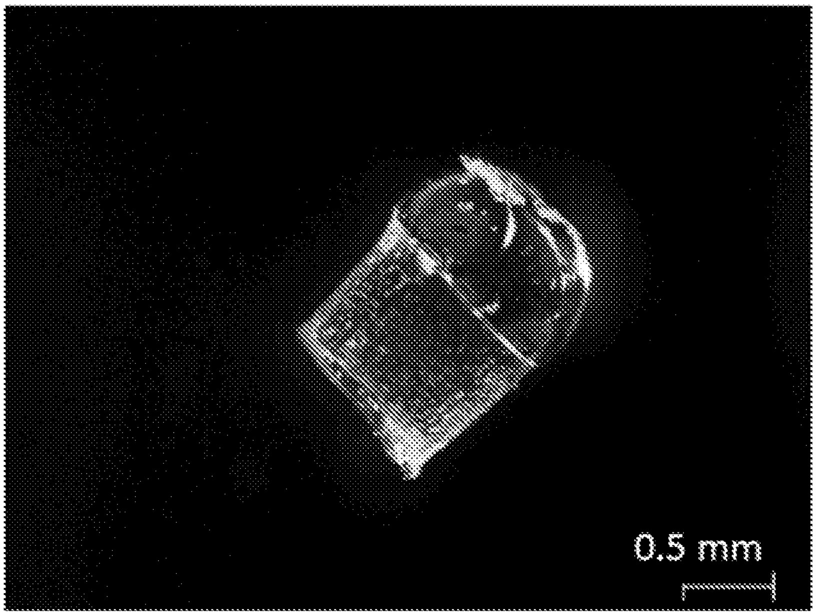
Figure 7C:
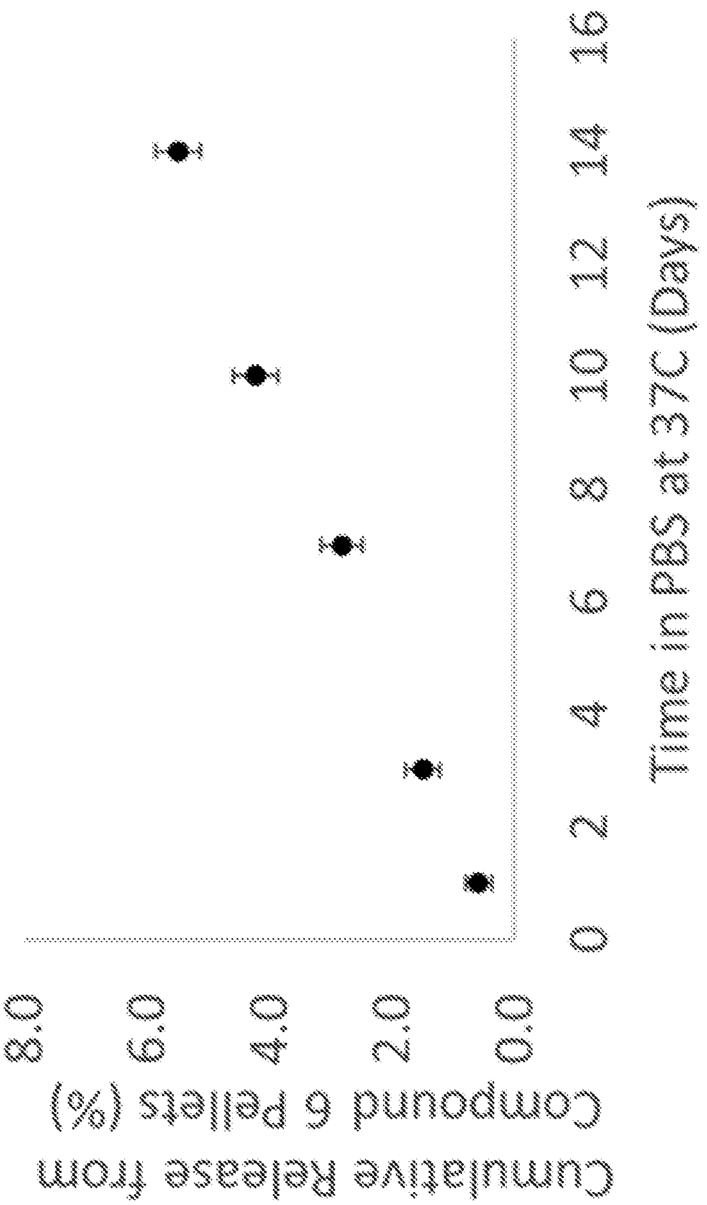
Figure 7D:
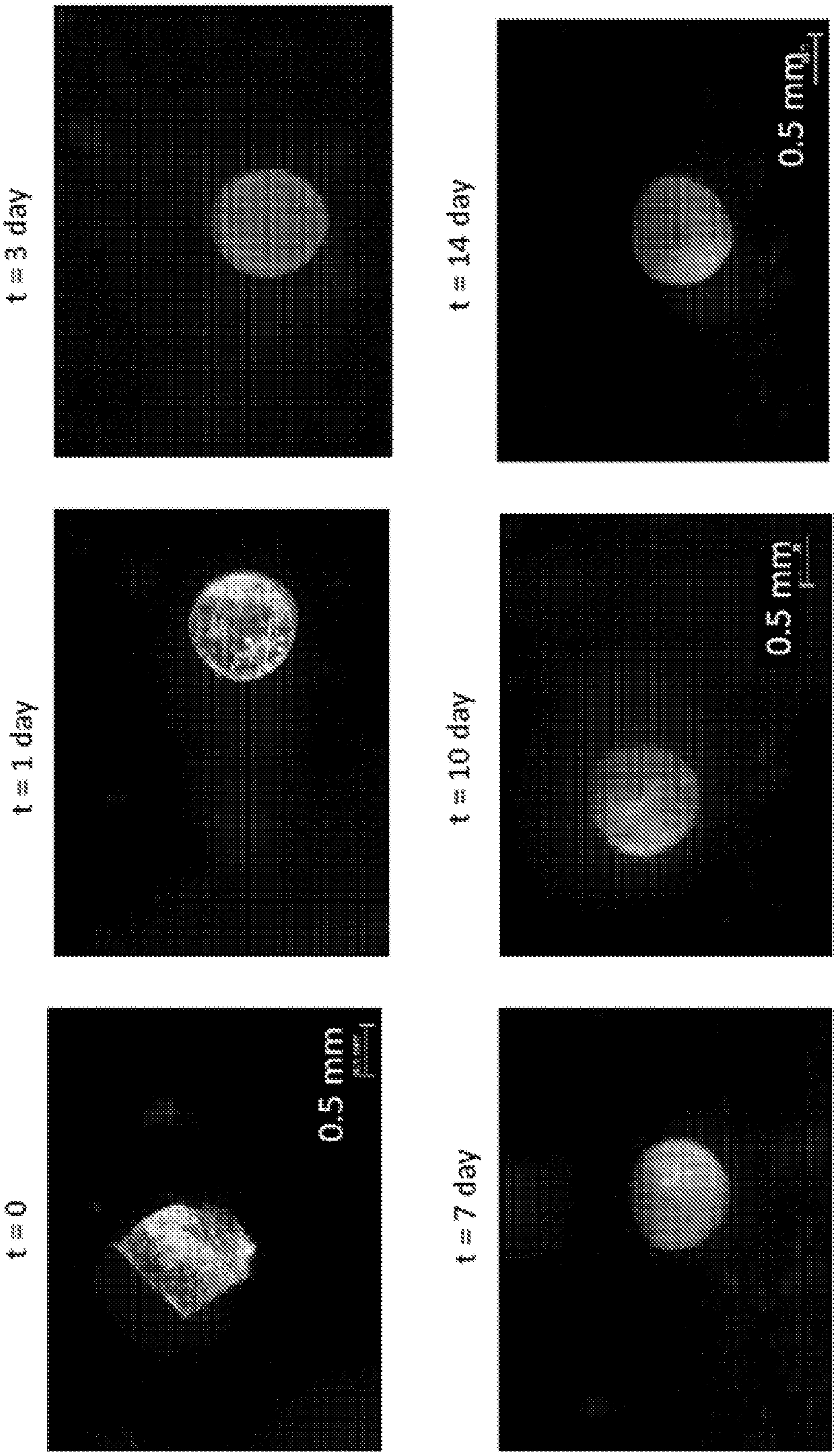
Figure 8A:
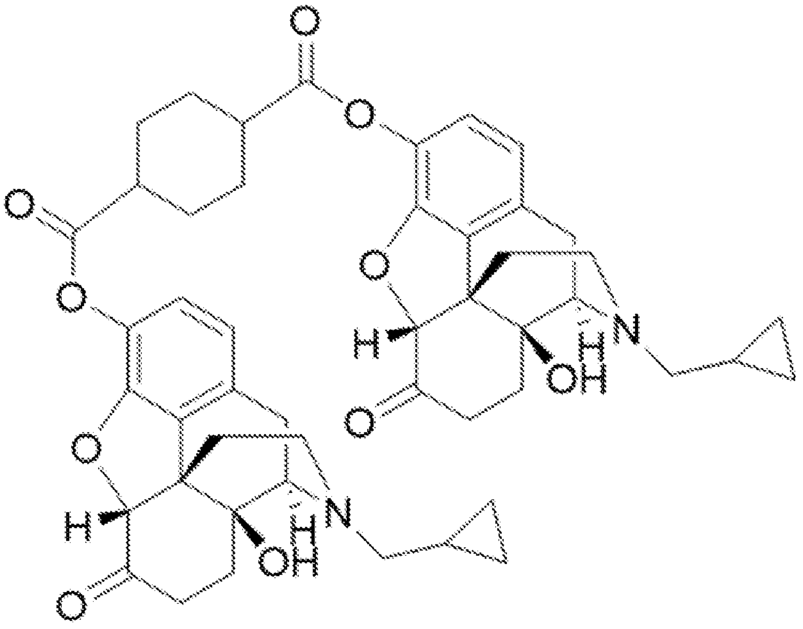
FIG. 8 shows the chemical structure (FIG. 8A) and the heat processed pellet (FIG. 8B) of an opioid composition (Naltrexone-1,4-cyclohexyl-Naltrexone, Compound 7) exemplified herein.
FIG. 8C shows the drug release profile for Compound 7 (pellet) in phosphate-buffered saline (PBS) over 14 days.
FIG. 8D represents the 14-day progression of the surface erosion drug release profile for the pellet of Compound 7 in PBS.
Figure 8B:
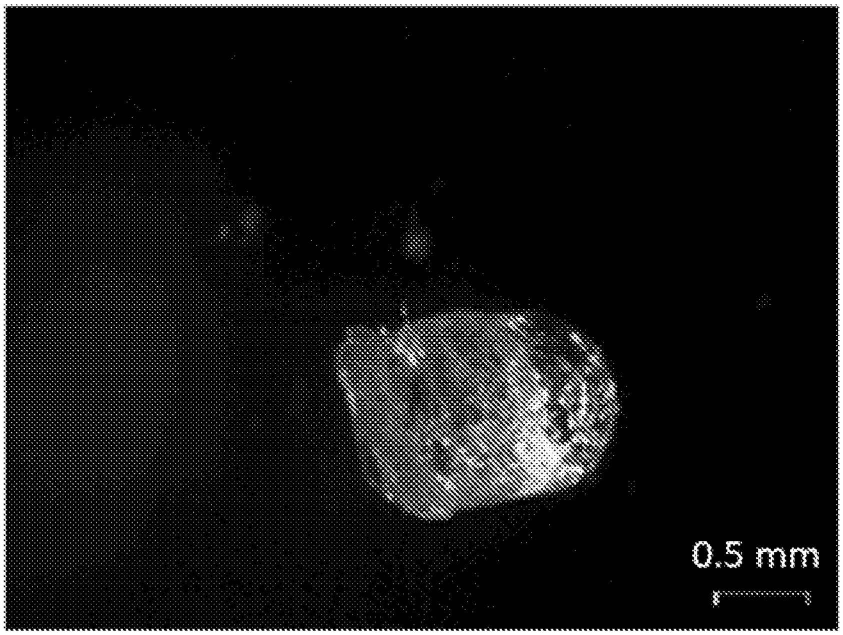
Figure 8C:
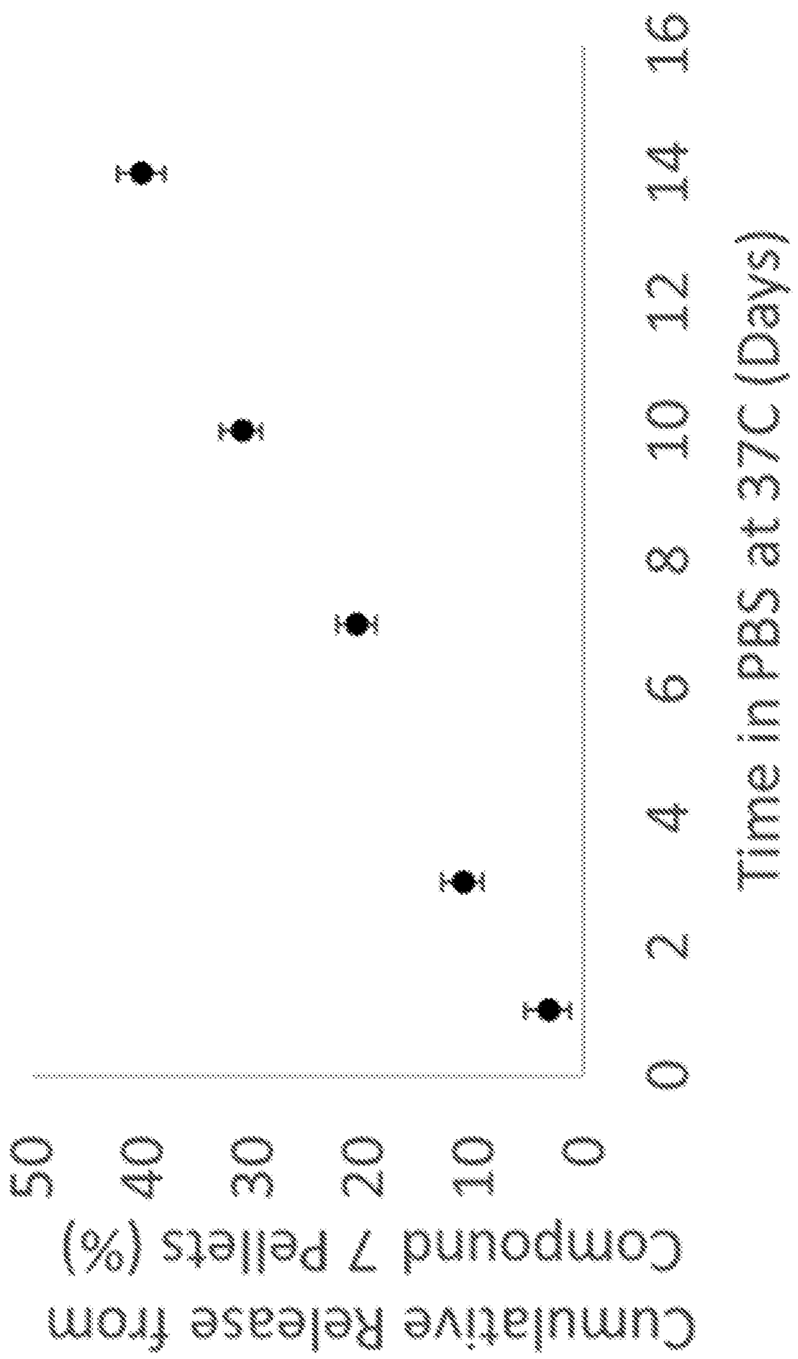
Figure 8D:
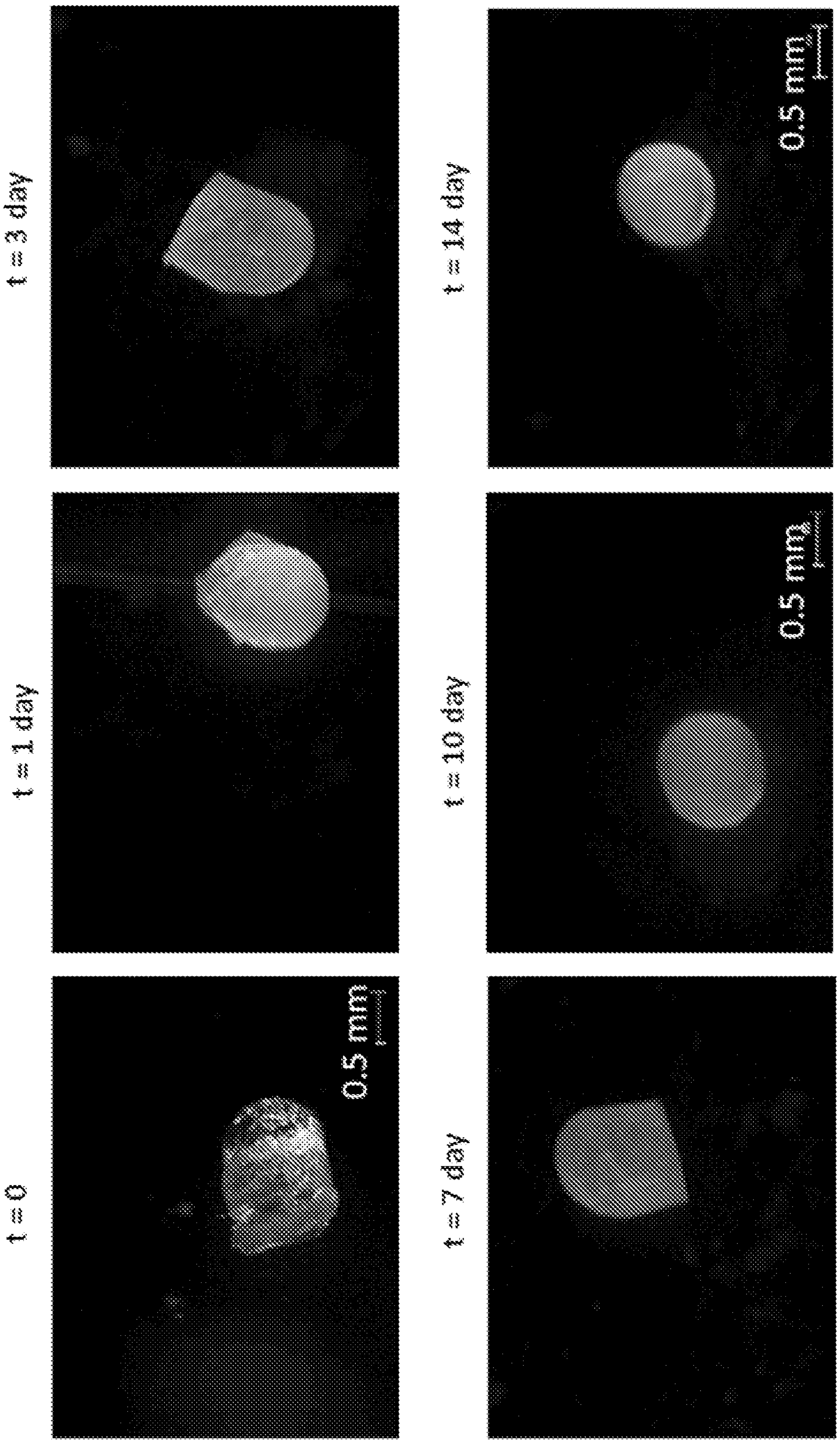
Figure 9:
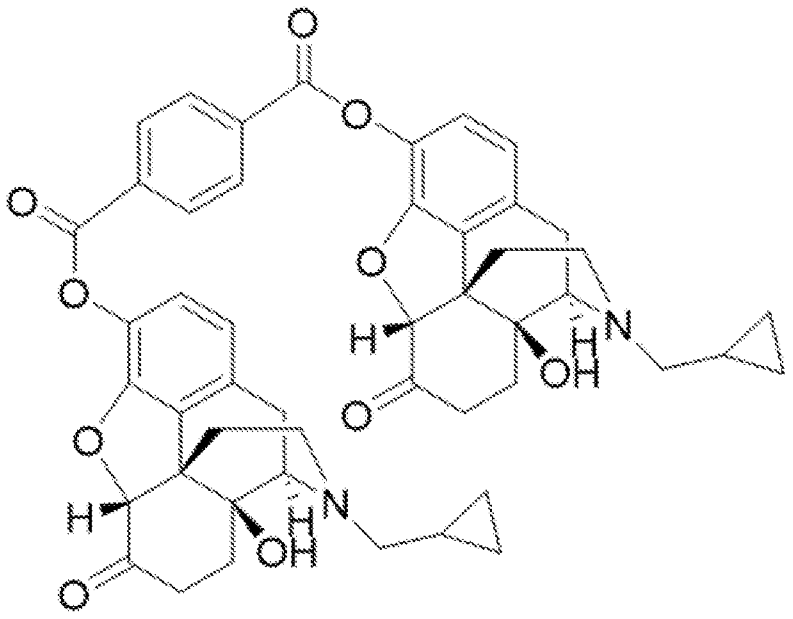
FIG. 9 shows the chemical structure of an opioid composition (Naltrexone-1,4-terephthalate-Naltrexone, Compound 8) that did not form a heat processed pellet exemplified herein.
Figure 10A:
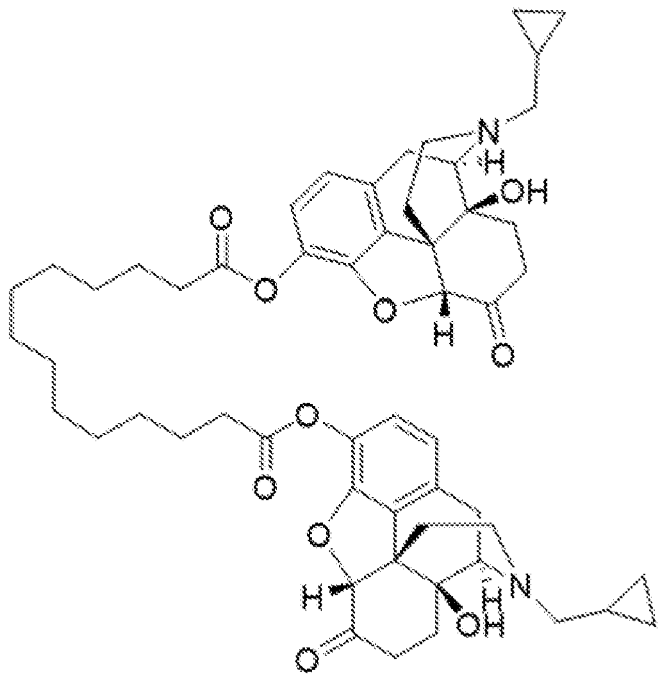
FIG. 10 shows the chemical structure (FIG. 10A) and the heat processed pellet (FIG. 10B) of an opioid composition (Naltrexone-dodecane-Naltrexone, Compound 9) exemplified herein.
FIG. 10C shows the drug release profile for Compound 9 (pellet) in phosphate-buffered saline (PBS) over 14 days.
FIG. 10D represents the 14-day progression of the surface erosion drug release profile for the pellet of Compound 9 in PBS.
Figure 10B:
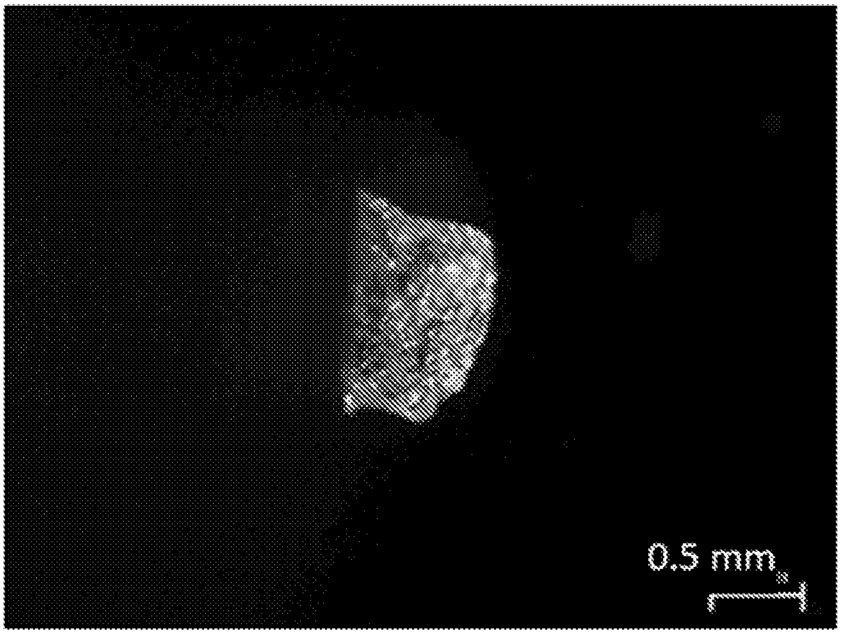
Figure 10C:
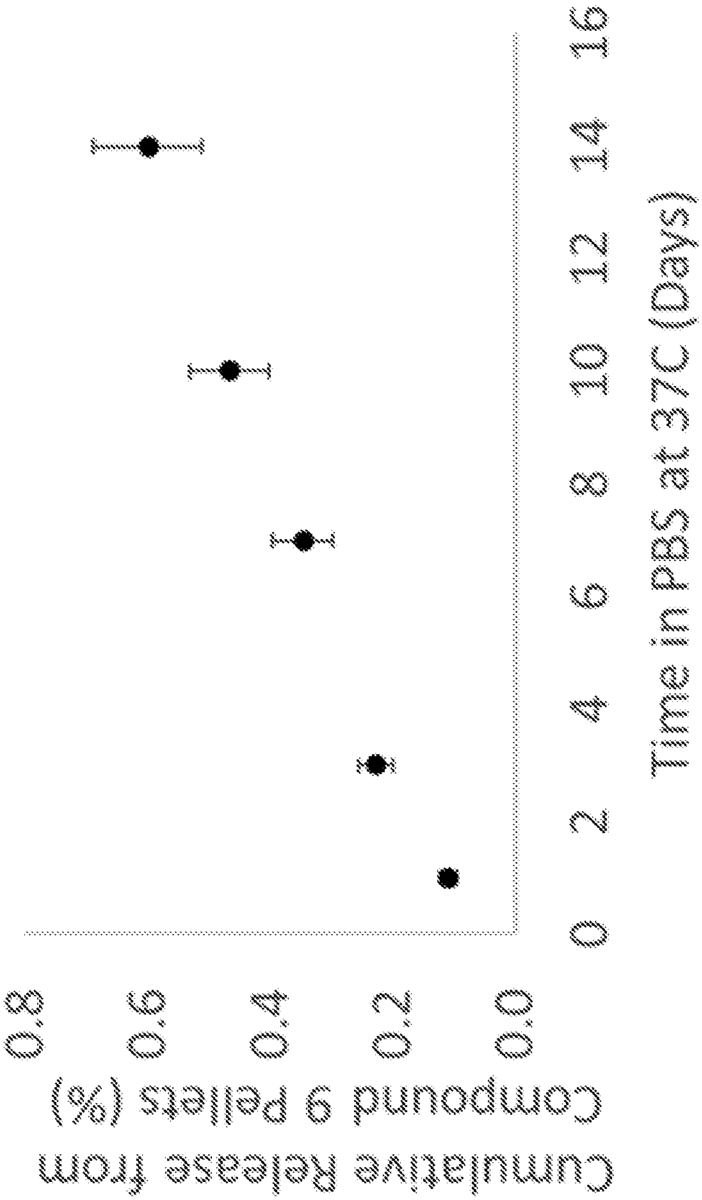
Figure 10D:
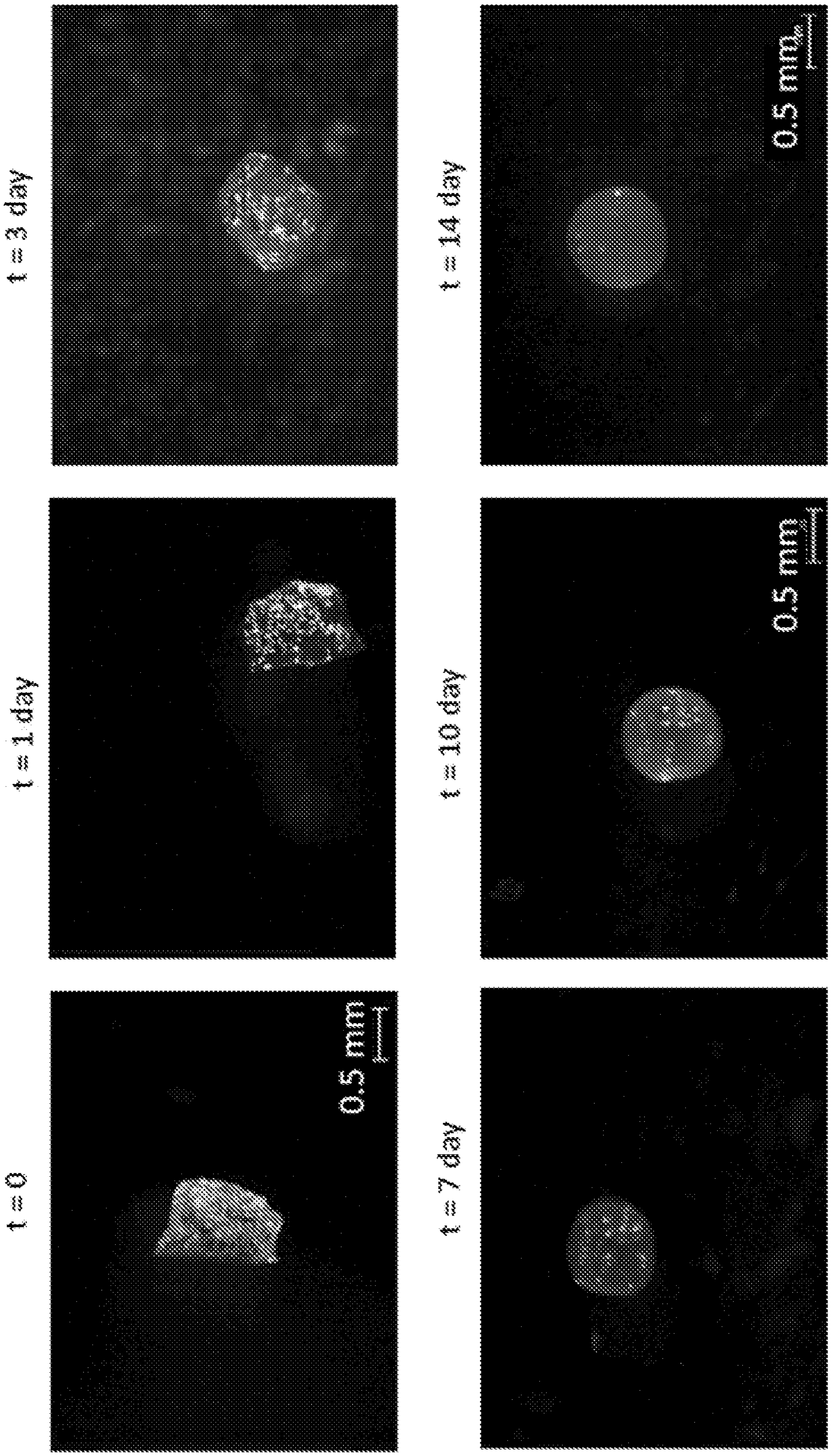
Figure 11A:
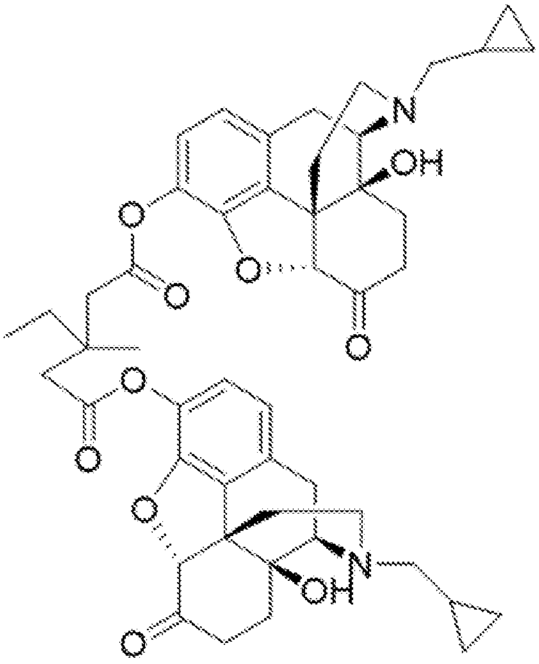
FIG. 11 shows the chemical structure (FIG. 11A) and the heat processed pellet (FIG. 11B) of an opioid composition (Naltrexone-3-ethyl-3-methylglutaric acid-Naltrexone, Compound 10) exemplified herein.
FIG. 11C shows the drug release profile for Compound 10 (pellet) in phosphate-buffered saline (PBS) over 14 days.
FIG. 11D represents the 14-day progression of the surface erosion drug release profile for the pellet of Compound 10 in PBS.
Figure 11B:
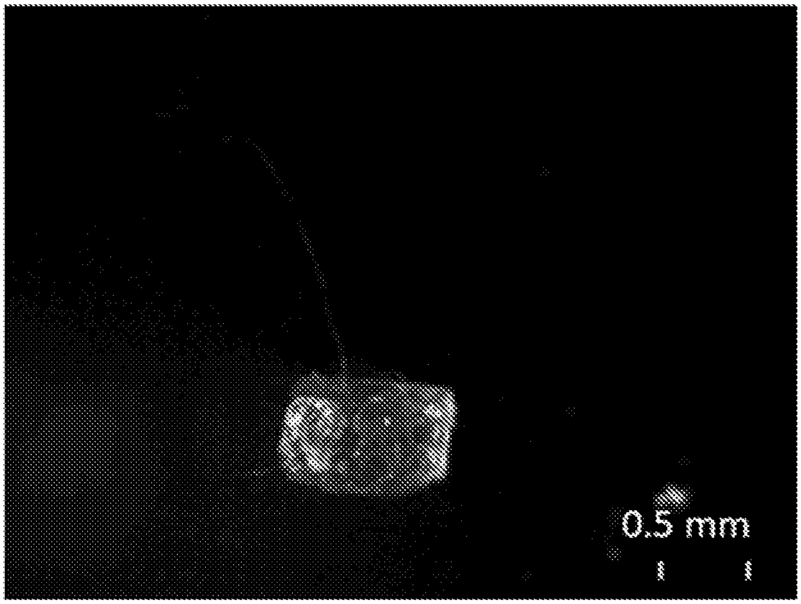
Figure 11C:
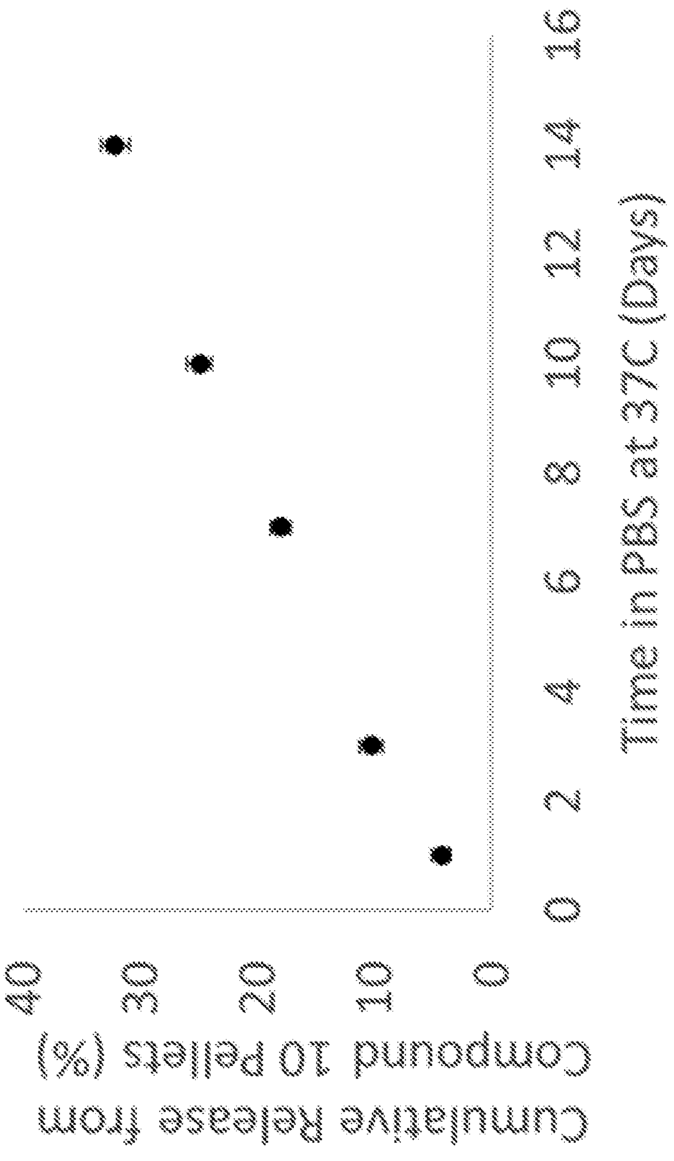
Figure 11D:
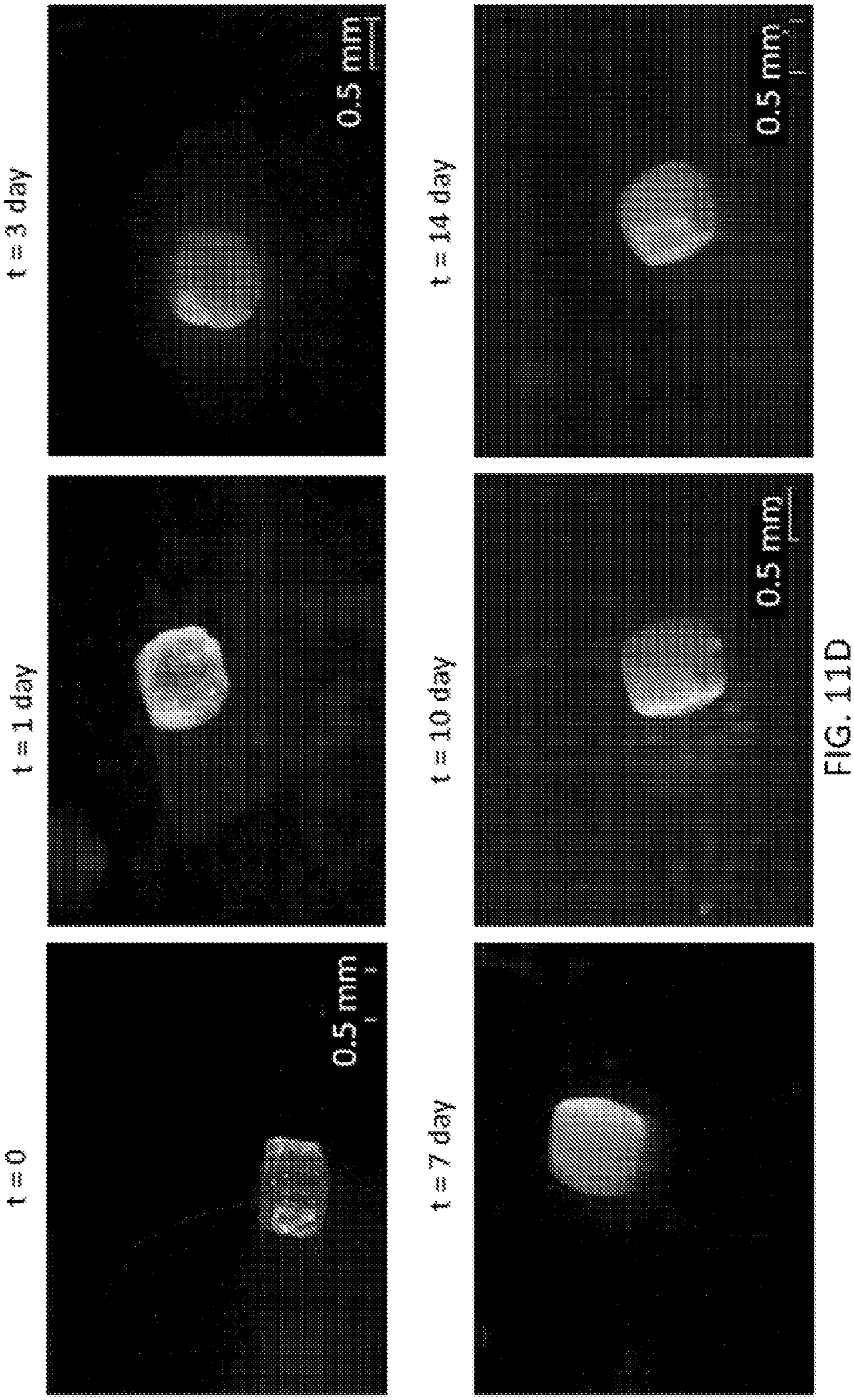
Figure 12A:
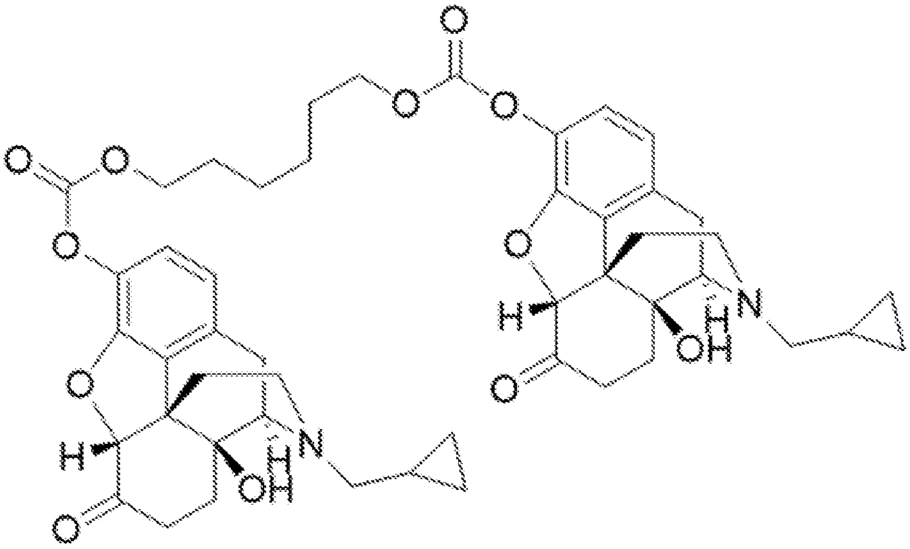
FIG. 12 shows the chemical structure (FIG. 12A) and the heat processed pellet (FIG. 12B) of an opioid composition (Naltrexone-Hex-Naltrexone, Compound 11) exemplified herein.
FIG. 12C shows the drug release profile for Compound 11 (pellet) in phosphate-buffered saline (PBS) over 14 days.
FIG. 12D represents the 14-day progression of the surface erosion drug release profile for the pellet of Compound 11 in PBS.
Figure 12B:
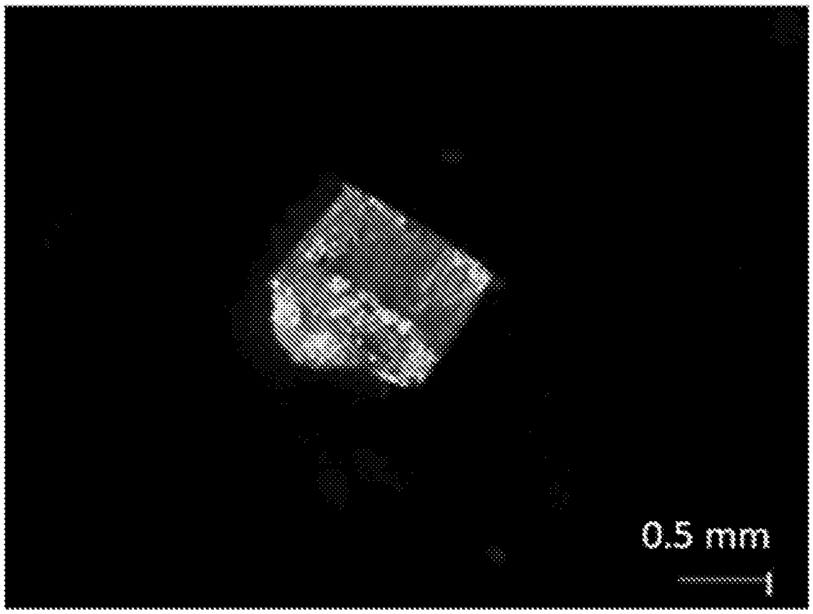
Figure 12C:
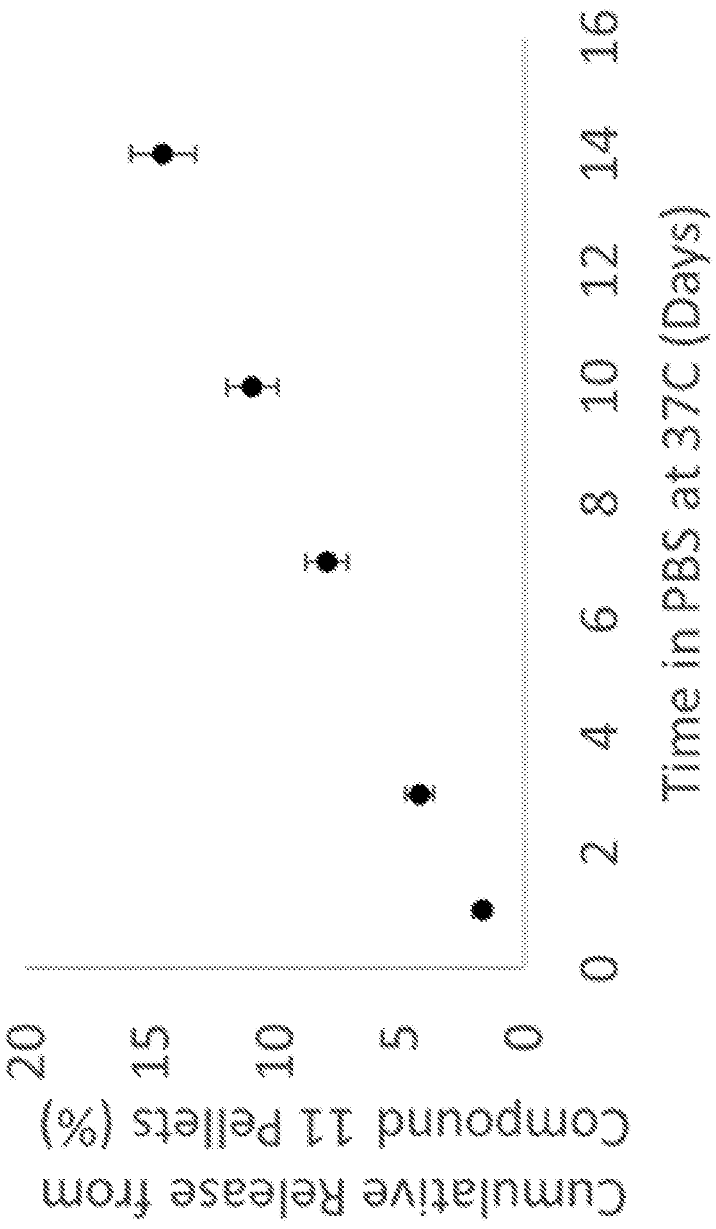
Figure 12D:
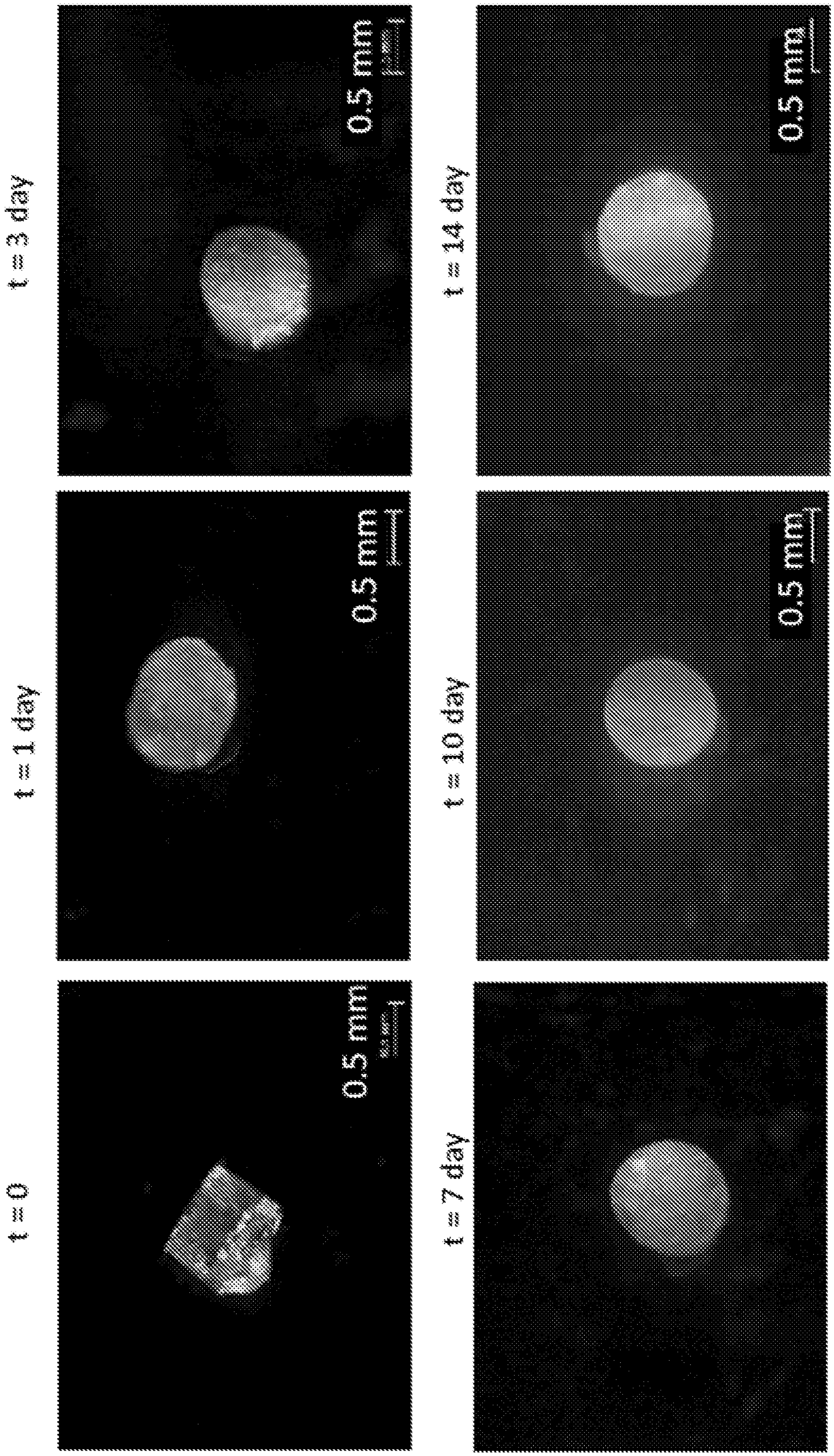
Figure 13A:
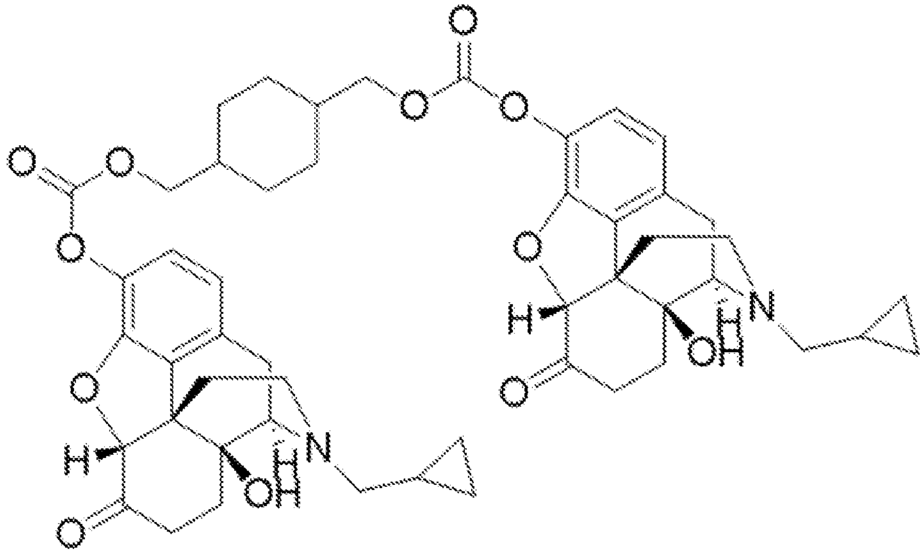
FIG. 13 shows the chemical structure (FIG. 13A) and the heat processed pellet (FIG. 13B) of an opioid composition (Naltrexone-CDM-Naltrexone, Compound 12) exemplified herein.
FIG. 13C shows the drug release profile for Compound 12 (pellet) in phosphate-buffered saline (PBS) over 14 days.
FIG. 13D represents the 14-day progression of the surface erosion drug release profile for the pellet of Compound 12 in PBS.
Figure 13B:
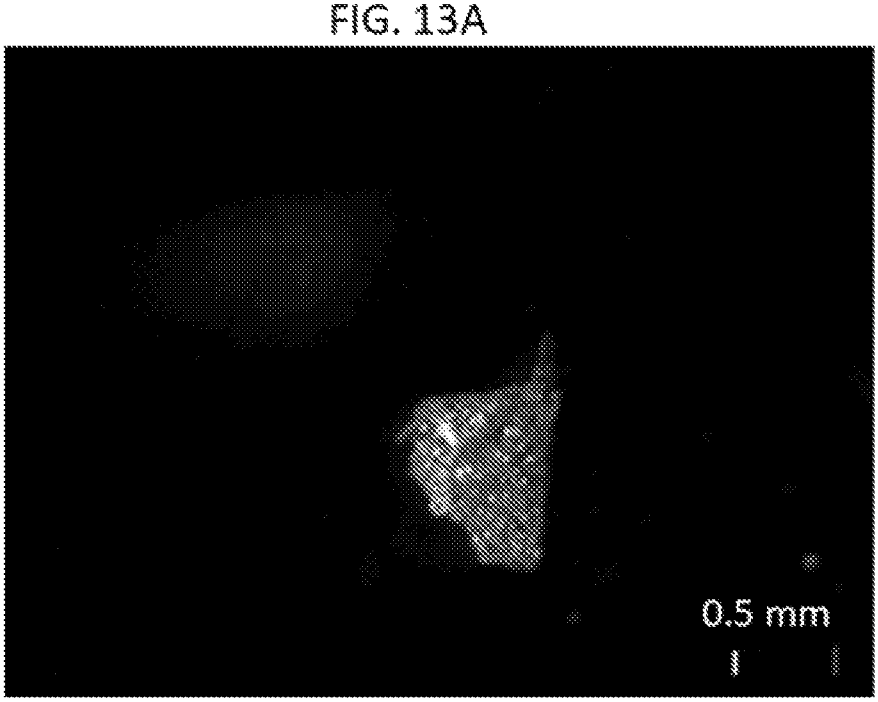
Figure 13C:
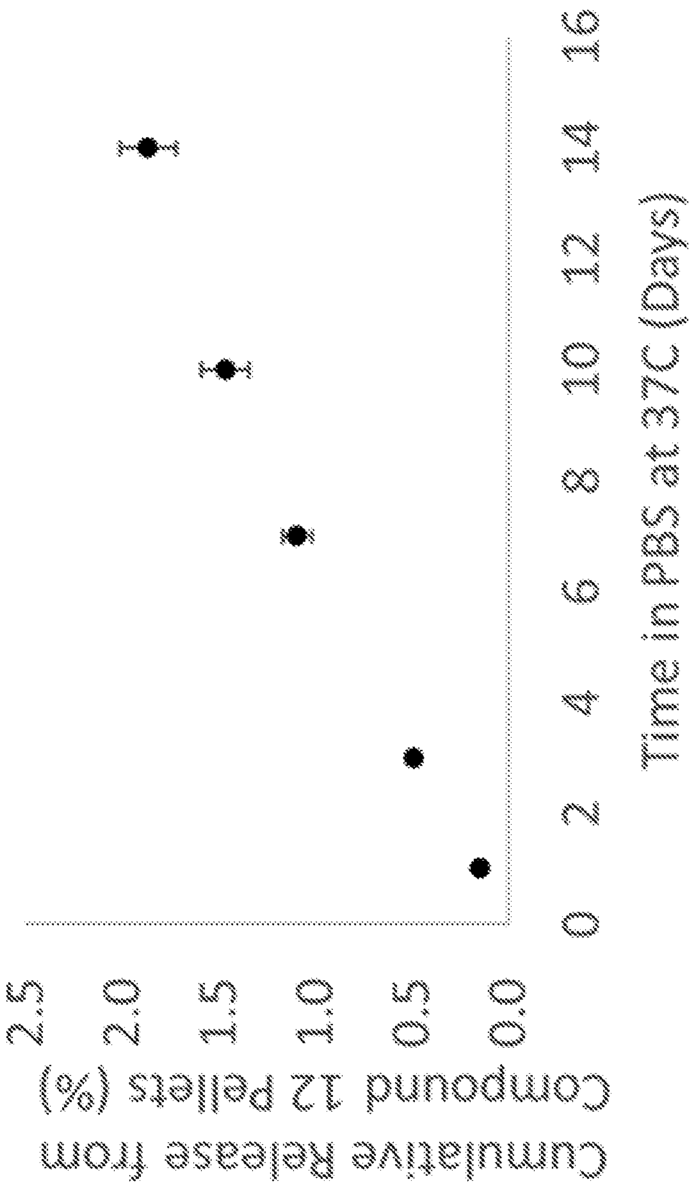
Figure 13D:
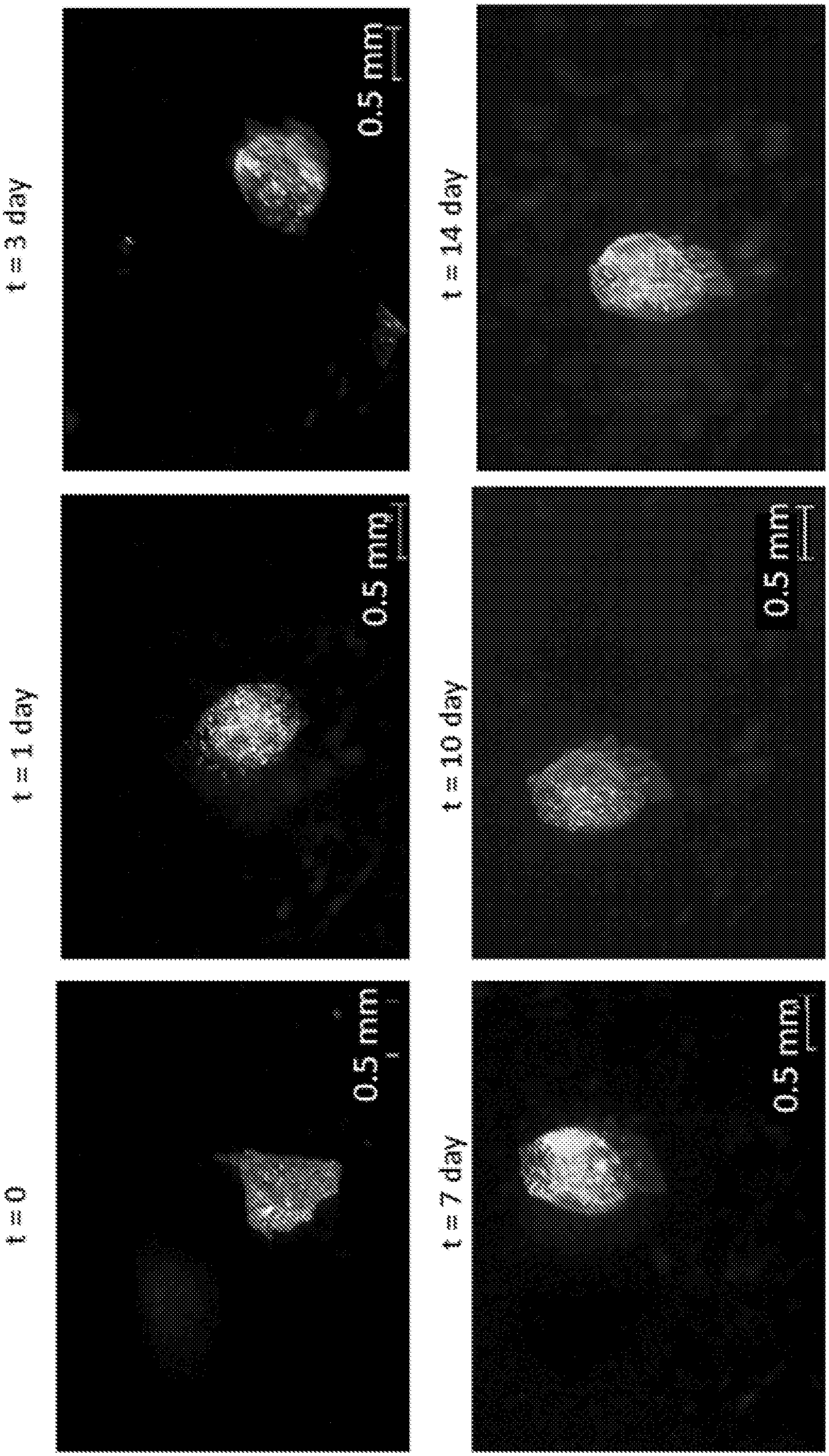
Figure 14:
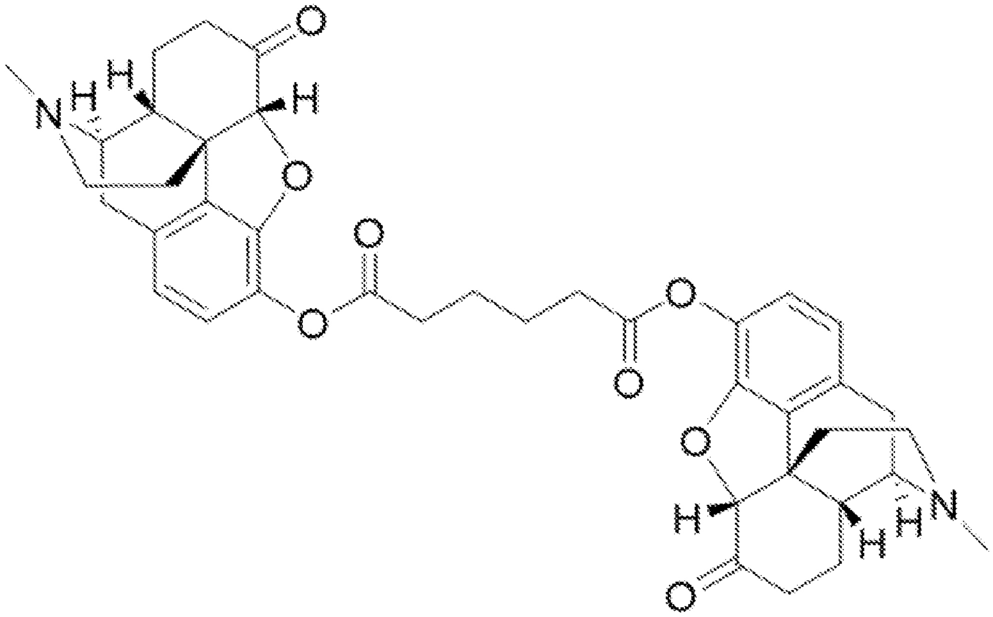
FIG. 14 shows the chemical structure of an opioid composition (Hydromorphone-Adip-Hydromorphone, Compound 13) exemplified herein.
Figure 15:
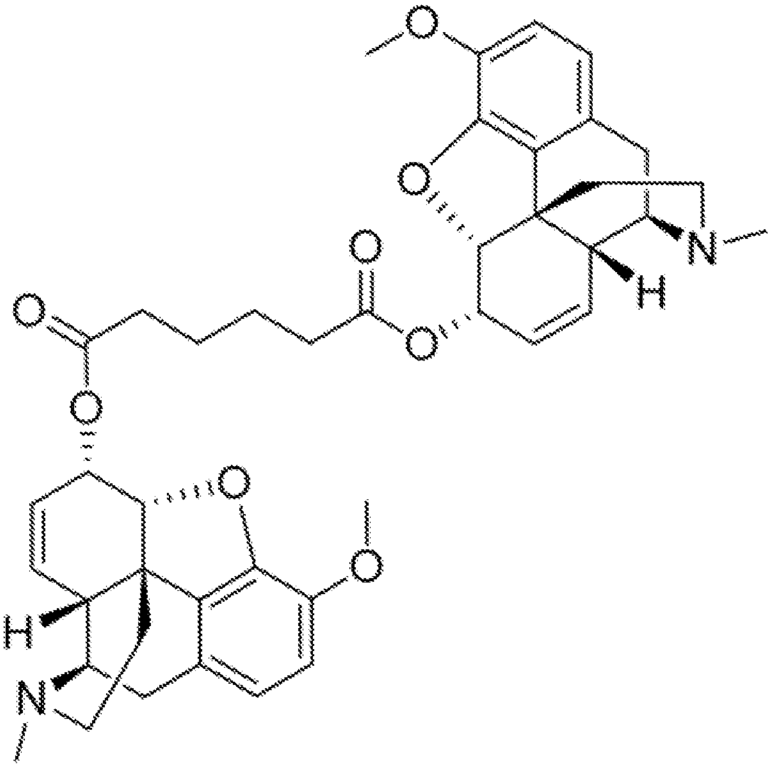
FIG. 15 shows the chemical structure of an opioid composition (Codeine-Adip-Codeine, Compound 14) exemplified herein.

| Compound | Melting point | Pellet formation? | Release in phosphate buffered saline (PBS) |
|---|---|---|---|
| 3 (FIG.4A) | 87° C. | ✓ (FIG. 4B) | Near zero order for > 7 days (FIG. 4C & FIG. 4D) |
| 4 (FIG. 5A) | 86° C. | ✓ (FIG. 5B) | Near zero order for > 7 days (FIG. 5C & FIG. 5D) |
| 5 (FIG. 6A) | 126° C. | ✓ (FIG. 6B) | Near zero order for > 7 days (FIG. 6C & FIG. 6D) |
| 6 (FIG. 7A) | 86° C. | ✓ (FIG. 7B) | Near zero order for > 7 days (FIG. 7C & FIG. 7D) |
| 7 (FIG. 8A) | 145° C. | ✓ (FIG. 8B) | Near zero order for > 7 days (FIG. 8C & FIG. 8D) |
| 8 (FIG. 9) | 240° C. | X | N/A |
| 9 (FIG. 10A) | 73° C. | ✓ (FIG. 10B) | Near zero order for > 7 days (FIG. 10C & FIG. 10D) |
| 10 (FIG. 11A) | 103° C. | ✓ (FIG. 11B) | Near zero order for > 7 days (FIG. 11C & FIG. 11D) |
| 11 (FIG. 12A) | 102° C. | ✓ (FIG. 12B) | Near zero order for > 7 days (FIG. 12C & FIG. 12D) |
| 12 (FIG. 13A) | 131° C. | ✓ (FIG. 13B) | Near zero order for > 7 days (FIG. 13C & FIG. 13D) |
| 13 (FIG. 14) | 112° C. | — | — |
| 14 (FIG. 15) | 209° C. | — | — |

In some embodiments, either one or both of the first and/or second radicals of the opioid conjugate, or pharmaceutically acceptable salt thereof, having a structure of any one of Formula (I'), Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, is released (e.g., in their free form), the release being controlled release (e.g., near zero-order) and/or extended release. In some embodiments, either one or both of the first and/or second radicals of the opioid conjugate, or pharmaceutically acceptable salt thereof, having a structure of any one of Formula (I'), Formula (I), Formula (IA), Formula (IA'), Formula (II), Formula (IIA), Formula (IIB), Formula (IIC), Formula (IID), Formula (IIE), or Formula (IIF), or provided in Table 1, Table 2, or Table 3, is released (e.g., in their free form) for at least 15 days (e.g., a buffer solution, serum, biological environment (e.g., under the skin or in the spine), in vivo, or the like).

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the dual-acting meibomian gland dysfunction pharmacological agent described herein is P. H. Stahl & C. G. Wermuth "Handbook of Pharmaceutical Salts", Verlag Helvetica Chimica Acta, Zurich, 2002.

Pharmaceutical Compositions

In some embodiments, the opioid conjugate described herein has a structure provided in any one of Formula (I), Formula (IA), Formula (IA'), Formula (II), Formula (IIA), Formula (IIB), Formula (IIC), Formula (IID), Formula (IIE), or Formula (IIF). In certain embodiments, the compound as described herein is administered as a pure (e.g., greater than 98 wt. %, greater than 99 wt. %, about 100 wt. %) chemical. In other embodiments, the opioid conjugate described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, $21^{st}$ Ed. Mack Pub. Co., Easton, PA (2005)).

In some embodiments, provided herein is a pharmaceutical composition comprising any compound provided herein, such as a compound that has the structure of any one of Formula (I'), Formula (I), Formula (IA), Formula (IA'), Formula (II), Formula (IIA), Formula (IIB), Formula (IIC), Formula (IID), Formula (IIE), or Formula (IIF), or a pharmaceutically acceptable salt thereof, and at least one pharmaceutically acceptable excipient. Another embodiment provides the pharmaceutical composition, wherein the pharmaceutical composition is suitable for subcutaneous administration. Another embodiment provides the pharmaceutical composition, wherein the pharmaceutical composition is suitable for intraspinal administration.

In certain embodiments, any compound provided herein, such as the opioid conjugate as described by any one of Formula (I), Formula (IA), Formula (IA'), Formula (II), Formula (IIA), Formula (IIB), Formula (IIC), Formula (IID), Formula (IIE), or Formula (IIF), (or pharmaceutically acceptable salt thereof) is substantially pure, in that it contains less than about 5%, or less than about 1%, or less than about 0.1%, of other organic small molecules, such as impurities, unreacted intermediates or (e.g., processing and/or synthesis) by-products that are created, for example, in one or more of the steps of a synthesis method and/or processing step (such as heat processing, solvent processing, and/or sterilization).

In certain embodiments, any compound provided herein, such as the opioid conjugate as described by any one of Formula (I), Formula (IA), Formula (IA'), Formula (II), Formula (IIA), Formula (IIB), Formula (IIC), Formula (IID), Formula (IIE), or Formula (IIF), (or pharmaceutically acceptable salt thereof) is a pharmaceutical implant or article. In some embodiments, the implant or article comprises at least 50 wt. % (at least 60 wt. %, at least 70 wt. %, at least 80 wt. %, at least 90 wt. %, at least 95 wt. %, at least 98 wt. %, or the like) of the compound and/or pharmaceutically acceptable salt thereof. In some embodiments, the implant or article undergoes surface erosion to release the compound, the first radical, and/or the second radical. In some embodiments, the first radical and the second radical are released from the pharmaceutical implant or article at near zero-order in solution (e.g., buffer solution, serum, biological environment, in vivo, or the like). In some embodiments, the first radical and the second radical are released from the pharmaceutical implant or article at 37° C. in 100% bovine serum or at 37° C. in phosphate buffered saline (PBS) at a rate such that $t_{10}$ is greater than or equal to $1/10$ of $t_{50}$.

In certain aspects, the pharmaceutical compositions provided herein include an article in the form of fibers, fiber meshes, woven fabrics, non-woven fabrics, pellets, cylinders, rods, hollow tubes, microparticles, nanoparticles, or other shaped articles. The term "pellet," as used herein, generally refers to the shape of the pharmaceutical compositions of the disclosure that is rounded, spherical, cylindrical, or a combination thereof. In some embodiments, the pellet has a mean diameter from about 0.2 to 5 mm, e.g., from about 0.2 to 1 mm, from about 0.2 to 2 mm, from about 0.3 to 3 mm, from about 1.5 to 5 mm, from about 2 to 5 mm, from about 2.5 to 5 mm, from about 3 to 5 mm, from about 3.5 to 5 mm, from about 4 to 5 mm, or from about 4.5 to 5 mm. In some embodiments, the pharmaceutical composition of the disclosure has a non-circular shape that affects, e.g., increases, the surface area (e.g., extruded through star-shaped dye or any other form shaping process with or without a dye mold). In some embodiments, suitable pharmaceutical compositions for use with this disclosure are small regularly or irregularly shaped particles, which can be solid, porous, or hollow.

In some embodiments, certain forms of pharmaceutical compositions described herein (e.g., fibers, fiber meshes, woven fabrics, non-woven fabrics, pellets, cylinders, rods, hollow tubes, microparticles (e.g., microbeads), nanoparticles (e.g., nanobeads), or other shaped articles) provide a controllable surface area. In some embodiments, the controllable surface area is injected, does not require removal after completion of drug release, and allows for tailoring of drug release rates for a given indication. In certain embodiments, methods provided herein do not require (or comprise) removal of an article or implant, or residual materials or components thereof (e.g., because the implant is completely or almost completely (e.g., bio- or physiologically) degraded or degradable (e.g., at least 80 wt. %, at least 85 wt. %, at least 90 wt. %, at least 95 wt. %, at least 98 wt. %, at least 99 wt. %, or the like)).

In some embodiments, the opioid conjugates described herein are used as a drug delivery device with a minimal need for additives. This may achieve a local, sustained release and a local biological effect, while minimizing a systemic response. In some embodiments, when present, the additives are in small amounts and do not affect the physical or bulk properties. In some embodiments, when present, the additives do not alter the drug release properties from the pharmaceutical composition but rather act to improve processing of the prodrug dimer into the shaped article. In some embodiments, the pharmaceutical compositions contain additives such as a plasticizer (e.g., to reduce thermal transition temperatures), an antioxidant (e.g., to increase stability during heat processing), a binder (e.g., to add flexibility to the fibers), a bulking agent (e.g., to reduce total drug content), a lubricant, a radio-opaque agent, or mixtures thereof. In some embodiments, the additives are present at 30% (w/w), e.g., 20% (w/w), 10% (w/w), 7% (w/w), 5% (w/w), 3% (w/w), 1% (w/w), 0.5% (w/w), or 0.1% (w/w). Non-limiting examples of plasticizers are polyols, e.g., glycerol, ethylene glycol, diethylene glycol, triethylene glycol, tetraethylene glycol, polyethylene glycol, propylene glycol, triacetin, sorbitol, mannitol, xylitol, fatty acids, monosaccharides (e.g., glucose, mannose, fructose, sucrose), ethanolamine, urea, triethanolamine, vegetable oils, lecithin, or waxes. Non-limiting examples of antioxidants are glutathione, ascorbic acid, cysteine, or tocopherol. The binders and bulking agents can be, e.g., polyvvinylpyrrolidone (PVP), starch paste, pregelatinized starch, hydroxypropyl methyl cellulose (HPMC), carboxymethyl cellulose (CMC), or polyethylene glycol (PEG) 6000.

In some embodiments, the implants, articles, or compositions described herein are amorphous. In some embodiments, the implants, articles, or compositions described herein are formed by heat-based and solvent based processing methods. Non-limiting examples of heat processing methods include heat molding, injection molding, extrusion, 3D printing, melt electrospinning, fiber spinning, fiber extrusion, and/or blow molding. Non-limiting examples of solvent processing include coating, micro printing, dot printing, micropatterning, fiber spinning, solvent blow molding, emulsion-based, electrospraying, and electrospinning. In some embodiments, processing methods to form an intermediate glassy state of any of the above heat and solvent based methods as well as heat and solvent based methods that lead to glassy state material with no defined shape (e.g. spray drying, lyophilization, powder melting, etc.).

The term "glassy state," as used herein, generally refers to an amorphous solid including greater than 70%, 80%, 90%, 95%, 98%, or 99% (w/w) of compositions, articles, or implants described herein. In some embodiments, the compositions, articles, or implants described herein exhibit a glass transition temperature above 38° C. In the glassy state, as measured by differential scanning calorimetry (DSC), X-ray powder diffraction (XRD), or polarized light microscopy (PLM), the level of crystallinity is, for example, from 0-15% (e.g., less than 1%, 0-1%, 0-3%, 0-5%, 0-7%, 0-9%, 0-10%, or 0-13%). In some embodiments, glass formulations are formed using heat processing or solvent processing methods described herein (e.g., in the examples).

In some embodiments, the pharmaceutical compositions described herein are prepared by electrospinning. In some embodiments, the pharmaceutical compositions of the disclosure are dissolved in a solvent (e.g., acetone) at concentrations ranging from, e.g., 10-30% w/v, and are electrosprayed to form micro- and nanobeads. In some embodiments, the solution is loaded into a syringe and injected at a rate (e.g., 0.5 mL/h) onto a stationary collection plate. In some embodiments, a potential difference (e.g., 18 kV) is maintained between the needle and collecting surface. For example, in certain embodiments, a concentration of 10% w/v is used to obtain nanoparticles. In other embodiments, a concentration of 30% w/v is used to obtain microbeads.

The pharmaceutical compositions of the disclosure are dissolved in a solvent (e.g., THF, or 1:1 ratio of DCM/THF). In some embodiments, the solution is loaded into a syringe and injected at a rate (e.g., 0.5 mL/h) onto a cylindrical mandrel rotating at a particular rotational speed, e.g., 1150 rpm, to obtain aligned fibers, or onto a stationary collector surface to obtain unaligned fibers. In some embodiments, a potential difference (e.g., 18 kV or 17 kV) is maintained between the needle and collecting surface for aligned and random fibers.

In some embodiments, provided herein is a method of forming an article provided herein comprising producing a glassy state (e.g., an intermediate glassy state or a melt) of a compound (e.g., a crystalline form (e.g., a solid or a powder)) provided herein using heat or solvent. In other embodiments, fibers are prepared from the melt or the glass at elevated temperatures, the glassy state intermediate, or from the solution by dissolving the pharmaceutical compositions described herein in a solvent (e.g., DCM, THF, or chloroform). As used herein, "melt spinning" describes heat processing from the melt state, "heat spinning" describes heat processing from the glassy state, and "wet", "dry", and "gel" spinning describe solution processing.

In some embodiments, the viscous melt, intermediate, or solution is fed through a spinneret and fibers are formed upon cooling (melt or heat spinning) or following solvent evaporation with warm air as the compound exits the spinneret (dry spinning). In some embodiments, wet spinning and gel spinning are used to produce the fibers disclosed herein. "Heat spinning," as used herein, describes a process that is similar to the melt spinning, but performed with a glassy state intermediate and heated above the glass transition temperature ($T_g$), obtaining the viscous fluid to extrude/spin instead of the melt. Alternatively, tweezers may be dipped into melted material or concentrated solutions and retracted slowly in order to pull fibers. The rate of pulling and distance pulled may be varied to yield fibers and columnar structures of different thickness.

In some embodiments, micro-particles or nano-particles made from the pharmaceutical composition are formed using an emulsion process. In some embodiments, the pharmaceutical composition is dissolved in an organic solvent (e.g. DCM, THF, etc.). In some embodiments, a surfactant (e.g. SDS, PVA, etc.) is added (e.g. 1%) to the solution/mixture. In some embodiments, the resulting mixture is stirred for the appropriate time at room temperature to form an emulsion. In some embodiments, the emulsion is subsequently added to Milli-Q water under stirring for an appropriate time (e.g., 1 h) to remove residual solvent. The resulting micro- or nano-particles may be collected by centrifugation and dried.

In some embodiments, injectable cylinders made from a pharmaceutical composition described herein is formed by heat extrusion. In some embodiments, the pharmaceutical composition is loaded into a hot melt extruder, heated to a temperature above the melting point (e.g., for crystalline compositions) or glass transition temperature (e.g., for premelted or amorphous compositions), and extruded using (i) a compressive force to push the material through the nozzle and (ii) a tensile force (or gravity) to pull the material out of the extruder. The extrudate may be cut to the desired length for suitable drug dosing for a medical indication.

In some embodiments, a milling process is used to reduce the size of an article described to form sized particles, e.g., beads, in the micrometer (microbeads) to nanometer size range (nanobeads). The milling process may be performed using a mill or other suitable apparatus. In some embodiments, dry and wet milling processes, such as, for example, jet milling, cryo-milling, ball milling, media milling, sonication, and homogenization are used in methods described herein. In some embodiments, heating of the milled microparticle above the $T_g$ is performed to achieve a spherical shape. In some embodiments, particles with non-spherical shapes are used as milled.

In certain embodiments, a composition described herein has a limited window (e.g., short timeframe of seconds to minutes) of thermal stability, whereby the purity of the dimer is affected (e.g., minimally) at elevated temperatures. In some embodiments, an intermediate glassy state form (e.g., film, surface coating, pellet, micro-particles, or other shaped article) is made to avoid decomposition. In some embodiments, heat or solvent processing is used to remove or reduce the crystallinity of the material to form a glassy state composition. In some embodiments, the glassy state composition is heat processed at a lower temperature (e.g., processing just above the glass transition temperature ($T_g$), and below the melt temperature ($T_m$)). In some embodiments, the lower temperature allows for a longer timeframe for heat processing the glassy state material into the final shaped article, while reducing the impact of processing conditions on the purity of the opioid dimer in the article.

In some embodiments, the compound provided by any one of Formula (I), Formula (IA), Formula (IA'), Formula (II), Formula (IIA), Formula (IIB), Formula (IIC), Formula (IID), Formula (IIE), or Formula (IIF), is formulated for administration by injection. In some instances, the injection formulation is an solid formulation. In some instances, the injection formulation is a non-aqueous formulation.

In certain aspects, the pharmaceutical compositions described herein provide an article (e.g., as described herein) with a controlled release profiled (e.g., by surface erosion). In some embodiments, the surface erosion allows the article to maintain its physical form, while gradually decreasing in size as the surface erodes (e.g., at a constant rate), rather than by, for example, bulk erosion that is characteristic of some polymer-based drug release vehicles (e.g., polylactic/glycolic acid). In some embodiments, the surface erosion inhibits burst release and/or reduces the formation of inflammatory particulates (e.g., no or minimal crystalline particulates are formed or released from the articles when drug is released as described herein). In some embodiments, compositions described herein are are delivered over a period of time. For example, a slower and steadier rate of delivery (e.g., release of less than 10% of the first radical or the second radical in their free form (as a percentage of the total drug, the first radical or the second radical in their free form, present in the article) at 37° C. in 100% bovine serum over 5 days) results in a reduction in the frequency with which the pharmaceutical composition is administered to a subject and/or improve the safety profile of the drug. In some embodiments, the drug release is tailored to avoid side effects of slower and longer release of the drug by engineering the article to provide constant release over a comparatively shorter period of time. In some embodiments, the drug release is tailored for dose and duration suitable for the indication or administration method.

In some embodiments, the release rate is related to, for example, the drug configuration of the dimer. In some embodiments, the drug release rate from an article described herein is modulated by the cleavage of dimer-linker bond through hydrolysis or enzymatic degradation. In some embodiments, the linking moiety (e.g., the linker) affects drug release rate. In some embodiments, the drug release rate is controlled by a functional group on the composition described herein to conjugate through to the linker, for example, a primary vs. a secondary hydroxyl group. In some embodiments, the release rate from a dimer is related to percentage of the loaded dimer compared to the final drug dimer formulation (e.g., by using a pharmaceutical excipient (e.g., bulking agent/excipient). In some embodiments, the release rate is controlled by the size of a microbead. In some embodiments, drug release is tailored based on the solubility of drug dimer (e.g., through selection of appropriate drug and/or linker) that will influence the rate of surface erosion (e.g., dissolution/degradation) from the article. In other embodiments, drug release is affected by changes in surface area of the formulation, e.g., by changing the diameter of the microbeads. By adjusting the vide supra factors, dissolution, degradation, diffusion, and controlled release may be varied over wide ranges. For example, release may be designed to be initiated over minutes to hours, and may extend over the course of days, weeks, months, or years.

In some embodiments, a pharmaceutical composition containing an opioid dimer described herein is administered to a subject by the following non-limiting examples oral, sublingual, nasal, intradermal, subcutaneous, intramuscular, rectal, vaginal, intravenous, intraarterial, intracisternal, intraperitoneal, intravitreal, topical (as by powders, creams, ointments, or drops), buccal and inhalational administration. In certain instances, the articles described herein are administered parenterally as injections (intravenous, intramuscular, or subcutaneous), or locally as injections (into a joint space). In some embodiments, the formulations described herein are admixed under sterile conditions with a pharmaceutically acceptable carrier, preservatives and/or buffers.

In some embodiments, the implant, article, or composition described herein is suitable for subcutaneous administration, or intraspinal administration.

The dose of the composition comprising at least one opioid conjugate as described herein differ, depending upon the individual's (e.g., human) condition, that is, general health status, age, and other factors.

Pharmaceutical compositions are administered in a manner appropriate to the disease to be treated (or prevented). An appropriate dose and a suitable duration and frequency of administration will be determined by such factors as the condition of the individual, the type and severity of the individual's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. The optimal dose depends upon the body mass, weight, or blood volume of the individual.

In other embodiments, the compositions described herein are combined with a pharmaceutically suitable or acceptable carrier (e.g., a pharmaceutically suitable (or acceptable) excipient, physiologically suitable (or acceptable) excipient, or physiologically suitable (or acceptable) carrier. Exemplary excipients are described, for example, in h*Remington: The Science and Practice of Pharmacy* (Gennaro, $21^{st}$ Ed. Mack Pub. Co., Easton, PA (2005)).

Methods of Treatment

In certain aspects, provided herein is a method of treating a CNS disease or disorder. In some embodiments, the CNS disease or disorder is pain (e.g., chronic pain), addiction (e.g., opioid addiction), or overdose. In some embodiments, the CNS disease or disorder is selected from chronic pain (e.g., cancer pain), acute pain, opioid addiction, alcohol addiction, alcohol dependence, opioid-induced constipation, gambling disorders, and narcotic depression.

In certain aspects, provided herein is a method of treating acute pain, chronic pain, post-operative pain, opioid dependence, opioid addiction, or the like in an individual in need of thereof, comprising administering to the individual any compound provided herein, or a pharmaceutically acceptable salt thereof, or a (e.g., pharmaceutical) composition comprising any compound provided herein, or a pharmaceutically acceptable salt thereof, such as a compound having a structure of any one of Formula (I'), Formula (I), Formula (IA), Formula (IA'), Formula (II), Formula (IIA), Formula (IIB), Formula (IIC), Formula (IID), Formula (IIE), or Formula (IIF). In certain aspects, provided herein is a method of treating acute pain, chronic pain, cancer pain, or post-operative pain in an individual in need of thereof, comprising administering to the individual any compound provided herein, or a pharmaceutically acceptable salt thereof, or a (e.g., pharmaceutical) composition comprising any compound provided herein, or a pharmaceutically acceptable salt thereof, such as a compound having a structure of any one of Formula (I'), Formula (I), Formula (IA), Formula (IA'), Formula (II), Formula (IIA), Formula (IIB), Formula (IIC), Formula (IID), Formula (IIE), or Formula (IIF). In certain aspects, provided herein is a method of treating opioid dependence, alcohol addiction, alcohol dependence, or opioid addiction in an individual in need thereof, comprising administering to the individual any compound provided herein, or a pharmaceutically acceptable salt thereof, or a (e.g., pharmaceutical) composition comprising any compound provided herein, or a pharmaceutically acceptable salt thereof, such as a compound having a structure of any one of Formula (I'), Formula (I), Formula (IA), Formula (IA'), Formula (II), Formula (IIA), Formula (IIB), Formula (IIC), Formula (IID), Formula (IIE), or Formula (IIF). In certain aspects, provided herein is a method of treating opioid-induced constipation or narcotic depression in an individual in need of thereof, comprising administering to the individual any compound provided herein, or a pharmaceutically acceptable salt thereof, or a (e.g., pharmaceutical) composition comprising any compound provided herein, or a pharmaceutically acceptable salt thereof, such as a compound having a structure of any one of Formula (I'), Formula (I), Formula (IA), Formula (IA'), Formula (II), Formula (IIA), Formula (IIB), Formula (IIC), Formula (IID), Formula (IIE), or Formula (IIF).

Another embodiment provides the method wherein the pharmaceutical composition is in the form of a solid suitable for subcutaneous administration (e.g., injection). Another embodiment provides the method wherein the pharmaceutical composition is in the form of a solid suitable for intraspinal administration (e.g., injection).

Methods involving treating a subject may include preventing a disease, disorder or condition from occurring in the subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected (e.g., such treating the pain of a subject by administration of an agent even though such agent does not treat the cause of the pain).

EXAMPLES

I. Analytical Methods

Analytical Example 1: High Performance Liquid Chromatography (HPLC)

Method 1: Samples (20.0 mg) are dissolved in acetonitrile (10.0 mL) to make 2 mg/mL solution. For the system: solvent A was Water+0.05% trifluoroacetic acid (TFA); solvent B was Acetonitrile+0.05% TFA; the flow rate was 1.0 mL/min; and the detection method was UV @232 nm and UV Spectra from 190 to 400 nm. The samples were loaded onto an Agilent 1100 series HPLC with either (i) a Phenomenex Gemini-NX C18 Column (5 μm; 110 Å; 250×4.6 mm; 00G-4454-E0) or (ii) Phenomenex SecurityGuard Analytical Guard Column (KJO-4282) with Gemini C18 4×3.0 mm Guard Cartridge (AJO-7597). The solvent gradient profile is shown in Table 5:

TABLE 5

| Time (min) | % A Solvent | % B Solvent |
|---|---|---|
| 0 | 98 | 2 |
| 3 | 90 | 10 |
| 15 | 80 | 20 |

Method 2: Samples (20.0 mg) were dissolved in methanol (10.0 mL) to make 2 mg/mL solutions. For the system: solvent A was 90% 10 mM potassium phosphate buffer (pH 6.6)+10% methanol (v/v); solvent B was 90% methanol+10% 10 mM potassium phosphate buffer (pH 6.6) (v/v); the flow rate was 1.0 mL/min and injection volume was 5 μL; detection method was UV @220 nm and UV Spectra from 190 to 400 nm. The samples were loaded onto an Agilent 1200 series HPLC with a Phenomenex Gemini-NX C18 Column (5 μm; 110 Å; 250×4.6 mm; 00G-4454-E0) equipped with a Phenomenex SecurityGuard Analytical Guard Pre-Column (KJO-4282) containing Gemini C18 4×3.0 mm Guard Cartridge (AJO-7597). The solvent gradient profile is shown in Table 6:

TABLE 6

| Time (min) | % A Solvent | % B Solvent |
|---|---|---|
| 0.0 | 50 | 50 |
| 3.5 | 15 | 85 |
| 9.5 | 0 | 100 |
| 26.5 | 0 | 100 |
| 32.5 | 50 | 50 |
| 40.0 | 50 | 50 |

Samples (20.0 mg) were dissolved in acetonitrile (10.0 mL) to make 2 mg/mL solutions. The samples were loaded onto an Agilent 1260 Series HPLC with a Phenomenex Gemini-NX C18 Column (5 μm; 110 Å; 250×4.6 mm; 00G-4454-E0) equipped with a Phenomenex SecurityGuard Analytical Guard Pre-Column (KJO-4282) containing Gemini C18 4×3.0 mm Guard Cartridge (AJO-7597). For the system: solvent A was Water+0.05% trifluoroacetic acid (TFA); solvent B was Acetonitrile+0.05% TFA; the flow rate was 1.0 mL/min and the injection volume was 5 μL. Solvent gradient profiles were designated as either Method 3 or Method 4, with the details shown in Tables 7 and 8, respectively. Detection method was UV @242 nm (Low Polarity) or UV @296 nm (Timolol), with UV Spectra from 190 to 400 nm collected in both cases.

TABLE 7

| Method 3 | | |
|---|---|---|
| Time (min) | % A Solvent | % B Solvent |
| 0 | 80 | 20 |
| 40 | 16 | 84 |
| 42 | 0 | 100 |
| 50 | 0 | 100 |

TABLE 8

| Method 4 | | |
|---|---|---|
| Time (min) | % A Solvent | % B Solvent |
| 0 | 98 | 2 |
| 30 | 68 | 32 |
| 35 | 0 | 100 |
| 45 | 0 | 100 |

Analytical Example 2: Nuclear Magnetic Resonance (NMR)

Compounds (10 mg) were dissolved in 666 μL of either $CDCl_3$ or DMSO-d6 and loaded in an 8-inch length, 5 mm diameter NMR tube. The instrument was a Varian Mercury 400 NMR spectrometer. Proton NMR spectra were obtained with 16 scans using the default method. FIDS were processed with MestRe-C software.

Analytical Example 3: Mass Spectrometry (MS)

Compounds were dissolved in acetonitrile at 1 mg/ml and used directly for analysis on an Agilent 6538 QTOF, using ESI MS+ as ion source.

Analytical Example 4: Melting Point

Compound powder was prepared neat in a glass capillary tube, and melting temperature was measured manually with standard glass capillary tube melting point apparatus.

Analytical Example 5: Differential Scanning Calorimetry 5-10 mg of compounds were weighed in an aluminum pan. Using a Hitachi Differential Scanning calorimeter DSC7020, samples were heated from room temperature to 110-280° C. at 10° C./min, cooled to −30° C. at 10° C./min, and heated again to 110-280° C. at 10° C./min.

Analytical Example 6: Light Microscopy

Heat molded pellets were imaged using a Leica DMV6 light microscope equipped with Leica application suite X software.

II. Chemical Synthesis

Solvents, reagents and starting materials were purchased from commercial vendors and used as received unless otherwise described. All reactions were performed at room temperature unless otherwise stated. Starting materials were purchased from commercial sources or synthesized according to the methods described herein or using literature procedures.

Chemical Synthesis Example 1 bis((4R,4aS,7aR,12bS)-4a-hydroxy-9-methoxy-3-methyl-2,3,4,4a,5,7a-hexahydro-1H-4,12-methanobenzofuro[3,2-e]isoquinolin-7-yl) adipate, Compound A)

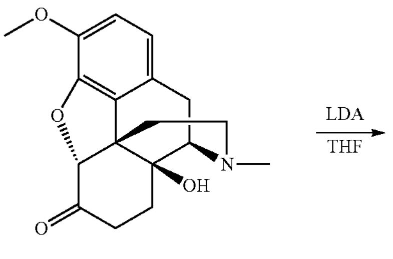

Oxycodone

-continued

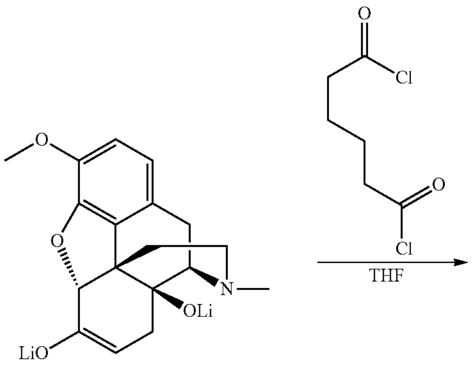

Oxycodone enolate

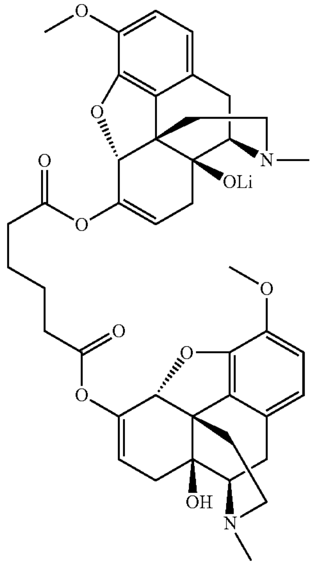

Dimeric compositions bearing an enolizable ketone (e.g., oxycodone) are prepared by reaction with lithium diisopropylamide (LDA, 2 equiv.) in tetrahydrofuran at −78° C. for 5 min to 1 hr, driving the enol tautomer to the formation of the lithium enolate. The appropriate linker precursor (e.g., adipoyl chloride, 0.5 eq.) is added and the reaction is stirred for 1 hr to 16 hrs at room temperature to form the drug dimer (e.g., oxycodone-adip-oxycodone).

Chemical Synthesis Example 2 bis((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl) adipate (naloxone-adipate-naloxone ester, Compound 1)

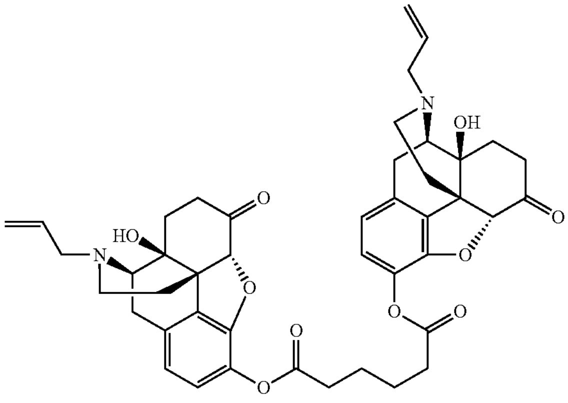 [SMILES: C=CCN1CC[C@]23c4c5ccc(OC(=O)CCCCC(=O)Oc6ccc7c8c6O[C@H]6C(=O)CC[C@@]9(O)[C@@H](C7)N(CC=C)CC[C@]869)c4O[C@H]2C(=O)CC[C@@]3(O)[C@H]1C5]

To a stirred suspension of naloxone hydrochloride (250 mg, 0.687 mmol) in dry DCM (50 mL) under nitrogen was added 4-(dimethylamino)pyridine (168 mg, 1.374 mmol), adipic acid (50 mg, 0.343 mmol) and N-(3-Dimethylaminopropyl)-N'-ethylcarbodiimide hydrochloride (263 mg, 1.374 mmol) and the mixture was stirred overnight. The mixture was concentrated onto 2 g reverse phase silica. Purification was performed by reverse phase chromatography (aqueous-MeCN gradient). Product containing fractions were combined, extracted with DCM, dried ($MgSO_4$) and concentrated to give Compound 1 (FIG. 1A) as an off-white solid (100 mg, 38%). Melting point: 120° C.; HPLC (Method 1) retention time: 6.75 min; ESI MS+ Found, $C_{44}H_{48}N_2NaO_{10}^+$, Mass: 787.32 g/mol; $^1H$ NMR (400 MHz, DMSO-$d_6$) δ 6.82 (2H, d, J=8.0 Hz); 6.74 (2H, d, J=8.0 Hz); 5.82 (2H, m, β-CH allyl); 5.21 (2H, d, J=16.8 Hz, γ-CH-allyl, trans); 5.12 (2H, d, J=10.0 Hz, γ-CH-allyl, cis); 5.04 (2H, s); 4.85 (2H, s); 3.10 (6H, m); 2.85 (6H, m); 2.54 (6H, m); 2.32 (2H, m); 2.03 (2H, m); 1.95 (2H, m); 1.74 (6H, m); 1.43 (2H, m); 1.22 (2H, m).

Chemical Synthesis Example 3 bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) adipate (naltrexone-adipate-naltrexone, Compound 2)

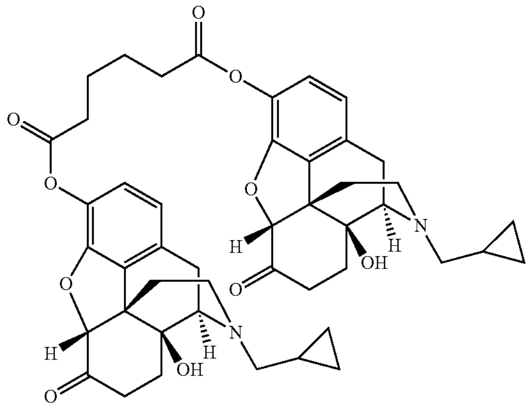 [SMILES: O=C(CCCCC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314]

To a solution of naltrexone hydrochloride (1.63 g, 4.31 mmol) in DCM (120 mL) under nitrogen was added 4-(dimethylamino)pyridine (1.00 g, 8.21 mmol), adipic acid (300 mg, 2.05 mmol) and dimethylaminopropyl-N'-ethylcarbodiimide hydrochloride (1.57 g, 8.21 mmol, 4.00 eq) at 0° C. The mixture was stirred at 25° C. for 8 h. The reaction mixture was concentrated under reduced pressure to give a residue. The crude product was purified by reversed-phase HPLC (column: Agela DuraShell C18 250*50 mm*10 um; mobile phase: [water (0.05% $NH_3H_2O$+10 mM $NH_4HCO_3$)-ACN]; B %: 55%-85%, 20 min) to give the product as an off-white solid (658 mg, 60%). Melting point: 187° C. HPLC (Method 2) retention time: 7.0 min, ESI MS+ Found, $C_{46}H_{53}N_2O_{10}^+$ Mass: 793.37 1H NMR (400 MHz, DMSO) δ 6.84 (d, J=8.2 Hz, 2H), 6.72 (d, J=8.3 Hz, 2H), 5.15 (s, 1H), 4.92 (s, 2H), 3.17 (d, J=5.6 Hz, 2H), 3.09 (s, 1H), 3.05 (s, 1H), 2.91 (td, J=14.3, 5.0 Hz, 2H), 2.70-2.52 (m, 8H), 2.38 (tt, J=11.2, 6.3 Hz, 6H), 2.11 (dt, J=12.6, 2.4 Hz, 2H), 1.95 (td, J=12.1, 3.8 Hz, 2H), 1.84-1.74 (m, 3H), 1.73 (d, J=3.3 Hz, 2H), 1.45 (td, J=14.0, 3.4 Hz, 2H), 1.33-1.21 (m, 2H), 0.95-0.81 (m, 2H), 0.55-0.42 (m, 4H), 0.20-0.07 (m, 4H).

Chemical Synthesis Example 4 bis((4R,4aS,7aS,12bS)-3-(cyclopropylmethyl)-4a-hydroxy-7-methylene-2,3,4,4a,5,6,7,7a-octohydro-1H-4,12-methanobenzofuro[3,2-e]isoquinolin-9-yl) adipate, Nalmefene-Adip-Nalmefene, Compound 3)

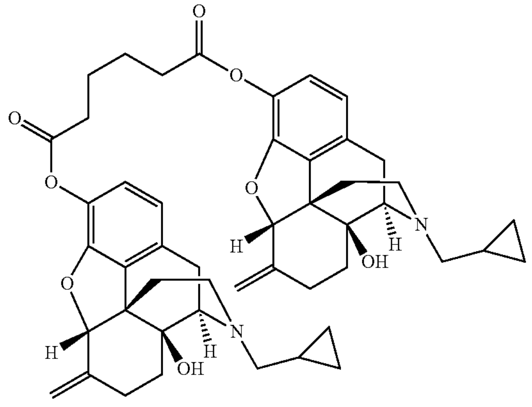 [SMILES: C=C1CC[C@@]2(O)[C@H]3Cc4ccc(OC(=O)CCCCC(=O)Oc5ccc6c7c5O[C@H]5C(=C)CC[C@@]8(O)[C@@H](C6)N(CC6CC6)CC[C@]758)c5c4[C@@]2(CCN3CC2CC2)[C@H]1O5]

To a solution of nalmefene (2.44 g, 7.18 mmol) in DCM (100 mL) was added 4-(dimethylamino)pyridine (1.25 g, 10.26 mmol), adipic acid (0.500 g, 3.42 mmol) and dimethylaminopropyl-N'-ethylcarbodiimide hydrochloride (2.62 g, 13.69 mmol) at 0° C. under $N_2$ atmosphere. The mixture was stirred at 20° C. for 10 h. The reaction mixture was concentrated under reduced pressure to give a residue. The crude product was purified by reversed-phase HPLC (column: Welch Xtimate C18 250*70 mm #10 um; mobile phase: [water (0.04% $NH_3H_2O$+10 mM NH4HCO3)-ACN]; B %: 80%-100%, 300 min) to give the product (1.30 g, 48% yield) as a light yellow solid. Melting point: 87° C. HPLC (Method 2) retention time: 9.0 min, ESI MS+ Found, $C_{48}H_{52}N_2O_8^+$ Mass: 789.41 $^1$H NMR (400 MHz, DMSO) δ 6.75 (d, J=8.11 Hz, 2H) 6.63 (d, J=8.11 Hz, 2H) 5.03 (d, J=1.10 Hz, 2H) 4.94 (s, 2H) 4.87 (s, 2H) 4.76 (d, J=1.75 Hz, 2H) 3.00 (br dd, J=11.95, 6.69 Hz, 4H) 2.48-2.71 (m, 8H) 2.15-2.46 (m, 8H) 1.87-2.07 (m, 4H) 1.64-1.78 (m, 4H) 1.43-1.55 (m, 2H) 1.10-1.28 (m, 4H) 0.74-0.89 (m, 2H) 0.36-0.54 (m, 4H) 0.00-0.16 (m, 4H)

Chemical Synthesis Example 5 bis((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl) decanedioate (Naloxone-Seb-Naloxone, Compound 4)

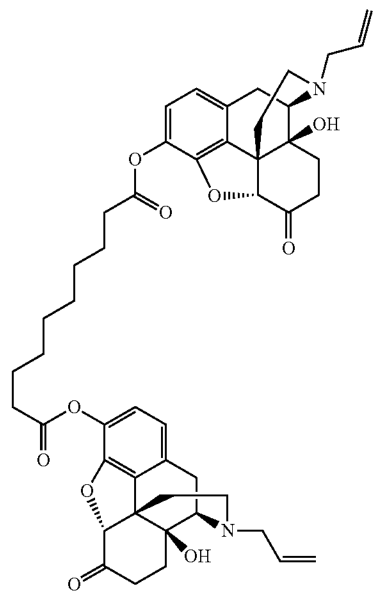 [SMILES: C=CCN1CC[C@]23c4c5ccc(OC(=O)CCCCCCCCC(=O)Oc6ccc7c8c6O[C@H]6C(=O)CC[C@@]9(O)[C@@H](C7)N(CC=C)CC[C@]869)c4O[C@H]2C(=O)CC[C@@]3(O)[C@H]1C5]

To a solution of naloxone hydrochloride dihydrate (1.04 g, 2.60 mmol) in DCM (100 mL) under nitrogen was added 4-(dimethylamino)pyridine (604 mg, 4.94 mmol), sebacic acid (250 mg, 1.24 mmol) and dimethylaminopropyl)-N'-ethylcarbodiimide hydrochloride (948 mg, 4.94 mmol) at 0° C. The mixture was stirred at 25° C. for 8 h. The reaction mixture was concentrated under reduced pressure to give a residue. The crude product was purified by reversed-phase HPLC (column: Agela DuraShell C18 250*80 mm*10 um; mobile phase: [water (10 mM $NH_4HCO_3$)-ACN]; B %: 55%-85%, 20 min) to give the product (855 mg, 84% yield) as a white solid. Melting point: 86° C. HPLC (Method 2) retention time: 8.8 min, ESI MS+ Found, $C_{48}H_{57}N_2O_{10}^+$ Mass: 821.40 $^1$H NMR (400 MHz, DMSO) δ ppm 6.83 (d, J=8.16 Hz, 2H) 6.73 (d, J=8.16 Hz, 2H) 5.86 (ddt, J=16.97, 10.38, 6.27, 6.27 Hz, 2H) 5.25 (br d, J=17.19 Hz, 2H) 5.15 (br d, J=10.42 Hz, 2H) 5.07 (s, 2H) 4.90 (s, 2H) 3.07-3.20 (m, 6H) 2.84-3.00 (m, 4H) 2.52-2.62 (m, 6H) 2.37 (td, J=12.49, 5.02 Hz, 2H) 2.09-2.13 (m, 2H) 2.07 (s, 2H) 1.95 (td, J=12.02, 3.45 Hz, 2H) 1.72-1.80 (m, 2H) 1.63 (quin, J=7.18 Hz, 4H) 1.25-1.48 (m, 12H)

Chemical Synthesis Example 6 bis((4R,4aS,7aR,12bS)-3-allyl-4a-hydroxy-7-oxo-2,3,4,4a,5,6,7,7a-octahydro-1H-4,12-methanobenzofuro[3,2-e]isoquinolin-9-yl) (cyclohexane-1,4-diylbis(methylene)) bis(carbonate) (Naloxone-CDM-Naloxone, Compound 5)

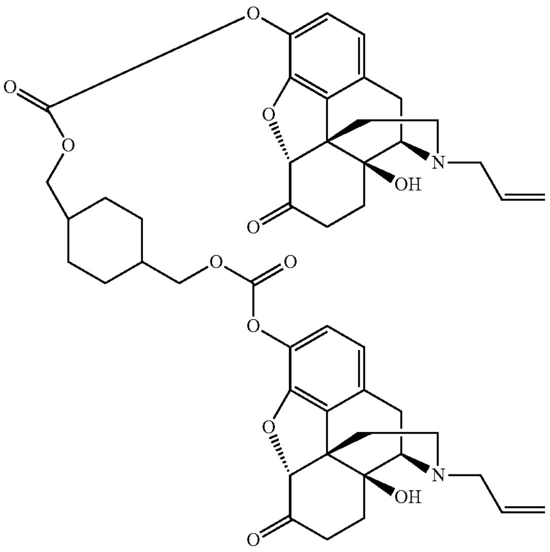 [SMILES: C=CCN1CC[C@]23c4c5ccc(OC(=O)OCC6CCC(COC(=O)Oc7ccc8c9c7O[C@H]7C(=O)CC[C@@]%10(O)[C@@H](C8)N(CC=C)CC[C@]97%10)CC6)c4O[C@H]2C(=O)CC[C@@]3(O)[C@H]1C5]

To a solution of cyclohexanedimethanol bis(4-nitrophenyl carbonate) (1.00 g, 2.11 mmol, 1.00 eq) and naloxone hydrochloride dihydrate (1.81 g, 4.53 mmol, 2.15 eq) in DMF (5 mL) was added diisopropylethylamine (1.63 g, 12.6 mmol, 6.00 eq) and 4-(dimethylamino)pyridine (25.7 mg, 211 umol) at 0° C., then stirred at 20° C. for 12 h. The reaction mixture was poured into water (50 mL), extracted with ethyl acetate (2×50 mL), the organic layer was washed with brine (3×50 mL), dried over $Na_2SO_4$, filtered and concentrated to give a residue. The residue was purified by prep-HPLC (column: Agela DuraShell C18 250*70 mm*10 um; mobile phase: [water (0.05% $NH_3H_2O$+10 mM $NH_4HCO_3$)-ACN]; B %: 68%-88%, 20 min) to give the product (1.00 g, 55% yield) as a light yellow solid. Melting point: 126° C. HPLC (Method 2) retention time: 8.3 min, ESI MS+ Found, $C_{48}H_{55}N_2O_{10}^+$ Mass: 851.38 $^1$H NMR (400 MHz, DMSO) δ 6.96 (d, J=8.33 Hz, 2H) 6.75 (d, J=8.11 Hz, 2H) 5.86 (ddt, J=16.96, 10.39, 6.17, 6.17 Hz, 2H) 5.25 (br d, J=17.32 Hz, 2H) 5.15 (br d, J=10.52 Hz, 2H) 5.08 (s, 2H) 4.96 (s, 2H) 3.99-4.18 (m, 4H) 3.07-3.22 (m, 6H) 2.86-3.02 (m, 4H) 2.52-2.65 (m, 4H) 2.32-2.45 (m, 2H) 2.10 (br d, J=14.03 Hz, 2H) 1.95 (td, J=12.06, 3.51 Hz, 2H) 1.76 (br d, J=8.11 Hz, 6H) 1.64 (br s, 2H) 1.37-1.56 (m, 4H) 1.28 (br d, J=10.74 Hz, 2H) 1.03 (br t, I=8.33 Hz, 2H).

Chemical Synthesis Example 7 bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) decanedioate (Naltrexone-Seb-Naltrexone, Compound 6)

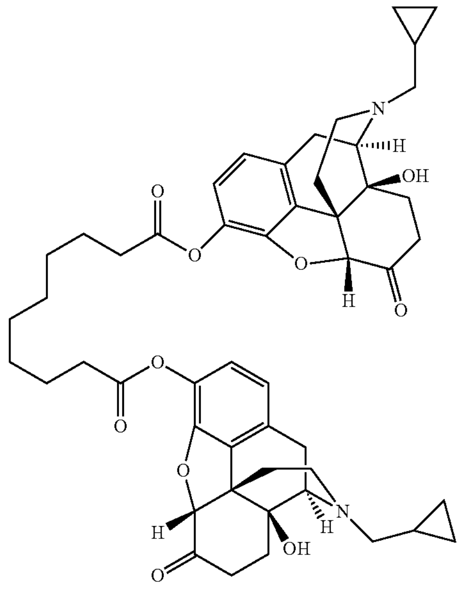 [SMILES: O=C(CCCCCCCCC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314]

To a stirred solution of naltrexone hydrochloride (378 mg, 1.00 mmol) in dry DCM (50 mL) under nitrogen was added 4-(dimethylamino)pyridine (244 mg, 2.0 mmol), sebacic acid (101 mg, 0.50 mmol) and N-(3-Dimethylaminopropyl)-N'-ethylcarbodiimide hydrochloride (383 mg, 2.00 mmol) and the mixture was stirred overnight. The mixture was concentrated onto 2 g reverse phase silica. Purification was performed by reverse phase automated chromatography (aqueous-MeCN gradient). Product containing fractions were combined and concentrated to give the product as an off-white solid (294 mg, 69%). Melting point: 86° C. HPLC (Method 2) retention time: 8.9 min, ESI MS+ Found, $C_{50}H_{61}N_2O_{10}^+$ Mass: 849.43 $^1$H NMR (400 MHz, DMSO) δ 6.82 (d, J=8.2 Hz, 2H), 6.71 (d, J=8.2 Hz, 2H), 5.14 (s, 2H), 4.91 (s, 2H), 3.17 (d, J=5.6 Hz, 2H), 3.09 (s, 2H), 3.04 (s, 2H), 2.97-2.84 (m, 4H), 2.67 (dd, J=12.0, 5.0 Hz, 2H), 2.64-2.51 (m, 8H), 2.44-2.31 (m, 6H), 2.15-2.05 (m, 4H), 1.95 (td, J=12.1, 3.8 Hz, 2H), 1.79 (dd, J=13.6, 4.8 Hz, 2H), 1.63 (p, J=7.2 Hz, 4H), 1.46 (dd, J=14.0, 3.4 Hz, 2H), 1.34 (s, 4H), 0.55-0.42 (m, 4H), 0.14 (t, J=5.6 Hz, 4H).

Chemical Synthesis Example 8 bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) cyclohexane-1,4-dicarboxylate (Naltrexone-1,4-cyclohexyl-Naltrexone, Compound 7)

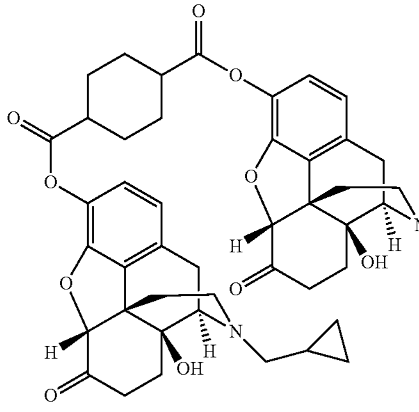

To a stirred solution of naltrexone hydrochloride (378 mg, 1.00 mmol) in dry DCM (50 mL) under nitrogen was added 4-(dimethylamino)pyridine (244 mg, 2.0 mmol), 1,4-cyclohexanedicarboxylic acid (86 mg, 0.50 mmol) and N-(3-dimethylaminopropyl)-N'-ethylcarbodiimide hydrochloride (383 mg, 2.00 mmol) and the mixture was stirred overnight. The mixture was concentrated onto 2 g reverse phase silica. Purification was performed by reverse phase automated chromatography (aqueous-MeCN gradient). Product containing fractions were combined and concentrated to give the product as an off-white solid (260 mg, 63%). Melting point: 145° C. HPLC (Method 2) retention time: 8.0 min, ESI MS+ Found, $C_{48}H_{55}N_2O_{10}^+$ Mass: 819.39 $^1$H NMR (400 MHz, DMSO) δ 6.83 (dd, J=8.2, 1.9 Hz, 2H), 6.72 (dd, J=8.3, 2.2 Hz, 2H), 5.15 (s, 2H), 4.93 (d, J=5.8 Hz, 2H), 3.17 (d, J=5.5 Hz, 2H), 3.09 (s, 1H), 3.05 (s, 1H), 2.94 (s, 1H), 2.89 (dd, J=14.3, 5.0 Hz, 2H), 2.72-2.59 (m, 3H), 2.57 (d, J=5.9 Hz, 1H), 2.38 (tt, J=11.0, 6.2 Hz, 6H), 2.17-2.09 (m, 2H), 2.07 (s, 3H), 2.01-1.91 (m, 5H), 1.89-1.75 (m, 4H), 1.58 (s, 1H), 1.45 (t, J=14.2 Hz, 2H), 1.30 (d, J=12.1 Hz, 2H), 0.87 (q, J=7.3 Hz, 2H), 0.55-0.43 (m, 4H), 0.19-0.09 (m, 4H).

Chemical Synthesis Example 9 bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) terephthalate (Naltrexone-1,4-terephthalate-Naltrexone, Compound 8)

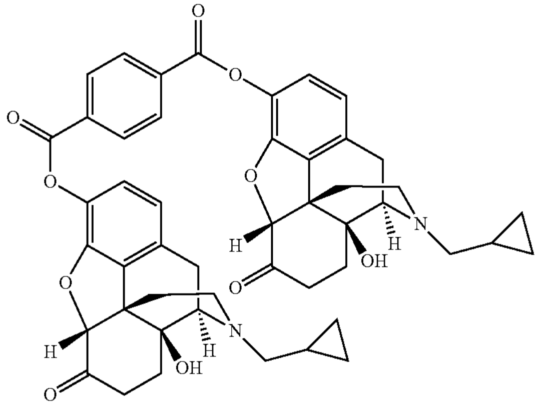 [SMILES: O=C(Oc1ccc2c3c1O[C@H]1C(=O)CC[C@@]4(O)[C@@H](C2)N(CC2CC2)CC[C@]314)c1ccc(C(=O)Oc2ccc3c4c2O[C@H]2C(=O)CC[C@@]5(O)[C@@H](C3)N(CC3CC3)CC[C@]425)cc1]

To a stirred solution of naltrexone hydrochloride (378 mg, 1.00 mmol) in dry DCM (50 mL) under nitrogen was added 4-(dimethylamino)pyridine (244 mg, 2.0 mmol), terephthalic acid (84 mg, 0.50 mmol) and N-(3-dimethylaminopropyl)-N'-ethylcarbodiimide hydrochloride (383 mg, 2.00 mmol) and the mixture was stirred overnight. The mixture was concentrated onto 2 g reverse phase silica. Purification was performed by reverse phase automated chromatography (aqueous-MeCN gradient). Product containing fractions were combined and concentrated to give the product as an off-white solid (180 mg, 44%). Melting point: 240° C. HPLC (Method 2) retention time: 8.9 min, ESI MS+ Found, $C_{48}H_{49}N_2O_{10}^+$ Mass: 813.34 $^1$H NMR (400 MHz, DMSO) δ 8.33 (d, J=2.2 Hz, 4H), 7.11-7.04 (m, 2H), 6.81 (d, J=8.0 Hz, 2H), 5.18 (s, 2H), 4.97 (d, J=2.2 Hz, 2H), 3.24-3.18 (m, 2H), 3.15 (s, 1H), 3.10 (s, 1H), 2.94 (d, J=2.2 Hz, 4H), 2.75-2.60 (m, 2H), 2.42 (d, J=6.9 Hz, 6H), 2.18-2.05 (m, 4H), 2.01 (t, J=11.7 Hz, 2H), 1.83 (d, J=13.2 Hz, 2H), 1.50 (t, J=13.8 Hz, 2H), 1.37 (d, J=12.5 Hz, 2H), 0.51 (d, J=8.1 Hz, 4H), 0.16 (d, J=5.0 Hz, 4H).

Chemical Synthesis Example 10 bis((4R,4aS,7aR,12bS)-3-(cyclopropylmethyl)-4a-hydroxy-7-oxo-2,3,4,4a,5,6,7,7a-octahydro-1H-4,12-methanobenzofuro[3,2-e]isoquinolin-9-yl) tetradecanedioate (Naltrexone-dodecane-Naltrexone, Compound 9)

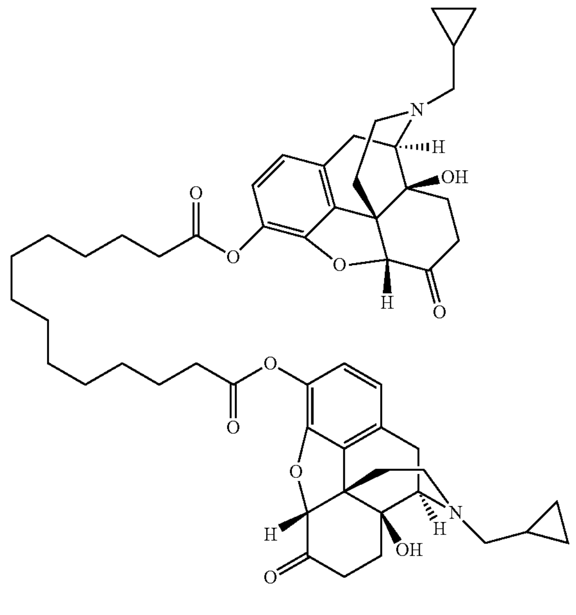 [SMILES: O=C(CCCCCCCCCCCCC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314]

To a stirred solution of naltrexone hydrochloride (378 mg, 1.00 mmol) in dry DCM (50 mL) under nitrogen was added 4-(dimethylamino)pyridine (244 mg, 2.0 mmol), 1,12-dodecanedicarboxylic acid (129 mg, 0.50 mmol) and N-(3-dimethylaminopropyl)-N'-ethylcarbodiimide hydrochloride (383 mg, 2.00 mmol) and the mixture was stirred overnight. The mixture was concentrated onto 2 g reverse phase silica. Purification was performed by reverse phase automated chromatography (aqueous-MeCN gradient). Product containing fractions were combined and concentrated to give the product as an off-white solid (248 mg, 55%). Melting point: 73° C. HPLC (Method 2) retention time: 12.9 min, ESI MS+ Found, $C_{54}H_{69}N_2O_{10}^+$ Mass: 905.50 $^1$H NMR (400 MHz, DMSO) δ 6.81 (d, J=8.2 Hz, 2H), 6.71 (d, J=8.3 Hz, 2H), 5.14 (s, 2H), 4.90 (s, 2H), 3.17 (d, J=5.6 Hz, 2H), 3.09 (s, 1H), 3.04 (s, 1H), 2.97-2.85 (m, 2H), 2.67 (dd, J=12.0, 4.9 Hz, 2H), 2.64-2.50 (m, 6H), 2.44-2.31 (m, 6H), 2.10 (dt, J=14.1, 3.2 Hz, 2H), 1.96 (td, J=12.1, 3.8 Hz, 2H), 1.79 (dt, J=13.2, 4.2 Hz, 2H), 1.61 (p, J=7.3 Hz, 4H), 1.45 (td, J=13.9, 3.3 Hz, 2H), 1.39-1.21 (m, 18H), 0.92-0.84 (m, 2H), 0.55-0.42 (m, 4H), 0.14 (p, J=6.4 Hz, 4H).

Chemical Synthesis Example 11 bis((4R,4aS,7aR,12bS)-3-(cyclopropylmethyl)-4a-hydroxy-7-oxo-2,3,4,4a,5,6,7,7a-octohydro-1H-4,12-methanobenzofuro[3,2-e]isoquinolin-9-yl) 3-ethyl-3-methylpentonedioate (Naltrexone-3-ethyl-3-methylglutaric acid-Naltrexone, Compound 10)

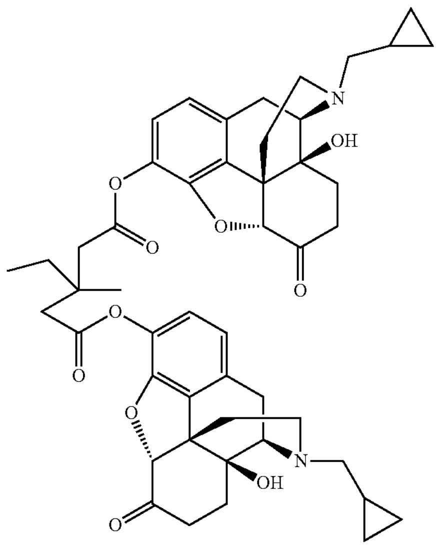 [SMILES: CCC(C)(CC(=O)Oc1ccc2c3c1O[C@H]1C(=O)CC[C@@]4(O)[C@@H](C2)N(CC2CC2)CC[C@]314)CC(=O)Oc1ccc2c3c1O[C@H]1C(=O)CC[C@@]4(O)[C@@H](C2)N(CC2CC2)CC[C@]314]

To a stirred solution of naltrexone hydrochloride (378 mg, 1.00 mmol) in dry DCM (50 mL) under nitrogen was added 4-(dimethylamino)pyridine (244 mg, 2.0 mmol), 3-Ethyl-3-methylglutaric acid (87 mg, 0.50 mmol) and N-(3-Dimethylaminopropyl)-N'-ethylcarbodiimide hydrochloride (383 mg, 2.00 mmol) and the mixture was stirred overnight. The mixture was concentrated onto 2 g reverse phase silica. Purification was performed by reverse phase automated chromatography (aqueous-MeCN gradient). Product containing fractions were combined and concentrated to give the product as an off-white solid (157 mg, 38%). Melting point: 103° C. HPLC (Method 2) retention time: 8.8 min, ESI MS+ Found, $C_{48}H_{57}N_2O_{10}$+ Mass: 821.40 $^1$H NMR (400 MHz, DMSO) δ 6.96-6.89 (m, 2H), 6.83 (d, J=8.2 Hz, 2H), 5.26 (s, 1H), 5.04 (d, J=2.3 Hz, 2H), 3.28 (d, J=5.6 Hz, 2H), 3.21 (s, 1H), 3.16 (s, 1H), 3.08-2.96 (m, 3H), 2.80 (d, J=16.3 Hz, 6H), 2.71 (dd, J=19.0, 5.9 Hz, 2H), 2.48 (s, 4H), 2.21 (dd, J=12.6, 2.5 Hz, 3H), 2.07 (t, J=12.2 Hz, 2H), 1.90 (d, J=13.4 Hz, 2H), 1.74 (d, J=8.0 Hz, 2H), 1.56 (t, J=13.9 Hz, 2H), 1.43 (d, J=12.7 Hz, 2H), 1.33 (s, 3H), 1.25 (d, J=2.3 Hz, 2H), 1.09-0.94 (m, 4H), 0.60 (d, J=8.1 Hz, 4H), 0.25 (d, J=4.9 Hz, 4H).

Chemical Synthesis Example 12 bis((4R,4aS,7aR,12bS)-3-(cyclopropylmethyl)-4a-hydroxy-7-oxo-2,3,4,4a,5,6,7,7a-octohydro-1H-4,12-methanobenzofuro[3,2-e]isoquinolin-9-yl) hexane-1,6-diyl bis(carbonate) (Naltrexone-Hex-Naltrexone, Compound 11)

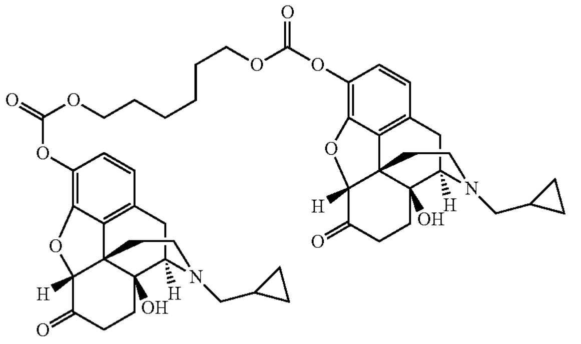 [SMILES: O=C(OCCCCCCOC(=O)Oc1ccc2c3c1O[C@H]1C(=O)CC[C@@]4(O)[C@@H](C2)N(CC2CC2)CC[C@]314)Oc1ccc2c3c1O[C@H]1C(=O)CC[C@@]4(O)[C@@H](C2)N(CC2CC2)CC[C@]314]

To a solution of 1,6-hexanediol (59 mg, 0.50 mmol), triethylamine (348 uL, 2.5 mmol) and 4-(dimethylamino) pyridine (3.0 mg, 0.025 mmol) in DCM (10 mL) was added 4-nitrophenylchloroformate (222 mg, 1.1 mmol) and the mixture stirred for 2d. Naltrexone hydrochloride (567 mg, 1.5 mmol) was added and the mixture stirred overnight. The mixture was concentrated onto 2 g reverse phase silica. Purification was performed by reverse phase automated chromatography (aqueous-MeCN gradient). Product containing fractions were combined and concentrated to give the product as an off-white solid (85 mg, 20%). Melting point: 102° C. HPLC (Method 2) retention time: 8.3 min, ESI MS+ Found, $C_{48}H_{57}N_2O_{12}^+$ Mass: 853.39 $^1H$ NMR (400 MHz, DMSO) δ 6.82 (d, J=8.2 Hz, 2H), 6.71 (d, J=8.2 Hz, 2H), 5.14 (s, 2H), 4.91 (s, 2H), 4.18 (m, 4H), 3.17 (d, J=5.6 Hz, 2H), 3.09 (s, 2H), 3.04 (s, 2H), 2.97-2.84 (m, 4H), 2.67 (dd, J=12.0, 5.0 Hz, 2H), 2.64-2.51 (m, 8H), 2.44-2.31 (m, 6H), 2.15-2.05 (m, 4H), 1.95 (td, J=12.1, 3.8 Hz, 2H), 1.79 (dd, J=13.6, 4.8 Hz, 2H), 1.63 (p, J=7.2 Hz, 4H), 1.46 (dd, J=14.0, 3.4 Hz, 2H), 1.34 (s, 2H), 0.55-0.42 (m, 2H).

Chemical Synthesis Example 13 cyclohexane-1,4-diylbis(methylene) bis((4R,4aS,7aR,12bS)-3-(cyclopropylmethyl)-4a-hydroxy-7-oxo-2,3,4,4a,5,6,7,7a-octohydro-1H-4,12-methanobenzofuro[3,2-e]isoquinolin-9-yl) bis(carbonate) (Naltrexone-CDM-Naltrexone, Compound 12)

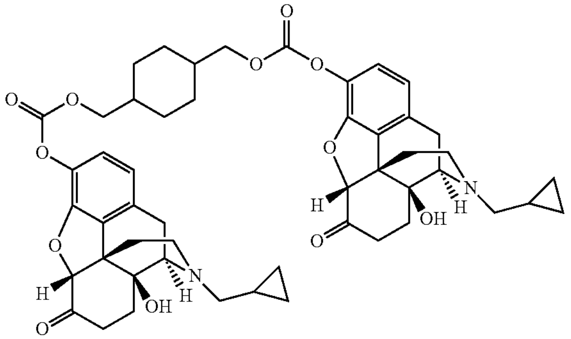 [SMILES: O=C(OCC1CCC(COC(=O)Oc2ccc3c4c2O[C@H]2C(=O)CC[C@@]5(O)[C@@H](C3)N(CC3CC3)CC[C@]425)CC1)Oc1ccc2c3c1O[C@H]1C(=O)CC[C@@]4(O)[C@@H](C2)N(CC2CC2)CC[C@]314]

To a solution of 1,4-cyclohexanedimethanol (72 mg, 0.50 mmol), triethylamine (348 uL, 2.5 mmol) and 4-(dimethylamino)pyridine (3.0 mg, 0.025 mmol) in DCM (10 mL) was added 4-nitrophenylchloroformate (222 mg, 1.1 mmol) and the mixture stirred for 2d. Naltrexone hydrochloride (567 mg, 1.5 mmol) was added and the mixture stirred overnight. The mixture was concentrated onto 2 g reverse phase silica. Purification was performed by reverse phase automated chromatography (aqueous-MeCN gradient). Product containing fractions were combined and concentrated to give the product as an off-white solid (90 mg, 20%). Melting point: 131° C. HPLC (Method 2) retention time: 8.8 min, ESI MS+ Found, $C_{50}H_{59}N_2O_{12}^+$ Mass: 879.41 $^1H$ NMR (400 MHz, DMSO) δ 6.81 (d, J=8.2 Hz, 2H), 6.70 (d, J=8.2 Hz, 2H), 5.14 (s, 2H), 4.91 (s, 2H), 3.98-4.17 (m, 4H) 3.07-3.22 (m, 6H) 2.86-3.02 (m, 4H) 2.52-2.65 (m, 4H) 2.32-2.45 (m, 2H) 2.10 (br d, J=14.03 Hz, 2H) 1.95 (td, J=12.06, 3.51 Hz, 2H) 1.76 (br d, J=8.11 Hz, 6H) 1.64 (br s, 2H) 1.37-1.56 (m, 4H) 1.28 (br d, J=10.74 Hz, 2H) 1.03 (br t, J=8.33 Hz, 2H), 0.87 (q, J=7.3 Hz, 2H), 0.55-0.43 (m, 4H), 0.19-0.09 (m, 4H).

Chemical Synthesis Example 14 bis((4R,4aR,7aR,12bS)-3-methyl-7-oxo-2,3,4,4a,5,6,7,7a-octahydro-1H-4,12-methanobenzofuro[3,2-e]isoquinolin-9-yl) adipate (Hydromorphone-Adip-Hydromorphone, Compound 13)

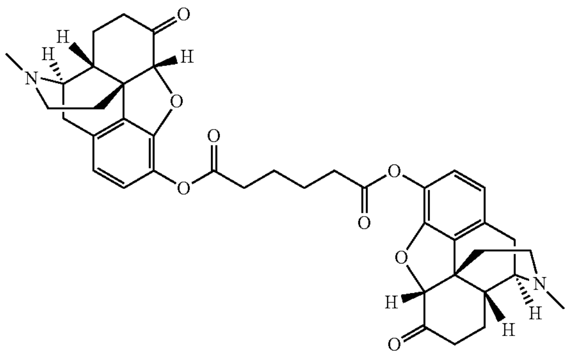

To a fine suspension of hydromorphone free base (456 mg, 1.60 mmol) in anhydrous THF (11.5 mL) was added 60% sodium hydride in mineral oil (64 mg, 1.60 mmol) portionwise and the mixture was stirred for 10 min under nitrogen. Adipoyl chloride (139 mg, 111 μL, 0.76 mmol) was added and stirring was continued overnight under nitrogen. The solution was quenched with saturated aqueous ammonium chloride (50 mL) and extracted with dichloromethane (3×40 mL). The combined organic layers were washed with saturated brine (50 mL), dried (MgSO4) and concentrated to give a white solid (550 mg). Purification was performed by reverse phase automated chromatography (aqueous HCl-MeCN gradient). Product containing fractions were combined, concentrated to ~50% volume, poured into saturated aqueous sodium bicarbonate (50 mL) and extracted with dichloromethane (4×50 mL). The combined organic layers were washed with saturated brine (50 mL), dried ($MgSO_4$) and concentrated to give a white glassy solid (408 mg) containing ~15% hydromorphone. A further purification was performed using reverse phase automated chromatography (aqueous HCl-MeCN gradient). Product containing fractions were combined, concentrated to ~50% volume, poured into saturated aqueous sodium bicarbonate (25 mL) and extracted with dichloromethane (3×20 mL). The combined organic layers were washed with saturated brine (20 mL), dried ($MgSO_4$) and concentrated and concentrated to give the product as a white glassy solid (230 mg, 44%). Melting point: 112° C. HPLC (Method 2) retention time: 8.1 min, ESI MS+ Found, $C_{40}H_{45}N_2O_8^+$ Mass: 681.32 $^1$H NMR (400 MHz, DMSO-d6) δ 6.82 (d, J=8.0 Hz, 2H), 6.71 (d, J=8.0 Hz, 2H), 4.97 (s, 2H), 3.14 (d, J=5.6 Hz, 2H), 2.98 (td, J=14.3, 5.0 Hz, 2H), 2.54 (m, 10H), 2.32 (m, 8H), 2.17 (dt, J=12.6, 2.4 Hz, 2H), 2.03 (td, J=12.1, 3.8 Hz, 2H), 1.95 (td, J=12.1, 3.8 Hz, 2H), 1.74 (m, 6H), 1.48 (td, J=14.0, 3.4 Hz, 2H), 1.00 (m, 2H).

Chemical Synthesis Example 15 bis((4R,4aR,7S,7aR,12bS)-9-methoxy-3-methyl-2,3,4,4a,7,7a-hexahydro-1H-4,12-methanobenzofuro[3,2-e]isoquinolin-7-yl) adipate (Codeine-Adip-Codeine, Compound 14)

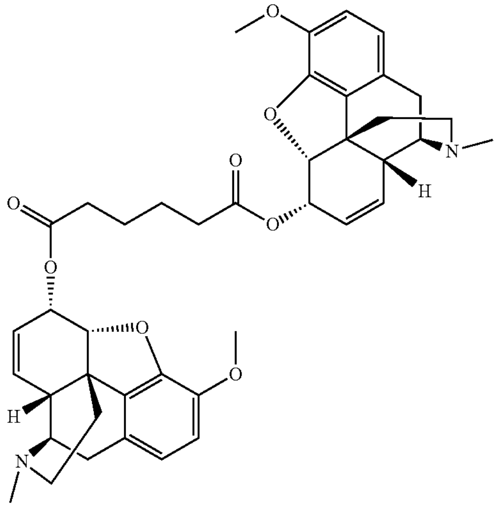

To a stirred solution of codeine free base (440 mg, 1.47 mmol) in anhydrous DMF (50 mL) was added adipic acid (102 mg, 0.70 mmol), N-(3-dimethylaminopropyl)-N'-ethylcarbodiimide hydrochloride (0.55 g, 2.87 mmol) and 4-(dimethylamino)pyridine (385 mg, 3.15 mmol) and the mixture was stirred overnight. The resulting solution was quenched with saturated aqueous ammonium chloride (50 mL) and extracted with dichloromethane (4×50 mL). The combined organic layers were washed with water (4×50 mL), saturated brine (50 mL), dried (MgSO4) and concentrated to give a white solid. Purification was performed by reverse phase automated chromatography (aqueous HCl-MeCN gradient). Product containing fractions were combined, concentrated to approximately 50% volume, poured into saturated aqueous sodium bicarbonate (100 mL) and extracted with dichloromethane (3×80 mL). The combined organic layers were washed with saturated brine (80 mL), dried (MgSO4) and concentrated to give the desired product as a white solid which was further purified by using an automated chromatography system under normal phase conditions (silica column, gradient of 2→30% methanol in dichloromethane) with detection at 254 nm to give the product (280 mg, 56%) as a white solid. Melting point: 209° C. HPLC (Method 2) retention time: 8.3 min, ESI MS+ Found, $C_{42}H_{49}N_2O_8^+$ Mass: 709.35 $^1$H NMR (400 MHz, $CDCl_3$) δ 6.58 (d, J=8.0 Hz, 2H), 6.47 (d, J=8.0 Hz, 2H), 5.56 (m, 2H), 5.35 (m, 2H), 5.10 (m, 2H), 5.01 (d, J=8.0 Hz, 2H), 3.76 (s, 6H), 3.28 (m, 2H), 2.97 (d, J=12.0 Hz, 2H), 2.68 (m, 2H), 2.54 (m, 2H), 2.41 (m, 10H), 2.25 (m, 4H), 2.01 (m, 2H), 1.77 (m, 2H), 1.71 (m, 4H).

Chemical Synthesis Example 16

(ethane-1,2-diylbis(oxy))bis(ethane-2,1-diyl) (25, 2'S)-bis(2-(6-methoxynaphthalen-2-yl)propanoate) (Naproxen-TEG-Naproxen, Compound 15)

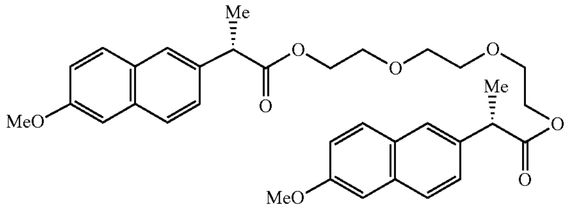 [SMILES: COc1ccc2cc([C@H](C)C(=O)OCCOCCOCCOC(=O)[C@@H](C)c3ccc4cc(OC)ccc4c3)ccc2c1]

To a stirred solution of naproxen (1.15 g, 5.0 mmol) in dry DCM (100 mL) under nitrogen was added 4-(dimethylamino)pyridine (1.22 g, 10.0 mmol), triethyleneglycol (375 mg, 2.5 mmol) and N-(3-dimethylaminopropyl)-N'-ethylcarbodiimide hydrochloride (1.92 g, 10.0 mmol) and the mixture was stirred overnight. The mixture was concentrated onto 5 g normal phase silica. Purification was performed by normal phase automated chromatography (ethyl acetate-hexane). Product containing fractions were combined and concentrated to give the product as a colorless oil (934 mg, 65%). HPLC retention time (Method 3): 39.0 min, ESI MS+ Found, $C_{34}H_{38}NaO_8^+$ Mass: 597.25 $^1$H NMR (400 MHz, DMSO-d6) δ (ppm); 7.75 (m, 6H), 7.38 (d, J=7.2 Hz, 2H), 7.23 (s, 2H), 7.12 (d, J=7.6 Hz, 2H), 4.08 (m, 4H), 3.85 (m, 8H), 3.42 (m, 4H), 3.31 (m, 4H), 1.41 (s, 6H).

Chemical Synthesis Example 17 cyclohexane-1,4-diylbis(methylene) (2S,2S)-bis(2-(6-methoxynaphthalen-2-yl)proponoote), (Naproxen-CDM-Naproxen, Compound 16)

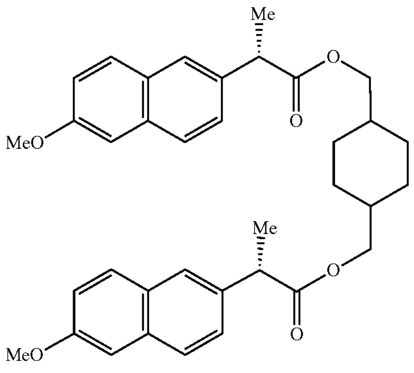 [SMILES: COc1ccc2cc([C@H](C)C(=O)OCC3CCC(COC(=O)[C@@H](C)c4ccc5cc(OC)ccc5c4)CC3)ccc2c1]

To a stirred solution of naproxen (1.15 g, 5.0 mmol) in dry DCM (100 mL) under nitrogen was added 4-(dimethylamino)pyridine (1.22 g, 10.0 mmol), cyclohexanedimethanol (361 mg, 2.5 mmol) and N-(3-dimethylaminopropyl)-N'-ethylcarbodiimide hydrochloride (1.92 g, 10.0 mmol) and the mixture was stirred overnight. The mixture was concentrated onto 5 g reverse phase silica. Purification was performed by reverse phase automated chromatography (water-acetonitrile). Product containing fractions were combined and concentrated to give the product as an off-white solid (881 mg, 62%). Melting point: 125° C. HPLC retention time (Method 3): 41.0 min, ESI MS+ Found, $C_{36}H_{40}NaO_6^+$ Mass: 591.27 $^1$H NMR (400 MHz, $CDCl_3$) δ (ppm); 7.75 (m, 6H), 7.38 (d, J=7.2 Hz, 2H), 7.05 (m, 4H), 3.82 (m, 10H), 1.65 (m, 3H), 1.59 (d, J=7.0 Hz, 6H), 1.43 (m, 2H), 1.31 (m, 2H), 1.22 (m, 2H), 0.81 (m, 3H).

Chemical Synthesis Example 18

(ethane-1,2-diylbis(oxy))bis(ethane-2,1-diyl) bis(2-(5H-chromeno[2,3-b]pyridin-7-yl)proponoote) (Pranoprofen-TEG-Pranoprofen, Compound 17)

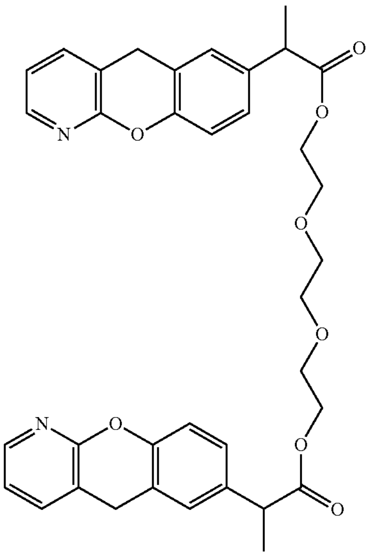 [SMILES: CC(C(=O)OCCOCCOCCOC(=O)C(C)c1ccc2c(c1)Cc1cccnc1O2)c1ccc2c(c1)Cc1cccnc1O2]

To a solution of pranoprofen (1.00 g, 3.93 mmol, 2.00 eq) in DMF (20.0 mL) was added $K_2CO_3$ (543 mg, 3.93 mmol, 2.0 eq) and triethylene glycol di(p-toluenesulfonate) (0.90 g, 1.96 mmol, 1.00 eq). The mixture was stirred at 80° C. for 10 h. The reaction mixture was poured into water (150 mL) and extracted with ethyl acetate (3×20 mL). The combined organic phase was washed with water (3×50.0 mL), dried with anhydrous $Na_2SO_4$, filtered and concentrated in vacuo to give the crude product which was purified by column chromatography ($SiO_2$, Petroleum ether: Ethyl acetate=5:1 to 1:1, TLC, Petroleum ether: Ethyl acetate=0:1, the product $R_f$=0.5) to give compound 5 (543 mg, 38%) as a colorless oil. HPLC retention time (Method 4): 37.1 min; $^1$H NMR (400 MHz, MeOD) δ (ppm) 8.17 (dd, J=4.80, 1.69 Hz, 2H), 7.53 (d, J=7.20 Hz, 2H), 7.14-7.19 (m, 2H), 7.08-7.14 (m, 4H), 7.03 (dd, J=7.20, 4.88 Hz, 2H), 4.17-4.26 (m, 4H), 4.08 (s, 4H), 3.71 (q, J=7.20 Hz, 2H), 3.61 (t, J=4.80 Hz, 4H), 3.50 (s, 4H), 1.64 (s, 4H), 1.50 (s, 3H), 1.48 (s, 3H) LCMS m/z: [M+H]+ Calcd for $C_{36}H_{32}N_2O_8$ 625.2; Found 625.3.

Chemical Synthesis Example 19 dodecane-1,12-diyl (2S,2'S)-bis(2-amino-3-(3,4-dihydroxyphenyl)proponoote) (L-DOPA-Dodec-L-DOPA, Compound 18)

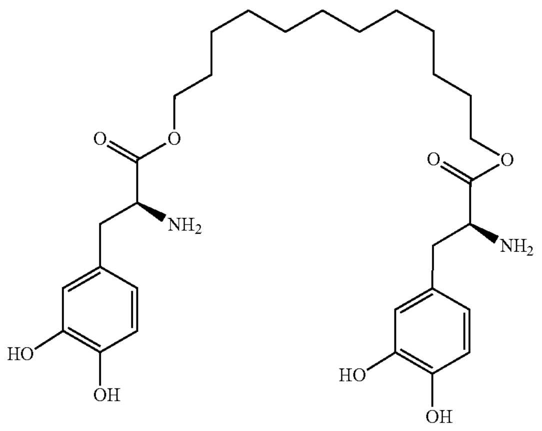 [SMILES: N[C@@H](Cc1ccc(O)c(O)c1)C(=O)OCCCCCCCCCCCCOC(=O)[C@@H](N)Cc1ccc(O)c(O)c1]

Procedure for Preparation of Boc-L-DOPA

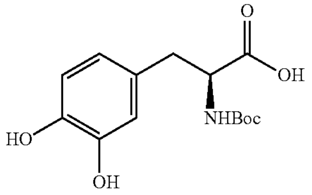 [SMILES: CC(C)(C)OC(=O)N[C@@H](Cc1ccc(O)c(O)c1)C(=O)O]

To a solution of L-DOPA (15.0 g, 76.1 mmol, 1.0 eq.) in dioxane (120 mL) and $H_2O$ (75 mL) was added NaOH (1.00 M, 120 mL, 1.58 eq.) and a solution of $Boc_2O$ (18.1 g, 82.7 mmol, 19 mL, 1.09 eq) in dioxane (20 mL). The mixture was stirred at 25° C. for 10 h. The mixture was concentrated in vacuo. The mixture was adjusted to pH 2 with HCl (1N), and extracted with ethyl acetate (3×200 mL). The combined organic layers were dried over $Na_2SO_4$, filtered and concentrated in vacuo to give Boc-L-DOPA (22 g, crude) as a brown oil which was used in the next step without further purification. LCMS: m/z=593.3 $(2M+1)^+$.

Procedure for Preparation of Tribenzyl-Boc-L-DOPA

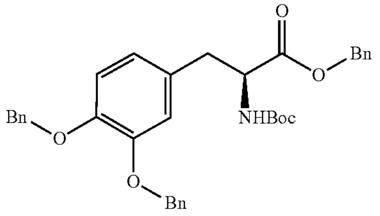 [SMILES: CC(C)(C)OC(=O)N[C@@H](Cc1ccc(OCc2ccccc2)c(OCc2ccccc2)c1)C(=O)OCc1ccccc1]

A solution of Boc-L-DOPA (17.0 g, 57.2 mmol, 1.00 eq), bromomethylbenzene (39.1 g, 229 mmol, 27.2 mL, 4.0 eq) and $K_2CO_3$ (31.6 g, 229 mmol, 4.00 eq) in MeCN (150 mL) was stirred at 80° C. for 10 h. The reaction mixture was filtered and the filtrate was concentrated in vacuo to give the tribenzyl-Boc-L-DOPA product (33.0 g, crude) as a white solid and was used in the next step without further purification.

Procedure for Preparation of Dibenzyl-Boc-L-DOPA

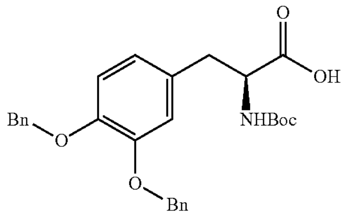 [SMILES: CC(C)(C)OC(=O)N[C@@H](Cc1ccc(OCc2ccccc2)c(OCc2ccccc2)c1)C(=O)O]

A mixture of tribenzyl-Boc-L-DOPA (32.9 g, 58.0 mmol, 1.0 eq) and NaOH (2M, 102 mL, 3.50 eq) in EtOH (150 mL) was stirred at 90° C. for 2 h. The reaction mixture was concentrated in vacuo to remove the EtOH, The mixture was diluted in $H_2O$ (200 mL) and the pH was adjusted to 4 with 1 M HCl. The resulting precipitate was filtered and the cake was pulled dry on the filter to give the product dibenzyl-Boc-L-DOPA (22 g, crude) as a white solid which was used in the next step without further purification. LCMS: m/z=476.2 $(M-1)^-$.

Procedure for Preparation of Dodecane bis(dibenzyl-Boc-L-DOPA) ester

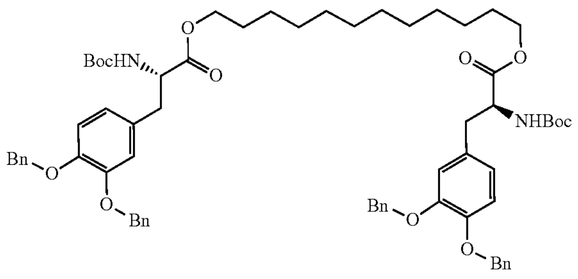 [SMILES: CC(C)(C)OC(=O)N[C@@H](Cc1ccc(OCc2ccccc2)c(OCc2ccccc2)c1)C(=O)OCCCCCCCCCCCCOC(=O)[C@H](Cc1ccc(OCc2ccccc2)c(OCc2ccccc2)c1)NC(=O)OC(C)(C)C]

A solution of dibenzyl-Boc-L-DOPA (8.50 g, 17.8 mmol, 2.4 eq.), dodecane-1,12-diol (1.50 g, 7.41 mmol, 1 eq) and DPTS (436.46 mg, 1.48 mmol, 0.2 eq) in DCM (100 mL) was stirred at 0° C. After all the solids were dissolved DIC (26.2 g, 208 mmol, 32.1 mL, 28.0 eq) was added in one portion and the mixture was stirred at 25° C. for 6 h under $N_2$. The reaction mixture was filtered and the filtrate concentrated in vacuo to give the crude product which was purified by column chromatography ($SiO_2$, Petroleum ether: Ethyl acetate=5:1 to 0:1, TLC, Petroleum ether:Ethyl acetate=5:1, the product $R_f$=0.5) to give the product as a white solid (10 g, crude). $^1H$ NMR: (400 MHz, $CDCl_3$) δ (ppm) 7.41-7.48 (m, 8H), 7.28-7.40 (m, 12H), 6.86 (d, J=8.40 Hz, 2H), 6.76 (d, J=2.00 Hz, 2H), 6.66 (dd, J=8.40, 1.75 Hz, 2H), 5.12 (s, 8H), 4.96 (br d, J=7.60 Hz, 2H), 4.46-4.59 (m, 2H), 4.04 (qt, J=10.80, 6.80 Hz, 4H), 2.91-3.18 (m, 4H), 1.57 (br d, J=6.80 Hz, 4H), 1.39-1.48 (m, 18H), 1.26 (br d, J=5.20 Hz, 12H), 1.15 (d, J=6.40 Hz, 4H).

Procedure for Preparation of Dodecane bis(Boc-L-DOPA) ester

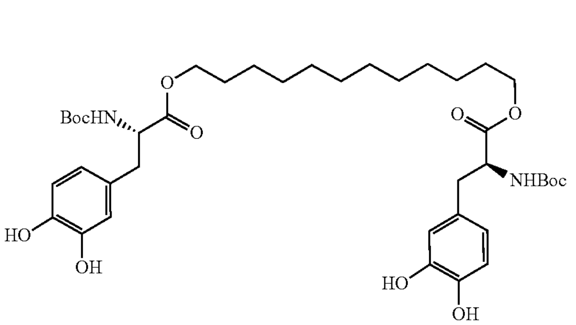 [SMILES: CC(C)(C)OC(=O)N[C@@H](Cc1ccc(O)c(O)c1)C(=O)OCCCCCCCCCCCCOC(=O)[C@H](Cc1ccc(O)c(O)c1)NC(=O)OC(C)(C)C]

A mixture of dodecane bis(dibenzyl-Boc-L-DOPA) ester (10.0 g, 8.92 mmol, 1.00 eq) and Pd/C (2 g, 10% w/w) in THF (100 mL) was degassed and purged with $H_2$ 3 times, and then the mixture was stirred at 20° C. for 6 h under $H_2$ atmosphere (50 psi). The reaction mixture was filtered and concentrated in vacuo to give the product (8.00 g, crude) as a yellow oil used in the next step directly.

Procedure for Preparation of L-DOPA-Dodec-L-DOPA

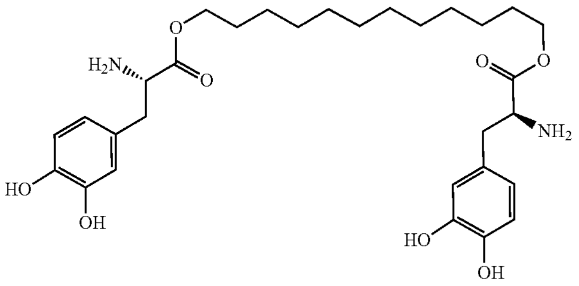 [SMILES: N[C@@H](Cc1ccc(O)c(O)c1)C(=O)OCCCCCCCCCCCCOC(=O)[C@@H](N)Cc1ccc(O)c(O)c1]

A solution of dodecane bis(Boc-L-DOPA) ester (8.00 g, 10.5 mmol, 1.0 eq) and HCl/dioxane (4.00 M, 100 mL, 38.1 eq) in dioxane (20.0 mL) was stirred at 25° C. for 2 h. The reaction mixture was concentrated in vacuo and the pH was adjusted to pH 7 with sat. $NaHCO_3$. The mixture was extracted with dichloromethane (3×100 mL). The combined organic phase was washed with brine (2×100 mL), dried with anhydrous $Na_2SO_4$, filtered and concentrated in vacuo to give the crude product which was purified by reversed phase prep-HPLC to give the product containing soln which was adjusted to pH 7 with sat.$NaHCO_3$. The mixture was extracted with dichloromethane (3×100 mL) and the combined organic phase was washed with brine (2×100 mL), dried with anhydrous $Na_2SO_4$, filtered and concentrated in vacuo to give compound 9 as a light yellow gum (732 mg, 12% yield). HPLC retention time (Method 4): 31.3 min; $^1H$ NMR (400 MHz, MeOD) δ (ppm) 6.69 (d, J=8.00 Hz, 2H), 6.61 (d, J=2.00 Hz, 2H), 6.49 (dd, J=8.00, 2.02 Hz, 2H), 4.06 (td, J=6.40, 1.28 Hz, 4H), 3.62 (t, J=6.40 Hz, 2H), 2.72-2.91 (m, 4H), 1.58 (br t, J=6.40 Hz, 4H), 1.30 (m, 16H). LCMS m/z: [M+H]+ Calcd for $C_{30}H_{45}N_2O_8$ 561.3; Found 561.3.

Chemical Synthesis Example 20 bis((S)-1-(tert-butylamino)-3-((4-morpholino-1,2,5-thiadiazol-3-yl)oxy)propon-2-yl) octanedioate (Timolol-HEX-Timolol, Compound 19)

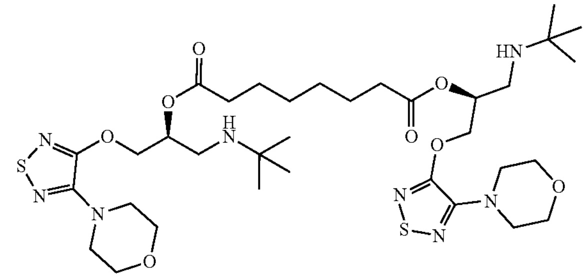 [SMILES: CC(C)(C)NC[C@@H](COc1nsnc1N1CCOCC1)OC(=O)CCCCCCC(=O)O[C@@H](CNC(C)(C)C)COc1nsnc1N1CCOCC1]

General Procedure for Preparation of Timolol Free Base

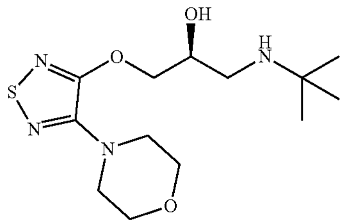 [SMILES: CC(C)(C)NC[C@H](O)COc1nsnc1N1CCOCC1]

To a solution of (S)-timolol maleate (5.00 g, 11.56 mmol) in $H_2O$ (45 mL) was added NaOH (1.39 g, 34.68 mmol) at 0° C. The mixture was stirred at 0° C. for 15 min. TLC (Petroleum ether/Ethyl acetate=0:1, material $R_f$=0.0, product $R_f$=0.3) showed the reaction was completed. The reaction was extracted with DCM (5×30 mL). The combined organic phase was dried over $Na_2SO_4$ and concentrated to give timolol free base (4.8 g, crude) as a colorless oil.

General Procedure for Preparation of Timolol-Hex-Timolol Ester

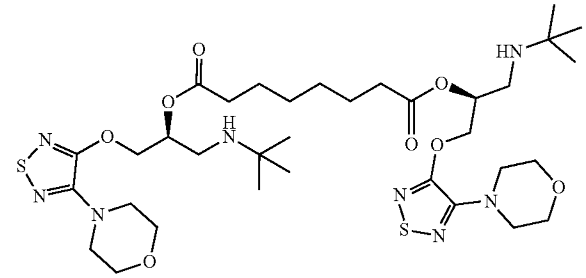 [SMILES: CC(C)(C)NC[C@@H](COc1nsnc1N1CCOCC1)OC(=O)CCCCCCC(=O)O[C@@H](CNC(C)(C)C)COc1nsnc1N1CCOCC1]

To a solution of timolol free base (1.82 g, 5.74 mmol) in DCM (20 mL) was added suberic acid (500 mg, 2.87 mmol), EDCI (2.20 g, 11.48 mmol) and DMAP (701.3 mg, 5.74 mmol) at 0° C., and then stirred at 15° C. for 2 hrs. The reaction mixture was added to water (30 mL), and then extracted with DCM (3×10 mL), combined the organic layer and dried over with $Na_2SO_4$, filtered and concentrated to give a residue. The residue was purified by prep-HPLC (column: Kromasil Eternity XT 250*80 mm*10 um; mobile phase: [water (0.05% ammonia hydroxide v/v)-ACN]; B %:

65%-95%, 20 min) to give the product (1.50 g, 68% yield) as a yellow oil. HPLC retention time (Method 4): 21.0 min; $^1$H NMR (400 MHz, $CDCl_3$) δ 5.16-5.18 (m, 2H), 4.54-4.58 (m, 2H), 4.46-4.50 (m, 2H), 3.70-3.73 (m, 8H), 3.40-3.44 (m, 8H), 2.73-2.74 (m, 4H), 2.20-2.25 (m, 4H), 1.50-1.53 (m, 4H), 1.23-1.27 (m, 4H), 1.07 (s, 18H) LCMS m/z: [M+H]+ Calcd for $C_{34}H_{59}N_8O_8S_2$ 771.39; Found 771.39.

Chemical Synthesis Example 21 bis((S)-1-(tert-butylamino)-3-((4-morpholino-1,2,5-thiadiazol-3-yl)oxy)propon-2-yl) succinate (Timolol-Succ-Timolol, Compound 20)

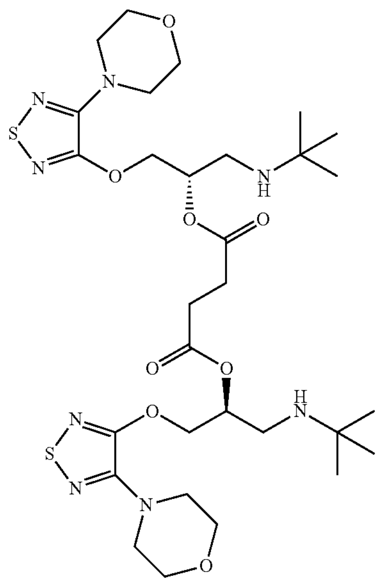 [SMILES: CC(C)(C)NC[C@@H](COc1nsnc1N1CCOCC1)OC(=O)CCC(=O)O[C@@H](CNC(C)(C)C)COc1nsnc1N1CCOCC1]

To a solution of timolol free base (1.82 g, 5.74 mmol) in DCM (20 mL) was added succinic acid (339 mg, 2.87 mmol), EDCI (2.20 g, 11.48 mmol) and DMAP (701 mg, 5.74 mmol) at 0° C., and then stirred at 15° C. for 2 hrs. The reaction mixture was added water (30 mL), and then extracted with DCM (3×10 mL), combined the organic layer and dried over with $Na_2SO_4$, filtered and concentrated onto 5 g reverse phase silica. Purification was performed by reverse phase automated chromatography (water-acetonitrile). Product containing fractions were combined and concentrated to give the product (1.72 g, 60% yield) as a colorless oil. HPLC retention time (Method 4): 30.1 min; $^1$H NMR (400 MHz, $CDCl_3$) δ 5.16-5.18 (m, 2H), 4.54-4.58 (m, 2H), 4.46-4.50 (m, 2H), 3.70-3.73 (m, 8H), 3.40-3.44 (m, 8H), 2.73-2.74 (m, 4H), 2.22 (s, 4H), 1.07 (s, 18H). ESI MS+ m/z: [M+H]+ Calcd for $C_{30}H_{51}N_8O_8S_2$ 715.33; Found 715.33.

Chemical Synthesis Example 22 hexane-1,6-diyl bis(2-((5-bromoquinoxalin-6-yl)amino)-4,5-dihydro-1H-imidazole-1-carboxylate) (Brimonidine-HEX-Brimonidine, Compound 21)

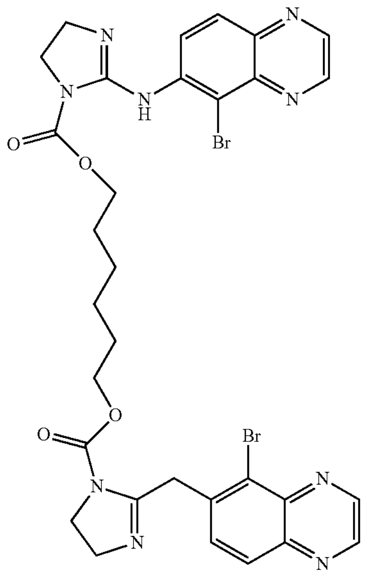 [SMILES: O=C(OCCCCCCOC(=O)N1CCN=C1Nc1ccc2nccnc2c1Br)N1CCN=C1Cc1ccc2nccnc2c1Br]

General Procedure for Preparation of 1,6-hexanediol bis 4-nitrophenylcarbonate

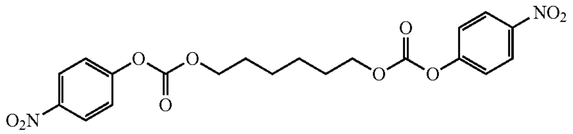 [SMILES: O=C(OCCCCCCOC(=O)Oc1ccc([N+](=O)[O-])cc1)Oc1ccc([N+](=O)[O-])cc1]

To a solution of 1,6-hexanediol (5.05 mL, 5.00 g, 42.3 mmol) in DCM (150 mL) was added pyridine (20.5 mL, 20.1 g, 253.9 mmol) and 4-nitrophenylchloroformate (18.8 g, 93.1 mmol) at 0° C. The mixture was stirred at 0° C. for 10 hr. The reaction was diluted with water (200 mL) and extracted with DCM (2×50 mL). The combined organic phase was dried over $Na_2SO_4$ and concentrated. The residue was purified by column chromatography ($SiO_2$, Petroleum ether/Ethyl acetate=20:1-2:1) to give 1,6-hexanediol bis 4-nitrophenylcarbonate (10.0 g, 53% yield) as a white solid. $^1$H NMR: (400 MHz, $CDCl_3$) δ 8.20-8.23 (m, 4H), 7.19-7.33 (m, 4H), 4.23-4.26 (m, 4H), 1.73-1.76 (m, 4H), 1.44-1.47 (m, 4H).

General Procedure for Preparation of Brimonidine-Hex-Brimonidine Carbamate

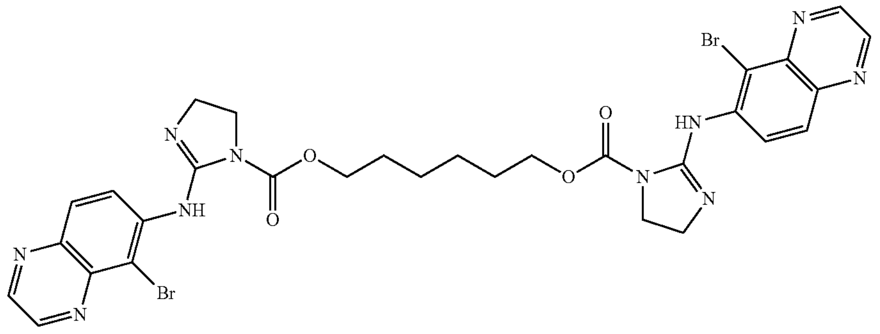 [SMILES: O=C(OCCCCCCOC(=O)N1CCN=C1Nc1ccc2nccnc2c1Br)N1CCN=C1Nc1ccc2nccnc2c1Br]

To a solution of compound 1,6-hexanediol bis(4-nitrophenyl)carbonate (307 mg, 685 umol) and brimonidine (500 mg, 1.7 mmol) in DCM (10 mL) was added DMAP (105 mg, 856 umol). The mixture was stirred at 30° C. for 1 h. The reaction was concentrated and the residue was purified by prep-HPLC (TFA) to give 1 g of TFA salt, the TFA salt was dissolved in MeOH (20 mL), then 30 mL of sat. $Na_2CO_3$ was added, the solid was filtered and dried under reduce pressure to give the product (186 mg, 36%) as a light yellow solid. HPLC retention time (Method 4): 26.7 min; $^1H$ NMR (400 MHz, MeOD) δ 8.93-8.95 (m, 4H), 8.17 (d, J=8.8 Hz, 2H), 7.87 (d, J=8.8 Hz, 2H), 4.35-4.38 (m, 4H), 4.19-4.24 (m, 4H), 3.70-3.74 (m, 4H), 1.77-1.80 (m, 4H), 1.46-1.50 (m, 4H). ESI MS+ m/z: [M+H]+ Calcd for $C_{30}H_{31}Br_2N_{10}O_4$ 753.09; Found 753.09.

Chemical Synthesis Example 23

8-(((((4S,6S)-4-(ethylamino)-6-methyl-7,7-dioxido-5,6-dihydro-4H-thieno[2,3-b]thiopyron-2-yl)sulfonyl)carbamoyl)oxy)octyl (((4S,6S)-4-(ethylamino)-6-methyl-7,7-dioxido-5,6-dihydro-4H-thieno[2,3-b]thiopyron-2-yl)sulfonyl)carbomate (Dorzolamide-Oct-Dorzolamide, Compound 22)

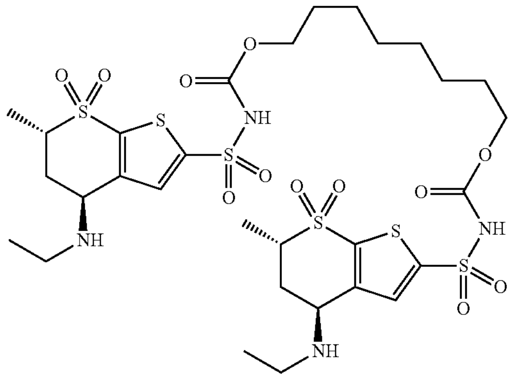 [SMILES: CCN[C@H]1C[C@H](C)S(=O)(=O)c2sc(S(=O)(=O)NC(=O)OCCCCCCCCOC(=O)NS(=O)(=O)c3cc4c(s3)S(=O)(=O)[C@@H](C)C[C@@H]4NCC)cc21]

General Procedure for Preparation of 1,8-octanediol bis(4-nitrophenyl) carbonate

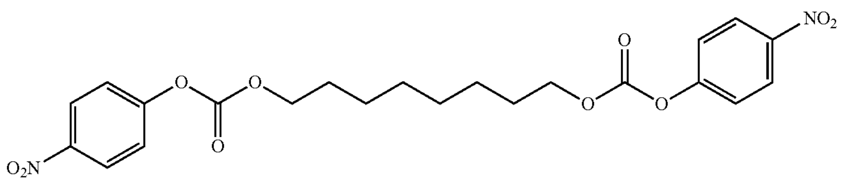 [SMILES: O=C(OCCCCCCCCOC(=O)Oc1ccc([N+](=O)[O-])cc1)Oc1ccc([N+](=O)[O-])cc1]

To a solution of 1,8-octanediol (5.05 mL, 5.00 g, 42.3 mmol) in DCM (150 mL) was added pyridine (16.6 mL, 16.2 g, 205.2 mmol) and 4-nitrophenylchloroformate (15.9 g, 78.6 mmol) at 0° C. for 4 h. The reaction was diluted with water (200 mL) and extracted with DCM (2×50 mL). The combined organic phase was dried over $Na_2SO_4$ and concentrated. The residue was purified by column chromatography ($SiO_2$, Petroleum ether/Ethyl acetate=50:1-5:1) to give 1,8-octanediol bis(4-nitrophenyl) carbonate (10.0 g, 22.3 mmol, 53% yield) as a white solid. $^1H$ NMR (400 MHz, $CDCl_3$) δ 8.19-8.22 (m, 4H), 7.30-7.32 (m, 4H), 4.21-4.24 (m, 4H), 1.68-1.70 (m, 4H), 1.32-1.34 (m, 4H).

General Procedure for Preparation of Dorzolamide-Oct-Dorzolamide Carbamate

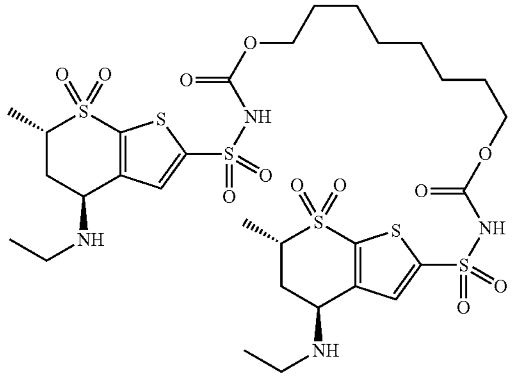 [SMILES: CCN[C@H]1C[C@H](C)S(=O)(=O)c2sc(S(=O)(=O)NC(=O)OCCCCCCCCOC(=O)NS(=O)(=O)c3cc4c(s3)S(=O)(=O)[C@@H](C)C[C@@H]4NCC)cc21]

A mixture of dorzolamide hydrochloride (1.57 g, 4.83 mmol), 1,8-octanediol bis(4-nitrophenyl) carbonate (1.00 g, 2.10 mmol), NaH (420 mg, 10.49 mmol, 60% purity) in DMF (10 mL) was stirred at 20° C. for 2 h under $N_2$ atmosphere. The reaction was purified by prep-HPLC (base condition) twice to give the product (1.00 g, 56%) as a white solid. HPLC retention time (Method 4): 33.4 min; $^1H$ NMR (400 MHz, DMSO-$d_6$) δ 8.84 (br s, 2H), 7.67 (s, 2H), 4.55-4.64 (m, 2H), 3.76-3.97 (m, 2H), 3.72-3.41 (m, 4H), 3.12-3.19 (m, 2H), 3.01-3.02 (m, 2H), 2.58-2.68 (m, 2H), 1.45 (s, 4H), 1.37 (d, J=6.4 Hz, 6H), 1.21-1.23 (m, 18H). LCMS+ m/z: [M+H]+ Calcd for $C_{30}H_{47}N_4O_{12}S_6$ 847.15; Found=847.15.

III. Formation and Evaluation of Processable Conjugates

Example 1: Heat Processing of Compounds

Compounds were formed into pellets by heat molding. Powders of Compound 1-7 and Compounds 9-12 were processed at a temperature from between about 10° C. to 30° C. above their thermal transitions (e.g., glass transition temperature (Tg) for amorphous powders or melting point (Tm) for crystalline powders) of the given compound (e.g., from about 70° C. (Compound 9) to about 220° C. (Compound 2)), and pressed into a cylindrical mold of ~1 mm in height×1 mm in diameter. Light microscopy was used to capture images of the heat-formed pellets.

All compounds tested, except for Compound 2, successfully formed a (e.g., glassy, mostly transparent) pellet and provided mechanical properties that allowed the pellets to be handled without breaking. These pellets had the appropriate processing properties to be tested as articles for drug delivery applications. Compound 2 was yellow upon heating and didn't form a viscous liquid that could be pressed into a pellet. The recovered form of Compound 2 was brittle and did not have mechanical properties that allowed the pellet to be handled without breaking.

Compounds 16, 22, and 23 were also tested for pellet formation using a similar method as compounds 1-7 and 9-12. Compound 16 formed a viscous liquid upon melting and flowed into the heat-mold template but displayed a softened state under ambient conditions and deformed during the process of removal from the mold. The recovered form was soft and tacky and could not be easily handled. Compound 22 and Compound 23 darkened significantly upon heating to melt the powders. Neither compound formed a viscous liquid that could be pressed into a pellet. Compounds that were oils do not have the appropriate physical properties to form pellets and were not tested.

Example 2: Solvent Processing for Compound 1

Compound 1 was formed into a thin film coating on a polymer surface by solvent casting. Compound 1 was dissolved in acetone at 100 mg/ml and 10 μl of the solution was cast onto a Dacron coupon and left to air dry at room temperature overnight. Images of the thin, transparent coating were captured by light microscopy.

IV. Drug Release Evaluation

Example 1: Drug Release from Pellets of Compound 1

Figure 1C:
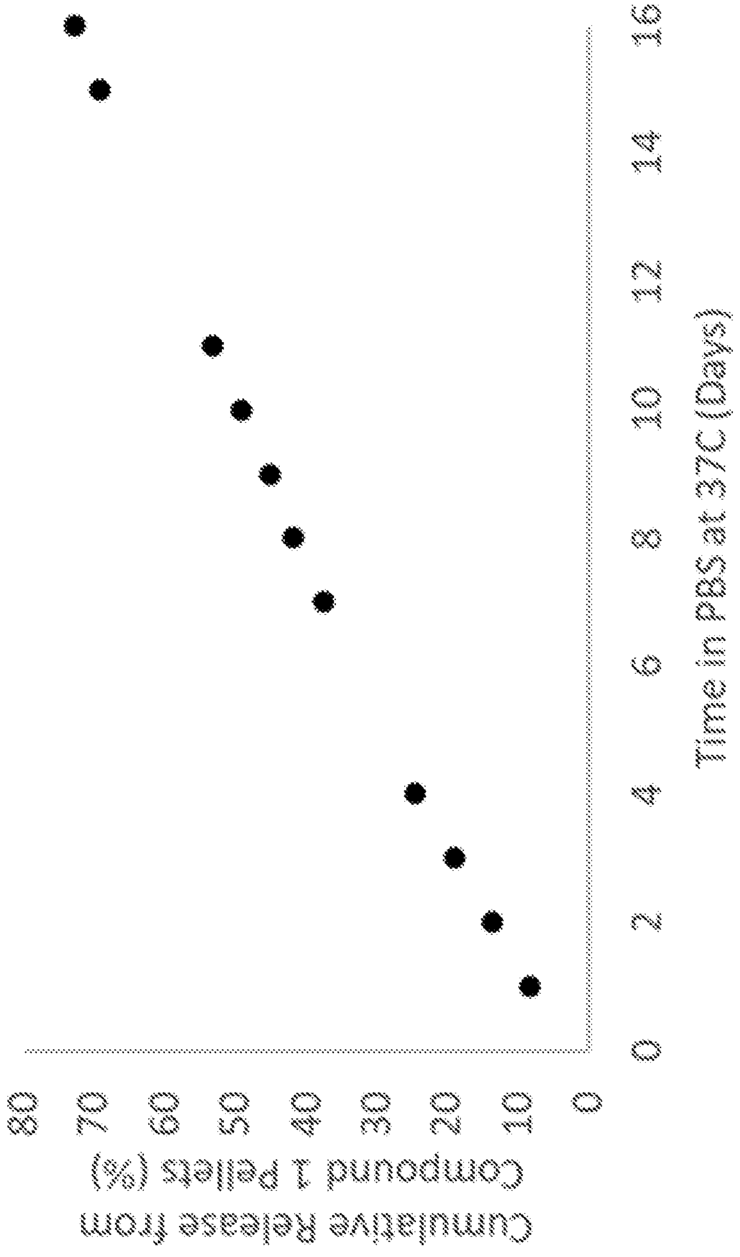
Figure 1D:
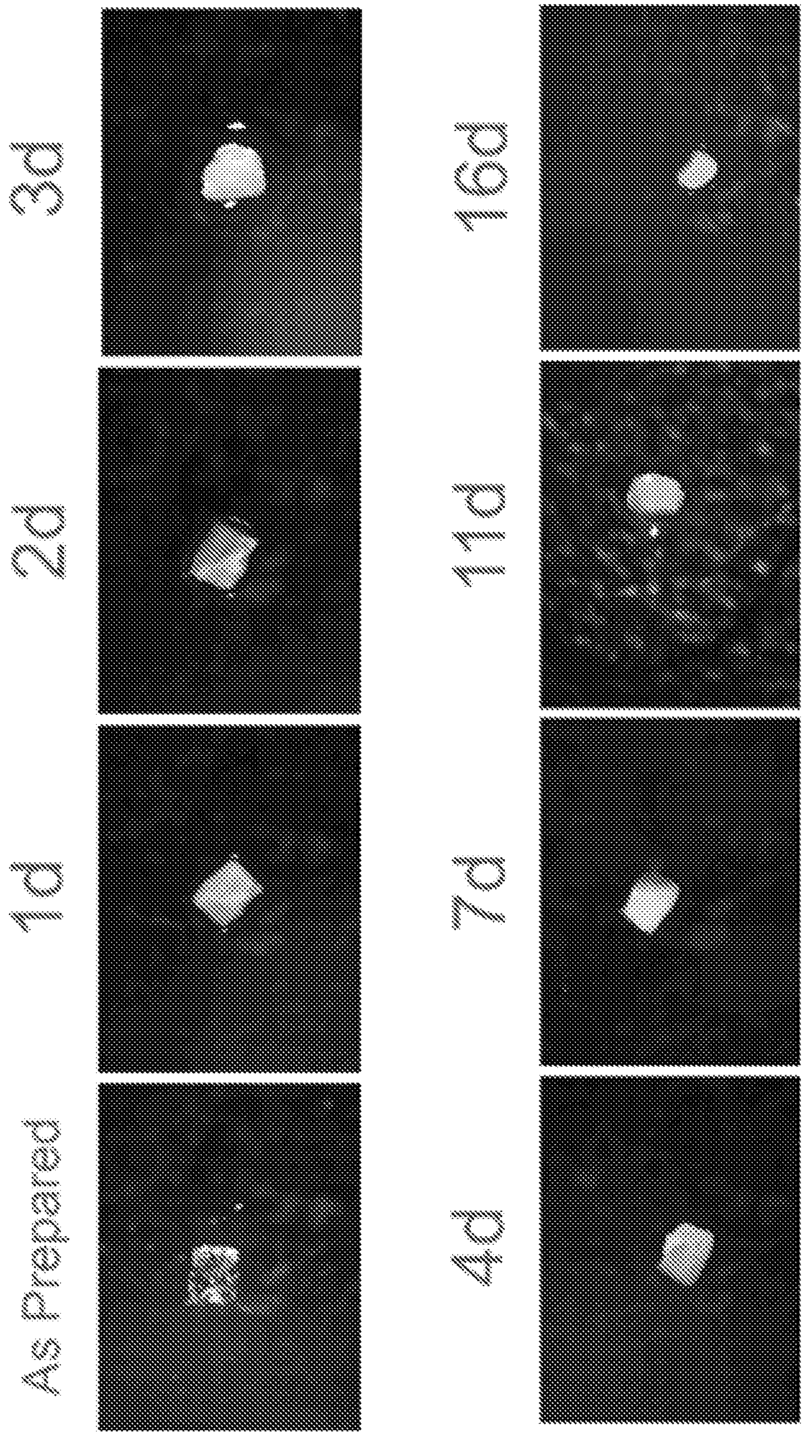
Figure 2A:
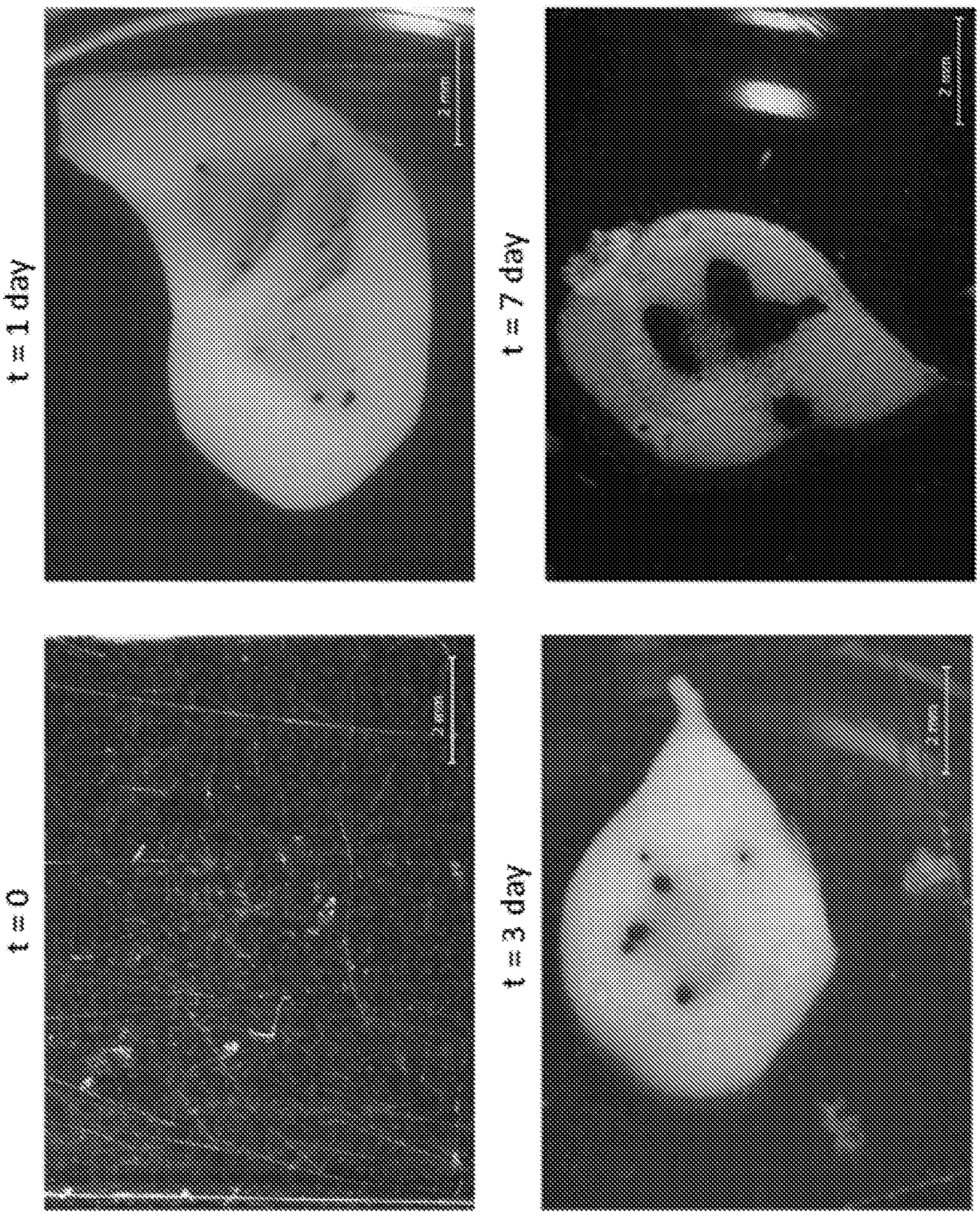
FIG. 2 shows 7-day progression of the surface erosion drug release profile for a surface coated with Compound 1 in fetal bovine serum (FBS) (FIG. 2A and FIG. 2B).
Figure 2B:
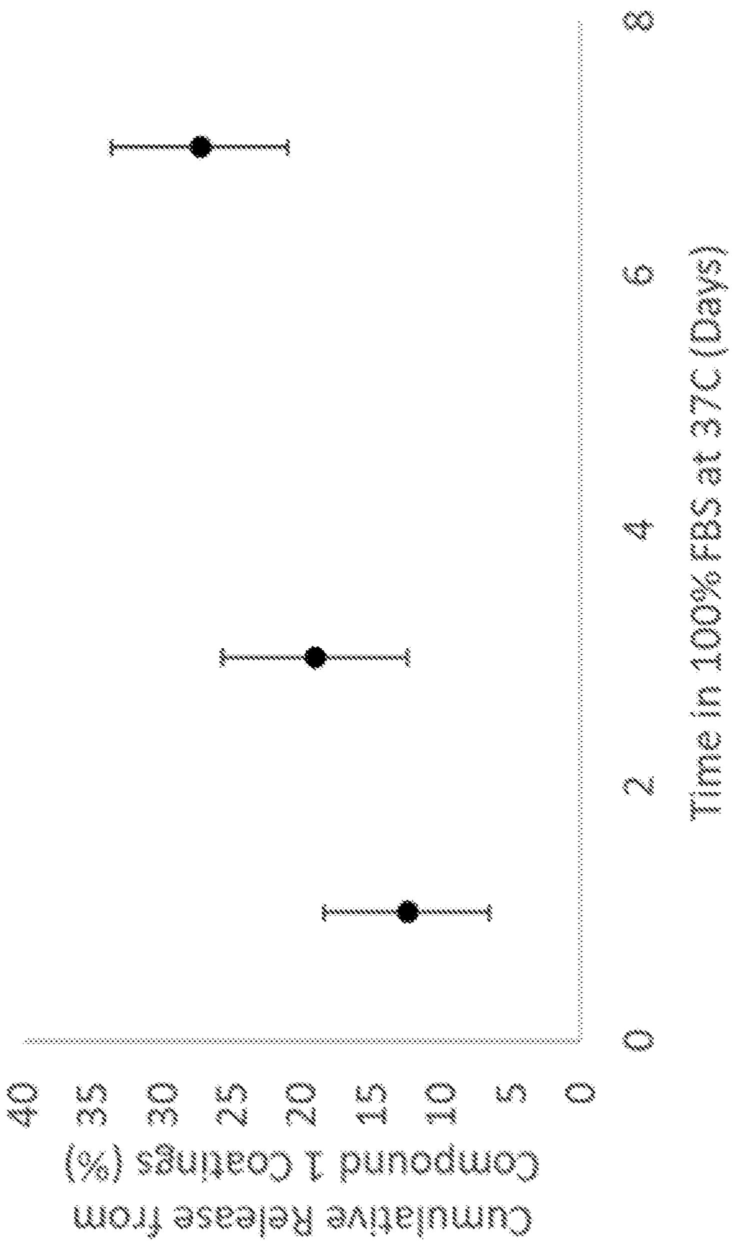

Drug release from heat-molded pellets of Compound 1 (FIG. 1A) was assessed in phosphate buffered saline (PBS). Heat-molded pellets (FIG. 1B) were placed in 20 ml glass vials and 2 ml of release buffer was added. Samples were incubated at 37° C. with constant agitation at 115 rpm. Release buffer was sampled and fully replaced with 2 ml of fresh buffer daily with the exception of days 5, 6, 12, 13, and 14 (FIG. 1C). Samples were analyzed by high performance liquid chromatography (HPLC) to quantify drug products (FIG. 1D). Cumulative release was calculated as a percentage of total mass of starting pellets and was plotted over time.

Example 2: Drug Release from a Polymer Surface Coated with Compound 1

Compound 1-coated Dacron films were placed into 20 mL vials, 2 mL fetal bovine serum (FBS) was added, and the samples were incubated at 37 C. At day 1, 3, and 7, the FBS was removed, proteins were precipitated with the addition of MeCN (2:1 ratio), and the suspension was transferred to a centrifuge tube. The tubes were centrifuged at 10,000 rpm for 6 min and the supernatant was analyzed by HPLC to quantify the release products. A fresh 2 mL of FBS was added and the sample was incubation at 37 C until the next timepoint.

Example 3: Drug Release from Pellets of Compound 3-7 and Compound 9-12

Drug release from heat-molded pellets of Compound 3-7 and Compound 9-12 were assessed in phosphate buffered saline (PBS). Heat-molded pellets were placed in 20 ml glass vials and 2 ml of release buffer was added. Samples were incubated at 37° C. with constant agitation at 115 rpm. Release buffer was sampled and fully replaced with 2 ml of fresh buffer on days 1, 3, 7, 10, and 14. Samples were analyzed by high performance liquid chromatography (HPLC) to quantify drug products. Cumulative release was calculated as a percentage of total mass of starting pellets and was plotted over time.

We claim:

1. A compound having a structure represented by Formula (IID):

Formula (IID)

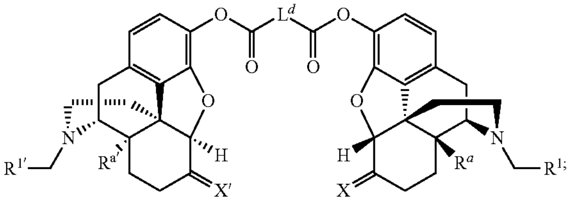

wherein:

$R^1$ and $R^{1'}$ are each independently unsaturated alkyl; or $R^1$ and $R^{1'}$ are each independently cycloalkyl;

$R^a$ and $R^{a'}$ are each independently H or —OH;

$L^d$ is selected from the group consisting of $—(CR_2)_y—$, $—O(CR_2)_yO—$, $—O(CR_2)_y—$, $—(CR_2)_yO—$, and $—O(CH_2CH_2O)_y—$, wherein y is 1-10 and each R is independently selected from the group consisting of H, hydroxyl, halogen, alkyl, or is taken together with another R to form an optionally substituted cycloalkyl; and X and X' are each independently O or $CH_2$, or a pharmaceutically salt thereof.

2. A compound having a structure represented by:

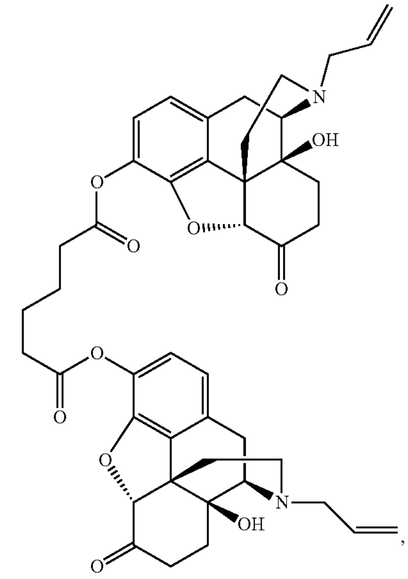

,

-continued

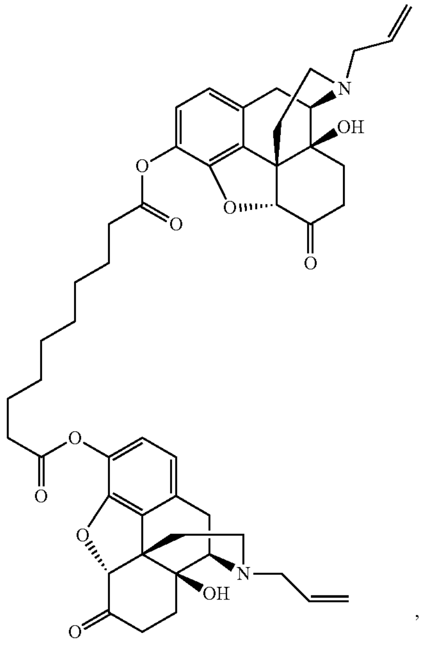

,

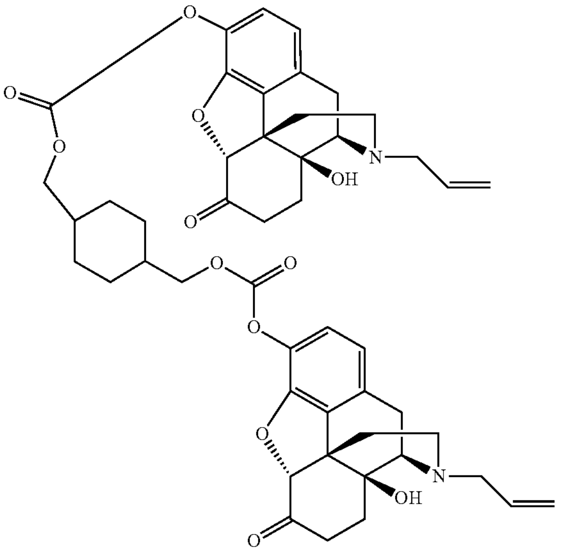

,

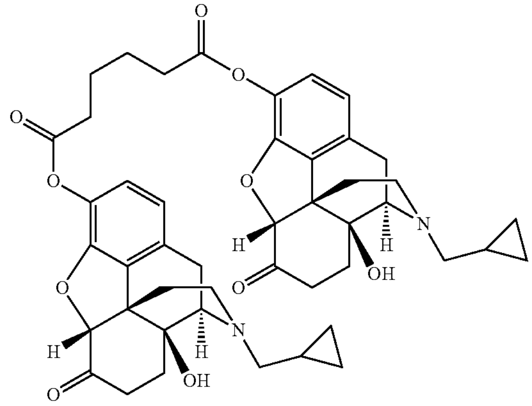

,

-continued
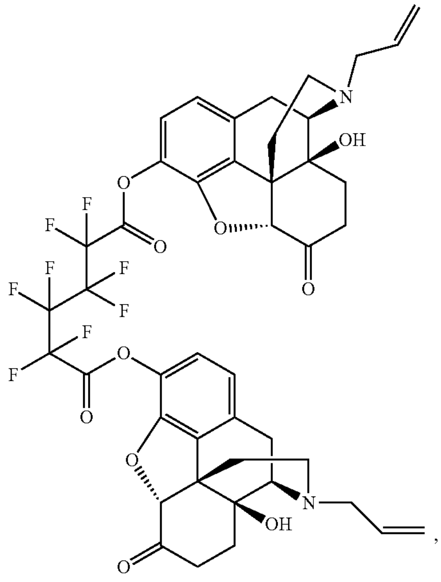
,
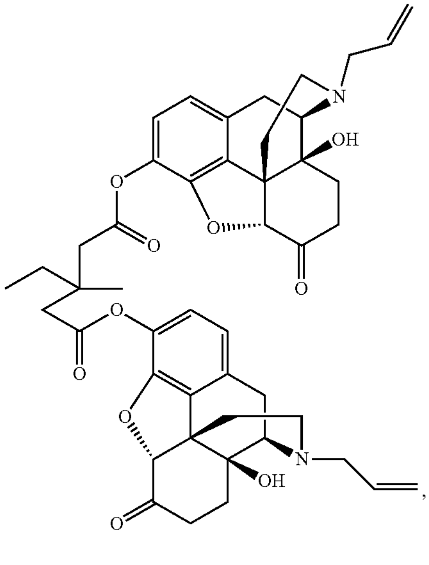
,
-continued
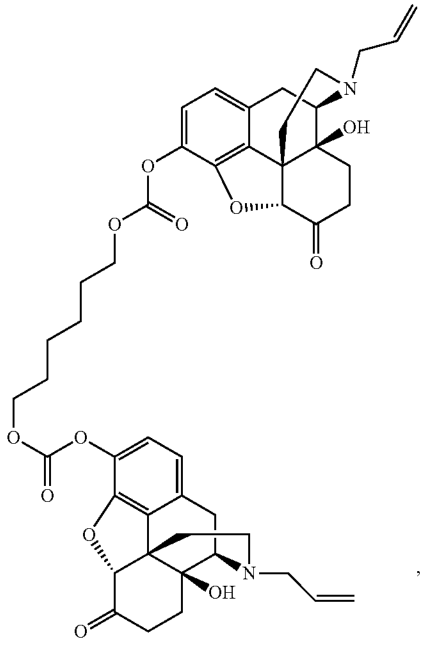
,
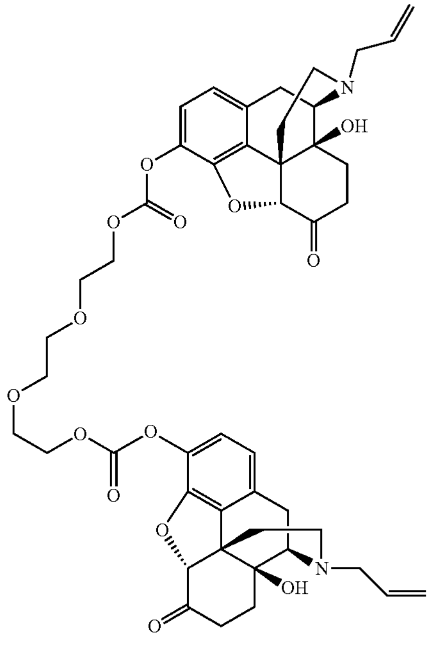
,

-continued
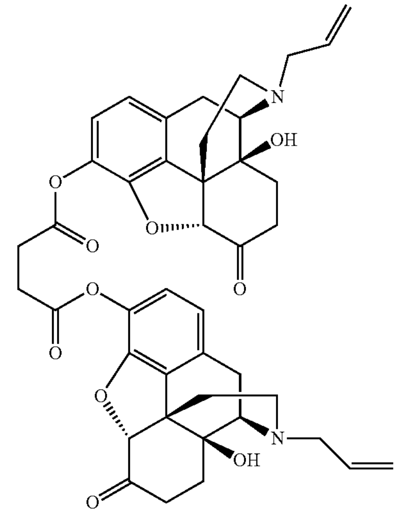
,
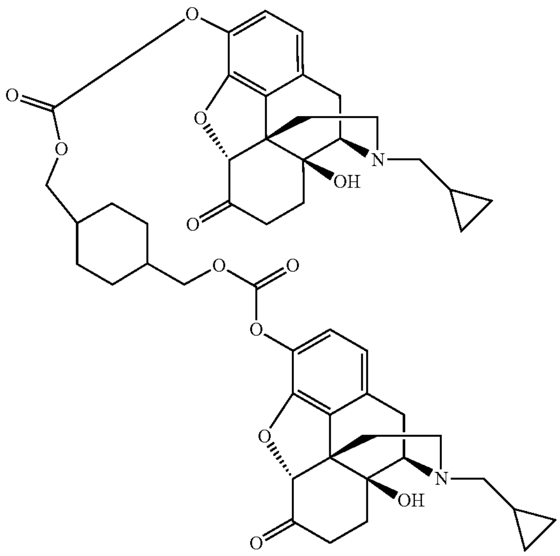
,
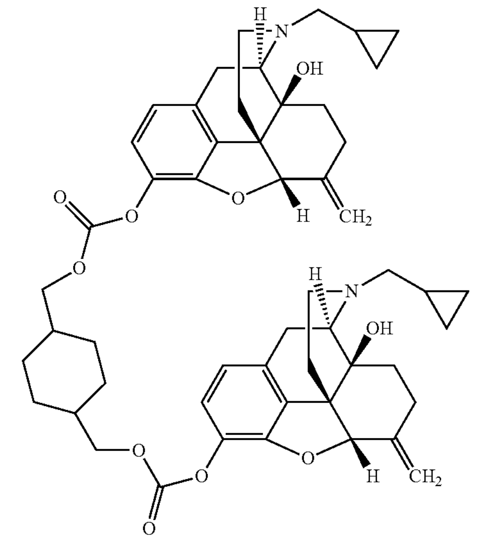
,
-continued
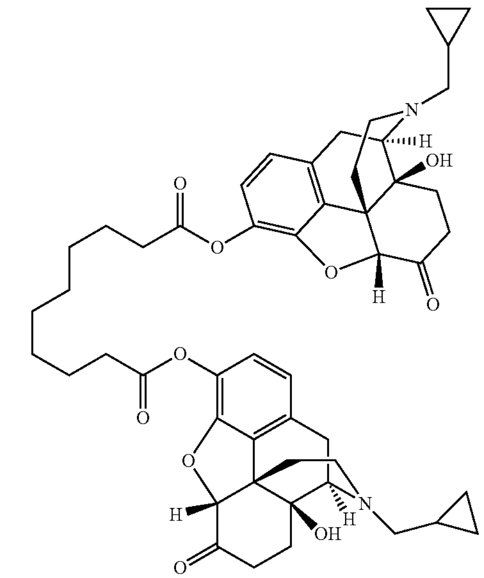
,
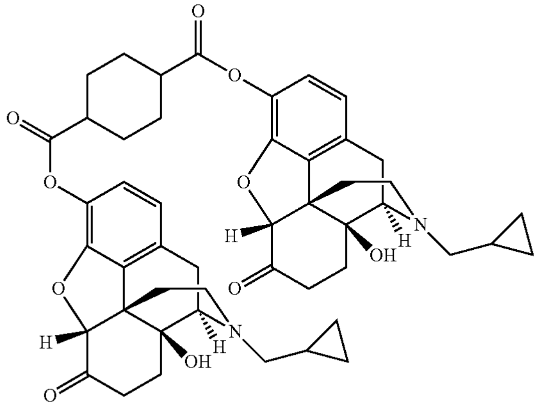
,
,
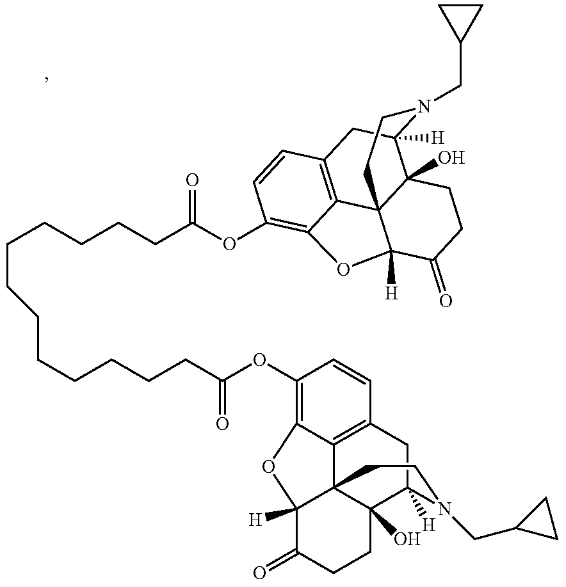
, -continued
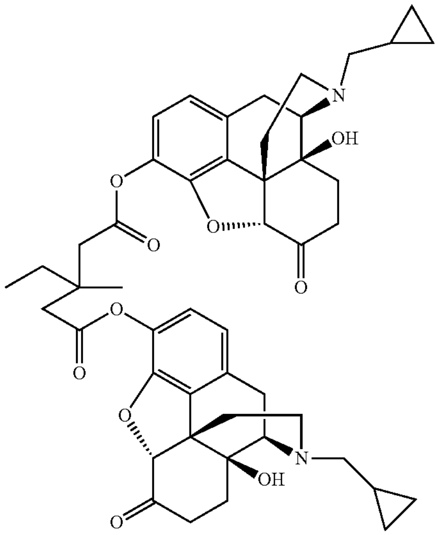
,
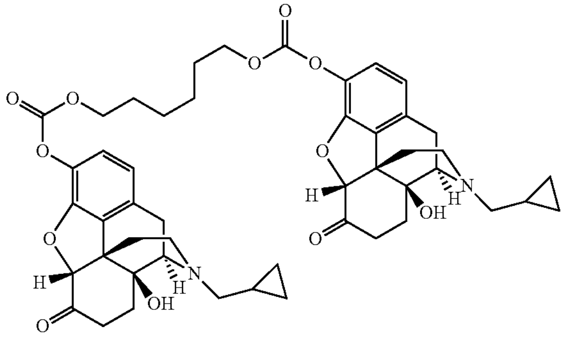
,
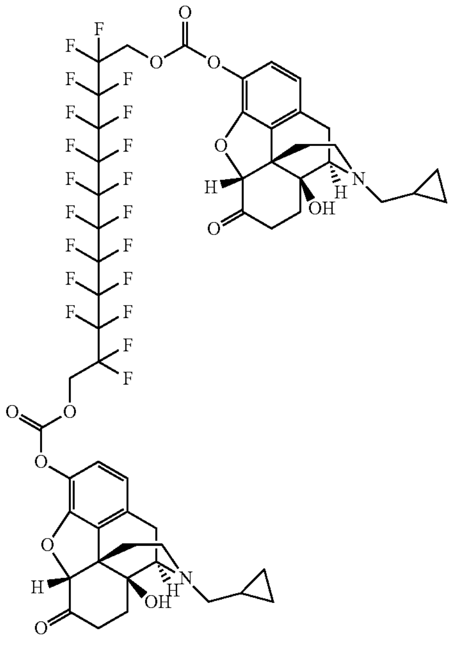
,
-continued
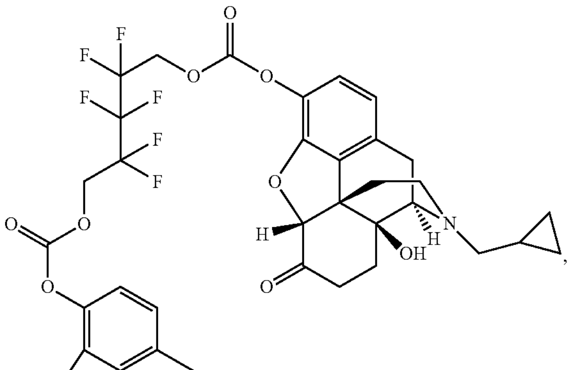
,
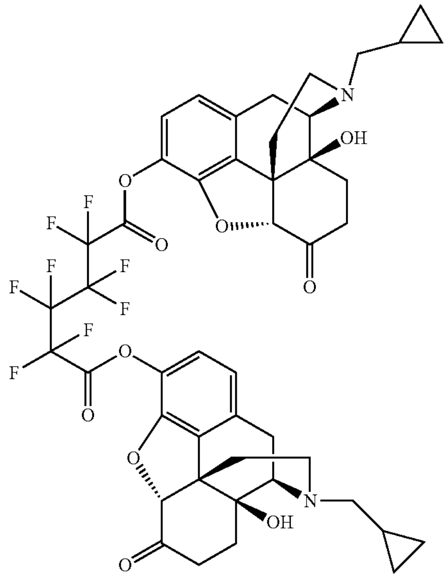
,
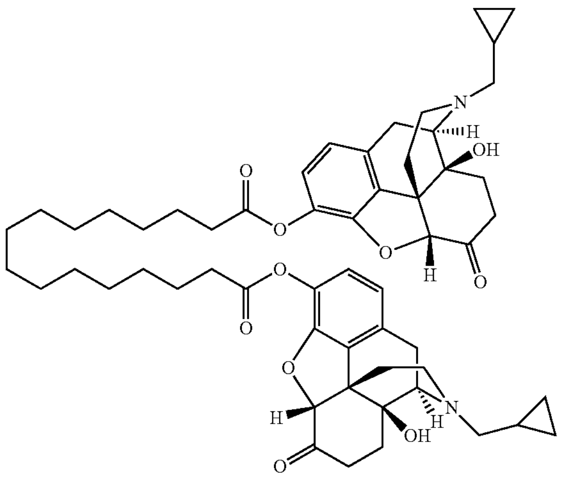
, -continued
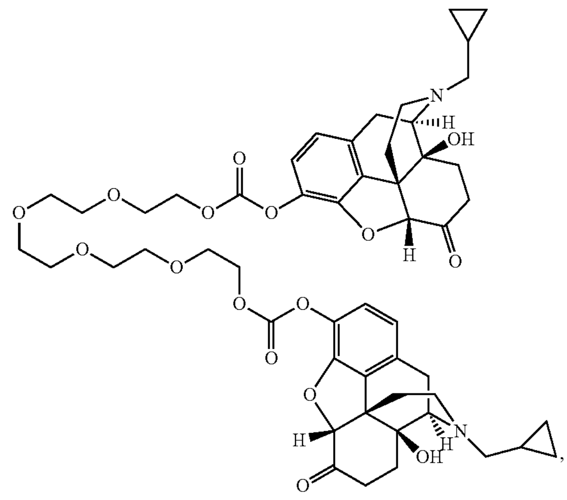
,
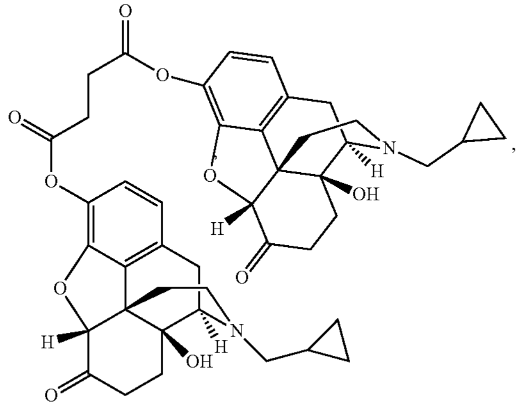
,
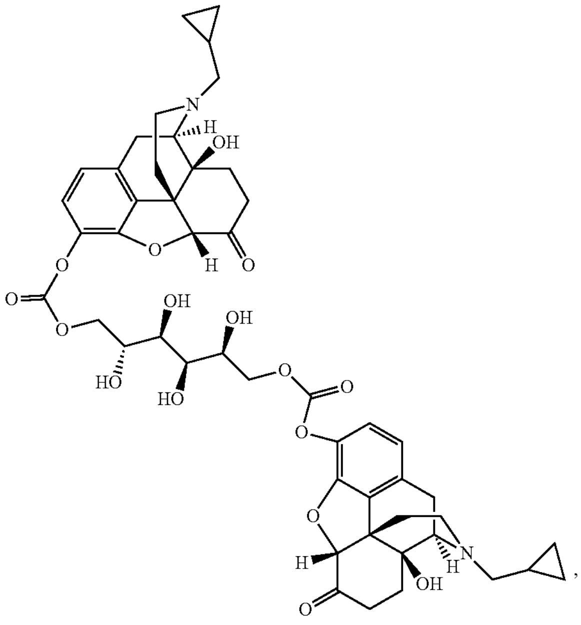
,
-continued
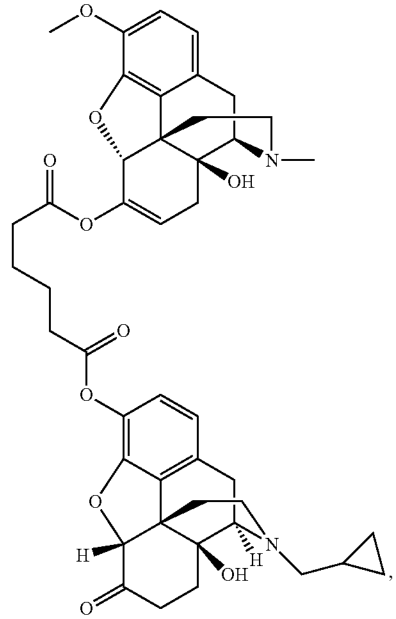
,
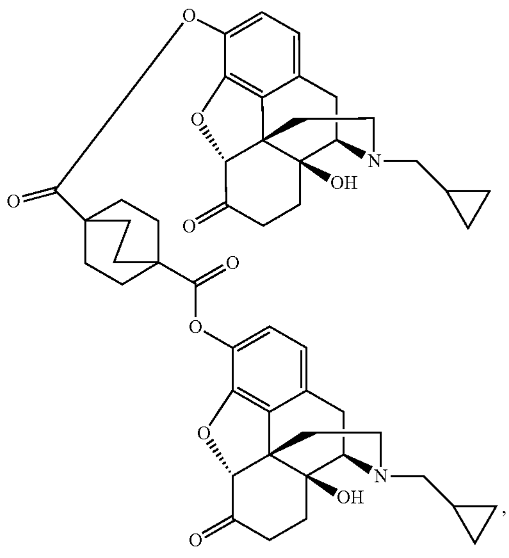
, -continued

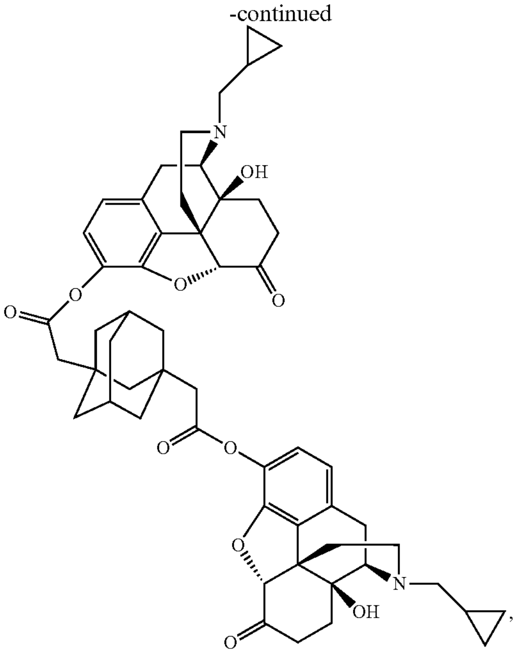

, or

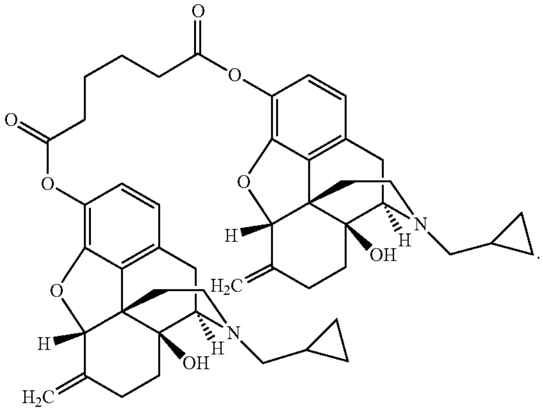

.

3. The compound of claim 1, wherein $R^1$ and $R^{1'}$ are each independently unsaturated alkyl.

4. The compound of claim 1, wherein $R^1$ and $R^{1'}$ are each independently cycloalkyl.

5. The compound of claim 1, wherein $R^a$ and $R^{a'}$ are each H.

6. The compound of claim 1, wherein $R^a$ and $R^{a'}$ are each —OH.

7. The compound of claim 1, wherein X and X' are each O.

8. The compound of claim 1, wherein X and X' are each $CH_2$.

9. The compound of claim 1, wherein $L^d$ is $-(CR_2)_y-$ or $-O(CR_2)_yO-$, wherein y is 1-10 and each R is independently selected from the group consisting of H, hydroxyl, halogen, alkyl, or is taken together with another R to form an optionally substituted cycloalkyl.

10. A pharmaceutical implant or article comprising a compound having a structure represented by Formula (IID):

Formula (IID)

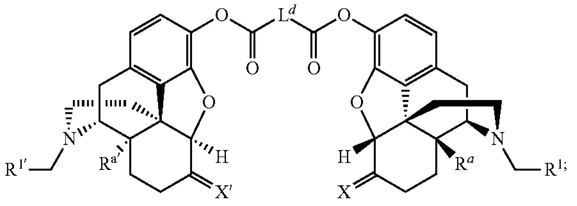

wherein:

$R^1$ and $R^{1'}$ are each independently unsaturated alkyl or cycloalkyl;

$R^a$ and $R^{a'}$ are each independently H or —OH;

$L^d$ is selected from the group consisting of $-(CR_2)_y-$, $-O(CR_2)_yO-$, $-O(CR_2)_y-$, $-(CR_2)_yO-$, and $-O(CH_2CH_2O)_y-$, wherein y is 1-10 and each R is independently selected from the group consisting of H, hydroxyl, halogen, alkyl, or is taken together with another R to form an optionally substituted cycloalkyl; and X and X' are each independently O or $CH_2$, or a pharmaceutically salt thereof.

11. The pharmaceutical implant or article of claim 10, wherein the implant or article comprises at least 50 wt. % of the compound and/or pharmaceutically acceptable salt thereof.

12. A pharmaceutical implant or article comprising a compound of claim 1, or a pharmaceutically acceptable salt thereof.

13. The pharmaceutical implant or article of claim 12, wherein the implant or article comprises at least 50 wt. % of the compound and/or pharmaceutically acceptable salt thereof.

* * * * *